US009556450B2

(12) United States Patent
Albertsen et al.

(10) Patent No.: US 9,556,450 B2
(45) Date of Patent: *Jan. 31, 2017

(54) DROUGHT TOLERANT PLANTS AND RELATED CONSTRUCTS AND METHODS INVOLVING GENES ENCODING DTP21 POLYPEPTIDES

(71) Applicants: E I DU PONT DE NEMOURS AND COMPANY, Wilmington, DE (US); JAPAN TOBACCO INC; PIONEER HI-BRED INTERNATIONAL INC, Johnston, IA (US)

(72) Inventors: Marc C Albertsen, Grimes, IA (US); Yukoh Hiei, Shizuoka (JP); Teruyuki Imayama, Shizuoka (JP); Masakazu Kashihara, Shizuoka (JP); Norio Kato, Shizuoka (JP); Toshihiko Komari, Tokyo (JP); Toshiyuki Komori, Shizuoka (JP); Stanley Luck, Wilmington, DE (US); Ichiro Oka, Shizuoka (JP); Hajime Sakai, Newark, DE (US); Yoshimitsu Takakura, Shizuoka (JP); Scott V Tingey, Rockdale, TX (US); Satoru Usami, Shizuoka (JP)

(73) Assignees: E I DU PONT DE NEMOURS AND COMPANY, Wilmington, DE (US); JAPAN TOBACCO INC (JP); PIONEER HI-BRED INTL INC., Johnston, IA (US)

( * ) Notice: Subject to any disclaimer, the term of this patent is extended or adjusted under 35 U.S.C. 154(b) by 36 days.

This patent is subject to a terminal disclaimer.

(21) Appl. No.: 14/570,267

(22) Filed: Dec. 15, 2014

(65) Prior Publication Data

US 2015/0101078 A1 Apr. 9, 2015

Related U.S. Application Data

(62) Division of application No. 12/915,547, filed on Oct. 29, 2010, now Pat. No. 8,916,746.

(60) Provisional application No. 61/256,348, filed on Oct. 30, 2009.

(51) Int. Cl.
*C12N 15/82* (2006.01)
*C07K 14/415* (2006.01)

(52) U.S. Cl.
CPC ......... *C12N 15/8273* (2013.01); *C07K 14/415* (2013.01); *C12N 15/821* (2013.01)

(58) Field of Classification Search
None
See application file for complete search history.

(56) References Cited

U.S. PATENT DOCUMENTS

| 7,834,146 B2 | 11/2010 | Kovalic et al. |
| 8,916,746 B2* | 12/2014 | Kashihara ............ C07K 14/415 435/419 |
| 2008/0801832 | 12/2008 | Kubo et al. |
| 2009/0144848 A1 | 6/2009 | Kovalic et al. |

OTHER PUBLICATIONS

"Hybridization Language" www.Patent Lens.net, Apr. 15, 2013.
Bedell et al., Sorghum Genome Sequencing by Methylation Filtration, PloS Biology, Jan. 2005, vol. 3(1: e13, pp. 103-115.
Bowers et al., Comparative physical mapping links conservation of microsynteny to chromosome structure and recombination in grasses, Proceedings of the National Academy of Science, Sep. 13. 2005, vol. 102(37) 13206-13211.
Guo et al., Protein tolerance to random amino acid change, Proceedings of the National Academy of Sciences, Jun. 22, 2004, vol. 101(25): 9205-9210.
Patterson et al., The weediness of wild plants: molecular analysis of genes influencing dispersal and persistence of johnsongrass, *Sorghum halepense* (L.) Pers, Proceedings of the National Academy of Sciences, Jun. 1995, vol. 92: 6127-6131.
USDA—Agricultural Research Service, National Genetic Resources Program, Germplasm Resources Information Network (GRIN) database. Entries for "Sorghum biocolor", "Suadangrass", "Switchgrass" and "Sugarcane", Apr. 11, 2013.
J.S. Boyer, "Plant Productivity and Environment", Science Magazine, vol. 28(4571):443-448, 1982.
M.M. Chaves et al., "Mechanisms Underlying Plant Resilience to Water Deficits: Prospects for Water Saving Agriculture", Journal of Experimental Botany, vol. 55(407):2365-2384, 2004
Yuji Ishida et al., "High Efficiency Transformation of Maize (*Zea Mays* L.) Mediated by Agrobacterium Tumefaciens", Nature Biotechnology, vol. 14:745-750, 1996.
Mie Kasuga et al., "Improving Plant Drought, Salt, and Freezing Tolerance by Gene Transfer of a Single Stress-Inducible Transcription Factor", Nature Biotechnology, vol. 17:287-291, 1999.
Toshihiko Komari et al., "Vectors Carrying Two Separate T-DNAs for Co-Transformation of Higher Plants Mediated by Agrobacterium Tumefaciens and Segregation of Transformants Free From Selection Markers", The Plant Journal, vol. 10(1):165-174, 1996.
Maurice S.B. Ku et al., "High-Level Expression of Maize Phosphoenolpyruvate Carboxylase in Transgenic Rice Plants", Nature Biotechnology, vol. 17:76-80, 1999.
National Center for Biotechnology Information General Identifier No. 124359063, Accession No. AC196837, Feb. 1, 2007, DOE Joint Genome Institute, "The Sequencing and Finishing of Large-Insert Genomic Clones".

(Continued)

*Primary Examiner* — Eileen B O Hara
(74) *Attorney, Agent, or Firm* — E I Du Pont de Nemours & Co.

(57) ABSTRACT

Isolated polynucleotides and polypeptides and recombinant DNA constructs useful for conferring drought tolerance, compositions (such as plants or seeds) comprising these recombinant DNA constructs, and methods utilizing these recombinant DNA constructs. The recombinant DNA construct comprises a polynucleotide operably linked to a promoter that is functional in a plant, wherein said polynucleotide encodes a DTP21 polypeptide.

27 Claims, 11 Drawing Sheets

(56) References Cited

OTHER PUBLICATIONS

National Center for Biotechnology Information General Identifier No. 124359064, Accession No, AC196847, Feb. 1, 2007, DOE Joint Genome Institute, "The Sequencing and Finishing of Large-Insert Genomic Clones".
Kazuo Shinozaki et al. "Regulatory Network of Gene Expression in the Drought and Cold Stress Responses", Current Opinion in Plant Biology, vol. 6:410-417, 2003.
Kazuko Yamaguchi-Shinozaki et al., "Organization of CIS-Acting Regulatory Elements in Osmotic-and Cold-Stress-Responsive Promoters", Trends in Plant Science, vol. 10(2):88-94, 2005.
Babu Valliyodan et al., "Understanding Regulatory Networks and Engineering for Enhanced Drought Tolerance in Plants", Current Opinion in Plant Biology, vol. 9:189-195, 2006
Basia Vinocur et al., "Recent Advances in Engineering Plant Tolerance to Abiotic Stress: Achievements and Limitations", Current Opinion in Biotechnology, vol. 16:123-132, 2005.
Wangxia Wang et al., "Plant Responses to Drought, Salinity and Extreme Temperatures: Towards Genetic Engineering for Stress Tolerance", Planta, vol. 218:1-14, 2003.
E.A. Bray, Biochemistry and Molecular Biology of Plants, Chapter 22, American Society of Biologists. 1158-1203, 2000.
Database EMBL, Data Accession No. ER758682, May 16, 2007.
G. P. Lodhi et al., Gene effects in interspecific crosses of Eu-Sorghun, Indan J. Agric Sci., Apr. 1978, pp. 201-204, vol. 48(4).
A. Egrnya Eneji et al., Growth and Nutent Use Four Grasses Under Drought Stress as Mediated by Silicon Fertilizers, Journal of Plant Nutrition, 2008, pp. 355-365, vol. 31(2).

\* cited by examiner

PCR primer pairs for genotyping

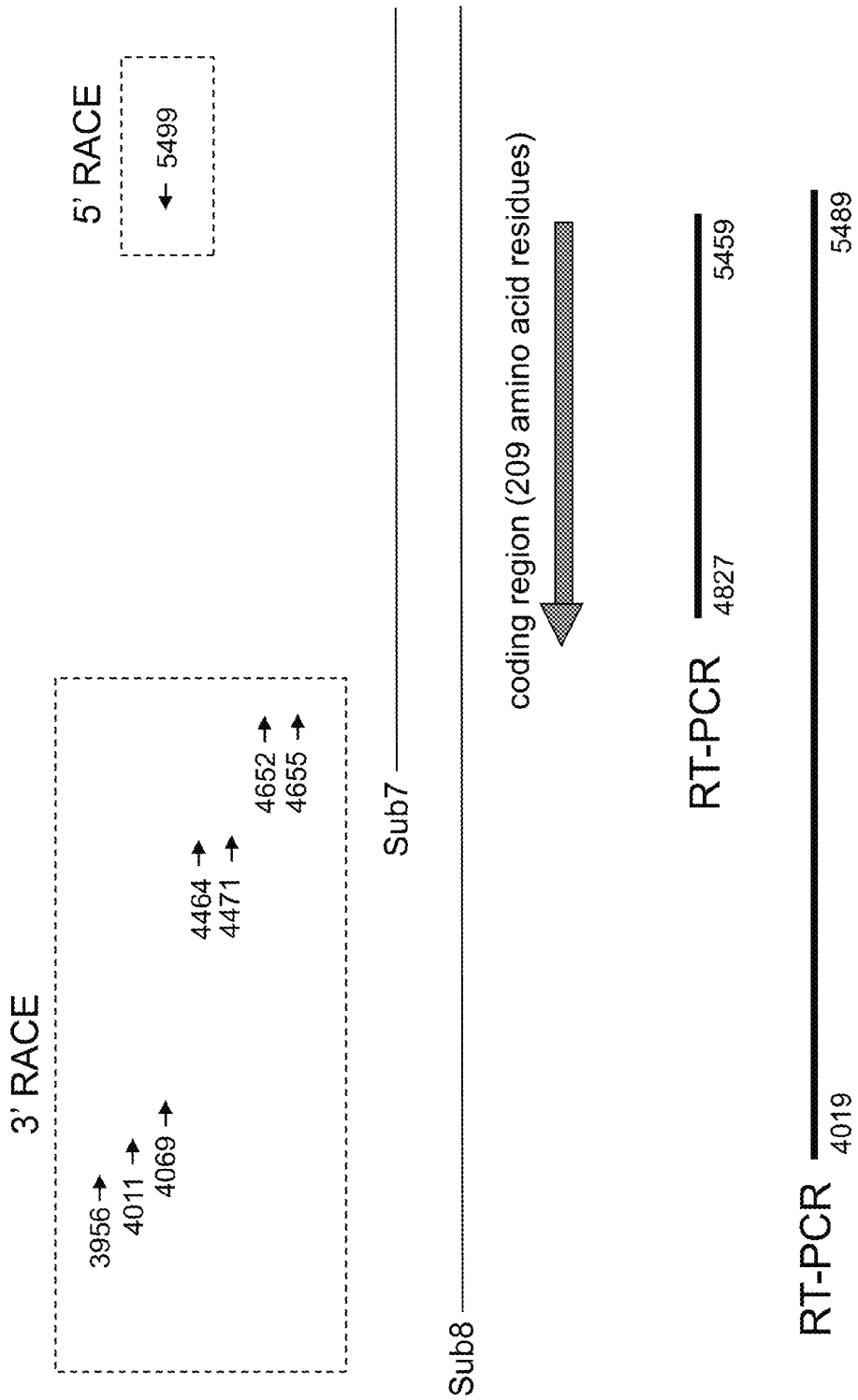

| | | | | | | | | | | |
|---|---|---|---|---|---|---|---|---|---|---|
| | . | . | H | . | . | . | . | . | I . . LE . . | |
| 201 | K | K | I | K | R | E | L | E | R R | Consensus #1 |
| 201 | K | K | I | K | K | E | L | E | R H | SEQ ID NO-27.pro |
| 201 | R | K | I | K | K | E | L | E | R Y | SEQ ID NO-32.pro |
| 201 | K | K | I | K | K | E | L | E | R H | SEQ ID NO-41.pro |
| 200 | K | K | I | K | K | E | L | E | R R | SEQ ID NO-42.pro |
| 201 | K | K | I | K | K | E | L | E | R R | SEQ ID NO-45.pro |
| 201 | K | K | I | K | K | E | L | E | R R | SEQ ID NO-46.pro |
| 201 | K | K | I | K | K | E | L | E | R C | SEQ ID NO-52.pro |
| 201 | K | K | I | K | K | E | L | E | R R | SEQ ID NO-54.pro |
| 201 | K | K | I | K | K | E | L | E | R H | SEQ ID NO-56.pro |
| 201 | K | K | I | K | K | E | L | E | R R | SEQ ID NO-58.pro |
| 201 | N | R | I | K | R | E | L | E | R H | SEQ ID NO-60.pro |
| 199 | A | R | I | R | R | E | D | L | E Q | SEQ ID NO-62.pro |
| 199 | A | R | I | R | R | E | D | L | E Q | SEQ ID NO-64.pro |
| 201 | K | K | I | K | K | E | L | E | R R | SEQ ID NO-66.pro |
| 201 | K | K | I | K | K | E | L | E | R R | SEQ ID NO-79.pro |
| 201 | M | K | I | K | K | E | L | E | R R | SEQ ID NO-81.pro |
| 200 | K | K | I | K | K | E | L | E | R R | SEQ ID NO-83.pro |
| 201 | K | K | I | K | K | E | L | E | R R | SEQ ID NO-85.pro |
| | | | | | | | | | | SEQ ID NO-87.pro |

FIG. 6A

Evaluation of Individual Gaspe Flint Derived Maize Lines Transformed with PHP29675*

| Treatment | Event name | % area chg_ start chronic - end chronic | % area chg_ start chronic - harvest | % area chg_ start chronic - recovery 24hr | % area chg_ start chronic - recovery 48hr | fv/fm_ acute1 | fv/fm_ acute2 |
|---|---|---|---|---|---|---|---|
| Reduce Water | EA2393.324.2.1 | 0.0832 | | | | 0.0288 | |
| Reduce Water | EA2393.324.3.2 | | 0.0661 | | | | |
| Reduce Water | EA2393.324.4.2 | | | | | | |
| Reduce Water | EA2393.324.5.1 | | | | | | |
| Well Water | EA2393.324.2.1 | (0.0372) | (0.0427) | | | 0.0009 | |
| Well Water | EA2393.324.3.2 | (0.0372) | | | | 0.0162 | |
| Well Water | EA2393.324.4.2 | | | | | (0.0245) | |
| Well Water | EA2393.324.5.1 | | | | | 0.0234 | |

* Significant positive effect has P-value less than or equal to 0.1; significant negative effect is in parenthesis; blank when difference not significant

FIG. 6B

Evaluation of Individual Gaspe Flint Derived Maize Lines Transformed with PHP29675*

| Treatment | Event name | leaf rolling_ recovery 24hr | leaf rolling_ recovery 48hr | psii_ acute1 | psii_ acute2 | sgr - r2 > 0.9 | shoot dry weight | shoot fresh weight |
|---|---|---|---|---|---|---|---|---|
| Reduce Water | EA2393.324.2.1 | | | 0.0072 | | | 0 | |
| Reduce Water | EA2393.324.3.2 | (0.0049) | | | | | | |
| Reduce Water | EA2393.324.4.2 | | | | | | | |
| Reduce Water | EA2393.324.5.1 | | | | | | | |
| Well Water | EA2393.324.2.1 | | | 0.0017 | | (0.0562) | | |
| Well Water | EA2393.324.3.2 | | | 0.0589 | | (0.0575) | 0.0513 | |
| Well Water | EA2393.324.4.2 | | | | | (0.0347) | | |
| Well Water | EA2393.324.5.1 | | | | | (0.0158) | | 0.0776 |

* Significant positive effect has P-value less than or equal to 0.1; significant negative effect is in parenthesis; blank when difference not significant

FIG. 7A

Summary Evaluation of Gaspe Flint Derived Maize Lines Transformed with PHP29675*

| Treatment | % area chg_ start chronic - end chronic | % area chg_ start chronic - harvest | % area chg_ start chronic - recovery 24hr | % area chg_ start chronic - recovery 48hr | fv/fm_acute1 | fv/fm_acute2 |
|---|---|---|---|---|---|---|
| Reduce Water | | | | | 0.0085 | |
| Well Water | | | | | | |

* Significant positive effect has P-value less than or equal to 0.1; significant negative effect in parenthesis; blank when difference not significant

FIG. 7B

Summary Evaluation of Gaspe Flint Derived Maize Lines Transformed with PHP29675*

| Treatment | leaf rolling_ recovery 24hr | leaf rolling_ recovery 48hr | psii_acute1 | psii_acute2 | sgr - r2 > 0.9 | shoot dry weight | shoot fresh weight |
|---|---|---|---|---|---|---|---|
| Reduce Water | (0.0151) | | 0.0085 | | | (0.0447) | |
| Well Water | | | | (0.0631) | | | |

* Significant positive effect has P-value less than or equal to 0.1; significant negative effect in parenthesis; blank when difference not significant

SEQUENCE LISTING

```
<160> NUMBER OF SEQ ID NOS: 91

<210> SEQ ID NO 1
<211> LENGTH: 42104
<212> TYPE: DNA
<213> ORGANISM: Artificial Sequence
<220> FEATURE:
<223> OTHER INFORMATION: Sorghum sudanense genomic fragment IS125 and
      adjacent vector sequence

<400> SEQUENCE: 1
gcggccgctt cgacgtctgc agtcgacggt tcaaagcaac ctcccctcg agctgagcct       60 gggcgttgcg agcctcggct tgggcggcca gaagctcatc cttaagccct gtgaacacca      120
atgcaaaaaa cgttagaaaa aaccaagcac acctcaaaat ggaattccga caatagaaac      180
```

```
ataccgcgga tgctctcctc cagggccgtg ttctcgccaa ccaatttagt gttggccctc    240
tcgatctccc tgttggagcg ggccagctca gtgttggcaa cacgcagatc ttcgatcgct    300
ttgccggctt gagcaatggc cccattcttc tccaatagct ctcccttcag atggtcgatg    360
tcatcggaga ggctacgaga ccgagcccgc tctgcttcga ggtcttcgag gccttcttc     420 ttggcttcct ccgcagcgct cctggcgatc tcgccgctca cgtgctccac cttcatcctc    480
tggaaggact ctcgaaggga gtccaggtta gtcttgagga gcccttctc cttgtccaga     540 tcagcaatga cgttcttata agacatggca tcctcccggg ctttcgaggc ggcctcctcg    600
accatcagag cccgcttcct cagcagcacg gcctcttcct cagccttcct tgaggcctct    660
cgagcctcaa ccagggcagc ttccctcgcc ttcttctcct cctcgagcgc tataaggtct    720
ttatatgctt taaggagttt ctcctgcgac tcgaggagtt ggtccttaag gacggggagc    780
tgctcccagc cgcctcttgt ggcatggatg aagctcgact tgatacggga ggtctctttc    840
atatcctatg aacgggtggt caaacagtta gaacacaaga ccaaaagctc cgtgaagatt    900
aaggaccgaa aagcacttac aaagtaggcc ggcccaagcc cgttattgat gacgtccgat    960
aggagcccca ccacgtgctt catccaaagg cggagctcct cgatgtgttc ccacttctca   1020
gcctccttcc gatcgtctag gaagatgtta ggcttggacg gatcggtgga agcacggatg   1080
cggatctgat cggggcacca gttttccatc tccaggtcag cccgcgcctt gacgccgtga   1140
atgagatcct cgacagcttc gagggatccc ccatggtgaa ggaacaagtc gacgaggaa    1200 gggaaccacc cgtcgtcgcc caccgtcttc caggtgccgt ccttgctacc cgatgtcccg   1260
gcctcgtctt cctcggcagg aatgcggtcc tcccacgccc ggcgctctcg gaggaaccct   1320
ggggcgatcc cgtccatgcc gtagatcgtc ctcctgatct cggactcggg gtcgacgggg   1380
gtgtgcatca tgcaggcaag cgtcactaca ccgtccgccc gccccgactc tgtcgggatc   1440
gcggcgggcg ccccggacg gagccacgct ggggtcggag ggccgaaaac cggcagaccc    1500
tcttcctggt ccccgggctc ttgcggcacc agtaacacca gatggggcgg actttgggga   1560
ggaggctcga gcggtccccc caacggctgg ccccctatt gctgctgctg ctgcctctcg    1620
agctcttgtg acccttgttg acggcccgc tcctgcagct gccgttgcgt ctcctgctct    1680
tgcagttgat gccttgcctc tcgctcccgc tcctcctctt cctccttctt cctctgctcc   1740
tcgagggagc gaagaccggc agggcaggc gtccgtcccg cgacaagaga ggtcgaggcc    1800
tcctcgtcca taggacgggc atccctcgac gtcccgttgc caccagatcc atcactgatg   1860
gtaatgggct cccctcgac ccccgatcga ggaggctcgg gggttccctc ttgtcgttgg    1920
gactggggcg cctcggcctg ttttggcgac gacggggcag actcagggcg gggtggagca   1980
ctctcagtgc cggtcaaagg ccgagggtcg gaggagcctg taatacgaga aacaaaagcc   2040
agtcactatg atgaccaacg taagaacaac cccagtccca tgaacaagcc acagacctgg   2100
ctccttggag gctgctccca ccttgagcct cttcgccatc gaaggctggg cctgctcaaa   2160
cgtccgcttc aacctgagga aagaagaacg agcataaaga ataccataat acgagaaaac   2220
atgaagaatc aggagaataa gaatcaccgc gtcgaaaaac ttaccccaca gggagtgttg   2280
atatttggga acgcaaaagg aattgatccg caagcgcacg gatatcggtg agcacttcac   2340
ccgggaagtt atccagagta tcgtatttat ttttttaaca ctaggagaaa gagtgcatct   2400
gactaaccgg tctattacta ctaaccctt aggcaacaaa gaatgtcttt cgatgtgagt    2460
gataaataga gaagactgca accgtagtct ccttctaacc ttggtaagga tgatctattg   2520
ttctattggg gaggctaacg gaatctagac accacaaagg atgttcaacc cgcacctata   2580
```

```
aaccctatcc ttcctgctaa cgagatatgg tctgcaaatg taacttggaa ttgtcacgtt    2640
cctcactact accacggtcc agctagtcag ggaatatcta tgagtacctc agcctaaaca    2700
ccacgtttac gccagcaatg attactctaa actctacgtg aagagattaa agtaaactca    2760
taaaccagaa gaacaataaa acaagaactt actagaattt agaagtccaa atactgaaga    2820
atcctaggag caagcttcgg gttaggtgaa cttgatcccg caggtacaag cttggagtag    2880
acaccgacag gccgggcttc ctccaatcta cacctccact ctatctctct caatctagta    2940
gaaactagaa gatctatttc tactttatat tggttgctaa gcctaaaaag aaatattaat    3000
tagagaagag gttttccttc gagggcaccc ctcaatctct atgataattt ctacatgcct    3060
tctgcagggg ccagggggtc tccttatata gtcctcctcc tctatgcgtt tttgggtcgc    3120
taggcgaggt ggtaccatgt tttccttgat ccaataggtc ggtggaatat cccgtgcgaa    3180
gagagtcctg attggcatct agcagggggc aggcgcccag gtcaccaggg cgggcgccct    3240
gggcctggcc cctttcggcc tctgtcttct tcccatggct tctggagtct tctagatggt    3300
agaaaatcac acggtgcgtt gatatctcta tgtaatcccg acatgtgggc ctttcttcct    3360
tatttcctga taaccccctg cagaaacaga taaacaacaa aactcgtgga attcgtcag    3420 atcaaaccct aattctaggt gttggttaca tattggtcct ttcccttgtt tatttgataa    3480
ttaaaattga tacttaagaa ccgtcaacaa ataccccccat acttaggctt ttactcgtcc    3540
tcgagaaaag gatggttaag aaaaatatct ggggtaaaca ttttaaagca ttctttatat    3600
ttgcagggtg ttaaaaattt cactgtgtac catagtcagg aaagtttatg gttaagagta    3660
aagatccttt cttctcaatc ctgtcacttg gagttttgt atattttga aagaaagtta    3720 gaataccttt ttatcctcat aggttcttct cagatcactc attatctttt atatatctca    3780
ctgaggttgt tttaatttgc aaaaattctc aagcatactt actttgcatt tattgcctga    3840
tcaaaacggg atccgaggag ggaaatgtca tactcttaga tcaaagactt tggaaattaa    3900
aatctttgtc aactcttgct ggcatattgc ttattagagg gaacatgggc tatcattttt    3960
tttaaatgga taccgaggta cccctaattc tactgccgga cacttgtcca tttttttttg    4020
cgaggttgtc gagcacttgc tcctttttat ttcctcgaat catctctatt tttgcatagc    4080
ccatgcctct aatgcaataa tacttcggaa gagtgaatat ttctgaataa atgtcttgat    4140
cttaggagca tgataaatct ctcaaaaagg gtctaactca ttttgaacaa actcaataca    4200
gagtagatag cttctataat cataattaat attttcagtt ttatcaggca tataaaacac    4260
tgaggatggt agctagaatt ttgaatatt tgaaataaat tctccaagta gcaatgatat    4320
caagaataag aaactcatac tctaccatca catattccat attgacttaa gtaacacagg    4380
gttttaaaat gattttataa taattgcaag ttttcaggaa atatcacaga ttgagattaa    4440
tcatgattag aaatattta atctttttaa tttatcatgt cggaaacaat attctgcata    4500
atccaaaata tgtgtaaagt aaagtgtgca gagtgtgtac ctgaatcgtg gagtggtgtg    4560
gtcggagtgt gtttggcatg tcgagggatc tcccccatac ttgttttctg ctttcttgca    4620
caaaaataaa gtagagacac acaagacata ataataataa taataatact ctttattaat    4680
cttgaggcat ttattacaaa agactagtag caaactgatg ataatagtaa actgatgata    4740
atagtaaacc taaaccgatt ttaaagatag ataactaaga tgcattgcct caatgtctaa    4800
tctagataaa ttagcggcgc tctaattccc taatcttctt gttggcactg gcaagatcct    4860
gcctaaggcc tagtataacg gtgttgtggt tagagagctg cctagtgagg gaattatcg    4920
```

```
aggactggag gtctatgata actctgtcta gtctatgaac gtcctcatca atatccatta    4980
tagtcttgcg acgcttggga ggtgtctcaa aagcaacgag agcgtgcttc ggggctgcct    5040
ttggagggat gaaacggact ttggctgctc taatcccttc aaagtaaggc ctttcttcct    5100
ccgtagtgta gcgaatactg ctgatctcac cgctccggtt ggtcttgact ccaacgaccc    5160
tctcattggg tctaggtgga aggatccttg tgccggttgg caccttgata gtggtcttca    5220
tcttggatga tgatcctttg aggagtaggg gttgtggcgg tgcggtgaga actggttgag    5280
catggtaaga ttgggcggag ctgcgttggc gtaatggcat ggcttctggc tgtcgctctg    5340
tgttggccgg gacgagagca cgggcatcgg ggtcttccac aggctccatg ctgaggttaa    5400
aggggaccac ttcccaatct tcgtggtact tctcggccat tggagcagca aggaactaat    5460
caagctctaa ctgaagaaga gaaggcttgg tggcttggtg tttgaaaact aaggtcaggg    5520
gtctgtttat ataggggtca aaaagtgcct ctatgggttg ttcgggttgc tcccatcgat    5580
gtgcatgcga aactttccat ctgagggatt attcaaatta ccataagtgc attttccata    5640
acaaataaaa ttgggaccga gggggaacag gagctgggcg cccgcccacc tgatctgggc    5700
gtccgccctc tctctggccc ctctgtgggc ccacttcctc gagcgcgttt ctagatgcga    5760
aattatttag aaaatatata tatatgaccc aaaaacatca gactaaaaag gtcgggcttt    5820
aattctccat gggaaagtaa aaatggacta cgtctatttc ttctaattca ttattgggct    5880
ctaaaaataa tttaagacat tgaccattta ccttgaataa cgtaccttcg tcattttgaa    5940
gtgtgatagc tccgtgggat gatgaattaa ttaccttgaa tggtccttcc cattcgctcc    6000
ggagttttcc atgcccgaaa agctttaccc tggacttaaa aattagtacc ttttctccgg    6060
gtgtgaactc cttcttcttg attctcttgc catgccacct tttgactctt tctttataga    6120
tctttgagtt gtgatatgcc ttctctcgcc attcttccaa ttccgatagt tgcattcttc    6180
tataatctcc agcaacatct aggtccatat tccatctctt tatggcccag tgtgctttga    6240
actctagttc aacgggtagg tggcaagtct tcccgtacac caattggtat ggagacattc    6300
caattggggt cttgtatgct gtccggtatg cccgtagtgc atcgggtaac ttgtctttcc    6360
acgccgttcc catttcattt actgtcttta gaagaatatt ctggatttgc ttgttggaag    6420
tttctgcttg gccacttgtc tgaggatgat aggggtagc gacgttgtga cggattccat    6480
gttttgatag atattgcttg aagcgtttgt cgatgaattg tgctcctcca tcacttatca    6540
ctactctggg gaatccaaat cgtggaaata taatttcttc aaacatcctc tttgaactga    6600
cgttgtcggc atgcttgcaa ggtaatgcct ctacccactt ggagacatag tcaactgcca    6660
ccaagatgta ctcacacttc tttgatggag gaaatggacc catgtagtct attccccata    6720
catcaaagag ctcaatctga aggttgttgg tgagtggcat tgcatccctt gtatttatgt    6780
ttctgtgtct ttaacatggc ccacatcttc tgatatattg cttcgtgtct tcaaacattg    6840
taggccagta gaatccacac tgccagatct ttgaatgcgt acgaaatgct ccatagtgac    6900
ctccatatgg tgatgaatga catctgtcga tgatcttcca tccttcctca gtggtcacac    6960
atctcctaag taagccatca gagcatactc ggaagaggta tggctcatcc catatatgtg    7020
aacgactttc ttgaataagc ttcttcttgt ttgctcctgg tggtacatac cctgaaacca    7080
taaaattaac aatatctgca taccagggt cagacctgtt aataacgtag agcatgtcgt    7140
cccggagtaa atcattgatg gggtttcct gtggattctt aaaatacatt ctagacaagt    7200
gatcagcaac agaatttct actccctttt tatcttttat ttctaagtca aattcttgga    7260
gtaataagat ccatctaatc aggcgaggtt tagcatcttt tttagtgagc aaatatttta    7320
```

```
gtgcagcatg atcagtgtaa acaattattt tagctccaac taaataagat ctaaatttat    7380
caatggcaaa gacaacagcc agaagctctt tttcagtggt tgtataatta agttgagctc    7440
gtgtcaaagt tttactggca taagcaattg catgatgctt cttatttta gtttgtccta     7500 aaactgcccc cacagcataa tcactagaat cacacaaaat ttcaaaaggc aacgaccaat    7560 caggggttg aatgattggt gcagagatga gtgctttctt taataaattg aaagatgtta     7620
gacatgcatc atcaaattca aaaggagcat ccttcgctag caaagagta agtggtctag     7680 caataaatga aaaatctttt atgaatctac gataaaaacg agcatggcca agaaagcttc    7740
gaatcccttt tatattcaca ggtggaggta gttgttcaat tacttcaatt ttagctttgt    7800
ctacctcaat acctctttca gacacttgtc ccagcactat tccttcccta accatgaaat    7860
gacatttttg caaaaacctt gtctaagtgc ttttctttac atctttgcaa aaccttgtct    7920
aagttttcaa gacaactatc aaagttttt ccataaacag agaaatcatc catgaaaact     7980
tccataatct cttcaatcat atcagaaaat atagacatca tgcatctttg aaaagaagct    8040
ggtgcattac ataacccaaa agacattcta cgataagcat aagttccata tgggcatgta    8100
aaagtggttt tgctttgatc atcgggatgg atcgggatct gatgataccc tgaatatcca    8160
tctaacaaac agaagaacga atggttcgct aaccgctcta gcatctcatc tataaaaggt    8220
aaaggaaagt gatcctttct cgtggctttg tttagtttc tatagtctat gcacatccgc     8280
catcctgtga cggtgcgttg cggaattagc tcgttctttt cattcataat aacagtcatg    8340 cctcccttt taggcacaac ttgaactggg cttacccact cactgtgcgg cacaggatat     8400
ataatccctg catgcagcaa ctttataact tccttttaa ctacctctct catagtgtta     8460
ttaagtctac gttggggttc tcgagagggt gaaacagaag gatctgttgg aatacgatgg    8520
gtacaaatca taggactgat tcctgtaaga tcttggagtg agtagccgaa aactgagtga    8580
tgtttctcaa gaatggtcat taatcgcaga gtttgaacct gagtgagttt atcgctaatg    8640
atcacaggaa tctctggatt attgtttagg aaagcatatg taagaccggg tggtaaagtt    8700
ttaagctcta tggggggtct aggtgtttct gcaaactcat ctaagggttc aggtttagaa    8760
ggttcggttt cttcttctgt gaagaaagga gtttcgtctt ctaagtctgg ttcatctaaa    8820
agctctagag atgcagcctt tacctcctcc ataggatcag gcaaaaaata tgattcggcc    8880
ttattattta aggagtgtta aattgttatt gggaatttaa aggttttcc aaaagaaatg     8940 tgtagctttc cagtatgacc ttcataaagg agtcttctaa aaggttgtcc tatcaacagg    9000
tcaaagtccc atgtatcaaa gatatagaag ttcaaatgaa ccatggagcc ttcaaccata    9060
agaggtaaga cattaataat tccaagactg gggactaatc gtcccgaaga ttcctttatg    9120
accttcgttg tgggggttaa gacaagattt taaaatagtt taagtgcaaa agattcagac    9180
atgatgtcga tccccacaac aggattataa agagcattaa atcgatcaga attataagca    9240
cagcgtatag ttatagaggg tgtgtccaaa cggatcacat tagaggaaag ctctgattcc    9300
tcctaccatt cgctactcaa gactgagata agctctctca attgatattc acttggtaaa    9360
taaatgctaa actagccgtt ttggggtttg ttaatagaat ggtagtttga aatgtttcca    9420
aaatcggcaa aaagatcgga ttctatatcc agcatgaagt ccgtgctgg atttttcttcc    9480 tcttgtggct cagaacttgg gatagctaaa gtagctgaag aatttggcag agtgtctaca    9540
tcggcttcgt aggtttcatc atgaagggta ttatccatct tagcttctag gattctatct    9600
aggatcactc tagcttcatc tgtagggatg cgaaagaaag aacctctaga cattgtgtgt    9660
```

```
agcatttgtt tgtgattttt ctgaagacct cgaaaaaagt gaaataaaag aacagggtct   9720
tcaagattaa ggtttgacca gattctaaaa gatcagaaaa acgtttccaa gattttccca   9780
aagtttcatt atcttttgt ttaaaagata ggacttcgag tctaaggttg gctatacggt   9840
caagggaata gaaatctaga caaaagttgg ctcgtaaaac tccccattca ccttgttgtt   9900
gacttacctt ctgactgtac cattgtctag cttctcccct taaagaaaaa ggaaaaagct   9960
tccaacgtaa agttttatca gaaatgcctt caatacgaag acaatcacat gtttgctcaa  10020
aatctctaat atgaaggtaa gggttttcgt cttcctttca cgaaaaagat aggttttgaa  10080
tcatggcaat caacctagaa cttaacttat actgggatgt ttggataggc tgtgatgatt  10140
cccatggtaa aaggttagtt actgaaggga tcgcagactc atggatcgat ttagaatttt  10200
ggttttccat aaggtaagac taagaaaat aagaaagaa tataaagat aagaacagat    10260 aaaagtatag atacaagcta gtagtaagac ttaggttatc tcagcaaccg tctttctccc  10320
cggcaacggc gccagaaatg cttgttgata tttgggaacg caataaggaa ttgatccgca  10380
agcgcacgga tatcggtgag cacttcaccc gggaaattat ccagagtatc gtatttattt  10440
ttttaccact aggagaaaga gtgcatctaa ctaaccggtc tattactact tacccttag   10500 gcaacaaaga atgtctttcg atgtgagtga taaatagaga agactgcaac cgtagtctcc  10560
ttctaacctt ggtaaggatg atctattgtt ctattgggga ggctaacgga atatagacac  10620
cacaaaggat gttcaacccg cacctataaa ccctatcctt cctgctaacg agatatggtc  10680
tgcaaaggta actcggaatt gtcacattcc tcactactac cacggtccag ctagtcaggg  10740
aatatctatg agtaccccag cctaaacacc acgtttacgc cagcaatgat tactctaaac  10800
tctacgcgaa gagattaaag taaactcata aaccagaaga acaataaaac aagaacttac  10860
tagaatttag aagtcgaaat actgaagaat cctaggagca agcttcggat taggagaact  10920
tgatcccgca ggtacaagct tggagtagac accgactagc cgggcttcct ccaatctaca  10980
cctccactct atctctctca atctagtaga aactagaaga tctatttcta ctttacattg  11040
gttgctaagc ctaaaaagaa atattaatta gagaagaggt tttccttcga gggcacccct  11100
caatctctat gataatttct tcatgtcttc tccaggggcc aggggtctc cttatatagt    11160 cctcctctat gcgttttggg gccggtaggc gaggtggtac catgtttcc ttgatcctat    11220 aggtcggtgg aacatcccgt gcgaagagag tcctgattgg catccagcag gaggcgggcg  11280
cccaggtcac cagggcgggc gccctgggcc tcgccccttt cggccctgt cttcttcccg    11340 tggcttctgg agtcttctag atggtagaaa atcatgcggt gcgttgatat ctctatgtaa  11400
tcccgacatg tggacctttc ttccttatta tctgataacc cctacagaa acagataaac    11460 aacaaaactc gtggaattct gtcagatcaa ccctaattc taggtgttgg ttgcatattg    11520
gtcatttccc ttgtttattt gataattaaa attgatactt aagaaccgtc aacagggaga  11580
acggctcatc tgacggtacc tcgaccagtg ggtctcgagc caccccgcgt caaggccca   11640 ggccctcga gggcaggcgt tggccttggc ctagcgtctc ccgcctggct gacaccggga   11700
ctggcgctcc ggcggccggc atctcccttc tcggaggccg cggcatgacc gcgggtcagc  11760
ggctccgtcg cctggggcct agcttgccca ctcgccttcg gtgcagggg aggctgtggg    11820 cgcggggcgg cccgactggc cgtgggcaca ggagggggtgt cggtgtgggg gcggagggcg  11880
cccgccctac ccccccttggc gcccgccctc ctctactggc caatcagcac gagtctcgcg  11940
gatcatgctc caccgaccta atggatcaag gagaaccgtt caatcaatgt cggtttgatc  12000
cgacggccta gattcatttg aaaatactat ataagcaagg cccctggcc cctagagaga   12060
```

```
agaatccaat tattcattag catattttcc aaacagaatt tagagagaga ggttccttag   12120
ggttcccacc tcatagggcg tagcatccaa tgtgagagta gactagttct actagattga   12180
gagagataga gtggaggtgt agatcggaga aagcctggcc tgtcggtgtc tactctaagg   12240
ttgtacctgc gggatcaagt ctcctaaccg gaggcttgct cctaggattc ttcagtattt   12300
tgatttctaa attctagtaa gttattcgtt ttattgttct ttggtttatg agtttacttt   12360
gatctcttcg cgtagagttt agtgtaatca tctctagcgt aaatgtggcg tttgggctag   12420
gatactcata gatatcccct gactagctgg accgtggtag tagcaaggaa cgtgatattt   12480
ccgagttacc tttgtagccc atatcacgtt agctggatcg atagggttta ttggtgcagg   12540
tcgaacatcc tctgtggtgt ctagattctg tgagcctccc caacaaaaca gtagatcatc   12600
cttaccaagg ttagaacgag agtgcagttg tagtcttctc tatacatcac tcacattgag   12660
tcacatagtt tgtagcctaa aggttagtag taatagaccg ggttagtcag atgcacgctt   12720
tctcctagtg gtaaaaatat aaatacgata ctcttgataa tatcctgggt gaagtgctca   12780
ccgatatccg tgcgcttgcg gattaatttt gattgcgtta ccaaatatca acaagcattt   12840
ctggcgtcgt tgcctgggtg aaagacaatt tgctaagata accttgagtc ttactactag   12900
cttgtattta tactttttatc ttatcttatc tttttacatt ctttatttc tttactctta   12960 ccttatggaa aaccaagatt ctaaatcgat ctatccattt gcaacacctt cggaaactga   13020
acttttacca tgggagtcat cacagcctat ccaaacatcc cagtataggt taagttccag   13080
gttgattgtc atgattcaaa acctatcttt ttcaggaaag gaagacgaaa acccttatat   13140
tagagatttt gagcaaacat gtgattgtct tcgcattaaa ggcatttcta ataagacttt   13200
acgttggaag ctttttcctt tttctttaag gggagaagct agacgatggt atagtcagaa   13260
gctaagtcaa caacaaggtg aatggggagt cttacgagcc aacttttgtc tagattttta   13320
ttccctcgac cgtatcggca accttagact cgaagtcgta tcttttaaac aaaaagataa   13380
tgaaactttg ggaaaatcct agaaacgttt ttctgatctt ttagaatctg gtccaaacct   13440
taatcttgaa gaccctgttc ttttatttca ctttttcgag gtcttcagaa agattataaa   13500
caaatgctac atactatgtc tagtggtttt ttctttcgca tccctactga taacactaga   13560
gtgatcctag atagaatcct agaagctgag atggataata accttcatga tgaaacccac   13620
aaagccgaag tagacactct gccaaattcc ccatctactt tagctatccc aagttctgag   13680
ccacaaaaga gagaaattcc accacctgat ttcatgctgg atatagaatc taatcttttt   13740
gccgattttg gaaacatttc aaactaccat tctatagaca gaccccagaa tggcaatttt   13800
agcatttgtt tgccaagtga acatcaattg agagagctta ttgtagtcat gagtagcgaa   13860
tggttggagg agtcagagct ttcctctgat gttatccgtt tggacacacc tcctatagct   13920
atacgatgta cttatgattc tgatcaattt gatgctctct ataatcctgt tgtggggatc   13980
aacattattt ctgaatctct tgcacttaaa ttatttaata atttggtttt aacctccata   14040
acaaaggtca taaggaatc ttcgagacga ttagtcccca gtctcagaat tattaatgtc   14100
ctacccttta tggtagaagg ctccatggtt catttgaact tctatatctt tgatacatgg   14160
gacttcgacc tattgatagg acaacctttt agaagacttg ttgatgcaaa actggtctgc   14220
aaacacaaag ggctaatacc cgattcaaac gttaaggcgt gccagccgat ttgaccctgc   14280
tatcggcaaa ggtgataact cgaatacttt agtcctgaca acagcgatgc gcccggatgt   14340
cacggctaag aggtactcac gcggaacttg agaacacgcc gagcttgagt cgacgaattc   14400
```

```
ctaagaactc gtaacaaaag gaaaaagtat gacgaagtcg tcgaaaagta aatgctggaa   14460
tatgagtaaa aacgtgtgtt tgatttcttg attgatttat tgattacaag gccctagggt   14520
ctacatttat accctgctca aagagctaca accagacacg attagaattc gaattccaaa   14580
ttacacggaa tccgtataca aaacgatgca ataattaag gaataacaa aactatccct     14640 cgtgacaaac cgaaactcct ccacataacg accggcagct tccagactcc ctctttgcat   14700
cattggcaga ccctttgcca tagtcatcgg cagactttct tatctagcca tcggcaccat   14760
attactgcct gtggacttaa tcacgttcaa cctctccctc atcggcaacc atcctcatcg   14820
gcaacccact ttgtaaacat cgtactgcca ccttatcctg ccatcccaga cacgtgccca   14880
aaaacggtgt caacacatgc cccccagttt cggagtataa aacattaatg ctccgaaatt   14940
ctctgcagta atgatgcctt tttccgcaat taatgctcct aatctggtaa ccgacaacct   15000
caatctgaac aactctgatc caattcctcc gcagatttct cgaaatcccc aactttctaa   15060
acgggcattt tttctcagcc gtacatcggc aacaataccg ttacaaagat ctgccgatgt   15120
tctgaccagg atattcacac aaacggttac ttcccctcta tccgcccatc ggcaatatga   15180
ccgttgtaga atattgccga tggaccgacc aggagatctc gcacagtaaa atatcttcag   15240
ataatgaccg cttcctatca aatcacctgc acaatccctg gattaccgtg cgaatagtta   15300
ccatatccac ctgagtaccc tcggatttct cggatgcagc aaagagataa gtcggatttg   15360
cccttgccca ttttgtccta taaatagttc cttctcgggt actccttccc catcacacca   15420
ttctactacc caactttact tttccagcgg cggcgccacc aaaaactccc aaggtctctg   15480
acaagtaccc ctcttcacca actccggcgc cttcaaacac ttccttcgca gctggatggc   15540
cgtcgggttc gtcgtccctg aggtcaaatc tccaccccgt cttctgtatt tttcttcata   15600
tccctgttca ctcgcaatcc attttactga acatcttcct tttcttttcct cttttttattt  15660 cttttttacgc ccaaaatcac taggaattgt ccaacaaaat tgtcatcccc accgatcaac  15720
cacaccttca atgcctcggc cctctagggg acccagatcc aactgacctt ctcaacgcag   15780
aaaccaacag gatccccttc agagccgaaa atttttcctt agatctgtgg aaggacacct   15840
tccgctcttg gccagcccca actgtagggt ggaaagactg gttcttgagg gtcagcaact   15900
ctaatgaagt tcagtggggt gaaaggaatc tagcccaatg catcagattg tccattgccg   15960
atatgcatag aaacgagtca ctgctgatag ctgcatccta cttttggtca gacaccctca   16020
atgcttttgc ctttggccac ggccctgctt ctcctactct tgccgatgta gccatgctta   16080
ctggtctaga tatatcttct gccgatagca ccctctttt tgatactgcc cctagtgcca    16140
aagtggagac tcgcgctatc ggcggttggt cggggtacat tcagaagtac cgtgggaaag   16200
gatctgtcac cataaaggaa caaaccacct ttctgaacat gtggctggac aagtttgtat   16260
tctgtggtcg atcggcagga ccgacttctg tctacctatc ggcagcagaa agactggcta   16320
atggtggccg attccctctc ggtcgatact tgcttggcgc tgcttaccac cttctccatc   16380
aagtagccca gaaacttctg ctcggccaat ccactggcaa cttgggaggc ccctggtggt   16440
ttgtcaacat gtggctcaat ctgcatctgc acaagcgtct caacttcaac ctgttcacac   16500
agcgtttccc aagagatata gctgaaaacc atgtattggg tgaagaggaa tcggcaacac   16560
gcgccccctt gaactttggc gaagctgtca tagttctgcc tggttcaggg ggtaatccag   16620
atcagatcgg ccgattcttc cagactctgt atgagggttt gaccagagac gaacgaccat   16680
ggttggctta tgatgaccca gatagcatgc tccctctgac cttcaatcca tttgatgaag   16740
ctctcgacag ggacaatgag gtgatcatgg caattgtgac tcccagaatc attccagtga   16800
```

```
atttctttgg tagcacaaaa acctccctc aaacttacga attttacaat ccatcggcat   16860
tagctcgcca gctagctttc ggccagttgc cgattgcact tccttatgcc gatgtgataa   16920
aacccagaga aactatcaac aaccttcttg agtggactcg agcagcccaa ctaccaccaa   16980
acgccgatat agatgtagat ctgtcagaat gggtcccggc tgcttttatc actcacgcat   17040
acaagttatg gtgggcagaa tggaaagagc atctgttctg tagatcggca ctttcattcc   17100
gcggcatgat tgactccgaa tacgaagttc ctgatgacac tgtaagtaat tcaaaccaac   17160
atttcgtttt ctcaatatta cctccatcgg cagcttaccc ttgtattcct tttgcaggtt   17220
gataatattc ctccgttggt tagcaggagt ggcaggccga tcaacttgtt tccatcaggc   17280
ccgatttcct caatcggcca caatgctccc actctagctt ccatcgtgca tcgggtgta   17340 cgcctcagga aagtcaccac cagaagaacc cagacatcac caacggtagc tgctgccact   17400
ctcgcgcggg ctttcaaggc aatttgtcaa atcttttcct ttatgctgac tatctttata   17460
tcggctatat ttatgcttat aaactcttgt tcattattgc agcaaaccgg cacatcggcg   17520
aaagccaggc gtgagagtac cgatgccccc cagtctagcc aacccaagag aaagggcacc   17580
acgggtgcta agactggaac aaagcgccag aaggtagcaa tccccctcc tcctccggta   17640 tctccaattc cggtggaatc ttctccttct tctccagaag cccagccaca gcaagcacca   17700
tctcccccac ctgtgcagga agcaccacag atagaagaac cccaacagga aggatctcaa   17760
acagaagata catcagttga catgggtgaa caaacaactg gcccggtgag tccagttata   17820
ccatcggcag ttcttccggt tcagacaact gttgtccctc ctccaggtaa catactttaa   17880
caatatcgct accgatgaac ttattcttat ttagtctcat aactcctttt gtcttttca   17940 gttgatattg ctccatcggc aatctcagcc gatcaacctg tagctccatc ggcatctttg   18000
gccgatcagc ctatagctcc gtcagtactt ctcagtcaaa gacaagagat cgccttgaag   18060
caagtaagtc accgtttacc gttagcatta tttgccgatt ctctgagtat gagctaattt   18120
tgctttccct cccaggaaca agattctccc gatagcctgt tctcctttgc catcgatctc   18180
tctgaagaag aaggtgaaga agcaagctct tctcagacgg tcggcatcac atcggcagag   18240
atcaaggtca ggctggaaga attgtcagct ctccttcacc aagacacagc gcaattggtt   18300
gatgattctg accctaccaa gaccctgttc agaactctca gaggccaaat cccagccgat   18360
gttgaagaaa tcctgttcca agccgctcat ctggagcgtc gccagctgca gtaccagaga   18420
gcttctcggc gccttgccga tagagccgct cagactcaac tctccgatga aatgaggaaa   18480
gagaagcttt tgaccgatga gaagcacaag gacatcggta tcctgagatc ttctcgagac   18540
gcgctgaagc agaagatatc cgatctatcg gcaagaaaag aatccctgtt ggcggaactc   18600
aaggaagtag agaacgctct gtcccaagcc aacaggaag agagccaatt gccagagacc   18660
atcaggcttc ttgagcacga gcgaaatgtt catggtcgca aggcacttca actgaagaag   18720
aagctgaagc cgatagaagg ttctgccgat gacgacatca aggagatgga agcagccaac   18780
caaattcggc tacgcgctat atcggcaatc cagacgctgc ttaacacata gagtttccat   18840
cggcattata tctgcgcttt ccttcttcct cagcttttag tctagccgat aggactgtta   18900
tcggcactta agcttttgaa acaccaagtc ttgtccccaa gcatttggat ccagccgata   18960
ggagtgttat cggcacctaa acttctatgc atcgacccat atactggggt agtacttctt   19020
taaatatttg ccgtttaatg ctctgggaaa ttcaattcct tcgagggttt ctagaatgta   19080
ggcattacca ggagccgatc aacttatccg ataaggaccc tcccaattag gagaccactt   19140
```

```
tccaaacttc gaacttttgg tcccaattgg taaaattaat ttccatacca aatccccatc   19200
ggcaaactct ttagccttca ctttcttatc ataccatcta gcaactctct tcttattttc   19260
ttctatactc attaaagctt ttaaccgatg ccctgctaga tcgtccaatt catcggtcat   19320
caaagtggca taaccatcgg aagttaattg atcttgaaaa gttaatcgcc tagatccagt   19380
cttaatctcc caaggcaaca ctgcatcatg tccatacacc aattgatagg gtgatacttt   19440
ggtcgatcca tgacaagcca tcctataaga ccacaatgct tcactcaata atgtgtgcca   19500
ccgcttagga ttttcttcaa tctttcgttt aataagcttg ataattcctt tgttagatgc   19560
ttcggcctgc ccattggctt gagcataata aggagaagaa ttcaacactt taattcccat   19620
accgattgcg aattcatcga actcccccga tgtgaacatg gtgccctgat cggtagtaat   19680
cgtttgggga atcccgaatc ggtaaataat atgctccttc acaaaatcaa tcatattggc   19740
cgatgtgact ttcttcaaag gaatagcttc aacccactta gtgaaatagt cagtggcaac   19800
tagaatgaac ttatgccctt tgctagatgg tggataaatc tggccgatca gatcgatggc   19860
ccatccccgg aacggccaag gctttattat aggattcata gccgatgcgg gtgctctctg   19920
gatattacca aacttttgac aaccttgaca tcccttgaaa tatttaaaac aatcttcaag   19980
tatggttggc caaaaatacc cattccttcg aatcatccac ttcatcttaa aagctgactg   20040
atgcgctcca catactcctt catggatttc ccccatcaaa cttctagcct catcatcgcc   20100
caagcatcgg agaagaattc cgtcgatagt tcgataatac aattcatttt caaggaacac   20160
atacttggtt gcttgaaatc gaacccgtct ttcaactttt ttggatggat cttttagata   20220
atcaataatt tctttcctcc aatcaccggc accgactgcc gatgtcgcat taatcattgg   20280
ctgatatccc gaggcacgct gagctaaccg attagcgtct tcattatgca atcggggaac   20340
atgctccaat cggaaatcct tgaattcctt taacagttgc atacttctct cgaaataagt   20400
tatgagaact tcacttcggc attcatagct tccggccaat tgatttataa ccaacataga   20460
atccccgaat atttcaacag catcagcacg aacttctctt aacaactcca atcccttgat   20520
cagagcctga tactcagcct gattatttgt tgatgtggca acaatcggca aggaaaactc   20580
atacttcctc cccttagggg aaactaatac aatgccgatt cctgccccct ggtcacaggt   20640
agatccatca agaagagcg tccagggtac aatctccaag gtttccacta gaccgcaatg   20700
ctgagtcaca aaatcggcca taatctgccc tttgactgcc ttagccgatt cgtaacgcaa   20760
atcgaactcc gacagcgcta aaatccattt accgatccta ccactcataa tcggcataga   20820
tagcatgtat cggaccacgt catctttgca acaacagtg cattcggccg ataacaggta   20880
atgtctcagc ttgatacatg aaaaatataa gcataagcat agtttctcaa tggccgaata   20940
cctggtttca gcatcaatca acctcctact caaataataa attaccctt ctttcccttc   21000 aaattcttga actaaagctg aaccgataac cgatccatcg gtagataaat acaatctgaa   21060
gggcttccct tgttgaggtg gaactagaac tggaggattt actagatact tcttgatttc   21120
atccagagcc aactgctgtt cttctcccca aataaactct tgatcggctt tcaatttaag   21180
aagaggactg aaagcacgaa tcctaccaga taaattcgat ataaatctcc tgatgaaatt   21240
taccttgccg atcaaggatt ggagctcggt tttgttggta ggggccacta ttttattgat   21300
ggcatcaaca gatcttcgac taatttcaat acccctctga tgtaccatga aaccaagaaa   21360
ctgccctgcc gatacaccaa atgcacactt gttgggattc atcttcaatc catgcttcct   21420
tgtgcattct aacactttt gtaaatcggc aagatgcttt gagaaatctc cagacttaac   21480
caccacatca tcaatataaa tctccacgag cttgccgatg aactcatgaa atataaaatt   21540
```

```
catagcccett tgataagtag caccagcatt cttcaaccca aaagtcatga ctatccactc   21600
aaatagccca acatgaccag gacacctgaa tgcggttttt ggaatatcct cctccgccat   21660
gaatatttga ttgtaacctg cattaccatc catgaagctg atgacctgat gaccagccgc   21720
agcatcaacc agtagatcgg cgacaggcat tgggtatcca tccatcggcg tagctttatt   21780
gagattcctg aaatcgatgc acacccgaag cttcccgttc ttcttgtaaa ccggaacaac   21840
attggaaatc cactcggcat accgacactg ccgaataaac ttagcttcaa taagtttggt   21900
gatttcggcc ttaatatcag gtagaatgtt aggattacat cggcgggctg gttgctgatg   21960
tggccgaaat ccagacttga tgggtaaccg atgttcaaca attgatcggt ctaaaccagg   22020
catctcagta taatcccaag caaagcaaac tttatattcc tttaacaaac tagtcaattg   22080
ttgcttactc tcaggatcta atttagcact aataaaagta ggcctaggct tatcaccact   22140
acctatatct acttctacca aatcatcggc cgatgtgaat ccctggccta attttccatc   22200
atcggcgaat ctatccatta aaaccgtcg tcagaaccga ctgcttggat cggtggaatc   22260
tcataatcgg caactttgag aaaatctttc tcccaaactt ctccagaaat gcacctggtc   22320
ctttcgtaag tatccgcttc tgccgacgcg ataacataag aagaatctcc tgggacaatc   22380
tcaatcttgt cacctaccca ctgaaccaag cattgatgca ttgtagatgg gatacaacaa   22440
ttggcatgaa tccaatctct tcccaacaat aagttgtaag cacctttttcc gctgatcacg   22500 aaaaaagttg tcggcaaggt tttgctgccg atggtcaact ctgcacatat cgccccttg   22560 actggagaca cgtttccttc aaagtctttg agcatcatat cggtcttggt caaatcttga   22620 tccccttttcc caagcttccg atatactgca tacggcataa tattaatagc agctccacca   22680
tcaactagga tcttggtcat tggctgccca tcaaccccttc ctttgaggaa cagagcttta   22740
agatgctgcc tctcgtcatc agcaggtttc tcaaatatag ccgtcatcgg atccagagcc   22800
aactgagcta tctgatcaga aaattccaac tcatcatcac tggctggtgc aagaaactcc   22860
atcggcaaca tgaagaccat gttgacgcct gccgatggac cttccctctt agtgtctgac   22920
ggctgccgac ttccagagtt ctctccccttg tttagctctt cttgcctttc acgttgcaat   22980
ctccttttct gtgtcttggt taatcctcca gggcaccatt gaggaagtgg cctttgcctt   23040
gccgtcgggc gtcggttctc ccttgactcc atacgatgcg tgttagcatc cctgcaaaat   23100
atgaattcat cgggaacccg cgcatcagcc attccctcga gctcctcttg ttcctgggga   23160
aaatactgga cacggtcact aagtctgtcg tgcccactaa atctgccccc cagccagtca   23220
tgaactgaca cccttcctct gatcggccca ttaaatcgcc gttcatcatc atgataatgc   23280
cgatcgatcc tatcgtaccg atcataaccg ttgcactcag ggcagtctct gacagtagga   23340
agcttgatat tttcctccca acaatggatg aagaatggac aattccaatg atccctgtgc   23400
cgattccact cctgtcggcg tctttcttct tcccgtcgat aatcttcctg ctggcgccga   23460
taccgatctt cccgttgttg ccattttttct cgaggccttc tatgagttat gacgatacca   23520
gagcgaggaa gccttcctga gctagttcct tcctggacca agcctttact tcttgcatcg   23580
gcagtagtaa cttgatgctg aggatctacc gatgcactct tctcagctgt ctccgatgtt   23640
aagaccttag ccttcccctt agcatccaac atgtttgtcg ggaaaggatg ttggtctatc   23700
ttcatcggct tctgggcttt ggaactgtca aacttgattc tccctgactc tatagccgat   23760
tgcagctgct gtctgaatac tttgcactcg ttggtgtcat gggaaattgc attatgccac   23820
ttgcaatatc tcatcctctt caactcttct gccgatggga tcacatggtt aggtgacagt   23880
```

```
ttgatctgac cttcctgaag tagaaagtca aatatcctat cagccttagc ggtgtcaaaa   23940
gcaaacttct ctggttcctt ctgcccaaaa ggacaagaca tcggcttctt gttttttacc   24000
cactctgcca agccgattac tggttcttca tcagaatctg agcttgttgc ttcatcaaca   24060
aatgacactt tcttattcca tgccctctta ggctcgaaag gcttgatgtc ttgatcagaa   24120
atcctctgca ccaaatgact taaactttcg aactcctagg aggcatactt gtccctgata   24180
tgtggcaaca aaccctggaa agccaaatcg gctagctgcc gatcatccag aaccaggcta   24240
tagcatttat tcttgacctc tcgtatcctc tgcacaaatc cctcaaccga ctcatcatta   24300
cgttgcctca acttgaccaa gtcggtgatc ttcttctcat gaaccccga gaagaagtat    24360
ttgtggaatt gcttctctag atcggcccaa gtaattactg agttgggagg taatgatatg   24420
aaccaagtaa aggccgatcc agacaatgat gatgaaaata gacgaaccct caattcgtcc   24480
ctgttaccag cctctccaca ttgaataatg aacctgttga catgctccat ggttgacgtg   24540
tcgtcctgtc cggaaaactt tgtaaaatcc ggtaccgtgt accgatgtgg aagcgggatc   24600
aaatcatacg cggaggata cggtgtccga taagagtaag tgttgacttt gcgttttatc     24660
ccaaattgtt ccctcattac ttcagcaatc ttatcggccc aatatgcatc ggcatcttgc   24720
cgatgaggct gcggatctgg tacttggtgg cgaacctcca cgtgtctgtt ggggacgtga   24780
tctgcgcgga acattgtatt gatcacctgt cctccaatct gcggaccacc aaactgctgt   24840
ccaccgattg gctgtcctcc gagttgctgt ccaaaattca ttggctggtt gggaatcccc   24900
tgaccttgga acccgggata gacctgccct tgctggaacc ctgtagtctg gtaactctgc   24960
tggggcgatt gtgaaaggc ttgttgtcca agccatccat tattagcgtt catcggcata    25020
ggtgctgccg atgattggta attgggtacc gtcgttgaat tgacataccc cgactgggcc   25080
ataggcctct gttgcatcag cattgactct gccgatgcgt tgggcatttg aacattgaa    25140
tcttgaggat ttctagtgtg aggccttgca gtagtagttg tggtataccg aggactctgg   25200
ttcaccggcg cattgagagg tgccgatgtc ataggagttt tgcctctcat gtcagttatt   25260
tgtgatgttc ccggcgtcaa ctctggaggc ataccgtaac cccaccagtt gggaggaaga   25320
gtcaaccctg acattgccga tgccaacata tctgttgtca gtttatgctg cccaactgaa   25380
atttgtgggt tggttgccat cggcatagat agtgcaccag tagtccccga tgtacttgga   25440
gggatggcag attgtgcact tgcattcgtc aaggcagccg atggagccgt gacctctggt   25500
gccgttggct gatgatggga ggggcccaca taatctggtg ggatttgtcc ttccttgaaa   25560
gttcttgcca cggcattgaa aaccgtatta gacagtacac cagcttggtt gatcaacgct   25620
cgattgatgg cattgtcaac catatcttga agcttgccag gattggcgtc aaaggtaacc   25680
tgctgtggtg ccggcagtgc atctttctgg accacttcgc cgctcctgtt tatgctgaaa   25740
gacctcaggc attgctgctt gaactcttcc atggcttggg caatagcttg cttctgctca   25800
tccttgaggt tggcctccgt cacggggatg acattctctt gatcgaggtc agagatcgac   25860
atgttgatct tgatcttgaa tcttgtccca ccgggcgtgc caaagatgt gttgatgcaa    25920
aactagtctg caaacacaaa gggctaatac gcgattcaaa cgttaaggcg tgccagccga   25980
tttgaccttg ctatcggcaa agtgataac tcgaatactt tagtcctgac aacagcgatg    26040
cgcccggatg tcacggctaa gaggtactca cgcggaactt gagaacacgc cgagcttgag   26100
tcgacaaatt cctaagaact cgtaacaaaa ggaaaaagga tgacgaagtc gtcgaaaagt   26160
aaatgctgga atatgagtaa aaacgtgtgt ttgatttctt gattgattta ttgattacaa   26220
ggccctaggg tctacattta ttccctgctc aaagagctac aaccagacac gattagaatt   26280
```

```
cgaattccaa attacacgga atccgtatac aaaacgatgc aaataattaa ggaaataaca    26340
aaactatccc tcgtgacaaa ccgaaactcc tccacataac gaccggcagc ttccagactc    26400
cctctttgca tcattggcag acccttttgcc atagtcattg gcagactttc ttatctagcc   26460
atcggcacca tattactgcc tgtggactta atcacgttca acctctccct catcggcaac    26520
ccactttgta aacatcgtac tgccaccttta tcctgccatc ccagacacgt gcccaaaaat   26580
ggtgtcaaca agactccttt acgaaggtca tactagaagg ctacacattt cttttggaaa    26640
aacttttaaa tttccaataa cgatttctca ctccttaaat aataagaccg agtcatatct    26700
tttgcctgat cctatggagg aggtaaaggc tgcatctcta gagcttttag atgaaccaga    26760
cttagaagac gaagctcctt tcttcacaga agaagaggct gaaccttctg aacctgaacc    26820
cttagatgag tttgcagaaa cacctagacc tcccatagag cttaaaactt taagacttgg    26880
tcttacctat gctttcctaa acaataatcc agagtttcct gtgatcatta gtgttaaact    26940
tactcaggag caaactagcg attgatgacc attcttgaga acatcactt agttttcggc     27000 tactcactcc aagatctcac aggaatcagt cctatgattt gtacccatcg tattccaata    27060
gatccttctg tttcacctc tcaagagccc aacgtagac ttaacaatgc gatgagagag     27120
gtagttaaaa aggaagttat aaagttgctg catgcaggga ttatatatcc tgtgccgcat    27180
agtgagtggg tgagcctagt ccaagttgtg cctaaaaagg gaggcatgac tgttgttacg    27240
aatgaaaaga acgagcaaat ttcataatgc accgtcacag ggtggcggat gtgaatagac    27300
tatagaaaac tgaacaaagc cacgaaaaag gatcattttc ctttaccttt catatatgag    27360
atgctagagc gattagcgaa ccattcgttc ttctgtttct tagatggata ttcagggtat    27420
caccagatcc caatccatcc cgatgatcaa agcaaaacca cttttacatg cccttacgga    27480
acttatgctt accgtagaat gtttttttggg ttatgtaatg caccagcttc ttttcaaaga    27540
tgcatgatgt ctatattttc tgatatcatc aaagagatta tggaagtttt catggatggt    27600
ttctatgtat atggaaaaaa cttttgatag ttgtcttgaa aacttagaca aggttttgca    27660
aagatgtgaa gaaaagcact taatcctaa ttgggaaaaa tgtcatttta tggttaggga     27720
aggaatagtg ttgggacacc tagtgtctaa aagaggtatt gaggtagaca aagctaaaat    27780
tgaagtaatt gaacaactac ctccacctgt gaatataaaa ggaattcgaa gctttcttgg    27840
ccatgctggt ttttatcgca aattcataaa agatttttca ttcattgcta gaccacttac    27900
tcttttgctg gccaaggatg ctccttttcga atttgatgat gcatccctaa catctttcaa    27960
cttattaaag aatccactca tctctgcacc aatcattcca ccccctgatt ggtcgttgcc    28020
ttttgaaatt atgtgtgatg ctagtgatta tgctgtgggg gcagttttgg gacaaactaa    28080
aaataagaag catcatgcaa ttgcttatgc tagtaaaact ttgaccggag ctcaacttaa    28140
ttatgcaacc actgaaaaag agcttctggc tattgttttt gccattgata aatttagatc    28200
ttatttagtt ggagctaaaa taattgttta cactgatcat ctgcactaa aatatctgct     28260 cactaaaaaa gatgctaaac ctcgcctgat tagatggatc ttattacttc aagaatttga    28320
ctccgggagt agaaaattct gttgctgatc acttgtctag aatgtatttt aagaatccac    28380
aaaaccccca tcaatgattc actccgggac gacatgctct atgggattaa catgtttgac    28440
ccctggtatg cagatattgt taattttatg gtttcagagt gtgtaccacc aggagcgaat    28500
aagaagaagc ttattcaaga aagtcgttca catttatggg atgagccata cctcttccga    28560
gtatgctctg atggcttact caggagatgt gtgaccacca aggaaggatg gaaaatcatc    28620
```

```
gacaggtgtc attcatcacc ttatggaggt cattatggag cattccatag acattgaaag   28680
atccggcaat gtggattcta ctggcctaca atgtatgaag acacgaagca atatatcaga   28740
agatgtgggc catgtcaaag gcacggaaac ataaacacaa gggatgcctc tccactcacc   28800
aacaaccttc agattgagct ctttgatgtc tggggaatag actacatggg tccatttccc   28860
ccatcaaaga agtgtgagtt catcttggtg gtagttgatt acgtctccaa gtgggtagag   28920
gcactacctt gcaagcacgc cgacaacatc agttcaaaga ggatgtttga agaaattata   28980
tttctaagat ttggagtccc tgaagtagtg ataagtgatg gaggagcaca cttcatcgac   29040
aaacgcttta agcactatct atcaaaacat ggaatccgtc acaacgtcgc tactccctac   29100
catcctcaga caagtggcca agcagagact tccaacaagc aaatcaagaa tattcttcaa   29160
aaatagtcaa tgagatggga acggcatgga aggacaagtt acccgatgca ctctgggcat   29220
accggacagc atacaagacc ccaattggaa tgtccccata ccaattgatg tacggaaaga   29280
ctttccacct acccgttgaa ttagagttca agaacacta ggccataagg agatggaata   29340
tggatctaga tgtcgctaga gatcatagaa gaatgcaatt atcagaattg gaagaatggc   29400
gagagaaagc ttatcacaac tcgaagatct acaaagaaag agtcaaaagg tggcatgaca   29460
agaggatcaa gaagaaggag ttcgctcccg gagataaggt attgcttttt aattctaggg   29520
tgaagctttt cgggcatgga aaactctgga gtaaatggga agggccattc aaggtaatca   29580
attcatcatc ccacggagct atcacacttc aaaatgacga aggtacgtta ttcaaggtaa   29640
atggtcaacg tcttaaatta tttttagagc ccaataaaga attagaagaa atagacgtga   29700
tccatttcta ccttcccatg gagaattaga gcccgacctt tttaatctga cgtttttggg   29760
ccacgtatat gttttcgaa taaagtctgc atctagaagc acgctcgagg aagcgggtcc   29820
acagagggc caggtacagg gcgggcgccc tgatgatgag ggcgggcgcc cagcccctgc   29880
ctcctctcag tcccgatttc ccccgtcgca ataaacccat ttatggtaaa ctaaaaaatc   29940
acacagatgg aaggtttcgc acgcatggcg gcgggagtag cctgagcaaa ccctataggc   30000
acttttgac ccctatataa acggacccct gacgtcggtt ttcaacacca atttattcaa   30060
gccttctctc cttcttctat tagagcttgc ttagtccctc gctgctccaa tggccgaaga   30120
gttccacaac gattgggaag tcatcccctt cgacctcaac aagaagccca aggaagaccc   30180
cgacgccgac gctctcgttc cggccaacac agagcgatag ctagcagcca tgccatcaca   30240
ccagcgcagc tctaccaatc ctaccatgct caaccagttc tcactgcacc cttgtagcct   30300
ctacttctca agggacagtc agccaagaag gaggccatcg tcaaggtgct agccggcaca   30360
aggatcctgc cacccagagc caatgagcgg ctcgttggag tcaagaccaa ccggagcggc   30420
gagatcagca gcatccgcta cactacggag gaggagaggc cttacttcga ggggattaga   30480
gcagccaaag tccgtttcat ctctccaaag gctgccccga agcatgctct caacactctt   30540
gagacacatc ctaagcgccg caagactata gtagatattg atgaggacat tcgtaggcta   30600
gacaaggtca tcatagagct ccagtcctcg gttaactcta tcactaggta gctctctaac   30660
caaaacacca ttatactagg tcttaggcat gatcttacta gtgccaataa gaagatcagg   30720
gagttagagc gacgctaagt tatctagatt agatcttgag gcagtacatc ttagttattc   30780
ttctttaaat tcggtttaga tctattatta gcttcagttc atcactagtc atttgtaata   30840
aatgcctcaa gattaataaa gattattatt atgtcttgtg tgtctctact ttatttttat   30900
gcaagaaagc agaaaacaag taaggggag atccctcgac atgccaacgc acttcgacta   30960
caccactcca tgattcaggt acatactcta cacactttac acatacacat atggtgaggt   31020
```

```
cgttgtcctg atcttcacga cgtaggataa ctagctgaag atcagccgat aacttgctgc   31080
aagcagcgag gataactagt gcaacctgac gacacgcaca aggagccaac caccgtctct   31140
atacggcagc ctgaaccaag gattcgccca accacactct caaagaacca acctacacaa   31200
cctgaactcg aggatcagga gcacggattg ggtgccgatg acgcggccgc ttctgtaatc   31260
tccacgaagg aaaacacaag agcaaagggg tagagatctc tctctgaatt tgttagcaca   31320
cagctgaaca aagtggtttg tattctcaat atcataagtc ttggattaca atgagtctta   31380
gggggtattt atactagcaa cagccctgct agataggtat gaaaacgaaa tagagtttct   31440
gagggaaggc aatgtgaaag gtcccctcga aatggattcc cgaagtggct tcgcgtgact   31500
gttggcctcc agagcagttt ccaataaact gacgataact ttttattggg aagtccaaat   31560
gatgaaccat ttcttgggtg tgaaactaga ctccaagagc tttccagcaa cgtatgccat   31620
gcaccacgaa actctgtaga ttggtacagt tttactttgc aagttgtacc aacattctgt   31680
cacgacaaac tgttgacctt ctgagcagtc tgtactaatt ctggtctgca ggaagtatgg   31740
agtatccaaa ctagtctcca ctagattcat tggaaggtag actcgaagag ctttccaaca   31800
aatgctcatg ggccttcata gcatctcgaa agtgaaagtt atgatctttt ctttcaactg   31860
gtccgttctg caccgtactg gtccgatctg cccttctttc aactggtccg ttctgcaccg   31920
tgttgttcca atccttgcga tccaggtcac ctccctcctc atgtgtatac ctaagcacaa   31980
ccaaagtaga acacttaggt agtataatat tctcattaac gttgatagaa ctctcacaaa   32040
gtagcacgtt cacctcttgt tgtagcttct tggctcggct acgtgtaatt gctctatcaa   32100
tggcttgggc tggtgccggc gtagtcggtg tagaggttgg catggaatta gagggagcat   32160
gcttggttgg gatgtcctca tcaacatata tcttggttta tgcagaatat tgtctccgac   32220
atgataaatt aacaagatta aaatgtttct aatcatgatt aatctcactc tatgatattt   32280
cctgaaaact tgcaattatt aaaaatcatt taaaaaccct atgtcactta agtcatttta   32340
agatggtaga gtatgagtac cttattctag atatcaatgt tgcttggaga atttatttca   32400
aaatcttcaa aaaattctag ctaacatccc cagtgtttta tatgcctgct aaacctaaaa   32460
atattaatta taataattat aaaagctatc tgctctgtat tgagtttgct taaaacgaga   32520
ttagacccct tgttgagaga ttatcatgct cctaagatca agacatttat tcagaaagat   32580
tcactcatcc gaagtattat tgcgttagag gcatgggcta ttcaaaaata tgaatatttc   32640
aaggaaataa aaaggagcaa gtgctcgata acctcgcaga aaaaatggac aagtgtccgg   32700
cagtagaatt aggggtacct cggtatccac ctgaaaaaaa agtgagagaa gaagatgata   32760
gcccatgctc cctctaataa gcaatatgcc agtaagagtt gacaagtttt taatttctaa   32820
agtctttgat ataagagtat ggcattcttc tcctcggata ccgttttgat caggcaacag   32880
atgcaaggta agtatgcttg agaatttctg caaattaaaa cagcctcagt gagatatata   32940
aaagataatg agtgacctaa gagaacatat gaggataaag gtacgctaaa tttcttttta   33000
aaaatataca aaaactctaa gtgacaggat taagaagaaa ggacctctac ttttggccat   33060
atttttccct gactacggta cacagtggat ttttacaaca ccctacaggt atgaagagaa   33120
tgctttacaa tgttttaacc ctagatattt ttcttaacca ttcttttctc gaggacgagt   33180
aaaagcctaa gtatgggggt gtttgttgac ggttcataag tatcaaattt aattatcaaa   33240
taaacaagga aaaggaccaa tgtacaaaca acacgtagaa ttagggtttg atctgacaga   33300
atgccacgag ttttgttgtt tatctatttc tgcatggggt tatcaggaaa taaggaagaa   33360
```

-continued

| | | | | | |
|---|---|---|---|---|---|
| aagcccacat | gtctggttta | catagagaat | ttaatgtgtt | gcgcaatttt | ctatcatcta | 33420 |
| gaagactcca | taagccacgg | gaacgaacgg | gaggccgatc | aggcttgggg | gcagggcgcc | 33480 |
| cgccctaacc | cccgaggcgc | ccgccctacc | ccccgaagcg | cccgccctcc | tctactggcc | 33540 |
| aatcagcacg | agtctcgcgg | atcatgctcc | accgacctaa | aggatcaagg | agaaccgttc | 33600 |
| aatcaatgtc | agtttgatcc | gacaacctat | attcatttga | aaagactata | taagcaaggc | 33660 |
| cccctagccc | ctggagagaa | gaatccaatt | attcattagc | atattttcta | gacaggattg | 33720 |
| agaaagagag | gttccttagg | gtttccacct | cataggagt | agcatccaat | gtgagagtac | 33780 |
| actagttcta | ctagattaag | aaagatagag | tggaggtgta | gatcggagaa | agcccggcct | 33840 |
| gtcggtgtct | actccgaggt | tgtacctgtg | ggatcaagtc | tcctaacccg | agactttctc | 33900 |
| ctaggattcc | tcagtatttc | gacttctaaa | ttctagtaag | ttcttctttt | tattgttctt | 33960 |
| tggtttatga | gtttactttg | atctcttcac | gtagagttta | gagtaatcat | ctctagcgta | 34020 |
| aacgtggtgt | ttgggctagg | atactcttag | atatcccatg | actagctgga | ccgtggtagt | 34080 |
| agcaaagaac | gtgacatttc | cgagttacct | ttgtagcccg | tatcccttta | gcaggatcga | 34140 |
| tagggtttat | aggtgcgggt | cgaacatcct | ctgtggtgtc | tagattccat | gagcctcccc | 34200 |
| aacagaacag | tagatcatca | ttaccaagtt | tagaacaaga | gtgcagttgt | agtcttctct | 34260 |
| atacatcact | cacatcgagt | cacatagttg | tagcctaaag | gttagtagta | atagaccggg | 34320 |
| ttagtcaaat | gcacgctttg | tcctagtggt | aaaaatataa | atacgatact | ctagataata | 34380 |
| tcccaggtga | agtgctcacc | gatatccgtg | cgcttgcgga | ttaattctga | ttgcgttact | 34440 |
| gttggtgcaa | aagctgatct | gcaatcacaa | agggctaata | cccgattcaa | acgttaacgc | 34500 |
| gtgccatccg | atttgacctt | gcaatcgacg | aaggtggtaa | ctcgaacacg | ttggtcccaa | 34560 |
| caagagcgat | gcgcccggat | gtcacggcca | agaggtgctc | acgcggaact | tgagaacaag | 34620 |
| ccgagattga | ctcgacgaat | tcttaagaac | tcgtagtaaa | aagaaaatat | gatgaagtcg | 34680 |
| tcaaaaaagt | agatgctgga | atatgagtaa | aaacttgtgt | tttattgatt | gatagatcat | 34740 |
| tcattacatt | gccctagggt | ctacatttat | accctatcca | aagagctaca | accagacaca | 34800 |
| actaggactc | gaattccaaa | ttaaacggaa | cccgtataca | aaatgaatcc | taataactaa | 34860 |
| ggaaaacatt | aaactatccg | ccgtaatcga | tcaggacact | gccacgaatc | aatcgtcaac | 34920 |
| ctccacgctt | ttcttaggg | tcatcggcaa | actacctgtt | acagccgtcg | gcaaacaccg | 34980 |
| acactggtca | tcggcatgaa | tacatcacca | cttctggact | tggtcatatt | tggttgtttc | 35040 |
| ccaatcagca | accaccttca | tcggcaactc | ccctatagac | tagtcaccat | tcctccacct | 35100 |
| gccgatctac | atcttattaa | ctctagacac | gtgcccaaag | atatgtgtcc | aaaaacgttg | 35160 |
| tcaacacatg | cccccaatt | tcagagtata | aaatcattaa | tgctccaaaa | ttctcctcat | 35220 |
| taatgatacc | tttccgcaat | tacttcctt | gattgataat | taattaccaa | atctaaacaa | 35280 |
| cctcggcctg | attctcctgc | agattctttg | aattcctcaa | cttcccgaac | tgaatctctc | 35340 |
| cagaacgctc | atcgacaata | ttaccgttag | agaaaactac | cgatggaccg | accacgcgat | 35400 |
| cttacacagt | aagaaatctt | caaaatcgtg | accgcttgct | gtcaaatcac | cagcaccatc | 35460 |
| ccttgattat | cgtgcgaaca | gttaccatat | ccacctgaac | accctcggat | ttcatggttg | 35520 |
| cggcaaagag | ataagtcaga | tttgcccctc | cccgttttgt | tctataaata | cttccttctt | 35580 |
| cggtactctt | tctccatctt | gtcattctac | agcctcaaat | ccaccttcct | ggtggcggca | 35640 |
| ttgcctgaga | actccaagaa | ctccagtaag | ggcctcctcc | atcaatcttc | caagtcttcg | 35700 |
| atctctcctc | ttccttggga | agaaatggca | atcaacttca | tcgttcctga | ggtcagccta | 35760 |

```
ccatctcctt tctgtacttt ttgttgtact cctgttcatc tgcgattctt tttactgagg    35820
accctccttt tttttctttt tgttccttca tcctcaaaac tctttaggat ttggccgata    35880
agatcgtaat tcctaccgat caacctcact tccaatgcct cggcctgtta ggaaatgcag    35940
atcccaccga tctgataaat gcagagacaa acagaatccc ctttagagcc gagaacttct    36000
ccttagatct gtggaaagat gcttttcgtt cctagcctag tcctaccaag ggatggaaag    36060
actggttcct gagagtcagt cattcaaatg aaatccaatg gggtgagcgg aaactagacc    36120
aatgcatcag attatccatt gccgatatgg agaggaacga gtcgctgctg atagctgcct    36180
cgtacttttg gtcagacaca cttaacgctt ttgtattcgg ccatggccat gcttcaccca    36240
ctcttgccga tgtactcatg cttactggct tacacatatc aactgccgat aatagtcatc    36300
tgtttgatac caagcccagt tcttaggtag agactcacgc tatcggcggt tggtctgggt    36360
atattcagaa ataccgaaaa acaggacctg ttggggaaag ggaacaagcc attttattga    36420
atatgtggct ggataagttt gtattctgtc accgatcggc aggaccaact tctgtctatc    36480
tattggcagt agaaagactg gccaatggtg gctgatttcc tcttggccga tatctgcttg    36540
gctctgttta tcacctcctt caccaggtag ctaagaaact cctgttaggc taacccatcg    36600
gcaacttagg gggaccctgg tggttcatca acatatggct tagtgttcac atgcataagc    36660
gccttcaatt caacctttc acacagcgct tccccaaaga tatagccgaa gatcatgagc    36720
tggatgaaga agaatcggca actcgctccc ccttgaacta tggtgaagct accatagttc    36780
tacctggtac cggtggtaat gaagatcagg ttagccgatt cttttagact ctttatgagg    36840
gtctgaccaa agaacagcgg gcatggatgc cttatgagga cccagacacc agatttccct    36900
tgactttcca tcccttttgat aatgctctca acaaggacca tgatctgatg atggcaatca    36960
tcaccccgag agctatacca gtgaacttct tcggtattgg gaaaacttcc aatcttacct    37020
atgagttctg caatccatcg acattggctc gccaattagc cttcggacaa ctgccgatcg    37080
cgctctgcta tgccgatgtg gtgaaaccaa gggagatcat caccagttgt cttgagtgga    37140
tcagaatagc tcaactccca ccaaatgccg atacatcaga tatcgactta ttagcttgga    37200
tcccaactct attcatcaca caggcgtaca acaatggtg ggcggagtgg aaagagcatt    37260
tgttctacag atcggctctt acataccgcg gtatgattga ctctgcgtac aaggtccccg    37320
aaaacactgt aagttttcaa ctgatgcgtc aatcctatta cttttgctct tatcggcaac    37380
ttacttcctc tgtgttacat aggtcaatga tactccacca tcagtaagca gaagtggcaa    37440
gctgatcgaa ctcctcccat cgggcccgat ctccttgatc ggcaacaacg caccaagttt    37500
ggcagctcta atgaaccggg gtgtgcgttt caagaagatc accaccaagc gggtcaagac    37560
atctccatcg gtcgctgctg ctgctttggc gcaagcttc aaggtagaaa gtttttatct    37620
cttcaattta taccgattcc attctatact tacacagttc tttcaggata catcggctgc    37680
tatggttact tcatcggtaa ctttcactgt ttcaaccaaa attccatcaa tactctgtta    37740
caattgtagt tatgaaactt ttatcgttgt atcagcaaac tggaaaatcg caaagacca    37800 gaagtaccaa gacaactgcc gatgccccc agtccagcca gtaaaaaga aggggtccca    37860 agagtactaa gtcacaagca aaacgccaga agacagcagc gcctcctcct cctcctcctc    37920
cagggtcacc gattcatgtg gaatcgtccc cttcttcacc agagactcag acacaacaag    37980
caccatctcc acctcagcca caagaagaac ctcagctaga agagacatta gccgatgtaa    38040
atgagcagac cgccgataca gtcggttcaa tcatagcatc ggtagtttcc tcaatccaga    38100
```

```
caagcactgc accccctcaa ggtaaagcat tgtctattaa atcattgccg atggacttaa   38160
ctttccaact tatgattatc tttattaatt ttcagctggc attgtcccag cggctccgac   38220
agatcaacct atggcactac cggcctcaac tagccagagg cgggagatag ctttgaaaca   38280
agtaagctat ttgattcatc ctttatttca ctaacattta gtcatcaaat aacctatctc   38340
cttttctttt acaggaacaa gattctcccg acagcctgtt ttccttcgct atcgaaattt   38400
ccgttgatga aggtgaagaa gcaagctcct ctcaagccat caggatttca tcagcaaaaa   38460
ttagagccaa gctggaagat ctgttggccc tgcttcatca agatacagct caactggttg   38520
atgactctga tccagcgaag gctttgttta agctctcag aggccaaatc cctgccaatg    38580
ccgaggagac tcttttttcag gctgcacact tagagagccg ccaacttcag tatcaaaaag  38640
ctgcccaacg ccttgccaat agaaccactc atgcccagct tttagaggag gtaatgaaag   38700
tgaagcacct tgccgatgag aaacacaaga gcatcggcat tctgaaatcc tccggagata   38760
cgctgaaaca aaagatctcc gacctatcag caaaaaggga agccctgttg gcagagctta   38820
agcaagtaga agaggctcta tcccaagctc aacaagaaga aactcaactg cttgaaatga   38880
tcaagaccct caaacaagag cgaaacattc tagcccgcaa ggcattgcag atgaagaaga   38940
agctgaagcc agtggagggt tctgccgatg aagacatcag ggagatagaa gaagccgatc   39000
aaattcgtct gcgcgctata tcggtgatcc aagctctact gaatgtataa gcttctcatc   39060
ggcggcgtgt tttgctcttt cttcaaaaac ttgttgattg ttttggtcta gccgatagga   39120
ctgttatcgg catcctttga aacatcgcat tcagtcccag atacatttca atccagccga   39180
taggagtgtt atcggcactt aaactttat gcatcgaccc atatgctcgg gtaatacttc    39240
tttaaatatt ttccatttaa tgctctggaa aattcaactc cttcgagagt ttccaaaata   39300
taggcattac caggagcaga ccgacttacc cgataaggac cttccaatt gggagaccac    39360
ttgccaaact ttgaactttt agtcccaatc ggtaatatta gtttccatac caaatctcca   39420
tcggcaaatt ccttagtctt tacctttta tcataccatc tggctactct cttttttattt   39480
tcttctatac ttatcaaagc cctcagccga tgcctggcta aatcatctaa ctcatctttc   39540
attaaagtag catagtcatc ggcagcgagc tgatcttgaa aagatagttg tctatatcct   39600
gtcttaattt cccatggtat catggcatcg tgtccataca ctaactgata aggtgaaact   39660
ttagttgacc catggcatgc catccgatac gaccataaag cctcacttag caatgtatgc   39720
catcttctag gatttt cttc aatctttcgt tgatgagtt tcataattcc tttgttagat    39780
gcttcggcct gcccattggc ttgagcataa taaggagaaa aattcaacac cttaattccc   39840
ataccgattg caaattcatc aaattctccc gatgtaaaca tagtaccctg atcggtagta   39900
attgtttgag gaataccaaa tcggtaaata atatgctctt tcacaaaacc aatcatatcg   39960
gtcgatgtaa ctttcttcaa aggaatagct tcaacccact tagtcaaata atcagtggca   40020
actaagataa atttatgccc tttgctcgaa gatgttaatt aacatcggta ccgagctcta   40080
gggataacag ggtaatagct cgaattctag cttgcatgcc tgcagtgcag cgtgacccgg   40140
tcgtgcccct ctctagagat aatgagcatt gcatgtctaa gttataaaaa attaccacat   40200
attttttttg tcacacttgt ttgaagtgca gtttatctat ctttatacat atatttaaac   40260
tttactctac gaataatata atctatagta ctacaataat atcagtgttt tagagaatca   40320
tataaatgaa cagttagaca tggtctaaag gacaattgag tattttgaca acaggactct   40380
acagttttat cttttttagtg tgcatgtgtt ctcctttttt tttgcaaata gcttcaccta   40440
tataatactt catccatttt attagtacat ccatttaggg tttagggtta atggttttta   40500
```

```
tagactaatt tttttagtac atctatttta ttctatttta gcctctaaat taagaaaact    40560
aaaactctat tttagttttt ttatttaata atttagatat aaaatagaat aaaataaagt    40620
gactaaaaat taaacaaata ccctttaaga aattaaaaaa actaaggaaa cattttcctt    40680
gtttcgagta gataatgcca gcctgttaaa cgccgtcgac gagtctaacg gacaccaacc    40740
agcgaaccag cagcgtcgcg tcgggccaag cgaagcagac ggcacggcat ctctgtcgct    40800
gcctctggac ccctctcgag agttccgctc caccgttgga cttgctccgc tgtcggcatc    40860
cagaaattgc gtggcggagc ggcagacgtg agccggcacg gcaggcggcc tcctcctcct    40920
ctcacggcac cggcagctac gggggattcc tttcccaccg ctccttcgct ttcccttcct    40980
cgcccgccgt aataaataga caccccctcc acaccctctt tccccaacct cgtgttgttc    41040
ggagcgcaca cacacacaac cagatctccc ccaaatccac ccgtcggcac ctccgcttca    41100
aggtacgccg ctcgtcctcc cccccccccc ctctctacct tctctagatc ggcgttccgg    41160
tccatggtta gggcccggta gttctacttc tgttcatgtt tgtgttagat ccgtgtttgt    41220
gttagatccg tgctgctagc gttcgtacac ggatgcgacc tgtacgtcag acacgttctg    41280
attgctaact tgccagtgtt tctctttggg gaatcctggg atggctctag ccgttccgca    41340
gacgggatcg atttcatgat tttttttgtt tcgttgcata gggtttggtt tgccctttc    41400 ctttatttca atatatgccg tgcacttgtt tgtcgggtca tcttttcatg cttttttttg    41460
tcttggttgt gatgatgtgg tctggttggg cggtcgttct agatcggagt agaattctgt    41520
ttcaaactac ctggtggatt tattaatttt ggatctgtat gtgtgtgcca tacatattca    41580
tagttacgaa ttgaagatga tggatggaaa tatcgatcta ggataggtat acatgttgat    41640
gcggttttta ctgatgcata tacagagatg cttttttgttc gcttggttgt gatgatgtgg    41700
tgtggttggg cggtcgttca ttcgttctag atcggagtag aatactgttt caaactacct    41760
ggtgtattta ttaattttgg aactgtatgt gtgtgtcata catcttcata gttacgagtt    41820
taagatggat ggaaatatcg atctaggata ggtatacatg ttgatgtggg ttttactgat    41880
gcatatacat gatggcatat gcagcatcta ttcatatgct ctaaccttga gtacctatct    41940
attataataa acaagtatgt tttataatta ttttgatctt gatatacttg gatgatggca    42000
tatgcagcag ctatatgtgg atttttttag ccctgccttc atacgctatt tatttgcttg    42060
gtactgtttc ttttgtcgat gctcaccctg ttgtttggtg ttac                     42104

<210> SEQ ID NO 2
<211> LENGTH: 24
<212> TYPE: DNA
<213> ORGANISM: Artificial sequence
<220> FEATURE:
<223> OTHER INFORMATION: M1 forward primer

<400> SEQUENCE: 2
ctgaaggcgg gaaacgacaa tctg                                            24

<210> SEQ ID NO 3
<211> LENGTH: 24
<212> TYPE: DNA
<213> ORGANISM: Artificial sequence
<220> FEATURE:
<223> OTHER INFORMATION: M1 reverse primer

<400> SEQUENCE: 3
ttccattttg aggtgtgctt ggtt                                            24
```

<210> SEQ ID NO 4
<211> LENGTH: 24
<212> TYPE: DNA
<213> ORGANISM: Artificial sequence
<220> FEATURE:
<223> OTHER INFORMATION: M2 forward primer

<400> SEQUENCE: 4
tccaagactg gggactaatc gtcc                                            24

<210> SEQ ID NO 5
<211> LENGTH: 24
<212> TYPE: DNA
<213> ORGANISM: Artificial sequence
<220> FEATURE:
<223> OTHER INFORMATION: M2 reverse primer

<400> SEQUENCE: 5
aagctaagat ggataatacc cttc                                            24

<210> SEQ ID NO 6
<211> LENGTH: 25
<212> TYPE: DNA
<213> ORGANISM: Artificial sequence
<220> FEATURE:
<223> OTHER INFORMATION: M3 forward primer

<400> SEQUENCE: 6
tatggtagaa ggctccatgg ttcat                                           25

<210> SEQ ID NO 7
<211> LENGTH: 24
<212> TYPE: DNA
<213> ORGANISM: Artificial sequence
<220> FEATURE:
<223> OTHER INFORMATION: M3 reverse primer

<400> SEQUENCE: 7
gcatcgtttt gtatacggat tccg                                            24

<210> SEQ ID NO 8
<211> LENGTH: 24
<212> TYPE: DNA
<213> ORGANISM: Artificial sequence
<220> FEATURE:
<223> OTHER INFORMATION: M4 forward primer

<400> SEQUENCE: 8
cactctgcca agccgattac tggt                                            24

<210> SEQ ID NO 9
<211> LENGTH: 24
<212> TYPE: DNA
<213> ORGANISM: Artificial sequence
<220> FEATURE:
<223> OTHER INFORMATION: M4 reverse primer

<400> SEQUENCE: 9
catcatcatt gtctggatcg gcct                                            24

<210> SEQ ID NO 10
<211> LENGTH: 24
<212> TYPE: DNA
<213> ORGANISM: Artificial sequence
<220> FEATURE:
<223> OTHER INFORMATION: M5 forward primer

```
<400> SEQUENCE: 10
gtagcctgag caaaccctat aggc                                          24

<210> SEQ ID NO 11
<211> LENGTH: 24
<212> TYPE: DNA
<213> ORGANISM: Artificial sequence
<220> FEATURE:
<223> OTHER INFORMATION: M5 reverse primer

<400> SEQUENCE: 11
tctaatcccc tcgaagtaag gcct                                          24

<210> SEQ ID NO 12
<211> LENGTH: 24
<212> TYPE: DNA
<213> ORGANISM: Artificial sequence
<220> FEATURE:
<223> OTHER INFORMATION: M6 forward primer

<400> SEQUENCE: 12
ctcagccgat gcctggctaa atca                                          24

<210> SEQ ID NO 13
<211> LENGTH: 24
<212> TYPE: DNA
<213> ORGANISM: Artificial sequence
<220> FEATURE:
<223> OTHER INFORMATION: M6 reverse primer

<400> SEQUENCE: 13
aactgcactt caaacaagtg tgac                                          24

<210> SEQ ID NO 14
<211> LENGTH: 23
<212> TYPE: DNA
<213> ORGANISM: Artificial sequence
<220> FEATURE:
<223> OTHER INFORMATION: M-hpt forward primer

<400> SEQUENCE: 14
gaaaaagcct gaactcaccg cga                                           23

<210> SEQ ID NO 15
<211> LENGTH: 22
<212> TYPE: DNA
<213> ORGANISM: Artificial sequence
<220> FEATURE:
<223> OTHER INFORMATION: M-hpt reverse primer

<400> SEQUENCE: 15 ctattcctttt gccctcggac ga                                           22

<210> SEQ ID NO 16
<211> LENGTH: 30
<212> TYPE: DNA
<213> ORGANISM: Artificial sequence
<220> FEATURE:
<223> OTHER INFORMATION: Sub8 forward primer

<400> SEQUENCE: 16
taccttgtta acctcatagg ttcttctcag                                    30

<210> SEQ ID NO 17
```

```
<211> LENGTH: 27
<212> TYPE: DNA
<213> ORGANISM: Artificial sequence
<220> FEATURE:
<223> OTHER INFORMATION: Sub8 reverse primer

<400> SEQUENCE: 17
tcccatggag agttaacgcc cgacctt                                          27

<210> SEQ ID NO 18
<211> LENGTH: 27
<212> TYPE: DNA
<213> ORGANISM: Artificial sequence
<220> FEATURE:
<223> OTHER INFORMATION: Sub7 forward primer

<400> SEQUENCE: 18
ccccatactt gttaactgct ttcttgc                                          27

<210> SEQ ID NO 19
<211> LENGTH: 27
<212> TYPE: DNA
<213> ORGANISM: Artificial sequence
<220> FEATURE:
<223> OTHER INFORMATION: Sub7 reverse primer

<400> SEQUENCE: 19
tcccatggag agttaacgcc cgacctt                                          27

<210> SEQ ID NO 20
<211> LENGTH: 24
<212> TYPE: DNA
<213> ORGANISM: Artificial sequence
<220> FEATURE:
<223> OTHER INFORMATION: Sub7 RT-PCR forward primer

<400> SEQUENCE: 20
tccctaatct tcttgttggc actg                                             24

<210> SEQ ID NO 21
<211> LENGTH: 24
<212> TYPE: DNA
<213> ORGANISM: Artificial sequence
<220> FEATURE:
<223> OTHER INFORMATION: Sub7 RT-PCT reverse primer

<400> SEQUENCE: 21
ttagttcctt gctgctccaa tggc                                             24

<210> SEQ ID NO 22
<211> LENGTH: 26
<212> TYPE: DNA
<213> ORGANISM: Artificial sequence
<220> FEATURE:
<223> OTHER INFORMATION: SS-DTP21-1 5-prime RACE primer

<400> SEQUENCE: 22
cctttggagg gatgaaacgg actttg                                           26

<210> SEQ ID NO 23
<211> LENGTH: 26
<212> TYPE: DNA
<213> ORGANISM: Artificial sequence
<220> FEATURE:
<223> OTHER INFORMATION: SS-DTP21-1 5-prime RACE nested primer

<400> SEQUENCE: 23
```

```
tgatctcacc gctccggttg gtcttg                                        26
```

<210> SEQ ID NO 24
<211> LENGTH: 26
<212> TYPE: DNA
<213> ORGANISM: Artificial sequence
<220> FEATURE:
<223> OTHER INFORMATION: SS-DTP21-1 3-prime RACE primer;DNA

<400> SEQUENCE: 24

```
tccttgctgc tccaatggcc gagaag                                        26
```

<210> SEQ ID NO 25
<211> LENGTH: 26
<212> TYPE: DNA
<213> ORGANISM: Artificial sequence
<220> FEATURE:
<223> OTHER INFORMATION: SS-DTP21-1 3-prime RACE nested primer

<400> SEQUENCE: 25

```
acctcagcat ggagcctgtg gaagac                                        26
```

<210> SEQ ID NO 26
<211> LENGTH: 630
<212> TYPE: DNA
<213> ORGANISM: Sorghum sudanense

<400> SEQUENCE: 26

```
atggccgaga agtaccacga agattgggaa gtggtcccct ttaacctcag catggagcct    60
gtggaagacc ccgatgcccg tgctctcgtc ccggccaaca cagagcgaca gccagaagcc   120
atgccattac gccaacgcag ctccgcccaa tcttaccatg ctcaaccagt tctcaccgca   180
ccgccacaac ccctactcct caaaggatca tcatccaaga tgaagaccac tatcaaggtg   240
ccaaccggca aaggatcct tccacctaga cccaatgaga gggtcgttgg agtcaagacc   300
aaccggagcg gtgagatcag cagtattcgc tacactacgg aggaagaaag gccttacttt   360
gaagggatta gagcagccaa agtccgtttc atccctccaa aggcagcccc gaagcacgct   420
ctcgttgctt ttgagacacc tcccaagcgt cgcaagacta taatggatat tgatgaggac   480
gttcatagac tagacagagt tatcatagac ctccagtcct cgataaattc cctcactagg   540
cagctctcta accacaacac cgttatacta ggccttaggc aggatcttgc cagtgccaac   600
aagaagatta gggaattaga gcgccgctaa                                    630
```

<210> SEQ ID NO 27
<211> LENGTH: 209
<212> TYPE: PRT
<213> ORGANISM: Sorghum sudanense

<400> SEQUENCE: 27

Met Ala Glu Lys Tyr His Glu Asp Trp Glu Val Val Pro Phe Asn Leu
1               5                   10                  15

Ser Met Glu Pro Val Glu Asp Pro Asp Ala Arg Ala Leu Val Pro Ala
                20                  25                  30

Asn Thr Glu Arg Gln Pro Glu Ala Met Pro Leu Arg Gln Arg Ser Ser
            35                  40                  45

Ala Gln Ser Tyr His Ala Gln Pro Val Leu Thr Ala Pro Pro Gln Pro
        50                  55                  60

Leu Leu Leu Lys Gly Ser Ser Ser Lys Met Lys Thr Thr Ile Lys Val
65                  70                  75                  80

-continued

```
Pro Thr Gly Thr Arg Ile Leu Pro Pro Arg Pro Asn Glu Arg Val Val
                85                  90                  95
Gly Val Lys Thr Asn Arg Ser Gly Glu Ile Ser Ser Ile Arg Tyr Thr
            100                 105                 110
Thr Glu Glu Arg Pro Tyr Phe Gly Ile Arg Ala Ala Lys Val
        115                 120                 125
Arg Phe Ile Pro Pro Lys Ala Ala Pro Lys His Ala Leu Val Ala Phe
    130                 135                 140
Glu Thr Pro Pro Lys Arg Arg Lys Thr Ile Met Asp Ile Asp Glu Asp
145                 150                 155                 160
Val His Arg Leu Asp Arg Val Ile Ile Asp Leu Gln Ser Ser Ile Asn
                165                 170                 175
Ser Leu Thr Arg Gln Leu Ser Asn His Asn Thr Val Ile Leu Gly Leu
            180                 185                 190
Arg Gln Asp Leu Ala Ser Ala Asn Lys Lys Ile Arg Glu Leu Glu Arg
        195                 200                 205
Arg
```

<210> SEQ ID NO 28
<211> LENGTH: 26
<212> TYPE: DNA
<213> ORGANISM: Artificial sequence
<220> FEATURE:
<223> OTHER INFORMATION: Sub5 RT-PCR forward primer

<400> SEQUENCE: 28
tgcgaggttg tcgagcactt gctcct                                        26

<210> SEQ ID NO 29
<211> LENGTH: 26
<212> TYPE: DNA
<213> ORGANISM: Artificial sequence
<220> FEATURE:
<223> OTHER INFORMATION: Sub5 RT-PCR reverse primer

<400> SEQUENCE: 29
caagccttct cttcttcagt tagagc                                        26

<210> SEQ ID NO 30
<211> LENGTH: 38671
<212> TYPE: DNA
<213> ORGANISM: Sorghum sudanense
<220> FEATURE:
<221> NAME/KEY: misc_feature
<222> LOCATION: (967)..(992)
<223> OTHER INFORMATION: n is a, c, g, or t

<400> SEQUENCE: 30
catcggtcca gacggccgcg cttctgcggg cgatttgtgt acgcccgaca gtcccggctc    60
cggatcggac gattgcgtcg catcgaccct gcgcccaagc tgcatcatcg aaattgccgt   120
caaccaagct ctgatagagt tggtcaagac caatgcggag catatacgcc cggagccgcg   180
gcgatcctgc aagctccgga tgcctccgct cgaagtagcg cgtctgctgc tccatacaag   240
ccaaccacgg cctccagaag aagatgttgg cgacctcgta ttgggaatcc ccgaacatcg   300
cctcgctcca gtcaatgacc gctgttatgc ggccattgtc cgtcaggaca ttgttggagc   360
cgaaatccgc gtgcacgagg tgccggactt cggggcagtc ctcggcccaa agcatcagct   420
catcgagagc ctgcgcgacg gacgcactga cggtgtcgtc catcacagtt tgccagtgat   480
```

```
acacatgggg atcagcaatc gcgcatatga aatcacgcca tgtagtgtat tgaccgattc    540
cttgcggtcc gaatgggccg aacccgctcg tctggctaag atcggccgca gcgatcgcat    600
ccatggcctc cgcgaccggc tgcagaacag cgggcagttc ggtttcaggc aggtcttgca    660
acgtgacacc ctgtgcacgg cgggagatgc aataggtcag gctctcgctg aattccccaa    720
tgtcaagcac ttccggaatc gggagcgcgg ccgatgcaaa gtgccgataa acataacgat    780
ctttgtagaa accatcggcg cagctattta cccgcaggac atatccacgc cctcctacat    840
cgaagctgaa agcacgagat tcttcgccct ccgagagctg catcaggtcg agacgctgt    900 cgaacttttc gatcagaaac ttctcgacag acgtcgcggt gagttcaggc ttttcatat    960 ctcattnnnn nnnnnnnnn nnnnnnnnnn nngatgatcc tctagagtcg acctgcagaa    1020
gtaacaccaa acaacagggt gagcatcgac aaaagaaaca gtaccaagca aataaatagc   1080
gtatgaaggc agggctaaaa aaatccacat atagctgctg catatgccat catccaagta   1140
tatcaagatc aaaataatta taaaacatac ttgtttatta taatagatag gtactcaagg   1200
ttagagcata tgaatagatg ctgcatatgc catcatgtat atgcatcagt aaaacccaca   1260
tcaacatgta tacctatcct agatcgatat ttccatccat cttaaactcg taactatgaa   1320
gatgtatgac acacacatac agttccaaaa ttaataaata caccaggtag tttgaaacag   1380
tattctactc cgatctagaa cgaatgaacg accgcccaac cacaccacat catcacaacc   1440
aagcgaacaa aaagcatctc tgtatatgca tcagtaaaac ccgcatcaac atgtatacct   1500
atcctagatc gatatttcca tccatcatct tcaattcgta actatgaata tgtatggcac   1560
acacatacag atccaaaatt aataaatcca ccaggtagtt tgaaacagaa ttctactccg   1620
atctagaacg accgcccaac cagaccacat catcacaacc aagacaaaaa aaagcatgaa   1680
aagatgaccc gacaaacaag tgcacggcat atattgaaat aaaggaaaag ggcaaaccaa   1740
accctatgca acgaaacaaa aaaaatcatg aaatcgatcc cgtctgcgga acggctagag   1800
ccatcccagg attccccaaa gagaaacact ggcaagttag caatcagaac gtgtctgacg   1860
tacaggtcgc atccgtgtac gaacgctagc agcacggatc taacacaaac acggatctaa   1920
cacaaacatg aacagaagta gaactaccgg gccctaacca tggaccggaa cgccgatcta   1980
gagaaggtag agagggggg gggggaggac gagcggcgta ccttgaagcg gaggtgccga    2040
cgggtggatt tggggagat ctggttgtgt gtgtgtgcgc tccgaacaac acgaggttgg    2100
ggaaagaggg tgtggagggg gtgtctattt attacggcgg gcgaggaagg gaaagcgaag   2160
gagcggtggg aaaggaatcc cccgtagctg ccggtgccgt gagaggagga ggaggccgcc   2220
tgccgtgccg gctcacgtct gccgctccgc cacgcaattt ctggatgccg acagcggagc   2280
aagtccaacg gtggagcgga actctcgaga ggggtccaga ggcagcgaca gagatgccgt   2340
gccgtctgct tcgcttggcc cgacgcgacg ctgctggttc gctggttggt gtccgttaga   2400
ctcgtcgacg gcgtttaaca ggctggcatt atctactcga aacaagaaaa atgtttcctt   2460
agttttttta atttcttaaa gggtatttgt ttaattttta gtcactttat tttattctat   2520
tttatatcta aattattaaa taaaaaaact aaatagagt tttagttttc ttaatttaga    2580
ggctaaaata gaataaaata gatgtactaa aaaattagt ctataaaaac cattaaccct    2640 aaccctaaa tggatgtact aataaaatgg atgaagtatt atataggtga agctatttgc    2700
aaaaaaaaag gagaacacat gcacactaaa aagataaaac tgtagagtcc tgttgtcaaa   2760
atactcaatt gtcctttaga ccatgtctaa ctgttcattt atatgattct ctaaaacact   2820
gatattattg tagtactata gattatatta ttcgtagagt aaagttaaa tatatgtata    2880
```

```
aagatagata aactgcactt caaacaagtg tgacaaaaaa aatatgtggt aatttttttat    2940 aacttagaca tgcaatgctc attatctcta gagaggggca cgaccgggtc acgctgcact    3000
gcaggcatgc aagctagaat tcgagctatt accctgttat ccctagagct cggtaccgat    3060
gttaattaac atcttcgaac aactcgcttc ttcgatgtca atgttgatca actgtctttt    3120
gagttggtca aagaaccgtt gcaactgttt gggcgacttt cccacttatt gaagacgtca    3180
agtctcactg atcgaagaag ctcaagacgg cgtgttacat cacaatacat ggtgctcggg    3240
gactagctgt gggggtataa accccctatac ccttacggct agacttcggc caggaggctt    3300
ggcccattac gagacgagtt caaggcttga tctgacaacc tgaagtttcg cgcaaggaaa    3360
caagatgtgg agatcaagca ggattccagt cggttagaat aggaattgat atcgaattat    3420
ccatggcaat tgtaaccgac taggattagt ttccagatct gtaaccctgc cctccagact    3480
atataaggag gggcaaggga cccccctagg acatcatatt ctctcagcac aaatcaatac    3540
aaccagacgc aggacgtagg tattacgcca actcggcggc cgaacctgga taaaaagctt    3600
gtccgtgtct tgcgtcacca tcgagttcgt agtttgcgca ccgtctaccg ataaactact    3660
accgtgggta taccccaagg tagactgccg actagctttc gtcgacattt agaatctggt    3720
ccaaaaccta atcttgaaga ccctgttctt ttattccact attttcgagg tcttcataaa    3780
aatcacaaat aaatgctaca cacaatgtct agaggttctt tctttcgcat ccctgctgat    3840
gaagcaagag tgatcctaga tagaatccta caagctgaga tggataatac ccttcatgat    3900
gaaaccaacg aagccgaagt agacactctg ccaaattctt catctacttt agctatccca    3960
agttctgagc cacaagagga agaaattcca ctaccggact tcatgctgga tatagaatcc    4020 gatcttttg ccgatttgg aaatatttca aactaccatt ctattgacaa accccaaaat    4080
ggccagttta gcatttattt accaagtgaa tatcaattga gagagcttat ctcaataatg    4140
agtagcgaat ggttggagga atcagagttt tcctctgatg tgatccgttt ggacacaccc    4200
tctataacta tacgctgtgc ttataattct gatcgattta atgctctta taatcctgtt    4260 gtggggatca acatcatgtc tgaatccttt gcacttaaac tatttaaaaa tcttgtctta    4320
acccccacaa caaaggtcat aaaggaatct tcgggacgat tagtccccag tcttggaatt    4380
attaatatcc tacctcttac ggtagaaggc tccatggttc atttgaactt ctatatcttt    4440
gatacatggg actttgacct gttgatagga caacctttta gaagactcct ttatgaaggt    4500
catactggaa agctacacat ttcttttaga aaatttttta aattcccgat aacaatttca    4560
cactccttaa ataataaggc cgagtcatat cttttgcctg atcctatgga ggaagtaaag    4620
gctgcatctc tagagctttt agatgaacca gacttagaag acgaaactcc tttcttcaca    4680
gaagaagaag acgaaccttc cgagcctgaa cccttagatg agtttgcaga acacctaga    4740 cctcccatag agcttaaaac tttaccaccc ggtcttacct atgctttcct aaacaataat    4800
ccagagttcc ctgtgatcat tagcgataaa ctcactcagg atcaaactct gcgattaatg    4860
accattcttg agaaacatca ctcggttttt ggctactcac ttcaagatct tacaggaatc    4920
agtcctatga tttgtaccca tcgtattcca acagatcctt ctgttacacc ctctcgagaa    4980
ccccaacgta gacttaacaa cactatgaga gaggtagtta aaaaggaagt tataaagttg    5040
ctgcatgcag ggattatata tcctgtgccg cacagtgagt gggtgagccc agtgcaagtt    5100
gtgcccaaaa agggaggcat gacagttatt atgaatgaaa agaatgagct aattccgcaa    5160
cgcaccgtca caggatggcg gatgtgcata gattatagaa aactaaacaa agccacgaga    5220
```

```
aaggatcact ttcctttgcc ttttatagat gagatgctag agcggttagc aaaccattcg    5280
ttcttctgtt tcttagatgg atactcagga tatcaccaaa tcccgatcca tcctgatgat    5340
caaagcaaaa ccacttttac atgcccatat ggaacttatg cttaccgtag aatgtctttt    5400
gggttatgta atgcaccagc ttcttttcaa agatgcatga tgtctatatt ttctgatatg    5460
attgaagaga ttatggaagt tttcatggat gatttctctg tttatggaaa aacttttgat    5520
agttgtcttg aaaacttaga caaggttttg caaagatgtg aagaaaagca cttagtcctt    5580
aattgggaaa aatgtcattt tatggttacg gaaggaatag tgctaggaca cttagtgtct    5640
gaaagaggga ttgaggtaga caaagctaaa attgaagtaa ttgaacaact acctccacct    5700
gtgaatataa aaggaattcg aagctttctt ggccatgctg ttttttatcg tagattcata    5760
aaagattttt catttattgc tagaccactt actcttttgc tagccaagga tgctcctttc    5820
gaatttgatg atgcatgttt aacatctttc aatttattaa agaaagcact catctctgca    5880
ccaatcattc aacccctga ttggtcgttg ccttttgaaa ttatgtgtga tgctagtgat    5940
tatgctgtgg gggcagtatt gggacaaact aaagataaga agcatcatgc aattgcttat    6000
gccagtaaaa ctttgacagg agctcaactt aattatgcaa ccactgaaaa agagcttctg    6060
gctgttgtct ttgccataga taaatttaga tcttatttag ttggagctaa ataattgtt    6120 tacactgatc atgctgcatt aaaatatttg ctcactaaaa aagatgctaa acctcgccta    6180
attagatgga tcttattact ccaagaattt gacttagaaa taaaagataa aaaaggagta    6240
gaaaattctg ttgctgatca cttgtctaga atgtatttta agaatccaca ggaaaccccc    6300
atcaatgatt cactccggga cgacatgctc tacgggatta acaggtctga ccctggtat    6360 gcagatattg ttaattttat ggtttcaggg tatgtaccac caggagcaaa caagaagaag    6420
cttattctag aaagtcgttc acatatatgg gatgagccta acctcttccg agtatgctct    6480
gatggcttac tcaggagatg tgtgaccact gaggaaggat ggaagatcat cgacagatgt    6540
cattcatcac catatggagg tcactatgga gcattccgta cacattcaaa gatctagcag    6600
tgtggattct attggcctac aatgtatgaa gacacgaagc aatatatcag aagttgtggg    6660
ccatgtcaaa ggcacggaaa cataaataca agggatgcaa tgccactcac caacaacctt    6720
cagattgagc tctttgatgt ctggggaata gactacatgg gtccatttcc tccatcaaag    6780
aagtgtgagt acatcttggt ggcagttgac tatgtctcca agtgggtaga agcattacct    6840
tgcaagcatg ccgacaacgt cagttcaaag aggatgtttg aagaaattat atttccaaga    6900
tttggagttc ccagagtagt gataagtgat ggaggagcac acttcatcga caacgcttc    6960 aagcaatacc tatcaagaca tggaatccgt cacaacgtcg ctaccccta tcatcctcag    7020 acaagtggcc aagcagagac ttccaacaaa caaatcaaga atattcttca gaagacagta    7080
aatgaaatgg aacggcatg gaaagacaag ttacccgatg cactctgggc ataccggaca    7140
gcatacaaga ccccaattgg aatgtctcca taccaattgg tgtacgggaa gacttgccat    7200
ctacctgttg aactagagtt caaagcacac tgggccataa agagatggaa tatgacccta    7260
gatgttgctg gagattatag aagaatgcaa ctatcagaat tggaagaatg gcgagagaag    7320
ccatatcaca attcaaagat ctacaaagaa agagtgaaga ggtggcatga caagagaatc    7380
aagaagaagg agttcacacc cagagataag gtattacttt ttaattccag ggtgaagctt    7440
ttcgggcatg gaaaactcta gagcaaatgg gaagggccat tcaaggtaat caattcatca    7500
tcccacggag ctatcacact gcaaaatagc gaaggtacgt tattcaaggt aaatggtcaa    7560
cgtcttaaat tattttttaga gcccaatgaa gaatttgaag aaatagacgt agtccatttt    7620
```

```
taccttccca tggagaatta gagcccgaca cttttggtct gatggttttg ggtgatatat    7680
atatttttct aaataatttc gcatctagaa acgcgctcgg agaagtgggc ccacagaggg    7740
gccagagaga gggcgggcgc ccagatcaag tgggcgggcg cccagcccct gttcccctc     7800 ggtcccgact ttctctgtta tggaaaatgc acttagggtg atccgaataa tccctcggat    7860
ggaaagtttc gcacgcacat tgacgggagc aacccgaaca acccatagag gcacccttt    7920 gaccctata taaacagacc cctgacctca gttttcaaac accaagccac caagctttct    7980
ctccttcaac tagagcttga ttagctctcc ttcaattaga gcttgattag ctctacttca    8040
attaaagttt tattagttcc ttgctgttcc aatggccgag aagtaccacc atgattggga    8100
agtcgtcccc ttcaacctca acatggagcc tgtggaagac cccgatgccc gtgctctcgt    8160
cccggccaac acagaaagac agctagaagc catgccatta cgccaacgta actccgccca    8220
atcttaccat gctcaaccag ttctcaccgc accaccacaa ccctactcc tcaaaggatc     8280 atcatccaag acgaagacca ctatcaaggt gccaatcggc acaaggatcc ttccacctag    8340
acccaatgag agggtcgttg gagtcaagac caaccgaagc ggcgagatca gcagtgttca    8400
ctacactacg gaggaggaaa ggccttactt tgaagggatt agagcagcca aagtccattt    8460
catccctcca aaggcagccc cgaagcactc tctcaatgct tttgagacac ctcccaagcg    8520
tcgcaagact ataatggaaa ttgatgagga agttcgcagg ctagatagag ttatcataga    8580
cctccagtcc tcgattaatt ccctcactag gcagctctct aaccacaaca ccattatact    8640
aggccttagg caggatcttg ccaatgccaa caagaagatc aaggaattag agcaccgcta    8700
agttatctag attagacctt gaggcaatgc atcttagtta tctatcttta aattcggttt    8760
aggtttacta ttattatcag tttgctatca gtcttttgta ataaatgcct caagatcaat    8820
aaagaatatt attattatta ttattattat tatgtcttgt gtgtctctac ttttgtaaga    8880
aagcagaaaa caagtatggg ggagatccct tgacatgcca aacacactcc aaacacacca    8940
ctccaccact caggtacaca ctctgcacac tttactttat acatacattt attctggatt    9000
atgcagacta ctatttccga catgataaaa taaaaggatt aaaatatttc taatcatgat    9060
taatctcaat ctatgatatt tcctgaaaac ttgcaattat tataaaatca ttttaaaacc    9120
ctgtgttact taagtcaatt ggaatatgtg atgatagagt atgagtttct tattctagat    9180
atcattgttg cttggagaat ttatttcaaa atattcaaat ttctagctac catcctcagt    9240
gttttatatg cctgataaaa ctaaaaatat taattatgat tataaaagct atctgctctg    9300
tattgagttt gttcaaaatg agttagaccc ttgttgagag atttatcatg ctcctaagat    9360
caagacatta tttcagtaag attcactctt ccgaagtatt attgcattag aggcatgggc    9420
tatgcaaaaa tagaaatatt tcgaggaaat aaaaggagc aagtgctcga taacctcgca     9480 gaaaaaaat ggataagtgt ccggcagtag aattaggggt acctcagtat ccacttaaaa     9540
aaagagagaa aaatgatagc ccatggtccc tctaataagc aatatgccag caagagttga    9600
caaagatttt aatttccaaa gtctttgatc taagagtatg acattcccct ccttggatcc    9660
cgttttgatc aggcaataaa tgcaaagtaa gaatgcttga gaattttgc aaaataaaac     9720 agcctcagtg agatatatgt aaaagctaat gagtgatctg agagaaccta tgaggataaa    9780
aaggtatgct aactttcttt caaaaatata caaaaactcc aagtggcagg attgagaaga    9840
aaggatcttt actcttaacc atatacttcc ctgactatgg tacacagtgg attttttga    9900 caccctgcaa attatataga gaatgcttta aaatgtttac cccagatatt attcttaacc    9960
```

```
atccttttct cgaggacgag taaaagccta agtatgggtg aatcttgttg acggttctta    10020
agtatcaatt ttaattatca aataaacaag agaaaggacc aatatgcaac caacacctag    10080
aattagggtt tgatctgaca gaattccacg agttttgttg tttatctgtt tctgcagggg    10140
gttatcagga aataaggaag aaaggcccac atgtcgggat tacatagaga tatcaacgca    10200
ccgcacgatt ttacatcatc tagaagactc cagaagccac gagaccgaag cggaggcgaa    10260
acggggccag gcccagggcg cccgccctgg tagcctgggc gccgccccc ctctggagcc     10320
agatcaggac tctcttcgct cgggatattc cactgaccta ttggatcaag aaaaacatag    10380
taccacctcg cctatcgacc caaaaacgca tagaagggga ggactatata agcaaggccc    10440
ccctggcccc tagagaagac atgaagaaat tatcatagag actgaggggt gccctcgaag    10500
gaaaacctct tctctaatta atatttcttt ttaggcttag caaccaatgt aaggtagaaa    10560
tagatcttct agtttctatt agattgagag agatagagtg gaggtgaaga gtggaggaag    10620
cccggcctgt cggtgtctac tccaagcttg tacctgcggg atcaagttct cctaacccga    10680
agcttgctcc taggattgtt cagtaattcg acttctaaat tctagtaagt tcttatttta    10740
ttgttcttat ggtttatgag tttacttaaa tctcttcgcg tagagtttag agtaatcatt    10800
gctggcgtaa acgtggtgtt taggctgggg tactcataga tattccctga ctagctggac    10860
cgtggtagta gtgaggaacg tgacaattcc gagctagctt tgtagatcac atctcgttag    10920
caggaaggat agggtttata ggtgcgggtt gaacatcctt tgtggtgtct agattccgtt    10980
agcctcccca ttagaacagt agatcatcct taccaaggtt agaaggagac tacggttgca    11040
gtcttctcta tttatcactc acatcgaaag acattctttg tgcctaaagg ttagtagtaa    11100
tagatcggtt agtcagatgc actctttctc ctagtggtaa aaaataaat acgatactct      11160
ggataaatttc ccgggtgaag tgctcaccga tatccgtgcg cttgcggatc aattccttat    11220
tgcgttccaa aatatcaaca aatctcacgg atcatgctcc accgacctaa aggatcaagg    11280
ataaccgttc aatcaatgtc ggtttgatcc gacggcccac gttcacctga ggggactata    11340
taagcagacc ccctggcccc tggaggagaa caagttcatt atagagttga gaggtgccct    11400
cgaaggataa cctttcctct acgtagactt agggcttagc atccaatgtg agagtagact    11460
agttctacta gattgagaga gatagagtgg aggtgtagat cagaggaagc ccggcctgtc    11520
ggtgtctact ccgaggttat acatgcggga tcaagtcttc taacccgagg cttgctccta    11580
ggattcttca atattttgac ttctaaattc tagtaagttc ttattgttct ttggtttatg    11640
agtttacttt gatctcttcg cgtagagttt agaataatca tctctacctt aaacgtggtg    11700
tttcggttag atactcata gatatcccct gactagctgg accgtggtag tagcgaggaa     11760
cgtgacattt tcgagttacc tttgtagccc atatccgtt agtaggatca atagggttta     11820
taggtgcggg tcgaacatcc tctgtggtgt ctagattccg taagcctccc caacagaaca    11880
gtatatcatc cttaccaagg ttagaacgag agtgcagttg tagtcttctc tatacatcac    11940
tcacatcaag tcgcattctt tgtagcctaa aggttagtag tataaaccgg gtcagtaaga    12000
tgcacgcttt ctcctagtgg taaaaatata aatatgatac tctggataac atcccgggtg    12060
aagtgctcac cgatattcgt gcgcttgcgg atcaattcct tattgcgtta ccaaatatca    12120
acaagcattt gtggctccgt tgccagggag aaagacggtt tgttgagata accttgagtc    12180
ttaatactag cttgtatcta tacttttatc ttttcttatc ttttatatt ctttattttc     12240
tttattctta ccttatggaa aaccaagatt gtaaatcgat ctatcaattt gcaacaccctt   12300
cggaaagtga cctttaccca tgggagtcat catagcctat ccaaacatcc cagtataggt    12360
```

```
taagttctag gttgattgcc atgattcaaa acctatcttt ttcaggaaag gaagacgaaa    12420
acccttacct tcatattaga gattttgagc aaacatgtga ttgtcttcgc attgaaggca    12480
tttctgataa aactttacgt tggaagcttt ttccttttc tttaagggga gaagctagac     12540
aatggtataa tcagaaggta agtcaacaac gaggtgaatg gggagtttta cgagctaact    12600
tttgcctaga tttttattcc ctcgaccgta tcagtgacct tagactcaaa gtcctatcct    12660
ttaaacaaaa agataatgaa actttgggaa atcctggaa acatttgtct gatcttttag     12720
aatctggtcc aaaccttaat cttgaagacc ctattctttt atttcacttt tttcgaggtc    12780
ttcaaaaaga tcataaacaa atgctacata caaagtctag aggttctttc tttcgcatcc    12840
ctactgatga cgctagagtg atcctagata gaatcctaga agctgagatg ataataccc     12900 ttcagatgaa acccacgaag ccgaagtaga cactctgcca aattctccat ctactttagc    12960
tatcccaagt tctgagccac aaaaggaaga aattccacca cctgatttca tgctggatat    13020
agaatctgat cttttttgccg attttggaaa catttcaaac taccattcta ttgacagacc   13080
ccaaaacggc catttagca tttgtttgcc aactgaacat caattaagag agcttatcgc    13140
agtcatgagt agcgaatggt tggaggagtc agagctttcc tctgatgtga tccgtttgga    13200
cacacctcct ataactatac gttgtgctta tgattctaat caatttgatg ctctctataa    13260
tcctgttgtg gggatcaaca tcatgtctaa atatttttgca cttaaattat ttaaaaattt   13320
agtcttaacc cccacaacaa aggtcataaa ggaatcttta ggacgattag tccccagtct    13380
tggaattatt aatgtcctac ctcttatggt agaaggctcc atggttcact tgaacttta     13440 tatctttgat acatgggact tcgacctgtt gataggacaa cctttagaa gactccttta     13500 tgaaggtcat actggaaagc tacacatttc ttttggaaaa gcttttaaat ttccaataac    13560
gatttctcac tccttaaata ataagaccga gtcatatctt tgcccgatc ctatggagga    13620 ggtaaaggct acatctctag agcttttaga tgaaccaaac ttagaagaag aagctccttt    13680
cttcacaaaa gaggaagttg aaccttctga accggaaccc ttagacgagt ttgcagaaac    13740
acctagacct cccatagagc ttaaaacttt accaccggt ctgacctatg ctttcctaaa     13800
gaataatcca gagattccta tgatcattag tgataaactc actcagtaga aaactctgcg    13860
attgatgacc attcttgaga aacatcacta agttttcggc tactcactcc aagatcttac    13920
aggaatcagt cctatgattt gtacccatcg tattccgaca gatccttctg tttcaccttc    13980
tcgagagccc caacatagac taaacaacgc gatgagagag gtagttaaaa aggaagttat    14040
gaagttgctg catgcaggga ttatatatcc tgtgccgcac agtgagtggg taagcccagt    14100
ccaagttgtg cctaaaaagg gaggcatgac tgttgttacg aatgaaaaga acgagctaat    14160
tccacaacgc accgtcacag ggtggcggat gtgcatagac tatagaaaac caaacaaagc    14220
cacgaaaaag gatcatttc ctttaccttt catagatgag atgctagagc gattagcgaa     14280
ccattcgttc ttctgtttct tagatggata ttcagggtat caccagatcc cgatccatcc    14340
cgatgatcaa agcaaaacca cttttacatg cccatatgga acttatgctt accgtagaat    14400
gtcttttggg ttatgtaatg cgccagcttc ttttcaaaga tgcatgatgt ctatatttc     14460 tgatataatt taagagatta tggaagtttt cagggatgat ttctctgtat atggaaaaac    14520
tttcgatggt tgtcttgaaa acttagacaa ggttttgcaa agatgtgaag aaaaacactt    14580 agtcttaat tgggaaaaat gtcatttat ggtttgggaa ggaatagtgg tgggacccct      14640
agtgtctgaa agaggtattg aggtagacaa agctaaaatt gaactaattg aacaactacc    14700
```

```
tccacctgtg aatataaaag gaattcgaag ctttcttagc catgctggtt tttatcacag    14760
attcataaaa gatttttcat ttattgctag accacttact cttttgctag ccaaggatgc    14820
tcctttcgaa tttgatgatg catgcctaac atctttcaat ttattaaaga atgcactcat    14880
ctctgcacca atcattcaac ccctaattg gtcgttgcct tttgaaatta tgtgtgatgc     14940
tagtgattat gctgtggggg cagttttggg acaaactaaa gataagaagc atcatgcaat    15000
tgcttatgcc agtaaacctt tggcaggagc tcaacttaat tatgcaacca ctaaaaaaga    15060
gcttctggct gttgtctttg ccattgataa atttagatct tatttagttg gagctaaaat    15120
aattgtttac actgatcatg ctgcactaaa atatctgctc actaaaaaag atgctaaacc    15180
tcgcctgatt agatggatct tattacttca agaatttgac ttagaaataa aagacaaaaa    15240
gggagtagag aattatgtcg ctaatcactt gtctagaatg tatttttaaga atccagagga  15300 aaccccatc aatgattcac tctaggacga catgctctac gagattaaca ggtctgaccc     15360
ctggtatgca gatattgtta ggagcgaaca agaagaagct tactcaagaa agtcgttcac    15420
atatatggga tgagccatac ctcttccgag tatgctctga tggcttactc acgaggtgtg    15480
tgaccactga ggaaggatgg aagatcatcg acagatgtca ttcatcacca tatggaggtc    15540 attatgagc attccgtaca cattcaaaga tctggcagtg tggattctac tggcctacaa     15600
tgtatgaaga cataaagcaa tatatcagaa gatgtgagcc atgtcaaagg cacgaaaaca    15660
taaacacaag agatgccatg ccactcacca acaaccttca aattgagctc tttgatgtct    15720
ggggaataga ttacatgggt ccatttcccc catcaaagaa gtgtgagttc atcttggtgg    15780
cagttgacta cgtctccaag tgggtagagg cactaccttg caagcatgcc gacaacatca    15840
gttcaaagag gacgtttgaa gaaattatat ttccaagatt agagtcccca gagtagtgat    15900
aagtgatgga ggagcacact tcatcgacaa acgcttcaag cactatctat caaaacatgg    15960
aatacgtcac aatgtcgcta cccccctacca tcctcagaca agtggtcaag cagagacttc   16020
caacaagcaa atcaagaata ttcttcgaaa aacagtcaat gagatgggaa cggcatggaa    16080
agacaagtta cctgatgcac tctgggcata ccggacagca taaaagaccc caattggaat    16140
gtccccatac caattggtgt acgggaagac ttgccaccta cctgttgaac tagaattcaa    16200
agcacactgg gccataagga gatggaatat ggacctagat gtcgctggag atcatagaag    16260
aatgcaacta tcagaattgg aagaatggcg agagaaagca tatcacaatt cgaagatcta    16320
taaagaaaga gtcaaaaggt ggcatgacaa gaggatcaag aagaaggagt tcgcgcccag    16380
agatagggta ttacttttta atttgagggt gaagcttttc gggcatgaaa aactccggag    16440
taaatgggaa ggaccattca aggtaaccaa ttcatcatcc cacggagcta tcacacttca    16500
aaatgacgaa ggtacgttat tcaaggtaaa tggtcaacgt cttaaattat ttttagagcc    16560
caataaagaa ttagaagaga tagacgtgat ccatttctac cttcccatgg agaattagag    16620
cccaactttt ttaatctgat gtttttgggc cacatatata ttttcgaat aaagtctgca    16680 tctagaagta cgctcgagga agcgggccta cagaggagcg aggcacaggg cgggcgccct    16740
gatgaagagg gcgggcgcct agccctgtc gcctctcagt cccgatttcc tccgtcgcgc     16800
taaacacatt tatggtaaac taaataatca tatagatgga aagtttcgca cgcacgacgg    16860
cgggagtagc ccgagcaaac cctagaggca cttttgacc cctatataaa cagacccctg     16920
acgtcagttt tcaaacacca attcatacaa gccttctctc cttcttcaac tagagcttgc    16980
ttagtccctc gctgctccaa tggccgaaga gttccacgac gattgggaag tcgtccccta    17040
cgacctcaac aaaaagccca aggaagaccc cgacgcccac gctctcgtcc cagccaacac    17100
```

```
tgagcgacag ctagaagcca tgccattacg ctagtgcagc tccgcccaat cctaccatgc   17160
tcaaccagtt ctcaccgcac cgccacagtc cctacttctc aagggaccgt caaggtgcca   17220
gccggcataa ggatcctgcc acccagaccc aatgagaggg tcgttggagt caataccaac   17280
cggagcggcg agatcagcag catccgctac actacgaggg aggagaggaa ttacttcgag   17340
ggggtttgag cagccaaagt ccgtttcatc cctcctaagg cagcccccaa gcatgctctc   17400
aatgctcttg agacacctcc taagcgtcgc aagactatag tagatattga tgaggacgtt   17460
cgtaggctag acagggtcat catagagctc cagtccttgg ttaactctgt cactaggcag   17520
ctctctaact agaacactgt tatactaggt cttaggcatg atcttgctag tgctaataag   17580
aagatcaggg agttagagcg ccgctaagtt atctagatta gatcttgagg cagtgcttct   17640
tagttattta tctttaaatt cggtttagat ctattattag cttcagttca ttactagtca   17700
tttgtaataa atgcctcaag attaataaag attactatta ttattattat tatgtcttgt   17760
gtgtctctac tttattatgc aagaaagcat aaaacaagta tgggggagat cccctgacat   17820
gccaaaagca cttcgacttc accactccac gattcaggta catactctac acactttaaa   17880
catactcata tatcttggtt catgcagaat attatctccg acatgataaa ttaacaaggt   17940
caaaatgttt ccaatcatga ttaatctcac tctgtgatat ttcctgaaaa cttgcaatta   18000
ttataaaatc atttaaaacc ctgtgttact taagtcactg tggaatgtaa gatggtagag   18060
tatgagttcc ttattcttga tatcattgtt gcttggagaa tttatttaaa aattctagct   18120
accatcctca gtgttttata tgcctgataa acctgaaaat attaatatga taattataaa   18180
agctatctac tctatattga gtttgttcaa aatgagttag acccttgttg agagatttat   18240
catgctccta agatcaagac atctattcaa aaagattcac tcttccgaag tattattgcg   18300
ttagaggcat gggctatgca aaaataagga tatctcgagg aaataaaaag gagcaagtgc   18360
tcgacaacct cgcagaaaaa atggacgagt gtccggcagt agaattaagg gtacctcggt   18420
atccacctga aaagaaaga gaaagaaag aaaatgatag cccatggtcc ctctaataag   18480
caatatgcca ataagagttg acaagttttt aattccaaag tctttgatct aagagtatga   18540
cattcctctc ctcggatcct gttttgatca ggcaataaat gcaaggtaag tatgcttgag   18600 aattttgca aattaaaaca gcctcagtga gatatacaaa agataatgag tgatttgaga   18660
gaacctatga ggataaaggt atgctaaatt tcttttcaaa aatatacaaa aactccaagt   18720
aacaggattg aaaagaaagg acctctactc ttgaccatat atttctctga ctacggtaca   18780
cagtgaattt ttacaacacc ctgcaggtat gaagagaatg ctttacaatg ttttaaccac   18840
agatattttt cttaaccatc cttttctcga ggacgagtaa aagcctaagt atggggtgt   18900 ttgttgacag ttcttaagta tcaattttaa ttatcaaata cacaagggaa atgactaata   18960
tacaaacaac acctagaatt agggtttgat ctgacagaat tccacgagtt ttgttgttta   19020
tctgtttctg caggaggtta tcaggaaata aggaagaaag gccacatgt cgggattaca   19080 tagagatatt aacgtaccgc gcaattttct atcatctaga agactccaga agccacggga   19140
acgaacagga agacgatcgg gcccgggagc agggcgcccg ccctaccccc ctgggcgccc   19200 gccccttcc tgtagccaaa cacggtgaat ctcgcggatc atgctccacc gacctaaagg   19260
atcaaggata accgttcaat caatgtcagt ttgatctgac ggcccacgtt cacttgaggg   19320
gactatataa gcagaccccc tggccctgg aggagaacaa gttcattata gagttgagag   19380
atgccctcga aggataacct ttcctctaca tagacttagg gcttagcatc caatgtgaga   19440
```

```
gtagactagt tctactagat tgagagagat agagtggagg tgtagatcag aggaagcccg    19500
gcctgtcgtt gtctactccg aggttgtacc tacgggatca agtcttctaa cccgaggctt    19560
gctcctagga ttcttcagta tttcgacttc taaattctag taagttcttg tttattgtt    19620
ctttggttta tgagtttact ttgatctctt cacgtagagt ttagagtaat catctctagc    19680
gtaaacttgg tgtttgggct aggatactca tagatatccc ctgactagct gaaccatggt    19740
agtagccagg aacgtgacat ttctgagtta cctttgtagc ccatatcccg ttagtaggat    19800
cgatagagtt tataggtgcg ggtcgaacat cctctgtggt gtctagattc cgtaagcctc    19860
cccaacagaa cagtgatca tccttaccaa ggttagaacg agagtgcagt tgtagtcttc    19920
tctatacatc actcacatcg agacgcattc tttgtagcct aaaggttagt agtaatagac    19980
cgggttagtc agatgcacga tactctggat aacatcccgg gtgaagtgct caccgatatc    20040
cgtgcgcttg cggatcaatt ccatattgtg ttactaaata tcaacagtag acacgcggcg    20100
ttgcagaggc gggccgagag atgggcactg tacgacacgc cccttccccc actgctgacg    20160
tgatggggca aagtagcgcg ccgacgagga cggaattcct cgtttctcat gcccggaaag    20220
gcgccccgtg acccgggcca agacgcggcc cagtagcgcc ggcgaacctc gttgtccgcg    20280
gccgcggccc acgactgttc cccccctcgaa gccagggtgg aaaccgttga agttgctgtc    20340
gtctgtcacc gtcggagccg ccaccatctc cgtcgtcgtc atccgacgac gatggcggcg    20400
gtgtgtgcca atcctgaaat tcgacgattc taagtcagac aaagtacctt agagcgggga    20460
tgtcgtcatg gatgacctct tccggtctta ggtataaggg cggtccaccg tcgtgcacct    20520
cctcaggctc cggcaccgcc atgatgacct cgtccggtat gaggtccaga tgtgcacacc    20580
aagtcgacac aaagaactcc cgctcgtcat cagggtcatc gaggccatcg gtgtcgacca    20640
actagatctt cgtcccccgca ttaccgagga tgcactgtgc cacttccgcg cagcgggcgt    20700
gcgacggaac acccttcatt ccgacgagcg cgcgataatg gaaggcgccc gaggagccca    20760
tgatcaagcg gttccagcgg cgccaccgca ggattagggg ggcacctgcg gggcgctggt    20820
tgttgaagac gagctccaga tcagccacct gtcggaaccg cacgatgaag tcgtcggggg    20880
tcgtcctgca gacagaaaca cggtcctccg agatgccgta gaactccgct agatggagcg    20940
tcacggcggc cggcgtgaca gccggcctgg tgcccaggac cagtgctagg agagccaacg    21000
acgaaagcat gtccttagca gcctgtagcc ttgccgtgcg aggaacaacc actagttgca    21060
gcagcggtgt gtgcgccctc gagtgtggcg acgccggagg cacctcggtc acacgccgaa    21120
gaaggtcgcg ggggaacccg cgtaaggggc ccgcgccatc agctccaccc tcggttgcca    21180
ccggcagagt gggggccggc catgtctggc gcccacaccc cagatcgata tatcctccac    21240
ggggcggctc cgaggaaggc ccgtcggcgg cgtgcacaag agtgggcgga gcgcagaccg    21300
gaggaacaga aggttcacgc cccgtggaag ccgagcgtgc cgagatggtg tctgcagacg    21360
acgagcaacg gggcgggcga cgggttgccg gacggaagcg ccgggagccc cggctatcag    21420
ccccacaacc cggcgagcgg ctgcgtttgc acgtcctccg gcccaagcgt ggatagagac    21480
gctcttggtg gccctcttcg aagcagtgga agcatctaga gggaaaagtg cagtccgcct    21540
tgacatggga atccgagaga cagttgaagc atttaccgac aaggtccgcg ggtaccgggc    21600
gacgaggcgg ggtagatctc ctccaacgcc tgtgactgtg aacttgacgg aagccgtcgg    21660
cgttggcctc ggcggccaga cgaggccggt gagtgacaag cctgactgga gcactgggtt    21720
gaaggggcga ggaggcaagc tgaggagccc cgcgacgagc atggcgacga cgcggcctac    21780
ggcgacgtcc acagagcttg gtgcgggatg ccgccgttgg acgcggcgac cggcagccag    21840
```

```
tgtcggagtc cccaaatgac tcctcggagt cagagaagtg gagcctcttt gaggcgccag   21900
gagaggcgaa gaacggcgcc gcctccgggt ccagcgaact caccctcaac acgaaggagg   21960
cgtgagcgac tgccgctagg ggaggaaggt caatggatct gcccgcagag cgaggcgcat   22020
ccatgtcctc aacctcatcg gcccagtgag gccttgggga gctagagctg ggatccatgt   22080
gaaggtgcac aggaagcagc gagggggaag gggtggccgt cgaggttacc tccggcgacg   22140
gacgcaggcg gcggcggcgg tcgcgagtgc ctactactat gtcccggcca ttagatgaac   22200
aagttgtgat gctcggaata tcacatcgga tgttaaaatc gaatggtgtc atctagattg   22260
gcaagtctaa gagcagagtt gtagaaacat tctgggtcaa tttattacgt gttttgggca   22320
agattttaga cctcccacag aataagacct atccacaccc cataaatata aagggccaag   22380
gatgattgtg gggcaaccaa tcgatgaaat catacataca aaatttacta ttttattcc   22440 tccaaactct aaacactttc aacctcaatc tatgttctct ctttgtctct atggtgactt   22500
gaggctttct aggtatcctt gctaacctta aaacaaacct agctaggtgc accaaccttA   22560
aaaataataa aacatcttat aatttggaat aaagggagta caaaactatt tatagaggtg   22620 catgttttt taatcagggc gactagtgat tcaaccacca ctattgtggc tcggtttggg   22680
ctccactaag tcaaccgcac ttacaaatgg atcagtagag gcagccgata ttacaccct   22740 aaaaatgggg gcacttgaag ggacgattgg ttatactagt gaccctctac cgatccattt   22800
gtaggagcag ctgacttttg agacacccct actaagctcc aaggcatata tagtaatcac   22860
cctccttctt ctaggctacc tcccaaaaat tgcaaatttg agggggggatt tgatttcttt   22920 ggtggaagag gttctagaag ataactaaat gctattccaa gcttcttttt tgaagttttt   22980
tttggtagac tagtgcttaa ttgtctcttt tgtttggtgg ttaaggcatt tatgaaagaa   23040
agcatgacca aatctttgga ggtactaggg taaatttagt agaacatgat tctacactta   23100
tttagtggcc atgtcttgat tttaattgac tattaattag tttttgagca gggatttggt   23160
ttttgtctag atctagatct atacataggt gtctgggatt acaattttt attagcaata   23220 atcatattat gtttgtttgc gaaatgagat taagtttgca taaacaatag cggtaaaata   23280
ttaatttggt gctaattgtt ttcttttgaat tcatttatca taataagaaa atgaaaaata   23340 tttcttttagt ggtacacatt agttgattaa ttaggttgtt tatttctct ctcttgcatg   23400 gtgattattt atggtacaaa ttagatcaaa actacatatt tattttcata attaagaaac   23460
aggattgcat aaacaatttg tagtaggtac tatgtgttt ttggacaaca tgattagaaa   23520
aggtgatcaa ttctatctat aattgaaata aaaatgacct tccacaatta cattgctata   23580
tactaattat attcttccta gttatttgat tcttatatct catttagtct tttttttctt   23640
ttgctttgat cgacatcgaa aaagattgac tacagaaact ccttcacgct tgagccgata   23700
ccgctgtcat cactgttttt gggatgcttt cagccctgat cccaatccat atgagttaat   23760
accgcatacg acatggcttt cccacggtct attctaaaaa ctggagtaaa taggtaggac   23820
cattgctaga gaggggagag ctatagctag ctaggtgaag agtgagaaat gtcggcactg   23880
tgggaaaaaa atgagagaga ggctagttga agaagccaag agggtagatg gacttattag   23940
ggtttttatc aggtctctat atatgatcta tttagactat cttcaacaat cgtcacccaa   24000
aatacaagac ccatttgtcc tttgggtagc actacaggta aaaggttcca tacttatttt   24060
tagtcttctc caacaataag acctaaaaga caacactctc tacaaatggg tctcgaagac   24120
agaggatacc caaatttggg ttatgtctct cctgataccc aaaatgggtc ttctggttgg   24180
```

```
gtactctgtt ggaggctata ggtattgtgt tggagaccca ttttagattt ggttgggtac    24240
tctgttggag gctataggta ttgtgttgga gacccatttt gggtttgggt tcgaaatggg    24300
tctcctattg agacagccgg cagatttttt ttttatcgat ctctataaat agatctgcta    24360
tctctatgac tatgagacac aaaacgtagc tctctctata ctttgtagct gaacggaacc    24420
tagctcctcg tccacatgca gtccctcgtc ttccttatta cggcagtgct cctgatcttg    24480
tcgacggcga cagccgacaa tgtgacgacg gagttcattc ctctatacta cacgtgcagc    24540
gaggatggtg gccggtacgg agaaaacagc acgtacttgt ccaacctgaa ggtgctggcc    24600
gggttgctct cggcgaacgc aagcacagcc aacttcgtct ccggcaccgc cggccaggcg    24660
cctgacgcgg tctacggctt cgtgctctgc cgcggggact acaccggcgc cgccacctgc    24720
ggcaagagca tctccatggc gttccgcaac accgtcgaca agggcttcct ctgccggttc    24780
tacaaggacg tgaccatcta ctacgacgac tacatgctcc gcttctccgg cgacgacgtc    24840
cgccggaacc tcaccaacag accggcatgg gtcgcgctga acatgaacag tgtgactcgt    24900
gtcgccggca agaattacgg cgagaaagtc gagaagctga ccaagatgat cgtggaggtg    24960
gccgcgagct cgccggcccg gtacggcacg ggggaggcgt gggtgggagg caacgacgtc    25020
gtcagcatgg cctacgggct gctgcagtgc acgcctgacc tccagacgga tgactgccgg    25080
agctgcctcg ccgatctcgt ctccatgatg ccggcgcact tcagccacga atccagtgac    25140
tactacgttg gcgggaggat tcttggcccc cggtgtaacc tgcgctacga gaagagctt    25200 ttcttccagg agaccaatgc cacgctcctg atcgatgtgc taaaagtaa gtacgtaagt    25260 gagtacaaat atatatatac ttatttttt tatttaagag agaaaacaat agatgtctag    25320
gtaataataa ctgcatgtag tcagtttttt taaaaaaaat tgggcataat aaagcgtgtc    25380
taccgtacct atttctatat aggatgacat tgttctagcc aaattcggaa ttcttttaca    25440
cttaagtaag gcctagcttg tttagttgac aaaaactttt acacaatttt taaaatttc    25500 cgtaaatctt gcgacatatg tatggagcat taaaatataga ttaaagatta ttaattaca    25560 caatttacct gtaacttgcg agacgaatct tttgagccta tataattaga caatttgtta    25620
aatataaacg aaagtgttat aatacttatt ttgcaaaaaa tttacaacta acaatacct    25680 tgacctggga aagctagtgt cccccaagtt gcacccatta ttaatatac aactactcgg    25740 tgccaactta actgctgctt tgtgttccgc acccgccggc cagcatctgt tcttcggttt    25800
ttgcattggc tgtgcataat tatcatgcgc attttatatc tataaagaaa gttgtttagg    25860
acggagatac ggtctccaag gtctaacttt aacttttttat ttttataaaa atatttataa    25920
aaaaagtgat atatgtatat ttttatgaaa gtattttca agacaaattt attcatttag    25980
tacgttttca tattttttaaa cacaacaact taaaagttat tcatgattta tattcccaat    26040
gtttgactca aaccttgtcc aaattaaaac gatttctttt atgggtatca agggagtagt    26100
ttttatagac attaatatac tgctgcctaa gcattttact aatgtgacaa gttagttatt    26160
gaagagagag caaaaataat agaaaccagg tctaagttag aaatcatgtc tacacaagaa    26220
ccaagacatg aagtaatatg attggttgag aatggagaga gaatgaatgt gattatataa    26280
aaaattattc tataaaaact atctattggg atcatggttt ctatatgtag tgtctataga    26340
aattaatagg tataaaacta catatagttt ctagcattgg actgccctta acattcatgc    26400
acctactaaa tcctttttga aatttagtgt tggtgaatga ttggagttaa ttagtcaaat    26460
atataccatg tattttcaca attaaaacaa attagttttg acttttttat catttacaga    26520
tcacctcggc aaaatagaga tcattctaat caccattgca gctgttctct ctatcatact    26580
```

```
ttttatagct ctactcggat ggatcataca atggaaagca ggtacgtata cagaggcctg   26640
tttggaatcc ctcctctaaa cttaagagca ctttacctca ttttttagtc taaagctcta   26700
atgtgaggtg gagctaaagt ttggagctaa ctttagacca tctattaatt agagctttag   26760
ctctaaagtt tagagggggg agatccaaac aggccctact ttggcttctg gaaaatatt    26820 aggtactgaa gagaaaacac atgtttctac ttcctcggaa aaaaaaacac atatgcatgt   26880
ttcttagagg aggaatgccc caccgcctat ctagctgccc cagcaaaaca tgttcaatga   26940
atgaagacat aaggttatca taaacttaaa cattttaacg aacatgattg tgtgctttct   27000
ctttgtaaat gatcgttgga aaatctttta aaatatatat tgtgtggtat ttgtgaagtc   27060
ttattcatgt ttcatgagaa acaaagccaa actgagtcca tataagaaac agtaactagc   27120
cacgccttca aatttaggtt ttgttggtgt aaatgctaaa ctaacagata atggtaatat   27180
tcattagttt ggtcctcagt atagtatagc tttactggtg caattgttta ggctatgcac   27240
ctggacaagt cttcagctgc attgcaatcc cttataattt ggaaggaaag tagtataaac   27300
aatggcctta ttaacttagt ttactgcaag tcctgccgct gtgtataata atatgacgcg   27360 agttttgtg ttatccaaaa gtttgtatta tataatataa gtgagcaaca ataatgtttt    27420
ctcaacttct tatttgtttt tgcactgctt gctgtgatgc tatttgcact gcaaaactag   27480
actcaaaaac cagaaatgag ctagaggaat ggacaagact ggttgctgtg gagataggaa   27540
cgatgtttac acactttact ttatctgaga taagaagtgc cactgacaat ttctcagaag   27600
caaagaaact tggagaagga gcttttggtc ccgtttactg ggtaagtgag ttataactgt   27660
atgccaacta tgttggacat tagcattatt ttttatacga taaataacat gaggaaagag   27720
aaacccaact atagtatcaa ttgtgataaa gaaaaaattg ggtgatgcat aaaaatcaca   27780
tataaaatag aaacacataa aagtagaggt tatagaggct agaagagtta ttttacacat   27840
cattagatta gatctgaaat tggttccttt ggctatgagt gtattcctgt tttccacacc   27900
aagatggaaa tcgtttagtg ggctattgtt ttgaaaacat actataaata agctaagatc   27960
tgttacttca ttcatcggca attcatgata tactactgaa tgtctcaaga tgtgtaggta   28020
aagcagctaa aatactagta ggaatagtag taggataatc agtgtcaaat cctaaaatga   28080
caaccaatga gctgttactt cattcatcgg caattcatga tatactactg aatgtctcaa   28140
gatgtgtagg taaagcagct aaaatagtag taggataatc agtgtcaaat cctaaaatga   28200
caaccaatga gctgacttt ctcgccattg ttgtattcca attatccatc ccattatgtt    28260
acatgttcaa aagcattaca agggtaacca agcaaactct ttcaaagcaa tctccaacaa   28320
gttcattcta ctgatagtaa actctcatca tccttatctc tatgtcatat gatcgtatta   28380
ctaaaatctc catagtgtag accgcatctt tatcaaatgt tcacaatgat tagcataatg   28440
ttgccatcat cttttctactt atatgaagaa cagtatgtgc agttagccaa ctgcttaggc   28500
cttgtttagt ttgggaaaaa ttttggattt cgctactgta gcactttcgt ttgtttgtgg   28560
caaatattat ccaaccatag actaactagg atcaaaagat tcgtctcgcg atttacaggt   28620
aaactgcgta attagttttt gttttcgtct atatttaatg cttcatgcat gtgccacaaa   28680
attcgatgtg acgggaatc ttgaaaaatt ttgggaacta acaaggcct taaaaacatg     28740 agtggctttt tgcacagggt aaattagctt atggagttgt ggcaatcaaa agattagcag   28800
catattcaag tcaaggtttg gaacagttca gaaatgaaat tagattcata gcaaagcttc   28860
aacatttaaa tcttgtcaag ctgattggtt tctgtatgca acaaaagag aagatactta    28920
```

-continued

```
tctatgagta catgcccaac aagagcttag atgacatttt caaaggtatg ctcaactgtt  28980 

aaccacaaga caacaccccc cccccccaa ccccaacccc cttttgatca agaaagttat  29040
atattgtcat tccaaaaatg tatccttgca gatgttgcga agtgggcatc gctaacatgg  29100
cctttgcgtc agaatataat tgatggcatc gctcaaggac ttctttacat acacaacttt  29160
tcacaatcag aaacatgcat tgtccacaga gacttgaaag caagtaacat tctattggac  29220
catcaaatga atccaaagat ttctgatttt gggatagcga tgcttagctc aagtgcaaca  29280
gaatcacaag atactgtacc aatgggaaca ctgtaagtac ataagtaaat ttgggttgct  29340
tagctcaagt gcagcagtac atatataagt aaatttgtat tgtcatggcc taaaattggg  29400
atgatacgga gatgcattat ataaaagtga atatagacaa gatacaattt gtaaggtttt  29460
tacagatgga tatatgtagt gtacatttca atatgcattt tatcttacct aggttatctg  29520
tatatcaact atcaagagag atcattatca gtgctggatg cagaaaaaaa atatttacca  29580
atagtggcgt ttagcttaca atataatgat agagtacaaa tagcaaagtt taactcaatt  29640
gcagcaggac atatatatgt aggcttgaat taccatggca aaaaatggga tatggagatg  29700
catcacatac aagggaacat aaacaagcta caattttta ctgtttcagg attggatatt  29760
gtagtataca tttcagtatg cattttattg cctaggatat cggtgcagga gagaacattt  29820
ttgtatgaaa aaatggaggg gaaaatagtg cacaaaagat aaatgatcaa catgtttttt  29880
ttgggacaaa ctggaaagaa aaaggtggcc tgccaggagg tgacaagtag cctccccggc  29940
agccagtaac aggagctcga gatgttcaaa ttggaagctg gcagttgact aaatttgcca  30000
tttactttg tatgactata tgaataaatt gctgatatat ttttctttca cagtggttac  30060
atggcacctg agtgcttcca tgggagtagc atctcagtga agtctgatgt ttttagcttt  30120
ggagtcttga ttttggagat aataagtgga aggaaagttg cgactagttt ccgtcgatac  30180
aaaagatcag acaatctgat ggcttacgtg agtattctct tgtacaaaag aacaattttg  30240
ttgagtaact gtaccacctg ctttcaaggc tatcaggcca aataatctac ttttggaaca  30300
ggcttggcga ctttgggaag atggaaattg taagcagctc atcgacaact ctctaagtgt  30360
tgaggaacat aacagtgagt cagagataat caggtgcatt cagattgcgc tcctatgtgt  30420
tcaggccaac ccagaggaca ggcctgacat ggtagaggtt gtcaggatgc taagcatcaa  30480
gggcacccag ctggacaatc ctaagcaacc tgcttatttt gatgaactca tcgtggcaac  30540
aacaagcaac cataccagta ctcggtacct cacagccata catgtccatc cagcttaata  30600
gatagtatct gaataatgca tagcaaaaga tgatttcatc tagggttgta tgcaattcct  30660
agcaaaagga aagatactaa tttcctgcaa ggttgatttg taaacagatc attcaaaagc  30720
ctataaattc ctaatctgat gaagcaaaac cagattatcc attcataaga aagatttcac  30780
acctcccaaa gatgaattgc ttgatgcgaa aatcagagaa cgtcctctgg acacaaggac  30840
gtgcacatat gctgatatgc ttctgcacct atcttcacct cagcttgttg gcctttctca  30900
gaacgtcttc aattgccggt gacatcgcta gctcccatct gatgtggaag cgtgtggttt  30960
ggtatctacg aacaaatcag ggagtcccgg aatccaaaat catttttta tattaaggaa  31020
aatgcttcca gcctaccccg gaatccaaaa tcatagggtt ccaaacaaat ttgaactgta  31080
aatagccaaa aaagctggag aattcaatca acctacggca ggaccagtgt tttaaatagc  31140
gtgctaagcc tattagcggc agcctctcta aaaggctaag aaaagctata gcgcgctaat  31200
agcgggctaa gccatttagc ggctgagcaa aaaatatgtt aaacatcatg taattttaca  31260
cataataaag atgaaaaata ttatgaatac caatagtgat agatatttca aaggattact  31320
```

```
aacatattac atcaaagttc gtagttcata catgatacat caataataac atacatcaca    31380 tagggcata tccctgctat ttgggcctcc aagttatttg ggtcgataga aatgattccc     31440
aaggccaaat agcggcgcta aactaaccca atttagcgaa attagcgtgc tattagctgc    31500
taatagcggg aacaatcatt tagcgttaaa atctccatag cttagcagtc ctcctccaca    31560
aacgctaaat agcgctatag cgtctgctat agcgcgctat ttagaacagg gggcaagaca    31620
ctagttcgtt tggctgataa gtcattgact gatcactgtt gaatagctag cagattcgcc    31680
tcttaaacaa acaaatacgg cggcagcagt agcattgcgt taatttacca tcagaattca    31740
aaaagggcag actggctgtg gaaagcataa ctagaaggct acagaaagat taaccttgta    31800
gtaatggcag gtgggattca tcgtggatga gccacccttg gctgaaagat gccctcaaac    31860
gacggagagc acggaaagcg caaccgctgc tgcgggagat cgccgggaca gtcaggtttc    31920
cgccgccgcg gagcttcgta tttggtgctt ccaccttgca agaatgaaag gtggtttggg    31980
ccatggcttg gtgcgttgca gcattgcagc aaccgacaat gggcttctct tgtttgggct    32040
ttggaaacga aataatgcca cggcccgtta tatgatctgg gtgggtccgg tggcttcttg    32100
ctatatttct gccgttttctt gcaatgttac ttgtattttt tagaacaaca agcacaagag   32160
ataagtgata tcagtttcat agacaaaaaa aaaatcattt ccatgcacga actaacaatt    32220
taatcggtgg cacataacca aacaatcctt agtttagtgg ccttttcttt ttacattatg    32280
cgtaagcagt actggtactt caaaactcca gagttccaag taatctgagt gtcaatacaa    32340
aaaagagagc gaattagaaa agaacaaagt aaaactaata acgactgaac atctactaaa    32400
tcacccagca gcagcagcag tagtaaataa gtaattccaa tcgacaaaaa tggttagtaa    32460
tggcacaagt tcattctaat gcactggaag cactccagtt gagatatttt tctatctcct    32520
gtccgttcaa agactgttcc atggtctaca gtcactatta tcgccgtgct tcaccctccg    32580
ccaagtcgcg atgttgagcg accattagtg gcctgcttgt gagccagatc cacggctgct    32640
cgtgcaagag aggccagatc catggccgct cgtggtaggg agaccggatc tgccacatcc    32700
tcgagtactt ctacctcacc ggcgccgtcg tgctatgacg tacatgggga atccaggtga    32760
ggtcctcagt atcaccctca atccccatgc ttctacctag cgtcactgct actgtgcatc    32820
tggagtttgg ccgctggaaa tcctctgctc gttgctctat tctgctgcca tgtgcttgtt    32880
gctctgccgc tgcatgcagt ctacgtgttt gatgaaatgt caatgcatgt tgactgttgt    32940
tttgcaattg accgttatgt gctagcttct gttagatggt gttgtgatta gatgcatcct    33000
catacaagag tatgcaatgt cattcccacc tggcccttgt ctgcttttg tacagttgtt     33060 tttgtaggag ttaggcaata gagagatgat ggaagtgacg agagaacaga agaaacattt    33120
aactggtgat gagattttct gaactaaacc atagaggaca aaatggttgg gagttgggac    33180
atttacttgc atcaaattac tgtccttggc tgtaagatca tataacctga ggcgttgata    33240
gcctccaaga aggaaagaaa tggctacttg taaattgcta aggagctata tgcttcaagc    33300
accaagtagt gacacaggct gagatgatga ccattaatat actagtattt tctgattgga    33360
tcatcaatct tcaaagccta caatctgaac ttagcgttcc tacatgatag aaacactaca    33420
aaatttatca ctctttggac catgtatagg ttcagtcttc aaattagcac tagcatgttt    33480
gactgtgtta catgaaaaaa aaccacaaat ttctatttca gctttataaa agtgtgatga    33540
tattaattac ctagttccaa catctattgc ttgcctttaa acactagtga aggttgccca    33600
aaactggttc atgcttgagt gagtttgatt tagggtattt ttggcctgag ctagttcact    33660
```

```
tttttagtag ttgcttttgt taggacaatg atctggtcat cttacagagc agctgctgca   33720
tactcccctt ctttctgaac attgcagacc aatgattggt gccttatata tcttagaatt   33780
agaattttca gttttgaaga tgcagtgatt tggttgatgt atcagactct gtaaggtgta   33840
ggctactagc agtagcacta gaacctgact aggaagatat gtcttgctac tctatctttc   33900
tgatatcgta catatgcaga tcatggtttc tctctaatta ctcaaactct ctaggaatag   33960
ctatactctg tactgagcta gttactatta ctattactag aaattgcttc gatcttgtta   34020
tgttctatcc gaacatagga atttcttgca tgttaataaa aaaacttaaa agttatagaa   34080
caaagcacca agggtgctta gagcactaag ttctgcatta ttcttttatc tcagttaata   34140
agtaaagtag cattattcac tgtccttttt tatttttta caagcactac tggagtgtaa   34200
gctctctgct tttctgaact ctgagcatac tttttcccgt gaactttgaa catgctatgc   34260
atccttttag atactgagtg tgttatgatc agcgccataa gttgttcact gatgaaataa   34320
ttactggtgc acacagctgt ctaggaagaa ggcaagctag ggttctttga ttgacaagca   34380
tccgcaagtc agcgagccac ccacgggtaa gtgagctgaa ctgaaatccc acaagtacaa   34440
gctgactagc tagagtttct gccttttgc tgtcagttag ataatttct gatagacact   34500 tctgctgtaa atacgtgaat tcaaacattt gatagtgtga aagaaattc agattttatt   34560 agcttgtaga atatcaattt ttgatgtagt tgaatgtgat gcactatttt tggcagagaa   34620
gtgattggtt cgagagccta gtggagtgtg gagaagagtt ctgatccaag ttctgcttca   34680
caggtatgga caatatatgg cttatgagca atgggtcaaa atacttattc tgtacgattg   34740
cagctccttt gtgttaaata cagtttgaaa gacaatttct aaatttgttt agtcagagtt   34800
gcatgcagag tgcttagctg gtgtcatagc tgtaaactta atcatctata tggtagacat   34860
atggttgaat atccttgtg agccttgctg gtgttatgtg gatatggtgt cctgttttat   34920
tcagccctac atactcctat aagctttcct agtgtcattg tcgttgttta tcatcattcc   34980
aaaatatcga ttagctatgt aaggccttgt gtgtatacat aagagtttca caatgacatt   35040
ccaaaatatt gattagctat cgctgtaaat aagcaggatt caaaggctca gatcagtgca   35100
actcacacct aataattggg atccttcagc tacatgcagg agcagtacaa caaggtacga   35160
tacaataata atgctaaact aatcaactag taattgtaca attccaaagt aatattttac   35220
ctgtgagctc ttgttacatc aaagcacaaa taaatcttta taaactcatc ctggtataaa   35280
agagtctgag agccttacat caattgtagt gttgcttaga atttttaata atatctattt   35340
gaaaatgtgt tctctgtata gagtggtctg ctgtgtagaa aggccacatt tatggatggc   35400
ataccgtttt gatattttct atattgattc agtaaggtaa gtcttattcc tagcatttta   35460
gatatgattg agcatgttgg ctgagactag gtgccttaaa tatattggat agaagttggt   35520
atttcttgca gcaactttt tttttgctat attagaacac aactgctgag catatcgaca   35580
tgctcaaatt tctgtagacg aatttatacc catttataaa tcactctcat cgaaccaagg   35640
ttgaaaattc aggctgtacc aagcctaatt attttctact ttgctgtagg ttcagaatag   35700
atttttcctt tgatatgaat tgcaaataca atggcaactt gcacgtgaag aaggtgtatc   35760
tttgtccttt ttaatgcctg ttcaagttaa gtataagttt cctcctccct ttagttactt   35820
tccaatgctc tgtgcatgtc caatgctgca agagagctgc tgcatatgtt gtcctttctg   35880
aacattgtca gccgcaaacc ttattgttta ttacattatt ctctgctcgc acttctaaat   35940
ttgtactttg gtttataatg gttttgcagg atctcaagaa cacctacac cttgtttagt   36000 tcaccccaaa atccaaaaac ttttcaagat ttccttgaca gcatatgcag accatcagtg   36060
```

```
cttcctgaca gctgcatgaa cagagtggac tttgcttgcc ctgttgtatg agctaggcct    36120
gcttataagt gctaccggat ttagtacaac catcagtgct tcctgagcct gtggcctctc    36180
actatacgct gaagtaagta gaaaaaatag tattctccta tgatctaaga ttaaacacca    36240
tttgctgcct ctcactatac aaggctaatt atttcccccc aacagtttct ttttataagt    36300
tggcatggtt ctactagtag tatactctat tttgttcact aataactaaa ctgtagtaat    36360
gggtttgtgg ggatcacatt gtttgtaatt gaccaaaact gcaggtactg atagaaaatt    36420
ataccataat cactgttggc cacagaaaaa aaataccaat aatgctaata ctgttaccca    36480
attgtaaaaa actgtggaga aaaaggggac tctgtaatgt ctattgtaat ttcaactttt    36540
agcagtggta gaacaactta ttgcactaga aacctattgg gcctgctaat actgtcacct    36600
gtccgttcaa atcttcagac cgctgatgaa atccgacagc cgttttccct ataaatcttt    36660
gggattttgt acccgttttc cgtattaatt acaattttgt tagtttggtt tgtgttgagg    36720
gtttccctat cctcacaaga gtcctaccta ctactactgc taccaccatg acttaaagtt    36780
catttcaggc ttgtcacagc taacagaaca acatgggag tggcagtgaa agcctccata    36840
gctcttcatc tcctccctat cctcctcctc actgccacca atgatgcagc cacgttcacc    36900
atcaccaaca attgcagctt caccgtgtgg ccagctgcca cgccagttgg tggtggcaca    36960
cagctcaacc ctgggcagac atggaccctc aacgtgcccg ccggcacctc tgccgggcgc    37020 ttgtggggc gcaccggctg ctcctttaga ggcggcagcg ggagatgtca aacaggcaat    37080
tgcggtggcg tgctttcctg caagctgagc cctcagccac ccgttacgct tgcagagttc    37140
acggtcaata gcggaacgtc tgatttcttt gatatctccg tcatcgatgg cttcaaccta    37200
cctatggact tcatgggagg ggcagggtgc agcaaggggc cacgctgcct gggcaactct    37260
acatcgcagt gctcggatgc atacaccaat cccagtgatg ataataaaac attcacttgt    37320
ccagcgggga ccgactacca gctcgttttc tgcccctcgg ttgatctaag acctacacca    37380
gtaactgtaa gtcctcaacc agcaccttct cctgcaactg taatccagat agcaccacca    37440
tcgccatcac ttgtgctatc acctcgtggg gcaacaacag caagatcatc ctcagcaaac    37500
caagttgttg tgattctagc tacggtaggt ggctttatct ttctagtgat cctttcatt    37560 gccattttct tcatgtgtaa acgaagaacc agacatcagg agatggagga aatggaagag    37620
tttgaggacc tacaaggaac accaatgaga ttcacttttc gaagcggccg caagcttgct    37680
gagtggctcc ttcaacgttg cggttctgtc agttccaaac gtaaacggc ttgtcccgcg    37740 tcatcggcgg gggtcataac gtgactccct taattctccg ctcatgatca gattgtcgtt    37800
tcccgccttc agtttaaact atcagtgttt gacaggatat attggcgggt aaacctaaga    37860
gaaaagagcg tttattagaa taatcggata tttaaagggt cgtgaaaagg tttatccgtt    37920
cgtccatttg tatgtgcatg ccaaccacag ggttcccctc gggagtgctt ggcattccgt    37980
gcgataatga cttctgttca accacccaaa cgtcggaaag cctgacgacg gagcagcatt    38040
ccaaaaagat cccttggctc gtctgggtcg gctagaaggt cgagtgggct gctgtggctt    38100
gatccctcaa cgcggtcgcg gacgtagcgc agcgccgaaa aatcctcgat cgcaaatccg    38160
acgctgtcga aaagcgtgat ctgcttgtcg ctctttcggc cgacgtcctg gccagtcatc    38220
acgcgccaaa gttccgtcac aggatgatct ggcgcgagtt gctggatctc gccttcaatc    38280
cgggtctgtg gcgggaactc cacgaaaata tccgaacgca gcaagatcgt cgaccaattc    38340
ttgaagacga aagggcctcg tgatacgcct atttttatag gttaatgtca tgataataat    38400
```

```
ggtttcttag acgtcaggtg gcacttttcg gggaaatgtg cgcggaaccc ctatttgttt    38460
atttttctaa atacattcaa atatgtatcc gctcatgaga caataaccct gataaatgct    38520
tcaataatat tgaaaaagga agagtatgag tattcaacat ttccgtgtcg cccttattcc    38580
cttttttgcg gcattttgcc ttcctgtttt tgctcaccca gaaacgctgg tgaaagtaaa    38640
agatgctgaa gatcagttgg gtgcacgagt g                                   38671

<210> SEQ ID NO 31
<211> LENGTH: 630
<212> TYPE: DNA
<213> ORGANISM: Sorghum sudanense

<400> SEQUENCE: 31
atggccgaga agtaccacca tgattgggaa gtcgtcccct tcaacctcaa catggagcct      60
gtggaagacc ccgatgcccg tgctctcgtc ccggccaaca cagaaagaca gctagaagcc     120
atgccattac gccaacgtaa ctccgcccaa tcttaccatg ctcaaccagt tctcaccgca     180
ccaccacaac ccctactcct caaaggatca tcatccaaga cgaagaccac tatcaaggtg     240
ccaatcggca aaggatcct tccacctaga cccaatgaga gggtcgttgg agtcaagacc     300
aaccgaagcg gcgagatcag cagtgttcac tacactacgg aggaggaaag gccttacttt     360
gaagggatta gagcagccaa agtccatttc atccctccaa aggcagcccc gaagcactct     420
ctcaatgctt ttgagacacc tcccaagcgt cgcaagacta atgaaaat tgatgaggaa      480 gttcgcaggc tagatagagt tatcatagac ctccagtcct cgattaattc cctcactagg     540
cagctctcta accacaacac cattatacta ggccttaggc aggatcttgc caatgccaac     600
aagaagatca aggaattaga gcaccgctaa                                    630

<210> SEQ ID NO 32
<211> LENGTH: 209
<212> TYPE: PRT
<213> ORGANISM: Sorghum sudanense

<400> SEQUENCE: 32

Met Ala Glu Lys Tyr His His Asp Trp Glu Val Val Pro Phe Asn Leu
1               5                   10                  15

Asn Met Glu Pro Val Glu Asp Pro Asp Ala Arg Ala Leu Val Pro Ala
            20                  25                  30

Asn Thr Glu Arg Gln Leu Glu Ala Met Pro Leu Arg Gln Arg Asn Ser
        35                  40                  45

Ala Gln Ser Tyr His Ala Gln Pro Val Leu Thr Ala Pro Pro Gln Pro
    50                  55                  60

Leu Leu Leu Lys Gly Ser Ser Ser Lys Thr Lys Thr Thr Ile Lys Val
65                  70                  75                  80

Pro Ile Gly Thr Arg Ile Leu Pro Pro Arg Pro Asn Glu Arg Val Val
                85                  90                  95

Gly Val Lys Thr Asn Arg Ser Gly Glu Ile Ser Ser Val His Tyr Thr
            100                 105                 110

Thr Glu Glu Glu Arg Pro Tyr Phe Glu Gly Ile Arg Ala Ala Lys Val
        115                 120                 125

His Phe Ile Pro Pro Lys Ala Ala Pro Lys His Ser Leu Asn Ala Phe
    130                 135                 140

Glu Thr Pro Pro Lys Arg Arg Lys Thr Ile Met Glu Ile Asp Glu Glu
145                 150                 155                 160

Val Arg Arg Leu Asp Arg Val Ile Ile Asp Leu Gln Ser Ser Ile Asn
```

165                 170                 175
Ser Leu Thr Arg Gln Leu Ser Asn His Asn Thr Ile Ile Leu Gly Leu
        180                 185                 190

Arg Gln Asp Leu Ala Asn Ala Asn Lys Lys Ile Lys Glu Leu Glu His
        195                 200                 205

Arg

<210> SEQ ID NO 33
<211> LENGTH: 30
<212> TYPE: DNA
<213> ORGANISM: Artificial sequence
<220> FEATURE:
<223> OTHER INFORMATION: SS-DTP21-2 forward primer

<400> SEQUENCE: 33
ataccttgtt aacctcatag gttctctcag                                    30

<210> SEQ ID NO 34
<211> LENGTH: 30
<212> TYPE: DNA
<213> ORGANISM: Artificial sequence
<220> FEATURE:
<223> OTHER INFORMATION: SS-DTP21-2 reverse primer

<400> SEQUENCE: 34
ccttcccatg gagagttaac gcccgacact                                    30

<210> SEQ ID NO 35
<211> LENGTH: 41
<212> TYPE: DNA
<213> ORGANISM: Artificial sequence
<220> FEATURE:
<223> OTHER INFORMATION: forward primer to prepare linearized vector

<400> SEQUENCE: 35
gctctaactg aagaagagaa ggcttggtgg cttggtgttt g                       41

<210> SEQ ID NO 36
<211> LENGTH: 40
<212> TYPE: DNA
<213> ORGANISM: Artificial sequence
<220> FEATURE:
<223> OTHER INFORMATION: reverse primer to prepare linearized vector

<400> SEQUENCE: 36
gctatcattt aaatcggttt aggtttacta ttatcatcag                         40

<210> SEQ ID NO 37
<211> LENGTH: 41
<212> TYPE: DNA
<213> ORGANISM: Artificial sequence
<220> FEATURE:
<223> OTHER INFORMATION: Sorghum DTP21 forward primer

<400> SEQUENCE: 37
ttcttcagtt agagcttgat tagttccttg ctgctccaat g                       41

<210> SEQ ID NO 38
<211> LENGTH: 68
<212> TYPE: DNA
<213> ORGANISM: Artificial sequence
<220> FEATURE:
<223> OTHER INFORMATION: Sorghum DTP21 reverse primer

<400> SEQUENCE: 38

```
aaacctaaac cgattttaaa gatagataac taagatgcat tgcctcaatg tctaatctag    60
ataaatta                                                              68

<210> SEQ ID NO 39
<211> LENGTH: 630
<212> TYPE: DNA
<213> ORGANISM: Sorghum bicolor

<400> SEQUENCE: 39
atggccgaga agttccacga tgattgggaa gtcgtcccct caacctcaa catggagcct     60 gcggaagacc ccgacgcccg tgctctcgtc ccggccaaca cagagcgaca gctagaagcc    120
atgccattac gccaacgcag ctccacccaa tcctaccatg ctcaaccagt tcttaccgca    180
ctgccacaac ccctacttct caagggatca tcatcgaaga cgaagaccac catcaaagtg    240
ccaaccttca cgaggatcct tctacctaga cctaatgaga gggtcgttga agtcaatacc    300
aactggagcg cgagatcca cagcattcgc tacactacag aggaggaaag gccttacttc    360 gagggggatta gagcagccaa agtccgtttc atccctccaa aggcagcccc gaagcattct    420
ctcaatgctt ttgagacacc tcctaagcgt cgcaagacta gtagatat tgatgaggac      480 gttcgcaggc tagacagagt tatcatagac ctccagtcct cgattaattc cctcactagg     540
cagctctgtg accacaacac cattatacta ggccttaggc aggatcttgc cagtgccaat    600
aggaagatta aggaattaga gcgctactaa                                      630

<210> SEQ ID NO 40
<211> LENGTH: 627
<212> TYPE: DNA
<213> ORGANISM: Sorghum bicolor

<400> SEQUENCE: 40
atggccgaaa agttccacga tgattgggaa gtcgtccgct ccacctcaa catgacgctt     60 gaggaagacc ccgatgcccg tgctctcgtc ccggccaaca cagagcgaca gctagaagcc    120
atgccattac gccagcgtag ctccgcccaa tcctaccata ctcaaccagt tctcaccgca    180
ctgccacaaa ccctactcct caagggatca tcatccaagg agaccaccat caaggtgcca    240
gccggcacga ggatccttcc acccagaccc aatgagaggg tcgttggagt caagaccaac    300
cggagcagtg agatcagcag catccgctac attacgagg aagagagacc ttactttgaa     360
gggattagag cagccgaagt ccgtttcatc cctccaaagg cagcctcgaa gcacgcactc    420
aatgcttttg agacacctcc taagcatcgc aagactatag tagatattga tgaggacatt    480
cgcaggctag acagagtcat catagacctc cagtcctcgg ttaattccat cactaggcag    540
ctctctaacc acaacaccgt tatactaggc cttaggcatg atcttcctag tgccaataag    600
aagatcaagg agttagagca ccgctaa                                         627

<210> SEQ ID NO 41
<211> LENGTH: 209
<212> TYPE: PRT
<213> ORGANISM: Sorghum bicolor

<400> SEQUENCE: 41

Met Ala Glu Lys Phe His Asp Asp Trp Glu Val Val Pro Phe Asn Leu
1               5                   10                  15

Asn Met Glu Pro Ala Glu Asp Pro Asp Ala Arg Ala Leu Val Pro Ala
            20                  25                  30
```

Asn Thr Glu Arg Gln Leu Glu Ala Met Pro Leu Arg Gln Arg Ser Ser
            35                  40                  45

Thr Gln Ser Tyr His Ala Gln Pro Val Leu Thr Ala Leu Pro Gln Pro
 50                  55                  60

Leu Leu Leu Lys Gly Ser Ser Lys Thr Lys Thr Thr Ile Lys Val
 65                  70                  75                  80

Pro Thr Phe Thr Arg Ile Leu Leu Pro Arg Pro Asn Glu Arg Val Val
                    85                  90                  95

Glu Val Asn Thr Asn Trp Ser Gly Glu Ile His Ser Ile Arg Tyr Thr
                100                 105                 110

Thr Glu Glu Arg Pro Tyr Phe Glu Gly Ile Arg Ala Ala Lys Val
            115                 120                 125

Arg Phe Ile Pro Pro Lys Ala Ala Pro Lys His Ser Leu Asn Ala Phe
            130                 135                 140

Glu Thr Pro Pro Lys Arg Arg Lys Thr Ile Val Asp Ile Asp Glu Asp
145                 150                 155                 160

Val Arg Arg Leu Asp Arg Val Ile Ile Asp Leu Gln Ser Ser Ile Asn
                165                 170                 175

Ser Leu Thr Arg Gln Leu Cys Asp His Asn Thr Ile Ile Leu Gly Leu
            180                 185                 190

Arg Gln Asp Leu Ala Ser Ala Asn Arg Lys Ile Lys Glu Leu Glu Arg
            195                 200                 205

Tyr

<210> SEQ ID NO 42
<211> LENGTH: 208
<212> TYPE: PRT
<213> ORGANISM: Sorghum bicolor

<400> SEQUENCE: 42

Met Ala Glu Lys Phe His Asp Asp Trp Glu Val Val Arg Phe His Leu
 1               5                  10                  15

Asn Met Thr Leu Glu Glu Asp Pro Asp Ala Arg Ala Leu Val Pro Ala
                20                  25                  30

Asn Thr Glu Arg Gln Leu Glu Ala Met Pro Leu Arg Gln Arg Ser Ser
            35                  40                  45

Ala Gln Ser Tyr His Thr Gln Pro Val Leu Thr Ala Leu Pro Gln Thr
 50                  55                  60

Leu Leu Leu Lys Gly Ser Ser Lys Glu Thr Thr Ile Lys Val Pro
 65                  70                  75                  80

Ala Gly Thr Arg Ile Leu Pro Pro Arg Pro Asn Glu Arg Val Val Gly
                    85                  90                  95

Val Lys Thr Asn Arg Ser Ser Glu Ile Ser Ser Ile Arg Tyr Ile Thr
                100                 105                 110

Glu Glu Glu Arg Pro Tyr Phe Glu Gly Ile Arg Ala Ala Glu Val Arg
            115                 120                 125

Phe Ile Pro Pro Lys Ala Ala Ser Lys His Ala Leu Asn Ala Phe Glu
            130                 135                 140

Thr Pro Pro Lys His Arg Lys Thr Ile Val Asp Ile Asp Glu Asp Ile
145                 150                 155                 160

Arg Arg Leu Asp Arg Val Ile Ile Asp Leu Gln Ser Ser Val Asn Ser
                165                 170                 175

Ile Thr Arg Gln Leu Ser Asn His Asn Thr Val Ile Leu Gly Leu Arg
            180                 185                 190

His Asp Leu Pro Ser Ala Asn Lys Lys Ile Lys Glu Leu Glu His Arg
        195                 200                 205

<210> SEQ ID NO 43
<211> LENGTH: 630
<212> TYPE: DNA
<213> ORGANISM: Sorghum bicolor

<400> SEQUENCE: 43

| | | | | | |
|---|---|---|---|---|---|
| atggccgaag | agttccacga | cgattgggaa | gtcattccct | acgacctcaa | caagaagccc | 60 |
| aaggaagacc | ccgacgcccg | agctctcgtc | ccggccaaca | cagagcgaca | gctagaagcc | 120 |
| atgccattac | gccaacacag | ctccgcacaa | tcctaccatg | ctcaaccagt | tctcatcaca | 180 |
| tcgccacaac | ccctacttct | caagggacca | tcagccaaga | aggagacctc | catcaaggtg | 240 |
| tcagccggca | cgaggatcct | tccacccaga | cccaatgtga | gggtcgttgg | agtcaagacc | 300 |
| aaccggagcg | gcgagatcag | caccatccgc | tacactaggg | aggaagagag | gccttacttt | 360 |
| gaagggatta | gagcagccaa | agtccatttc | atccctccaa | aggctgcccc | aaagcacgct | 420 |
| ctcaatgctc | tcgagacacc | ccctaagcgt | cgcaagacta | tagtagatat | tgatgaggac | 480 |
| gttcgcaggc | tagacagagt | tatcatagac | ctccagtcct | cagttaactc | catcactagg | 540 |
| cagctctcta | accacaacac | catgatacta | ggtcttaggc | atgatcttgc | cagtgccaac | 600 |
| aagaagatca | agaattaga | gcgccgctaa | | | | 630 |

<210> SEQ ID NO 44
<211> LENGTH: 630
<212> TYPE: DNA
<213> ORGANISM: Sorghum bicolor

<400> SEQUENCE: 44

| | | | | | |
|---|---|---|---|---|---|
| atggccgaga | agtaccacga | tgattgggaa | gtcgtcccct | tcaacctcaa | catggagcct | 60 |
| gtggaagacc | ccgatgcccg | tgctctcgtc | ccggccaaca | cagagcgaca | acttgaagcc | 120 |
| atgccattac | gccaacgcag | ctccgcccaa | ccctaccatg | atcaaccagt | tctcaccgca | 180 |
| ccgccacaac | ccctactcct | caaaggatca | tcatccaaga | cgaagaccac | catcaaggtg | 240 |
| ccaaccggca | cgaagatcct | tccacctaga | cccaatgaga | gggtcgttgg | agtcaagacc | 300 |
| aaccggagcg | gcgaggtcag | cagcattcgc | tacaccacgg | aggagggaag | gccttacttc | 360 |
| gaagggatta | gagcagccaa | agtccgtttc | atccctccaa | aggcagcccc | gaagcacgct | 420 |
| ctcaatactt | ttgagacacc | tcccaagcgt | cgcaaaacta | atggatat | tgatgaggac | 480 |
| gttcgcagac | tagacagagt | tatcatagac | ctccagtcct | cgattaattc | cctcactagg | 540 |
| cagctctcta | accacaacac | cgttatatta | ggccttaggc | atgatcttgc | cagtgccaac | 600 |
| aagaagatta | aggaattaga | gcgccgctaa | | | | 630 |

<210> SEQ ID NO 45
<211> LENGTH: 209
<212> TYPE: PRT
<213> ORGANISM: Sorghum bicolor

<400> SEQUENCE: 45

Met Ala Glu Glu Phe His Asp Asp Trp Glu Val Ile Pro Tyr Asp Leu
1               5                   10                  15

Asn Lys Lys Pro Lys Glu Asp Pro Asp Ala Arg Ala Leu Val Pro Ala
            20                  25                  30

Asn Thr Glu Arg Gln Leu Glu Ala Met Pro Leu Arg Gln His Ser Ser
        35                  40                  45

Ala Gln Ser Tyr His Ala Gln Pro Val Leu Ile Thr Ser Pro Gln Pro
            50                  55                  60

Leu Leu Leu Lys Gly Pro Ser Ala Lys Lys Glu Thr Ser Ile Lys Val
65                  70                  75                  80

Ser Ala Gly Thr Arg Ile Leu Pro Pro Arg Pro Asn Val Arg Val Val
                85                  90                  95

Gly Val Lys Thr Asn Arg Ser Gly Glu Ile Ser Thr Ile Arg Tyr Thr
            100                 105                 110

Arg Glu Glu Glu Arg Pro Tyr Phe Glu Gly Ile Arg Ala Ala Lys Val
            115                 120                 125

His Phe Ile Pro Pro Lys Ala Ala Pro Lys His Ala Leu Asn Ala Leu
            130                 135                 140

Glu Thr Pro Pro Lys Arg Arg Lys Thr Ile Val Asp Ile Asp Glu Asp
145                 150                 155                 160

Val Arg Arg Leu Asp Arg Val Ile Ile Asp Leu Gln Ser Ser Val Asn
                165                 170                 175

Ser Ile Thr Arg Gln Leu Ser Asn His Asn Thr Met Ile Leu Gly Leu
            180                 185                 190

Arg His Asp Leu Ala Ser Ala Asn Lys Lys Ile Lys Glu Leu Glu Arg
            195                 200                 205

Arg

<210> SEQ ID NO 46
<211> LENGTH: 209
<212> TYPE: PRT
<213> ORGANISM: Sorghum bicolor

<400> SEQUENCE: 46

Met Ala Glu Lys Tyr His Asp Asp Trp Glu Val Val Pro Phe Asn Leu
1               5                   10                  15

Asn Met Glu Pro Val Glu Asp Pro Asp Ala Arg Ala Leu Val Pro Ala
            20                  25                  30

Asn Thr Glu Arg Gln Leu Glu Ala Met Pro Leu Arg Gln Arg Ser Ser
            35                  40                  45

Ala Gln Pro Tyr His Asp Gln Pro Val Leu Thr Ala Pro Pro Gln Pro
            50                  55                  60

Leu Leu Leu Lys Gly Ser Ser Lys Thr Lys Thr Thr Ile Lys Val
65                  70                  75                  80

Pro Thr Gly Thr Lys Ile Leu Pro Pro Arg Pro Asn Glu Arg Val Val
                85                  90                  95

Gly Val Lys Thr Asn Arg Ser Gly Glu Val Ser Ser Ile Arg Tyr Thr
            100                 105                 110

Thr Glu Glu Gly Arg Pro Tyr Phe Glu Gly Ile Arg Ala Ala Lys Val
            115                 120                 125

Arg Phe Ile Pro Pro Lys Ala Ala Pro Lys His Ala Leu Asn Thr Phe
            130                 135                 140

Glu Thr Pro Pro Lys Arg Arg Lys Thr Ile Met Asp Ile Asp Glu Asp
145                 150                 155                 160

Val Arg Arg Leu Asp Arg Val Ile Ile Asp Leu Gln Ser Ser Ile Asn
                165                 170                 175

Ser Leu Thr Arg Gln Leu Ser Asn His Asn Thr Val Ile Leu Gly Leu
            180                 185                 190

Arg His Asp Leu Ala Ser Ala Asn Lys Lys Ile Lys Glu Leu Glu Arg
            195                 200                 205

Arg

<210> SEQ ID NO 47
<211> LENGTH: 627
<212> TYPE: DNA
<213> ORGANISM: Sorghum bicolor

<400> SEQUENCE: 47

```
atggccgaga agttccacga tgattgggaa gtcgtcccct tcaacctcaa catggagcct        60
gaagaagacc ccgacgcccg tgctctcgtc ccggccagca cagagcgaca gctagaagcc       120
atgccattac gccagcgcag ctccacccaa tcctaccatg ctcaaccagt tctcaccgca       180
ccgccacaac ccctacttct caagggatca tcatccaaga cgaagaccac catcaaggtg       240
ccaaccggca cgaggatcct tccacccaga cccaatgaga gggtcgttgg agtcaagacc       300
aaccggagcg gcgagatcag cagcatcccc tacactacgg aggaggagag gccttacttt       360
gaagggatta gagtagccaa agtctgtttc atccctccaa aggcagcccc gaagcacgct       420
ctcaatgctt ttgagacacc tcctaagcgt cgcaagacta tagtagacat tgatgagaac       480
gttcgcaggc tagacagagt catcatagac ctccagtcct cagttaactc catcactagg       540
cagctctcaa accacaacac cgttatatta ggccttaggc atgatcttgc tagtgccaat       600
aagaagatca aggaattaga gcgccgc                                           627
```

<210> SEQ ID NO 48
<211> LENGTH: 627
<212> TYPE: DNA
<213> ORGANISM: Sorghum bicolor

<400> SEQUENCE: 48

```
atggccgaga agttccacga tgattgggaa gtcgtcccct tcaacctcaa catggagcct        60
gaagaagacc ccgacgtccg tgctctcgtc ccggccaaca cagagtgaca gctagaagcc       120
atgccattac accagcgcag ctccacccaa tcctaccatg ctcaaccagt tctcaccaca       180
ccgccacaac ccctacttct caagggatca tcatccaaga cgaagaccac catcaaggtg       240
ccagccggca cgaggatcct tccacctaga cccaatgaca gggtcgtttg agtcaagacc       300
aaccagagtg cgcagatcag cagcattcgc tacactacag aggaggagag accttacttt       360
gaagggatta gagcagccaa agtccgtttc atccctccaa aggcagcccc gaagcacgct       420
ctcaatgctt ttgagacacc tcctaagtgt cgcaagacta taatagatat tgatgaggac       480
gttcgtaggc tagacagagt catcatagac ctccagtcct cagttaattc catcactagg       540
cagctctcta accacaacac cgttatacta ggccttaggc atgatcttgc caatgccaat       600
aagaagatca aggaattaga gcgccgc                                           627
```

<210> SEQ ID NO 49
<211> LENGTH: 209
<212> TYPE: PRT
<213> ORGANISM: Sorghum bicolor

<400> SEQUENCE: 49

```
Met Ala Glu Lys Phe His Asp Asp Trp Glu Val Val Pro Phe Asn Leu
 1               5                  10                  15

Asn Met Glu Pro Glu Glu Asp Pro Asp Ala Arg Ala Leu Val Pro Ala
             20                  25                  30

Ser Thr Glu Arg Gln Leu Glu Ala Met Pro Leu Arg Gln Arg Ser Ser
         35                  40                  45
```

```
Thr Gln Ser Tyr His Ala Gln Pro Val Leu Thr Ala Pro Pro Gln Pro
         50                  55                  60

Leu Leu Leu Lys Gly Ser Ser Lys Thr Lys Thr Thr Ile Lys Val
 65                  70                  75                  80

Pro Thr Gly Thr Arg Ile Leu Pro Pro Arg Pro Asn Glu Arg Val Val
                 85                  90                  95

Gly Val Lys Thr Asn Arg Ser Gly Glu Ile Ser Ser Ile Pro Tyr Thr
                100                 105                 110

Thr Glu Glu Arg Pro Tyr Phe Glu Gly Ile Arg Val Ala Lys Val
                115                 120                 125

Cys Phe Ile Pro Pro Lys Ala Ala Pro Lys His Ala Leu Asn Ala Phe
                130                 135                 140

Glu Thr Pro Pro Lys Arg Arg Lys Thr Ile Val Asp Ile Asp Glu Asn
145                 150                 155                 160

Val Arg Arg Leu Asp Arg Val Ile Ile Asp Leu Gln Ser Ser Val Asn
                165                 170                 175

Ser Ile Thr Arg Gln Leu Ser Asn His Asn Thr Val Ile Leu Gly Leu
                180                 185                 190

Arg His Asp Leu Ala Ser Ala Asn Lys Lys Ile Lys Glu Leu Glu Arg
                195                 200                 205

Arg

<210> SEQ ID NO 50
<211> LENGTH: 209
<212> TYPE: PRT
<213> ORGANISM: Sorghum bicolor
<220> FEATURE:
<221> NAME/KEY: misc_feature
<222> LOCATION: (36)..(36)
<223> OTHER INFORMATION: Xaa can be any naturally occurring amino acid
<220> FEATURE:
<221> NAME/KEY: misc_feature
<222> LOCATION: (97)..(97)
<223> OTHER INFORMATION: Xaa can be any naturally occurring amino acid

<400> SEQUENCE: 50

Met Ala Glu Lys Phe His Asp Asp Trp Glu Val Val Pro Phe Asn Leu
 1               5                  10                  15

Asn Met Glu Pro Glu Glu Asp Pro Asp Val Arg Ala Leu Val Pro Ala
                 20                  25                  30

Asn Thr Glu Xaa Gln Leu Glu Ala Met Pro Leu His Gln Arg Ser Ser
             35                  40                  45

Thr Gln Ser Tyr His Ala Gln Pro Val Leu Thr Thr Pro Pro Gln Pro
         50                  55                  60

Leu Leu Leu Lys Gly Ser Ser Lys Thr Lys Thr Thr Ile Lys Val
 65                  70                  75                  80

Pro Ala Gly Thr Arg Ile Leu Pro Pro Arg Pro Asn Asp Arg Val Val
                 85                  90                  95

Xaa Val Lys Thr Asn Gln Ser Gly Glu Ile Ser Ser Ile Arg Tyr Thr
                100                 105                 110

Thr Glu Glu Arg Pro Tyr Phe Glu Gly Ile Arg Ala Ala Lys Val
                115                 120                 125

Arg Phe Ile Pro Pro Lys Ala Ala Pro Lys His Ala Leu Asn Ala Phe
                130                 135                 140

Glu Thr Pro Pro Lys Cys Arg Lys Thr Ile Ile Asp Ile Asp Glu Asp
145                 150                 155                 160
```

```
Val Arg Arg Leu Asp Arg Val Ile Ile Asp Leu Gln Ser Ser Val Asn
            165                 170                 175

Ser Ile Thr Arg Gln Leu Ser Asn His Asn Thr Val Ile Leu Gly Leu
        180                 185                 190

Arg His Asp Leu Ala Asn Ala Asn Lys Lys Ile Lys Glu Leu Glu Arg
    195                 200                 205

Arg
```

<210> SEQ ID NO 51
<211> LENGTH: 630
<212> TYPE: DNA
<213> ORGANISM: Sorghum sudanense

<400> SEQUENCE: 51

```
atggccgaca agtaccacga cgattgggaa gtcgtcccct tcaacctcaa catggagcct      60
gtggaagacc ccgatgctcg tgctctcgtc ccggccaaca tagagcgtca gctagaagcc     120
atgccattac gtcaacgcag ctccgcccaa tcctaccatg ctcaaccagt tctcaccgca     180
ccaccacaac ccctactcct caaggaccac tcatccaaga cgaagaccac tatcaaggtg     240
ccaaccggca aaggatcctc tccacctaga cccaatgaga gggtcgttgg agtcaagacc     300
aaccgaagcg gcgagatcag cagtattcgc tacactacag aggaggaaag gccttacttt     360
gaagggatta gagcatccaa agtctgtttc atccctccaa aggcagcccc gaaacactct     420
ctcaatgctt ttgagacacc tcccaagcgt cgcaagacta tagtcgatat tgatgaggaa     480
gttcacaggc tagatagagt tatcatagac ctccagtcct caattaattc cctcactagg     540
cagctctcta accacaacac cgttatacta ggctttaggc aggatcttgc cagtgccaac     600
aagaagatca aggaattaga gcgccgctaa                                     630
```

<210> SEQ ID NO 52
<211> LENGTH: 209
<212> TYPE: PRT
<213> ORGANISM: Sorghum sudanense

<400> SEQUENCE: 52

```
Met Ala Asp Lys Tyr His Asp Asp Trp Glu Val Val Pro Phe Asn Leu
1               5                   10                  15

Asn Met Glu Pro Val Glu Asp Pro Asp Ala Arg Ala Leu Val Pro Ala
            20                  25                  30

Asn Ile Glu Arg Gln Leu Glu Ala Met Pro Leu Arg Gln Arg Ser Ser
        35                  40                  45

Ala Gln Ser Tyr His Ala Gln Pro Val Leu Thr Ala Pro Pro Gln Pro
    50                  55                  60

Leu Leu Leu Lys Gly Pro Ser Ser Lys Thr Lys Thr Thr Ile Lys Val
65                  70                  75                  80

Pro Thr Gly Thr Arg Ile Leu Pro Pro Arg Pro Asn Glu Arg Val Val
                85                  90                  95

Gly Val Lys Thr Asn Arg Ser Gly Glu Ile Ser Ser Ile Arg Tyr Thr
            100                 105                 110

Thr Glu Glu Glu Arg Pro Tyr Phe Glu Gly Ile Arg Ala Ser Lys Val
        115                 120                 125

Cys Phe Ile Pro Pro Lys Ala Ala Pro Lys His Ser Leu Asn Ala Phe
    130                 135                 140

Glu Thr Pro Pro Lys Arg Arg Lys Thr Ile Val Asp Ile Asp Glu Glu
145                 150                 155                 160
```

```
Val His Arg Leu Asp Arg Val Ile Ile Asp Leu Gln Ser Ser Ile Asn
            165                 170                 175

Ser Leu Thr Arg Gln Leu Ser Asn His Asn Thr Val Ile Leu Gly Phe
        180                 185                 190

Arg Gln Asp Leu Ala Ser Ala Asn Lys Lys Ile Lys Glu Leu Glu Arg
    195                 200                 205

Arg
```

```
<210> SEQ ID NO 53
<211> LENGTH: 630
<212> TYPE: DNA
<213> ORGANISM: Sorghum sudanense

<400> SEQUENCE: 53
atggccgaga agttccacga tgattgggaa gtcatcccct tcaacctcaa catggagcct      60
gtggaagacc ccgatgcccg tgctctcgtc ccggctaaca cagagcgaca gctagaagcc    120
atgccattac gccaacgcag ctccgcccaa tcctaccatg ctcaaccggt tctcaccgca    180
ccgccacaac ccctactcct caagggatca tcatccaaga cgaagaccac catcaaggtg    240
ccaactggca cgaaaatcct cccacctaga cccaatgaga gggtcgttgg agtcaagacc    300
aaccggagcg gcgagatcag cagcattcgc tacactacgg aggaggaaag gccttacttc    360
gaagggatta gagcagccaa agtctgtttt atccctccaa aggcagcccc aaagcacgct    420
ctcaatgctt ttgagacacc tcccaagcgt cgcaagacta tagtagatat tgatgaggac    480
gtttgcaggc tagacagagt tatcatagac ctccagtcct cgattaattc cctcactagg    540
cagctctcta accacaacac cgttatacta agccttaggc atgatcttgc cagtgacaac    600
aagaagatta aggaattaga gcgctgctaa                                      630
```

```
<210> SEQ ID NO 54
<211> LENGTH: 209
<212> TYPE: PRT
<213> ORGANISM: Sorghum sudanense

<400> SEQUENCE: 54

Met Ala Glu Lys Phe His Asp Asp Trp Glu Val Ile Pro Phe Asn Leu
1               5                  10                  15

Asn Met Glu Pro Val Glu Asp Pro Asp Ala Arg Ala Leu Val Pro Ala
            20                  25                  30

Asn Thr Glu Arg Gln Leu Glu Ala Met Pro Leu Arg Gln Arg Ser Ser
        35                  40                  45

Ala Gln Ser Tyr His Ala Gln Pro Val Leu Thr Ala Pro Pro Gln Pro
    50                  55                  60

Leu Leu Leu Lys Gly Ser Ser Lys Thr Lys Thr Thr Ile Lys Val
65                  70                  75                  80

Pro Thr Gly Thr Lys Ile Leu Pro Pro Arg Pro Asn Glu Arg Val Val
                85                  90                  95

Gly Val Lys Thr Asn Arg Ser Gly Glu Ile Ser Ser Ile Arg Tyr Thr
            100                 105                 110

Thr Glu Glu Glu Arg Pro Tyr Phe Glu Gly Ile Arg Ala Ala Lys Val
        115                 120                 125

Cys Phe Ile Pro Pro Lys Ala Ala Pro Lys His Ala Leu Asn Ala Phe
    130                 135                 140

Glu Thr Pro Pro Lys Arg Arg Lys Thr Ile Val Asp Ile Asp Glu Asp
145                 150                 155                 160
```

```
Val Cys Arg Leu Asp Arg Val Ile Ile Asp Leu Gln Ser Ser Ile Asn
            165                 170                 175

Ser Leu Thr Arg Gln Leu Ser Asn His Asn Thr Val Ile Leu Ser Leu
        180                 185                 190

Arg His Asp Leu Ala Ser Asp Asn Lys Lys Ile Lys Glu Leu Glu Arg
    195                 200                 205

Cys

<210> SEQ ID NO 55
<211> LENGTH: 630
<212> TYPE: DNA
<213> ORGANISM: Sorghum sudanense

<400> SEQUENCE: 55
atggccgaca gtaccacga tgattgggaa gtcgtcccct tcaacctcaa catggagcca      60
gtggaagacc ccgatgcccg tgctctcgtc ccggccaaca cagagcgtca gctagaagcc     120
atgccattac gtcaacgcag ctccgcccaa tcttaccatg ctcaaccagt tctcaccgca     180
ccaccacaac ccctactcct caaggaccaa tcatccaaga cgaagacccc tatcaaggtg     240
ccaatcggca aaggatcct tccacctaga cccaatgaga gggtcgttgg agtcaagacc      300
aaccggagcg gcgagatcag cagcgtacgc tacacttcag aggaggaaag gccttacttt     360
gaagggatta gagcagccaa agtccgtttc atccctccaa aggcagcccc gaagcatgct     420
ctcaacgctt ttgagacacc tcccaagcgt cgcaagacta atggatat catgaggaa        480 gttcgcaggc tagatagaat tatcatagac cttcagacct cgattaattc cctcactaga     540
cagctctcta accacaacac cattatactt ggccttaggc aggatcttgc cagtgccaac     600
aagaagatca aggaattaga gcgccgctaa                                      630

<210> SEQ ID NO 56
<211> LENGTH: 209
<212> TYPE: PRT
<213> ORGANISM: Sorghum sudanense

<400> SEQUENCE: 56

Met Ala Asp Lys Tyr His Asp Asp Trp Glu Val Val Pro Phe Asn Leu
1               5                   10                  15

Asn Met Glu Pro Val Glu Asp Pro Asp Ala Arg Ala Leu Val Pro Ala
            20                  25                  30

Asn Thr Glu Arg Gln Leu Glu Ala Met Pro Leu Arg Gln Arg Ser Ser
        35                  40                  45

Ala Gln Ser Tyr His Ala Gln Pro Val Leu Thr Ala Pro Pro Gln Pro
    50                  55                  60

Leu Leu Leu Lys Gly Pro Ser Lys Thr Lys Thr Pro Ile Lys Val
65                  70                  75                  80

Pro Ile Gly Thr Arg Ile Leu Pro Pro Arg Pro Asn Glu Arg Val Val
                85                  90                  95

Gly Val Lys Thr Asn Arg Ser Gly Glu Ile Ser Ser Val Arg Tyr Thr
            100                 105                 110

Ser Glu Glu Glu Arg Pro Tyr Phe Glu Gly Ile Arg Ala Ala Lys Val
        115                 120                 125

Arg Phe Ile Pro Pro Lys Ala Ala Pro Lys His Ala Leu Asn Ala Phe
    130                 135                 140

Glu Thr Pro Pro Lys Arg Arg Lys Thr Ile Met Asp Ile His Glu Glu
145                 150                 155                 160
```

```
Val Arg Arg Leu Asp Arg Ile Ile Ile Asp Leu Gln Thr Ser Ile Asn
                165                 170                 175

Ser Leu Thr Arg Gln Leu Ser Asn His Asn Thr Ile Ile Leu Gly Leu
            180                 185                 190

Arg Gln Asp Leu Ala Ser Ala Asn Lys Lys Ile Lys Glu Leu Glu Arg
        195                 200                 205

Arg

<210> SEQ ID NO 57
<211> LENGTH: 630
<212> TYPE: DNA
<213> ORGANISM: Sorghum sudanense

<400> SEQUENCE: 57
atggccaaag agttccacga cgattgggaa gtcgtcccct acgacctcaa caagaagccc      60
aaggaagatc ccgacaccca cgctctcatc ccggccaaca cagagcgaca gtttgaagcc     120
atgccattac gccagtgcag ctccgtccaa tcctaccatg ctcaaccagt tctcaccgca     180
ccgccacagc ccctacttct caagggacca tcagccaaga aggaggccac cgtcaaggtg     240
ccagccggca cgaggatcct gccacccaga cccaatgaga gggtcgttgg agtcaagacc     300
aaccggagcg gtgagatcag cagcattcgc tacactacgg aggaggaaaa gccttacttt     360
gaagggatta gagtagccaa agtctgtttc atccctccaa aggcagcccc gaagcacgct     420
ctcaatgctt ttgagacacc tcccaagcgt cgtaagacta tagtagatac tgatgaggac     480
gttcgcaggc tagacagagt tatcatagac ctccagtcct cgattaattc cctcactagg     540
cagctctcta accacaacac cgttatacta ggccttaggc aggatcttgc cagtgccaat     600
aagaagatca aggaattaga gcaccgctaa                                      630

<210> SEQ ID NO 58
<211> LENGTH: 209
<212> TYPE: PRT
<213> ORGANISM: Sorghum sudanense

<400> SEQUENCE: 58

Met Ala Lys Glu Phe His Asp Asp Trp Glu Val Val Pro Tyr Asp Leu
1               5                   10                  15

Asn Lys Lys Pro Lys Glu Asp Pro Asp Thr His Ala Leu Ile Pro Ala
            20                  25                  30

Asn Thr Glu Arg Gln Phe Glu Ala Met Pro Leu Arg Gln Cys Ser Ser
        35                  40                  45

Val Gln Ser Tyr His Ala Gln Pro Val Leu Thr Ala Pro Pro Gln Pro
    50                  55                  60

Leu Leu Leu Lys Gly Pro Ser Ala Lys Lys Glu Ala Thr Val Lys Val
65                  70                  75                  80

Pro Ala Gly Thr Arg Ile Leu Pro Pro Arg Pro Asn Glu Arg Val Val
                85                  90                  95

Gly Val Lys Thr Asn Arg Ser Gly Glu Ile Ser Ser Ile Arg Tyr Thr
            100                 105                 110

Thr Glu Glu Glu Lys Pro Tyr Phe Glu Gly Ile Arg Val Ala Lys Val
        115                 120                 125

Cys Phe Ile Pro Pro Lys Ala Ala Pro Lys His Ala Leu Asn Ala Phe
    130                 135                 140

Glu Thr Pro Pro Lys Arg Arg Lys Thr Ile Val Asp Thr Asp Glu Asp
145                 150                 155                 160
```

```
Val Arg Arg Leu Asp Arg Val Ile Ile Asp Leu Gln Ser Ser Ile Asn
            165                 170                 175

Ser Leu Thr Arg Gln Leu Ser Asn His Asn Thr Val Ile Leu Gly Leu
        180                 185                 190

Arg Gln Asp Leu Ala Ser Ala Asn Lys Lys Ile Lys Glu Leu Glu His
    195                 200                 205

Arg

<210> SEQ ID NO 59
<211> LENGTH: 630
<212> TYPE: DNA
<213> ORGANISM: Sorghum halepense

<400> SEQUENCE: 59
atggcggaca agtaccacga cgattgggaa gtcgtcccct tcaacctcaa catggagcca      60
atggaagacc ccgatgcccg tgctctcgtc ccggccaaca cagagcgtca gctagaagcc     120
atgccactac gccaacgcag ctccgcccaa tcttaccatg ctcaaccagt tctcaccgca     180
ccaccacaaa ccctactcct cacaggatca tcatccaaga cgaagaccac catcaaggtg     240
ccaaccggca aaggattct  tccacctaga cccaatgaga gggtcgttgg agtcaagacc     300
aaccgaagca gcgagatcag cagcgtacgc tacactacgg aggaagaaag accttacttt     360
gaagggatta gagcagccaa agtccgtttc atccctccaa aggcagcccc gaagcactct     420
ctcaatgctt ttgagatacc tcccaagcgt cgcaagacta atggacat  tgatgaggaa      480 gttcgcaggc tagatagaat tatcatagac ctccagtcct cgattaattc cctcactagg     540
cagctctcta accacaacac cgttatacta ggccttaggc aggatcttgc cagtgccaac     600
aagaagatta aggaattaga gcgccgctaa                                      630

<210> SEQ ID NO 60
<211> LENGTH: 209
<212> TYPE: PRT
<213> ORGANISM: Sorghum halepense

<400> SEQUENCE: 60

Met Ala Asp Lys Tyr His Asp Asp Trp Glu Val Val Pro Phe Asn Leu
1               5                   10                  15

Asn Met Glu Pro Met Glu Asp Pro Asp Ala Arg Ala Leu Val Pro Ala
            20                  25                  30

Asn Thr Glu Arg Gln Leu Glu Ala Met Pro Leu Arg Gln Arg Ser Ser
        35                  40                  45

Ala Gln Ser Tyr His Ala Gln Pro Val Leu Thr Ala Pro Pro Gln Thr
    50                  55                  60

Leu Leu Leu Thr Gly Ser Ser Lys Thr Lys Thr Thr Ile Lys Val
65                  70                  75                  80

Pro Thr Gly Thr Arg Ile Leu Pro Pro Arg Pro Asn Glu Arg Val Val
                85                  90                  95

Gly Val Lys Thr Asn Arg Ser Ser Glu Ile Ser Ser Val Arg Tyr Thr
            100                 105                 110

Thr Glu Glu Glu Arg Pro Tyr Phe Glu Gly Ile Arg Ala Ala Lys Val
        115                 120                 125

Arg Phe Ile Pro Pro Lys Ala Ala Pro Lys His Ser Leu Asn Ala Phe
    130                 135                 140

Glu Ile Pro Pro Lys Arg Arg Lys Thr Ile Met Asp Ile Asp Glu Glu
145                 150                 155                 160
```

Val Arg Arg Leu Asp Arg Ile Ile Ile Asp Leu Gln Ser Ser Ile Asn
                165                 170                 175

Ser Leu Thr Arg Gln Leu Ser Asn His Asn Thr Val Ile Leu Gly Leu
            180                 185                 190

Arg Gln Asp Leu Ala Ser Ala Asn Lys Lys Ile Lys Glu Leu Glu Arg
        195                 200                 205

Arg

<210> SEQ ID NO 61
<211> LENGTH: 630
<212> TYPE: DNA
<213> ORGANISM: Sorghum halepense

<400> SEQUENCE: 61
atggccgaga agtaccacga taattgggaa gtcgtcccct tcaacctcaa catggagcct      60
gtggaagatc ccgatgcccg tgctctcgtc ccggccaaca cagagcgaca gctagaagcc     120
atgccattac gccagcgcag ctccgcccaa tcctaccatg ctcaaccagt tctcaccgca     180
ccgccacaac ccctactcct caagggatca tcatgcaaga cgaagaccac catcaaggtg     240
ccaaccggca cgaggatcct tccacctaga cccaatgaga gggtcgttgg agtcaagacc     300
aaccggagcg gcgagatcag cagcgttcgc tacactacgg aggaggaaag gcctcacttt     360
gaagggatta gagcagccaa agtccgtttc atccctccaa aggcagcccc gaagcacgct     420
ctcaatgctt ttgagacacc tcccaaacgt cgcaagacta atggatatat tgatgaggac     480
gttcgcagac tagacagaat tatcatagac ctccagtcct cgattaattc cctcactagg     540
cagttctcta accacaacac ggtgatacta ggtcttaggc atgatcttgc tagtgccaat     600
aagaatatta gggagttaga gcgccgctaa                                      630

<210> SEQ ID NO 62
<211> LENGTH: 209
<212> TYPE: PRT
<213> ORGANISM: Sorghum halepense

<400> SEQUENCE: 62

Met Ala Glu Lys Tyr His Asp Asn Trp Glu Val Val Pro Phe Asn Leu
1               5                   10                  15

Asn Met Glu Pro Val Glu Asp Pro Asp Ala Arg Ala Leu Val Pro Ala
            20                  25                  30

Asn Thr Glu Arg Gln Leu Glu Ala Met Pro Leu Arg Gln Arg Ser Ser
        35                  40                  45

Ala Gln Ser Tyr His Ala Gln Pro Val Leu Thr Ala Pro Pro Gln Pro
    50                  55                  60

Leu Leu Leu Lys Gly Ser Ser Cys Lys Thr Lys Thr Thr Ile Lys Val
65                  70                  75                  80

Pro Thr Gly Thr Arg Ile Leu Pro Pro Arg Pro Asn Glu Arg Val Val
                85                  90                  95

Gly Val Lys Thr Asn Arg Ser Gly Glu Ile Ser Ser Val Arg Tyr Thr
            100                 105                 110

Thr Glu Glu Glu Arg Pro His Phe Glu Gly Ile Arg Ala Ala Lys Val
        115                 120                 125

Arg Phe Ile Pro Pro Lys Ala Ala Pro Lys His Ala Leu Asn Ala Phe
    130                 135                 140

Glu Thr Pro Pro Lys Arg Arg Lys Thr Ile Met Asp Ile Asp Glu Asp
145                 150                 155                 160

```
Val Arg Arg Leu Asp Arg Ile Ile Ile Asp Leu Gln Ser Ser Ile Asn
            165                 170                 175

Ser Leu Thr Arg Gln Phe Ser Asn His Asn Thr Val Ile Leu Gly Leu
        180                 185                 190

Arg His Asp Leu Ala Ser Ala Asn Lys Asn Ile Arg Glu Leu Glu Arg
    195                 200                 205

Arg

<210> SEQ ID NO 63
<211> LENGTH: 624
<212> TYPE: DNA
<213> ORGANISM: Saccharum officinarum

<400> SEQUENCE: 63
atggccgaca agacccaccg caactgggag atcgtccctt acgacctcaa ccacaagccc      60
aaggatgacc ccgacgccta cgtcccggcc aacacagagc gacagctagc agccccacca     120
tcaaaccagc gcagctcaat ctcatcctac tacgcccaac cagttcttac tgcaccaccg     180
cagccccttc ttctcaaggg accgtcgtcc aagcaagaag ccatcgtcaa ggtaccagcc     240
ggcacgaaaa tcctgccacc taaacccact gagcgggttg taggtgtcaa gaccaaccgg     300
agcggcgaga tcagcagcgt ccactacact acggagaagg agaggccccg cttcgaagga     360
gttaggacag taaagttcg cttcatccca ccaaaggaag ctcctaagca cgctctcaat     420
tcgtttgaga caccaccgaa cgccgcagg accatagcag atgtggatga ggacatcagg     480
acagcaaata gacatattat ggaacttcag tccacagtta gctcccttag taggcaggtc     540
tccaacctga acactactgt gctcgcgttt aaacgtgacc tttctgatgc ccttgctagg     600
atcagggatt tagagcaaca ctaa                                             624

<210> SEQ ID NO 64
<211> LENGTH: 207
<212> TYPE: PRT
<213> ORGANISM: Saccharum officinarum

<400> SEQUENCE: 64

Met Ala Asp Lys Thr His Arg Asn Trp Glu Ile Val Pro Tyr Asp Leu
1               5                   10                  15

Asn His Lys Pro Lys Asp Asp Pro Asp Ala Tyr Val Pro Ala Asn Thr
            20                  25                  30

Glu Arg Gln Leu Ala Ala Pro Pro Ser Asn Gln Arg Ser Ser Ile Ser
        35                  40                  45

Ser Tyr Tyr Ala Gln Pro Val Leu Thr Ala Pro Pro Gln Pro Leu Leu
    50                  55                  60

Leu Lys Gly Pro Ser Ser Lys Gln Glu Ala Ile Val Lys Val Pro Ala
65                  70                  75                  80

Gly Thr Lys Ile Leu Pro Pro Lys Pro Thr Glu Arg Val Val Gly Val
                85                  90                  95

Lys Thr Asn Arg Ser Gly Glu Ile Ser Ser Val His Tyr Thr Thr Glu
            100                 105                 110

Lys Glu Arg Pro Arg Phe Glu Gly Val Arg Thr Val Lys Val Arg Phe
        115                 120                 125

Ile Pro Pro Lys Glu Ala Pro Lys His Ala Leu Asn Ser Phe Glu Thr
    130                 135                 140

Pro Pro Lys Arg Arg Arg Thr Ile Ala Asp Val Asp Glu Asp Ile Arg
145                 150                 155                 160
```

```
Thr Ala Asn Arg His Ile Met Glu Leu Gln Ser Thr Val Ser Ser Leu
            165                 170                 175

Ser Arg Gln Val Ser Asn Leu Asn Thr Thr Val Leu Ala Phe Lys Arg
        180                 185                 190

Asp Leu Ser Asp Ala Leu Ala Arg Ile Arg Asp Leu Glu Gln His
        195                 200                 205

<210> SEQ ID NO 65
<211> LENGTH: 624
<212> TYPE: DNA
<213> ORGANISM: Saccharum officinarum

<400> SEQUENCE: 65
atggccgaca agacccaccg caactggaag atcgtccctt acgacctcaa ccgcaagccc      60
aaggatgacc ccgacgccta cgtcccggcc aacacagagc gacagctagc agccccacca     120
tcaaaccagc gcagctcaat ctcatcctac tacgcccaac cagttcttac tgcaccaccg     180
cagccccttc ttctcaaggg accgtcatcc aagcaagaag ccatcatcaa ggtaccagcc     240
ggcacgaaaa tcctgccacc taaacccaat gagcgggttg taggcgtcaa gaccaaccgg     300
agcggcgaga tcagcagcgt ccactacact acggagaagg agaggccccg cttcgaagga     360
gttaggacag caaaagttca cttcatccca ccaaaggaag ctcctaagca cgctctcaat     420
tcgtttgaga caccaccgaa gcgccgcagg accatagcag atgtggatga ggatatcagg     480
acagcaaata gacatattat ggaacttcag tccacagtta gcttccttag taggcaggtc     540
ttcaacctga acactactgt gctcgcgctt aaacgtgacc tttctgatgc ccttgctagg     600
atcagggatt tagagcaaca ctaa                                            624

<210> SEQ ID NO 66
<211> LENGTH: 207
<212> TYPE: PRT
<213> ORGANISM: Saccharum officinarum

<400> SEQUENCE: 66

Met Ala Asp Lys Thr His Arg Asn Trp Lys Ile Val Pro Tyr Asp Leu
1               5                   10                  15

Asn Arg Lys Pro Lys Asp Asp Pro Asp Ala Tyr Val Pro Ala Asn Thr
            20                  25                  30

Glu Arg Gln Leu Ala Ala Pro Pro Ser Asn Gln Arg Ser Ser Ile Ser
        35                  40                  45

Ser Tyr Tyr Ala Gln Pro Val Leu Thr Ala Pro Pro Gln Pro Leu Leu
    50                  55                  60

Leu Lys Gly Pro Ser Ser Lys Gln Glu Ala Ile Ile Lys Val Pro Ala
65                  70                  75                  80

Gly Thr Lys Ile Leu Pro Pro Lys Pro Asn Glu Arg Val Val Gly Val
                85                  90                  95

Lys Thr Asn Arg Ser Gly Glu Ile Ser Ser Val His Tyr Thr Thr Glu
            100                 105                 110

Lys Glu Arg Pro Arg Phe Glu Gly Val Arg Thr Ala Lys Val His Phe
        115                 120                 125

Ile Pro Pro Lys Glu Ala Pro Lys His Ala Leu Asn Ser Phe Glu Thr
    130                 135                 140

Pro Pro Lys Arg Arg Arg Thr Ile Ala Asp Val Asp Glu Asp Ile Arg
145                 150                 155                 160

Thr Ala Asn Arg His Ile Met Glu Leu Gln Ser Thr Val Ser Phe Leu
                165                 170                 175
```

```
Ser Arg Gln Val Phe Asn Leu Asn Thr Thr Val Leu Ala Leu Lys Arg
            180                 185                 190

Asp Leu Ser Asp Ala Leu Ala Arg Ile Arg Asp Leu Glu Gln His
        195                 200                 205

<210> SEQ ID NO 67
<211> LENGTH: 51
<212> TYPE: DNA
<213> ORGANISM: Artificial Sequence
<220> FEATURE:
<223> OTHER INFORMATION: SS-DTP21-1 attB forward primer

<400> SEQUENCE: 67
ggggacaagt ttgtacaaaa aagcaggcta tggccgagaa gtaccacgaa g            51

<210> SEQ ID NO 68
<211> LENGTH: 54
<212> TYPE: DNA
<213> ORGANISM: Artificial Sequence
<220> FEATURE:
<223> OTHER INFORMATION: SS-DTP21-1 attB reverse primer;DNA

<400> SEQUENCE: 68
ggggaccact ttgtacaaga aagctgggtt tagcggcgct ctaattccct aatc         54

<210> SEQ ID NO 69
<211> LENGTH: 25
<212> TYPE: DNA
<213> ORGANISM: Artificial sequence
<220> FEATURE:
<223> OTHER INFORMATION: attB1 site

<400> SEQUENCE: 69
acaagtttgt acaaaaaagc aggct                                        25

<210> SEQ ID NO 70
<211> LENGTH: 25
<212> TYPE: DNA
<213> ORGANISM: Artificial sequence
<220> FEATURE:
<223> OTHER INFORMATION: attB2 site

<400> SEQUENCE: 70
accactttgt acaagaaagc tgggt                                        25

<210> SEQ ID NO 71
<211> LENGTH: 16843
<212> TYPE: DNA
<213> ORGANISM: Artificial Sequence
<220> FEATURE:
<223> OTHER INFORMATION: pBC-Yellow destination vector

<400> SEQUENCE: 71
ccgggctggt tgccctcgcc gctgggctgg cggccgtcta tggccctgca acgcgccag    60 aaacgccgtc gaagccgtgt gcgagacacc gcggccgccg gcgttgtgga tacctcgcgg  120
aaaacttggc cctcactgac agatgagggg cggacgttga cacttgaggg gccgactcac  180
ccggcgcggc gttgacagat gaggggcagg ctcgatttcg gccggcgacg tggagctggc  240
cagcctcgca aatcggcgaa aacgcctgat tttacgcgag tttcccacag atgatgtgga  300
caagcctggg gataagtgcc ctgcggtatt gacacttgag gggcgcgact actgacagat  360
gaggggcgcg atccttgaca cttgaggggc agagtgctga cagatgaggg gcgcacctat  420
```

```
tgacatttga ggggctgtcc acaggcagaa aatccagcat ttgcaagggt ttccgcccgt     480
ttttcggcca ccgctaacct gtcttttaac ctgcttttaa accaatattt ataaaccttg     540
tttttaacca gggctgcgcc ctgtgcgcgt gaccgcgcac gccgaagggg ggtgcccccc     600
cttctcgaac cctcccggcc cgctaacgcg ggcctcccat cccccagggg gctgcgcccc     660
tcggccgcga acggcctcac cccaaaaatg gcagcgctgg cagtccttgc cattgccggg     720
atcggggcag taacgggatg ggcgatcagc ccgagcgcga cgcccggaag cattgacgtg     780
ccgcaggtgc tggcatcgac attcagcgac caggtgccgg gcagtgaggg cggcggcctg     840
ggtggcggcc tgcccttcac ttcggccgtc ggggcattca cggacttcat ggcggggccg     900
gcaattttta ccttgggcat tcttggcata gtggtcgcgg gtgccgtgct cgtgttcggg     960
ggtgcgataa acccagcgaa ccatttgagg tgataggtaa gattataccg aggtatgaaa    1020
acgagaattg gacctttaca gaattactct atgaagcgcc atatttaaaa agctaccaag    1080
acgaagagga tgaagaggat gaggaggcag attgccttga atatattgac aatactgata    1140
agataatata tcttttatat agaagatatc gccgtatgta aggatttcag ggggcaaggc    1200
ataggcagcg cgcttatcaa tatatctata gaatgggcaa agcataaaaa cttgcatgga    1260
ctaatgcttg aaacccagga caataacctt atagcttgta aattctatca taattgggta    1320
atgactccaa cttattgata gtgttttatg ttcagataat gcccgatgac tttgtcatgc    1380
agctccaccg attttgagaa cgacagcgac ttccgtccca gccgtgccag gtgctgcctc    1440
agattcaggt tatgccgctc aattcgctgc gtatatcgct tgctgattac gtgcagcttt    1500
cccttcaggc gggattcata cagcggccag ccatccgtca tccatatcac cacgtcaaag    1560
ggtgacagca ggctcataag acgccccagc gtcgccatag tgcgttcacc gaatacgtgc    1620
gcaacaaccg tcttccggag actgtcatac gcgtaaaaca gccagcgctg gcgcgattta    1680
gccccgacat agccccactg ttcgtccatt ccgcgcagac gatgacgtc actgcccggc    1740
tgtatgcgcg aggttaccga ctgcggcctg agttttttaa gtgacgtaaa atcgtgttga    1800
ggccaacgcc cataatgcgg gctgttgccc ggcatccaac gccattcatg gccatatcaa    1860
tgattttctg gtgcgtaccg ggttgagaag cggtgtaagt gaactgcagt tgccatgttt    1920
tacggcagtg agagcagaga tagcgctgat gtccggcggt gcttttgccg ttacgcacca    1980
ccccgtcagt agctgaacag gagggacagc tgatagacac agaagccact ggagcacctc    2040
aaaaacacca tcatacacta aatcagtaag ttggcagcat cacccataat tgtggtttca    2100
aaatcggctc cgtcgatact atgttatacg ccaactttga aaacaacttt gaaaaagctg    2160
ttttctggta tttaaggttt tagaatgcaa ggaacagtga attggagttc gtcttgttat    2220
aattagcttc ttggggtatc tttaaatact gtagaaaaga ggaaggaaat aataaatggc    2280
taaaatgaga atatcaccgg aattgaaaaa actgatcgaa aaataccgct gcgtaaaaga    2340
tacgaaagga atgtctcctg ctaaggtata taagctggtg ggagaaaatg aaaacctata    2400
tttaaaaatg acgacagcc ggtataaagg gaccacctat gatgtggaac gggaaaagga    2460
catgatgcta tggctggaag gaaagctgcc tgttccaaag gtcctgcact ttgaacggca    2520
tgatggctgg agcaatctgc tcatgagtga ggccgatggc gtcctttgct cggaagagta    2580
tgaagatgaa caaagccctg aaaagattat cgagctgtat gcggagtgca tcaggctctt    2640
tcactccatc gacatatcgg attgtcccta tacgaatagc ttagacagcc gcttagccga    2700
attggattac ttactgaata cgatctggcc gatgtggat tgcgaaaact gggaagaaga    2760
cactccattt aaagatccgc gcgagctgta tgattttta aagacggaaa agcccgaaga    2820
```

```
ggaacttgtc ttttcccacg gcgacctggg agacagcaac atctttgtga aagatggcaa    2880
agtaagtggc tttattgatc ttgggagaag cggcagggcg acaagtggt atgacattgc     2940
cttctgcgtc cggtcgatca gggaggatat cggggaagaa cagtatgtcg agctattttt    3000
tgacttactg gggatcaagc ctgattggga gaaaataaaa tattatattt tactggatga    3060
attgttttag tacctagatg tggcgcaacg atgccggcga caagcaggag cgcaccgact    3120
tcttccgcat caagtgtttt ggctctcagg ccgaggccca cggcaagtat ttgggcaagg    3180
ggtcgctggt attcgtgcag ggcaagattc ggaataccaa gtacgagaag gacggccaga    3240
cggtctacgg gaccgacttc attgccgata aggtggatta tctggacacc aaggcaccag    3300
gcgggtcaaa tcaggaataa gggcacattg ccccggcgtg agtcggggca atcccgcaag    3360
gagggtgaat gaatcggacg tttgaccgga aggcatacag gcaagaactg atcgacgcgg    3420
ggttttccgc cgaggatgcc gaaaccatcg caagccgcac cgtcatgcgt gcgccccgcg    3480
aaaccttcca gtccgtcggc tcgatggtcc agcaagctac ggccaagatc gagcgcgaca    3540
gcgtgcaact ggctccccct gccctgcccg cgccatcggc cgccgtggag cgttcgcgtc    3600
gtctcgaaca ggaggcggca ggtttggcga agtcgatgac catcgacacg cgaggaacta    3660
tgacgaccaa gaagcgaaaa accgccggcg aggacctggc aaaacaggtc agcgaggcca    3720
agcaggccgc gttgctgaaa cacacgaagc agcagatcaa ggaaatgcag ctttccttgt    3780
tcgatattgc gccgtggccg gacacgatgc gagcgatgcc aaacgacacg gcccgctctg    3840
ccctgttcac cacgcgcaac aagaaaatcc cgcgcgaggc gctgcaaaac aaggtcattt    3900
tccacgtcaa caaggacgtg aagatcacct acaccggcgt cgagctgcgg gccgacgatg    3960
acgaactggt gtggcagcag gtgttggagt acgcgaagcg cacccctatc ggcgagccga    4020
tcaccttcac gttctacgag cttgccagg acctgggctg gtcgatcaat ggccggtatt     4080
acacgaaggc cgaggaatgc ctgtcgcgcc tacaggcgac ggcgatgggc ttcacgtccg    4140
accgcgttgg gcacctggaa tcggtgtcgc tgctgcaccg cttccgcgtc ctggaccgtg    4200
gcaagaaaac gtcccgttgc caggtcctga tcgacgagga atcgtcgtg ctgtttgctg      4260
gcgaccacta cacgaaattc atatgggaga agtaccgcaa gctgtcgccg acggcccgac    4320
ggatgttcga ctatttcagc tcgcaccggg agccgtaccc gctcaagctg gaaaccttcc    4380
gcctcatgtg cggatcggat tccacccgcg tgaagaagtg gcgcgagcag gtcggcgaag    4440
cctgcgaaga gttgcgaggc agcggcctgg tggaacacgc ctgggtcaat gatgacctgg    4500
tgcattgcaa acgctagggc cttgtggggt cagttccggc tgggggttca gcagccagcg    4560
ctttactggc atttcaggaa caagcgggca ctgctcgacg cacttgcttc gctcagtatc    4620
gctcgggacg cacggcgcgc tctacgaact gccgataaac agaggattaa aattgacaat    4680
tgtgattaag gctcagattc gacggcttgg agcggccgac gtgcaggatt ccgcgagat     4740
ccgattgtcg gccctgaaga agctccagaa gatgttcggg tccgtttacg agcacgagga    4800
gaaaaagccc atggaggcgt tcgctgaacg gttgcgagat gccgtggcat tcggcgccta    4860
catcgacggc gagatcattg gctgtcggt cttcaaacag gaggacggcc ccaaggacgc      4920
tcacaaggcg catctgtccg gcgttttcgt ggagcccgaa cagcgaggcc gaggggtcgc    4980
cggtatgctg ctgcgggcgt tgccggcggg tttattgctc gtgatgatcg tccgacagat    5040
tccaacggga atctggtgga tgcgcatctt catcctcggc gcacttaata tttcgctatt    5100
ctggagcttg ttgtttattt cggtctaccg cctgccgggc ggggtcgcgg cgacggtagg    5160
```

```
cgctgtgcag ccgctgatgg tcgtgttcat ctctgccgct ctgctaggta gcccgatacg    5220
attgatggcg gtcctggggg ctatttgcgg aactgcgggc gtggcgctgt tggtgttgac    5280
accaaacgca gcgctagatc ctgtcggcgt cgcagcgggc ctggcggggg cggtttccat    5340
ggcgttcgga accgtgctga cccgcaagtg gcaacctccc gtgcctctgc tcacctttac    5400
cgcctggcaa ctggcggccg gaggacttct gctcgttcca gtagctttag tgtttgatcc    5460
gccaatcccg atgcctacag gaaccaatgt tctcggcctg gcgtggctcg gcctgatcgg    5520
agcgggttta acctacttcc tttggttccg ggggatctcg cgactcgaac ctacagttgt    5580
ttccttactg ggcttctca gccccagatc tggggtcgat cagccgggga tgcatcaggc    5640
cgacagtcgg aacttcgggt ccccgacctg taccattcgg tgagcaatgg ataggggagt    5700
tgatatcgtc aacgttcact tctaaagaaa tagcgccact cagcttcctc agcggcttta    5760
tccagcgatt tcctattatg tcggcatagt tctcaagatc gacagcctgt cacggttaag    5820
cgagaaatga ataagaaggc tgataattcg gatctctgcg agggagatga tatttgatca    5880
caggcagcaa cgctctgtca tcgttacaat caacatgcta ccctccgcga gatcatccgt    5940
gtttcaaacc cggcagctta gttgccgttc ttccgaatag catcggtaac atgagcaaag    6000
tctgccgcct tacaacggct ctcccgctga cgccgtcccg gactgatggg ctgcctgtat    6060
cgagtggtga ttttgtgccg agctgccggt cggggagctg ttggctggct ggtggcagga    6120
tatattgtgg tgtaaacaaa ttgacgctta gacaacttaa taacacattg cggacgtttt    6180
taatgtactg gggtggtttt tcttttcacc agtgagacgg gcaacagctg attgcccttc    6240
accgcctggc cctgagagag ttgcagcaag cggtccacgc tggtttgccc cagcaggcga    6300
aaatcctgtt tgatggtggt tccgaaatcg gcaaaatccc ttataaatca aaagaatagc    6360
ccgagatagg gttgagtgtt gttccagttt ggaacaagag tccactatta agaacgtgg    6420
actccaacgt caagggcga aaaccgtct atcagggcga tgcccacta cctgtatggc    6480
cgcattcgca aaacacacct agactagatt tgttttgcta acccaattga tattaattat    6540
atatgattaa tatttatatg tatatggatt tggttaatga aatgcatctg gttcatcaaa    6600
gaattataaa gacacgtgac attcatttag gataagaaat atggatgatc tctttctctt    6660
ttattcagat aactagtaat tacacataac acacaacttt gatgcccaca ttatagtgat    6720
tagcatgtca ctatgtgtgc atccttttat ttcatacatt aattaagttg gccaatccag    6780
aagatggaca agtctaggtt aaccatgtgg tacctacgcg ttcgaatatc catgggccgc    6840
ttcaggccag ggcgctgggg aaggcgatgg cgtgctcggt cagctgccac ttctggttct    6900
tggcgtcgct ccggtcctcc cgcagcagct tgtgctggat gaagtgccac tcgggcatct    6960
tgctgggcac gctcttggcc ttgtacacgg tgtcgaactg gcaccggtac cggccgccgt    7020
ccttcagcag caggtacatg ctcacgtcgc ccttcaggat gccctgctta ggcacgggca    7080
tgatcttctc gcagctggcc tcccagtgg tggtcatctt cttcatcacg gggccgtcgg    7140
cggggaagtt cacgccgttg aagatgctct tgtggtagat gcagttctcc ttcacgctca    7200
cggtgatgtc cacgttacag atgcacacgg cgccgtcctc gaacaggaag ctccggcccc    7260
aggtgtagcc ggcggggcag ctgttcttga agtagtccac gatgtcctgg gggtactcgg    7320
tgaagatccg gtcgccgtac ttgaagccgg cgctcaggat gtcctcgctg aagggcaggg    7380
ggccgccctc gatcacgcac aggttgatgg tctgcttgcc cttgaagggg tagccgatgc    7440
cctcgccggt gatcacgaac ttgtggccgt tcacgcagcc ctccatgtgg tacttcatgg    7500
tcatctcctc cttcaggccg tgcttgctgt gggccatggt ggcgaccggt gaattcgagc    7560
```

```
tcggtacccg gggatcctga gtaaaacaga ggagggtctc actaagttta tagagagact   7620
gagagagata aagggacacg tatgaagcgt ctgttttcgt ggtgtgacgt caaagtcatt   7680
ttgctctcta cgcgtgtctg tgtcggcttg atcttttttt ttgcttttg gaactcatgt    7740 cggtagtata tcttttattt attttttctt ttttccctt ttctttcaaa ctgatgtcgg    7800
tatgatattt attccatcct aaaatgtaac ttactattat tagtagtcgg tccatgtcta   7860
ttggcccatc atgtggtcat tttacgttta cgtcgtgtgg ctgttattta taacaaacgg   7920
cacatccttc tcattcgaat tgtatttctc cttaatcgtt ctaataggta tgatcttta    7980 ttttatacgt aaaattaaaa ttgaatgatg tcaagaacga aaattaattt gtatttacaa   8040
aggagctaaa tattgtttat tcctctactg gtagaagata aagaagtag atgaaataat    8100 gatcttacta gagaatattc ctcatttaca ctagtcaaat ggaaatcttg taaacttta    8160 caataattta tcctgaaaat atgaaaaaat agaagaaaat gtttacctcc tctctcctct   8220
taattcacct acgatcggtg cgggcctctt cgctattacg ccagctggcg aaaggggat    8280 gtgctgcaag gcgattaagt tgggtaacgc cagggttttc ccagtcacga cgttgtaaaa   8340
cgacggccag tgaattcgag ctcggtaccc ggggatcctc tagagtcgac ctgcaggcat   8400
gcaagcttgt tgaaacatcc ctgaagtgtc tcattttatt ttatttattc tttgctgata   8460
aaaaaataaa ataaagaag ctaagcacac ggtcaaccat tgctctactg ctaaagggt     8520 tatgtgtagt gttttactgc ataaattatg cagcaaacaa gacaactcaa attaaaaaat   8580
ttcctttgct tgtttttttg ttgtctctga cttgactttc ttgtggaagt tggttgtata   8640
aggattggga cacaccattg tccttcttaa tttaatttta tttctttgct gataaaaaaa   8700
aaaaatttca tatagtgtta ataataatt tgttaaataa ccaaaaagtc aaatatgttt    8760
actctcgttt aaataattga gagtcgtcca gcaaggctaa acgattgtat agatttatga   8820
caatatttac tttttatag ataaatgtta tattataata aatttatata catatattat    8880
atgttattta ttatttatta ttatttaaa tccttcaata ttttatcaaa ccaactcata    8940
attttttttt tatctgtaag aagcaataaa attaaataga cccactttaa ggatgatcca   9000 accttatac agagtaagag agttcaaata gtacccttc atatacatat caactaaaat     9060
attagaaata tcatggatca aaccttataa agacattaaa taagtggata agtataatat   9120
ataaatgggt agtatataat atataaatgg atacaaactt ctctctttat aattgttatg   9180
tctccttaac atcctaatat aatacataag tgggtaatat ataatatata aatggagaca   9240
aacttcttcc attataattg ttatgtcttc ttaacactta tgtctcgttc acaatgctaa   9300
agttagaatt gtttagaaag tcttatagta cacatttgtt tttgtactat ttgaagcatt   9360
ccataagccg tcacgattca gatgatttat aataataaga ggaaatttat catagaacaa   9420
taaggtgcat agatagagtg ttaatatatc ataacatcct ttgtttattc atagaagaag   9480
tgagatggag ctcagttatt atactgttac atggtcggat acaatattcc atgctctcca   9540
tgagctctta cacctacatg cattttagtt catacttcat gcacgtggcc atcacagcta   9600
gctgcagcta catatttaca ttttacaaca ccaggagaac tgccctgtta gtgcataaca   9660
atcagaagat ggccgtggct actcgagtta tcgaccact tgtacaaga aagctgaacg     9720 agaaacgtaa aatgatataa atatcaatat attaaattag attttgcata aaaaacagac   9780 tacataaatac tgtaaaacac aacatatcca gtcactatgg tcgacctgca gactggctgt   9840
gtataaggga gcctgacatt tatattcccc agaacatcag gttaatggcg tttttgatgt   9900
```

```
cattttcgcg gtggctgaga tcagccactt cttccccgat aacggagacc ggcacactgg   9960
ccatatcggt ggtcatcatg cgccagcttt catcccccgat atgcaccacc gggtaaagtt  10020
cacgggagac tttatctgac agcagacgtg cactggccag ggggatcacc atccgtcgcc  10080
cgggcgtgtc aataatatca ctctgtacat ccacaaacag acgataacgg ctctctcttt  10140
tataggtgta aaccttaaac tgcatttcac cagtccctgt tctcgtcagc aaaagagccg  10200
ttcatttcaa taaaccgggc gacctcagcc atcccttcct gattttccgc tttccagcgt  10260
tcggcacgca gacgacgggc ttcattctgc atggttgtgc ttaccagacc ggagatattg  10320
acatcatata tgccttgagc aactgatagc tgtcgctgtc aactgtcact gtaatacgct  10380
gcttcatagc acacctcttt ttgacatact tcgggtatac atatcagtat atattcttat  10440
accgcaaaaa tcagcgcgca aatacgcata ctgttatctg ctttttagta agccggatcc  10500
tctagattac gccccgccct gccactcatc gcagtactgt tgtaattcat taagcattct  10560
gccgacatgg aagccatcac agacggcatg atgaacctga atcgccagcg gcatcagcac  10620
cttgtcgcct tgcgtataat atttgcccat ggtgaaaacg ggggcgaaga agttgtccat  10680
attggccacg tttaaatcaa aactggtgaa actcacccag ggattggctg agacgaaaaa  10740
catattctca ataaaccctt tagggaaata ggccaggttt tcaccgtaac acgccacatc  10800
ttgcgaatat atgtgtagaa actgccggaa atcgtcgtgg tattcactcc agagcgatga  10860
aaacgtttca gtttgctcat ggaaaacggt gtaacaaggg tgaacactat cccatatcac  10920
cagctcaccg tctttcattg ccatacggaa ttccggatga gcattcatca ggcgggcaag  10980
aatgtgaata aaggccggat aaaacttgtg cttatttttc tttacggtct ttaaaaaggc  11040
cgtaatatcc agctgaacgg tctggttata ggtacattga gcaactgact gaaatgcctc  11100
aaaatgttct ttacgatgcc attgggatat atcaacggtg gtatatccag tgatttttttt 11160
ctccatttta gcttccttag ctcctgaaaa tctcgccgga tcctaactca aaatccacac  11220
attatacgag ccggaagcat aaagtgtaaa gcctggggtg cctaatgcgg ccgccatagt  11280
gactggatat gttgtgtttt acagtattat gtagtctgtt ttttatgcaa aatctaattt  11340
aatatattga tatttatatc attttacgtt tctcgttcag cttttttgta caaacttgtt  11400
tgataaccgg tactagtgtg cacgtcgagc gtgtcctctc caaatgaaat gaacttcctt  11460
atatagagga agggtcttgc gaaggatagt gggattgtgc gtcatccctt acgtcagtgg  11520
agatgtcaca tcaatccact tgctttgaag acgtggttgg aacgtcttct ttttccacga  11580
tgctcctcgt gggtggggt ccatctttgg gaccactgtc ggcagaggca tcttgaatga  11640
tagcctttcc tttatcgcaa tgatggcatt tgtaggagcc accttccttt tctactgtcc  11700
tttcgatgaa gtgacagata gctgggcaat ggaatccgag gaggtttccc gaaattatcc  11760
tttgttgaaa agtctcaata gccctttggt cttctgagac tgtatctttg acatttttgg  11820
agtagaccag agtgtcgtgc tccaccatgt tgacgaagat tttcttcttg tcattgagtc  11880
gtaaaagact ctgtatgaac tgttcgccag tcttcacggc gagttctgtt agatcctcga  11940
tttgaatctt agactccatg catggcctta gattcagtag aactacctt tttagagact   12000
ccaatctcta ttacttgcct tggtttatga agcaagcctt gaatcgtcca tactggaata  12060
gtacttctga tcttgagaaa tatgtctttc tctgtgttct tgatgcaatt agtcctgaat  12120
cttttgactg catctttaac cttcttggga aggtatttga tctcctggag attgttactc  12180
gggtagatcg tcttgatgag acctgctgcg taggcctctc taaccatctg tgggtcagca  12240
ttctttctga aattgaagag gctaaccttc tcattatcag tggtgaacat agtgtcgtca  12300
```

```
ccttcacctt cgaacttcct tcctagatcg taaagataga ggaaatcgtc cattgtaatc    12360 tccgggcaa aggagatctc ttttggggct ggatcactgc tgggccttttt ggttcctagc    12420 gtgagccagt gggcttttttg ctttggtggg cttgttaggg ccttagcaaa gctcttgggc    12480
ttgagttgag cttctccttt ggggatgaag ttcaacctgt ctgtttgctg acttgttgtg    12540
tacgcgtcag ctgctgctct tgcctctgta atagtggcaa atttcttgtg tgcaactccg    12600
ggaacgccgt ttgttgccgc ctttgtacaa ccccagtcat cgtatatacc ggcatgtgga    12660
ccgttataca caacgtagta gttgatatga gggtgttgaa tacccgattc tgctctgaga    12720
ggagcaactg tgctgttaag ctcagatttt tgtgggattg gaattggatc ctctagagca    12780
aagcttggcg taatcatggt catagctgtt tcctgtgtga aattgttatc cgctcacaat    12840
tccacacaac atacgagccg gaagcataaa gtgtaaagcc tggggtgcct aatgagtgag    12900
ctaactcaca ttaattgcgt tgcgctcact gcccgctttc cagtcgggaa acctgtcgtg    12960
ccagctgcat taatgaatcg gccaacgcgc ggggagaggc ggtttgcgta ttgggccaaa    13020
gacaaaaggg cgacattcaa ccgattgagg gagggaaggt aaatattgac ggaaattatt    13080
cattaaaggt gaattatcac cgtcaccgac ttgagccatt tgggaattag agccagcaaa    13140
atcaccagta gcaccattac cattagcaag gccggaaacg tcaccaatga aaccatcatc    13200
tagtaacata gatgacaccg cgcgcgataa tttatcctag tttgcgcgct atattttgtt    13260
ttctatcgcg tattaaatgt ataattgcgg gactctaatc ataaaaaccc atctcataaa    13320
taacgtcatg cattacatgt taattattac atgcttaacg taattcaaca gaaattatat    13380
gataatcatc gcaagaccgg caacaggatt caatcttaag aaactttatt gccaaatgtt    13440
tgaacgatct gcttcgacgc actccttctt taggtacgga ctagatctcg gtgacgggca    13500
ggaccggacg gggcggtacc ggcaggctga agtccagctg ccagaaaccc acgtcatgcc    13560
agttcccgtg cttgaagccg gccgcccgca gcatgccgcg gggggcatat ccgagcgcct    13620
cgtgcatgcg cacgctcggg tcgttgggca gcccgatgac agcgaccacg ctcttgaagc    13680
cctgtgcctc cagggacttc agcaggtggg tgtagagcgt ggagcccagt cccgtccgct    13740
ggtggcgggg ggagacgtac acggtcgact cggccgtcca gtcgtaggcg ttgcgtgcct    13800
tccaggggcc cgcgtaggcg atgccggcga cctcgccgtc cacctcggcg acgagccagg    13860
gatagcgctc ccgcagacgg acgaggtcgt ccgtccactc ctgcggttcc tgcggctcgg    13920
tacggaagtt gaccgtgctt gtctcgatgt agtggttgac gatggtgcag accgccggca    13980
tgtccgcctc ggtggcacgg cggatgtcgg ccgggcgtcg ttctgggctc atggatctgg    14040
attgagagtg aatatgagac tctaattgga taccgagggg aatttatgga acgtcagtgg    14100 agcattttttg acaagaaata tttgctagct gatagtgacc ttaggcgact tttgaacgcg    14160
caataatggt ttctgacgta tgtgcttagc tcattaaact ccagaaaccc gcggctgagt    14220
ggctccttca acgttgcggt tctgtcagtt ccaaacgtaa aacggcttgt cccgcgtcat    14280 cggcggggggt cataacgtga ctcccttaat tctccgctca tgatcagatt gtcgtttccc    14340
gccttcagtt taaactatca gtgtttgaca ggatatattg gcgggtaaac ctaagagaaa    14400
agagcgttta ttagaataat cggatatttta aagggcgtg aaaaggttta ccgttcgtc    14460 catttgtatg tgcatgccaa ccacaggggtt ccccagatct ggcgccggcc agcgagacga    14520
gcaagattgg ccgccgcccg aaacgatccg acagcgcgcc cagcacaggt gcgcaggcaa    14580
attgcaccaa cgcatacagc gccagcagaa tgccatagtg ggcggtgacg tcgttcgagt    14640
```

```
gaaccagatc gcgcaggagg cccggcagca ccggcataat caggccgatg ccgacagcgt    14700
cgagcgcgac agtgctcaga attacgatca ggggtatgtt gggtttcacg tctggcctcc    14760
ggaccagcct ccgctggtcc gattgaacgc gcggattctt tatcactgat aagttggtgg    14820
acatattatg tttatcagtg ataaagtgtc aagcatgaca aagttgcagc cgaatacagt    14880
gatccgtgcc gccctggacc tgttgaacga ggtcggcgta gacggtctga cgacacgcaa    14940
actggcggaa cggttggggg ttcagcagcc ggcgctttac tggcacttca ggaacaagcg    15000
ggcgctgctc gacgcactgg ccgaagccat gctggcggag aatcatacgc attcggtgcc    15060
gagagccgac gacgactggc gctcatttct gatcgggaat gcccgcagct caggcaggc    15120 gctgctcgcc taccgcgatg gcgcgcgcat ccatgccggc acgcgaccgg gcgcaccgca    15180
gatggaaacg gccgacgcgc agcttcgctt cctctgcgag gcgggttttt cggccgggga    15240
cgccgtcaat gcgctgatga caatcagcta cttcactgtt ggggccgtgc ttgaggagca    15300
ggccggcgac agcgatgccg gcgagcgcgg cggcaccgtt gaacaggctc cgctctcgcc    15360
gctgttgcgg gccgcgatag acgccttcga cgaagccggt ccggacgcag cgttcgagca    15420
gggactcgcg gtgattgtcg atggattggc gaaaaggagg ctcgttgtca ggaacgttga    15480
aggaccgaga aagggtgacg attgatcagg accgctgccg gagcgcaacc cactcactac    15540
agcagagcca tgtagacaac atcccctccc cctttccacc gcgtcagacg cccgtagcag    15600
cccgctacgg gcttttttcat gccctgccct agcgtccaag cctcacgcc gcgctcggcc    15660 tctctggcgg ccttctggcg ctcttccgct tcctcgctca ctgactcgct gcgctcggtc    15720
gttcggctgc ggcgagcggt atcagctcac tcaaaggcgg taatacggtt atccacagaa    15780
tcaggggata acgcaggaaa gaacatgtga gcaaaaggcc agcaaaaggc caggaaccgt    15840
aaaaaggccg cgttgctggc gttttttccat aggctccgcc cccctgacga gcatcacaaa    15900
aatcgacgct caagtcagag gtggcgaaac ccgacaggac tataaagata ccaggcgttt    15960 cccccttggaa gctccctcgt gcgctctcct gttccgaccc tgccgcttac cggatacctg    16020
tccgcctttc tcccttcggg aagcgtggcg ctttttccgct gcataaccct gcttcggggt    16080
cattatagcg atttttttcgg tatatccatc cttttttcgca cgatatacag gattttgcca    16140
aagggttcgt gtagactttc cttggtgtat ccaacggcgt cagccgggca ggataggtga    16200
agtaggccca cccgcgagcg ggtgttcctt cttcactgtc ccttattcgc acctggcggt    16260
gctcaacggg aatcctgctc tgcgaggctg gccggctacc gccggcgtaa cagatgaggg    16320
caagcggatg gctgatgaaa ccaagccaac caggaagggc agcccaccta tcaaggtgta    16380
ctgccttcca gacgaacgaa gagcgattga ggaaaaggcg gcggcggccg gcatgagcct    16440
gtcggcctac ctgctggccg tcggccaggg ctacaaaatc acgggcgtcg tggactatga    16500
gcacgtccgc gagctggccc gcatcaatgg cgacctgggc cgcctgggcg gctgctgaa    16560 actctggctc accgacgacc cgcgcacggc gcggttcggt gatgccacga tcctcgccct    16620
gctggcgaag atcgaagaga agcaggacga gcttggcaag gtcatgatgg gcgtggtccg    16680
cccgagggca gagccatgac tttttttagcc gctaaaacgg ccggggggtg cgcgtgattg    16740
ccaagcacgt cccatgcgc tccatcaaga agagcgactt cgcggagctg gtgaagtaca    16800
tcaccgacga gcaaggcaag accgagcgcc tttgcgacgc tca                      16843
```

<210> SEQ ID NO 72
<211> LENGTH: 51
<212> TYPE: DNA
<213> ORGANISM: Artificial sequence

```
<220> FEATURE:
<223> OTHER INFORMATION: SS-DTP21-2 attB forward primer

<400> SEQUENCE: 72
ggggacaagt ttgtacaaaa aagcaggcta tggccgagaa gtaccaccat g      51

<210> SEQ ID NO 73
<211> LENGTH: 51
<212> TYPE: DNA
<213> ORGANISM: Artificial sequence
<220> FEATURE:
<223> OTHER INFORMATION: SS-DTP21-2 attB reverse primer

<400> SEQUENCE: 73
ggggaccact ttgtacaaga aagctgggtt tagcggtgct ctaattcctt g      51

<210> SEQ ID NO 74
<211> LENGTH: 23
<212> TYPE: DNA
<213> ORGANISM: Artificial Sequence
<220> FEATURE:
<223> OTHER INFORMATION: GeneRacer 5-prime primer

<400> SEQUENCE: 74
cgactggagc acgaggacac tga                                      23

<210> SEQ ID NO 75
<211> LENGTH: 26
<212> TYPE: DNA
<213> ORGANISM: Artificial Sequence
<220> FEATURE:
<223> OTHER INFORMATION: GeneRacer 5-prime nested primer

<400> SEQUENCE: 75
ggacactgac atggactgaa ggagta                                   26

<210> SEQ ID NO 76
<211> LENGTH: 25
<212> TYPE: DNA
<213> ORGANISM: Artificial Sequence
<220> FEATURE:
<223> OTHER INFORMATION: GeneRacer 3-prime primer

<400> SEQUENCE: 76
gctgtcaacg atacgctacg taacg                                    25

<210> SEQ ID NO 77
<211> LENGTH: 23
<212> TYPE: DNA
<213> ORGANISM: Artificial Sequence
<220> FEATURE:
<223> OTHER INFORMATION: GeneRacer 3-prime nested primer

<400> SEQUENCE: 77
cgctacgtaa cggcatgaca gtg                                      23

<210> SEQ ID NO 78
<211> LENGTH: 630
<212> TYPE: DNA
<213> ORGANISM: Sorghum sudanense

<400> SEQUENCE: 78
atggccgaga agtaccacga tgattgggaa gtcgtcccct tcaacctcaa catggagcct   60
gtggaagacc ccgatgcccg tgctttcgtc ccggccaaca cagagcgaca gctagaagcc  120
```

```
atgccattac gccagcatag ctccgcccaa tcctaccatg ctcaaccagt tctcaccgca    180
ccgccacaac ccctactcct cacgggatca tcatccaaga cgaagaccac catcaaggtg    240
ccaaccggca cgaggatcct tccacctaga cccaatgaga gggtcattgg agtcaagacc    300
aaccggagcg gcgagatcag cagcgttcgc tacactatag aggaggaaag accttacttt    360
gaagggatta gagcagccaa agtccgtttc atccctccaa aggcagcctc gaagcacgct    420
ctcaatgctt ttgagacacc tcccaagcgt cgcaagacta atatggatat tgatgaggac    480
gctcgcagac tagacagaat tatcatagac ctccagtcct cgattaactc cctcactagg    540
cagctctcta accacaacac catcatacta ggcctcaggc aggatcttgc taatgccaac    600
aagaagatta aggaattaga gcgccgctaa                                    630
```

<210> SEQ ID NO 79
<211> LENGTH: 209
<212> TYPE: PRT
<213> ORGANISM: Sorghum sudanense

<400> SEQUENCE: 79

```
Met Ala Glu Lys Tyr His Asp Asp Trp Glu Val Val Pro Phe Asn Leu
1               5                   10                  15

Asn Met Glu Pro Val Glu Asp Pro Asp Ala Arg Ala Phe Val Pro Ala
                20                  25                  30

Asn Thr Glu Arg Gln Leu Glu Ala Met Pro Leu Arg Gln His Ser Ser
            35                  40                  45

Ala Gln Ser Tyr His Ala Gln Pro Val Leu Thr Ala Pro Pro Gln Pro
        50                  55                  60

Leu Leu Leu Thr Gly Ser Ser Lys Thr Lys Thr Thr Ile Lys Val
65                  70                  75                  80

Pro Thr Gly Thr Arg Ile Leu Pro Pro Arg Pro Asn Glu Arg Val Ile
                85                  90                  95

Gly Val Lys Thr Asn Arg Ser Gly Glu Ile Ser Ser Val Arg Tyr Thr
            100                 105                 110

Ile Glu Glu Glu Arg Pro Tyr Phe Glu Gly Ile Arg Ala Ala Lys Val
        115                 120                 125

Arg Phe Ile Pro Pro Lys Ala Ala Ser Lys His Ala Leu Asn Ala Phe
    130                 135                 140

Glu Thr Pro Pro Lys Arg Arg Lys Thr Ile Met Asp Ile Asp Glu Asp
145                 150                 155                 160

Ala Arg Arg Leu Asp Arg Ile Ile Ile Asp Leu Gln Ser Ser Ile Asn
                165                 170                 175

Ser Leu Thr Arg Gln Leu Ser Asn His Asn Thr Ile Ile Leu Gly Leu
            180                 185                 190

Arg Gln Asp Leu Ala Asn Ala Asn Lys Lys Ile Lys Glu Leu Glu Arg
        195                 200                 205

Arg
```

<210> SEQ ID NO 80
<211> LENGTH: 630
<212> TYPE: DNA
<213> ORGANISM: Sorghum bicolor

<400> SEQUENCE: 80

```
atggccgaga agttccacga tgattgggaa gtcgtcccct tcaacctcaa catgaagcct    60
gaggaagacc ccgacgcccg tgctctcgtc ccggccaaca cagagcgaca actagaagcc    120
```

```
atgccattac gccaacgcag ctccgctcaa acctatcatg ctcaaccagt tcttaccgca    180
ccgccacaac cccaactcct caagggatca tcatccaaga caaagaccac catcaaggtg    240
ccaactggca cgaggatcct tccacctaga cccaatgaga gggtcgttgg agtcaagacc    300
aaccgaagcg gtgagatcaa cagcatccgc tacactacgg aggaggagag acattacttt    360
gaagggatta gagcagccaa agtccgtttc atccctccaa aggcagcccc gaagcacgct    420
ctcaatgctt ttgagacacc tcccaagcgt cgcaagacta tagtagatat tgatgaggac    480
gttcgcaggc tagacagagt tatcatagac ctccagtcct cggttaattc cctcactagg    540
cagctctcta accacaacac cgttatatta ggccttaggc atgatcttgc tagtgccaat    600
aagaagatta aggaattaga gcgccgctaa                                     630
```

<210> SEQ ID NO 81
<211> LENGTH: 209
<212> TYPE: PRT
<213> ORGANISM: Sorghum bicolor

<400> SEQUENCE: 81

```
Met Ala Glu Lys Phe His Asp Asp Trp Glu Val Val Pro Phe Asn Leu
1               5                   10                  15

Asn Met Lys Pro Glu Glu Asp Pro Asp Ala Arg Ala Leu Val Pro Ala
            20                  25                  30

Asn Thr Glu Arg Gln Leu Glu Ala Met Pro Leu Arg Gln Arg Ser Ser
        35                  40                  45

Ala Gln Thr Tyr His Ala Gln Pro Val Leu Thr Ala Pro Pro Gln Pro
    50                  55                  60

Gln Leu Leu Lys Gly Ser Ser Ser Lys Thr Lys Thr Thr Ile Lys Val
65                  70                  75                  80

Pro Thr Gly Thr Arg Ile Leu Pro Pro Arg Pro Asn Glu Arg Val Val
                85                  90                  95

Gly Val Lys Thr Asn Arg Ser Gly Glu Ile Asn Ser Ile Arg Tyr Thr
            100                 105                 110

Thr Glu Glu Glu Arg His Tyr Phe Glu Gly Ile Arg Ala Ala Lys Val
        115                 120                 125

Arg Phe Ile Pro Pro Lys Ala Ala Pro Lys His Ala Leu Asn Ala Phe
    130                 135                 140

Glu Thr Pro Pro Lys Arg Arg Lys Thr Ile Val Asp Ile Asp Glu Asp
145                 150                 155                 160

Val Arg Arg Leu Asp Arg Val Ile Ile Asp Leu Gln Ser Ser Val Asn
                165                 170                 175

Ser Leu Thr Arg Gln Leu Ser Asn His Asn Thr Val Ile Leu Gly Leu
            180                 185                 190

Arg His Asp Leu Ala Ser Ala Asn Lys Lys Ile Lys Glu Leu Glu Arg
        195                 200                 205

Arg
```

<210> SEQ ID NO 82
<211> LENGTH: 630
<212> TYPE: DNA
<213> ORGANISM: Sorghum bicolor

<400> SEQUENCE: 82

```
atggccgaga agtaccacga tgattgggaa gtcgtcccct ttaacctcaa catggagcca     60
gtggaagacc ccgatgcccg tgctctcgtc ccggccaaca cagaaagaca gctagaagcc    120
```

| | | |
|---|---|---|
| ataccattac gccaacgcag ctccgcccaa tcttaccatg ctcaaccagt tctcaccgca | 180 | |
| ccaccacaac ccctactcct caaaggatca tcatccaaga cgaagaccac tataaaggtg | 240 | |
| ccaatcggca caaggatcct tccacctaga cccaatgaga gggtcgttgg agtcaagacc | 300 | |
| aaccggagcg gcgagatcag cagtgtacgc tacactacag aggaggaaag gccttacttt | 360 | |
| gaagggatta gagcatccaa agtccgtttc atccctccaa aggcagcccc gaagcactct | 420 | |
| ctcaatgctt ttgagacacc tcccaagcgt cgcaagacta atggatat tgatgaggaa | 480 | |
| gttcacaggc tagatagagt tatcatagac ctccagtcct cgattaattc cctcactagg | 540 | |
| cagctctcta accacaacac cattatacta ggccttaggc aggatcttgc cagtgccaac | 600 | |
| aagatgatca aggaattaga gcgccgctaa | 630 | |

<210> SEQ ID NO 83
<211> LENGTH: 209
<212> TYPE: PRT
<213> ORGANISM: Sorghum bicolor

<400> SEQUENCE: 83

```
Met Ala Glu Lys Tyr His Asp Asp Trp Glu Val Val Pro Phe Asn Leu
1               5                   10                  15
Asn Met Glu Pro Val Glu Asp Pro Ala Arg Ala Leu Val Pro Ala
            20                  25                  30
Asn Thr Glu Arg Gln Leu Glu Ala Ile Pro Leu Arg Gln Arg Ser Ser
        35                  40                  45
Ala Gln Ser Tyr His Ala Gln Pro Val Leu Thr Ala Pro Pro Gln Pro
    50                  55                  60
Leu Leu Leu Lys Gly Ser Ser Lys Thr Lys Thr Thr Ile Lys Val
65                  70                  75                  80
Pro Ile Gly Thr Arg Ile Leu Pro Pro Arg Pro Asn Glu Arg Val Val
                85                  90                  95
Gly Val Lys Thr Asn Arg Ser Gly Glu Ile Ser Ser Val Arg Tyr Thr
            100                 105                 110
Thr Glu Glu Glu Arg Pro Tyr Phe Glu Gly Ile Arg Ala Ser Lys Val
        115                 120                 125
Arg Phe Ile Pro Pro Lys Ala Ala Pro Lys His Ser Leu Asn Ala Phe
    130                 135                 140
Glu Thr Pro Pro Lys Arg Arg Lys Thr Ile Met Asp Ile Asp Glu Glu
145                 150                 155                 160
Val His Arg Leu Asp Arg Val Ile Ile Asp Leu Gln Ser Ser Ile Asn
                165                 170                 175
Ser Leu Thr Arg Gln Leu Ser Asn His Asn Thr Ile Ile Leu Gly Leu
            180                 185                 190
Arg Gln Asp Leu Ala Ser Ala Asn Lys Met Ile Lys Glu Leu Glu Arg
        195                 200                 205
Arg
```

<210> SEQ ID NO 84
<211> LENGTH: 627
<212> TYPE: DNA
<213> ORGANISM: Sorghum bicolor

<400> SEQUENCE: 84

| | | |
|---|---|---|
| atggccgaga agtaccacga tgattgggaa gtcgtcccct tcaacctcaa catggagcct | 60 | |
| gtagaagacc ccgatgcccg tgctctcgtc ccggccaaca cagagcgaca gctagaagcc | 120 | |

```
atgccattac gccaacgcag ctccgcccaa tcctaccatg ctcaaccagt tctcaccgca      180
ccgccacaac ccctactcct caaaggatca tcatccaaga cgaagaccac tatcaaggtg      240
ccaaccggca caaggatcct tccacctaga cccaatgaga gggtcgttgg agtcaagacc      300
aaccggagcg gcgagatcag cagtgtacgc tacactacgc aggaaaggcc ttactttgaa      360
gggattcgag cagccaaagt ccgtttcatc cctccaaagg cagccccgaa gcacgctctc      420
aatgcttttg agacacctcc caagcgtcgc aagactatag tagacattga tgaggacgtt      480
cgcagactag acagagttat catagatctc cagtcctcaa ttaattccct cactaggcag      540
ctctctaaca acaacaccat tatactaggc cttaggcagg atcttgccag tgccaacaag      600
aagattaagg aattagagcg ccgctaa                                         627
```

<210> SEQ ID NO 85
<211> LENGTH: 208
<212> TYPE: PRT
<213> ORGANISM: Sorghum bicolor

<400> SEQUENCE: 85

```
Met Ala Glu Lys Tyr His Asp Asp Trp Glu Val Val Pro Phe Asn Leu
1               5                   10                  15

Asn Met Glu Pro Val Glu Asp Pro Ala Arg Ala Leu Val Pro Ala
            20                  25                  30

Asn Thr Glu Arg Gln Leu Glu Ala Met Pro Leu Arg Gln Arg Ser Ser
        35                  40                  45

Ala Gln Ser Tyr His Ala Gln Pro Val Leu Thr Ala Pro Pro Gln Pro
    50                  55                  60

Leu Leu Leu Lys Gly Ser Ser Lys Thr Lys Thr Thr Ile Lys Val
65                  70                  75                  80

Pro Thr Gly Thr Arg Ile Leu Pro Pro Arg Pro Asn Glu Arg Val Val
                85                  90                  95

Gly Val Lys Thr Asn Arg Ser Gly Glu Ile Ser Ser Val Arg Tyr Thr
            100                 105                 110

Thr Gln Glu Arg Pro Tyr Phe Glu Gly Ile Arg Ala Ala Lys Val Arg
        115                 120                 125

Phe Ile Pro Pro Lys Ala Ala Pro Lys His Ala Leu Asn Ala Phe Glu
    130                 135                 140

Thr Pro Pro Lys Arg Arg Lys Thr Ile Val Asp Ile Asp Glu Asp Val
145                 150                 155                 160

Arg Arg Leu Asp Arg Val Ile Ile Asp Leu Gln Ser Ser Ile Asn Ser
                165                 170                 175

Leu Thr Arg Gln Leu Ser Asn Asn Asn Thr Ile Ile Leu Gly Leu Arg
            180                 185                 190

Gln Asp Leu Ala Ser Ala Asn Lys Lys Ile Lys Glu Leu Glu Arg Arg
        195                 200                 205
```

<210> SEQ ID NO 86
<211> LENGTH: 630
<212> TYPE: DNA
<213> ORGANISM: Sorghum bicolor

<400> SEQUENCE: 86

```
atggccgaga agtaccacga tgattgggaa gtcgtcccct tcaacctcaa catggagcct      60
gtggaagacc ccgatgctcg tgctctcgtc ccggccaaca cagagcgaca gctagaagcc      120
atgccattac gccaacgcag cttcgcccaa tcttaccatg ctcaaccagt tctcaccgca      180
```

```
ccaccacaac ccctactcct caaaggatca tcatccaaaa cgaagaccac tatcaaggtg    240
ccaatcggca ctaggatcct tccacctaga ccccatgaga gggtcgttgg agtcaagacc    300
aaccgaagcg gcgagatcag cagcgtacgc tacactacgg aggaggaaag gccttacttt    360
gaagggatta gagcagccaa agtccgtttc atccctccaa aggtagcccc gaagcatgct    420
ctcaacgctt ttgagacacc tcccaagcgt cgcaagacta taatggatat tgatgaggaa    480
gttcgcaggc tagatagagt tatcatagac atccagtcct tgattaattc cctcactagg    540
cagctctcta accacaacac cattatacta ggccttaggc aggatcttgc cagtgccaac    600
aagaaaatca aggaattaga gcgccgctaa                                     630
```

<210> SEQ ID NO 87
<211> LENGTH: 209
<212> TYPE: PRT
<213> ORGANISM: Sorghum bicolor

<400> SEQUENCE: 87

```
Met Ala Glu Lys Tyr His Asp Asp Trp Glu Val Val Pro Phe Asn Leu
1               5                   10                  15

Asn Met Glu Pro Val Glu Asp Pro Ala Arg Ala Leu Val Pro Ala
            20                  25                  30

Asn Thr Glu Arg Gln Leu Glu Ala Met Pro Leu Arg Gln Arg Ser Phe
        35                  40                  45

Ala Gln Ser Tyr His Ala Gln Pro Val Leu Thr Ala Pro Pro Gln Pro
    50                  55                  60

Leu Leu Leu Lys Gly Ser Ser Lys Thr Lys Thr Thr Ile Lys Val
65                  70                  75                  80

Pro Ile Gly Thr Arg Ile Leu Pro Pro Arg Pro His Glu Arg Val Val
                85                  90                  95

Gly Val Lys Thr Asn Arg Ser Gly Glu Ile Ser Ser Val Arg Tyr Thr
            100                 105                 110

Thr Glu Glu Arg Pro Tyr Phe Glu Gly Ile Arg Ala Ala Lys Val
        115                 120                 125

Arg Phe Ile Pro Pro Lys Val Ala Pro Lys His Ala Leu Asn Ala Phe
130                 135                 140

Glu Thr Pro Pro Lys Arg Arg Lys Thr Ile Met Asp Ile Asp Glu Glu
145                 150                 155                 160

Val Arg Arg Leu Asp Arg Val Ile Ile Asp Ile Gln Ser Leu Ile Asn
                165                 170                 175

Ser Leu Thr Arg Gln Leu Ser Asn His Asn Thr Ile Ile Leu Gly Leu
            180                 185                 190

Arg Gln Asp Leu Ala Ser Ala Asn Lys Lys Ile Lys Glu Leu Glu Arg
        195                 200                 205

Arg
```

<210> SEQ ID NO 88
<211> LENGTH: 30
<212> TYPE: DNA
<213> ORGANISM: Artificial sequence
<220> FEATURE:
<223> OTHER INFORMATION: first primer to amplify a region of Sub8
      plasmid DNA

<400> SEQUENCE: 88

```
acctttttat cctcaaagct tcttctcaga                                      30
```

```
<210> SEQ ID NO 89
<211> LENGTH: 30
<212> TYPE: DNA
<213> ORGANISM: Artificial sequence
<220> FEATURE:
<223> OTHER INFORMATION: second primer to amplify a region of Sub8
      plasmid DNA

<400> SEQUENCE: 89
acccctgacc tcaattgtca aacaccaagc                                         30

<210> SEQ ID NO 90
<211> LENGTH: 30
<212> TYPE: DNA
<213> ORGANISM: Artificial sequence
<220> FEATURE:
<223> OTHER INFORMATION: first primer to amplify a region of pSB31

<400> SEQUENCE: 90
gggcgtcgtt ctgggtcaat tgttatagag                                         30

<210> SEQ ID NO 91
<211> LENGTH: 30
<212> TYPE: DNA
<213> ORGANISM: Artificial sequence
<220> FEATURE:
<223> OTHER INFORMATION: second primer used to amplify a region of pSB31
      plasmid DNA

<400> SEQUENCE: 91
ggacgttttt aaggtaccga attccaatcc                                         30
```

US 9,556,450 B2

DROUGHT TOLERANT PLANTS AND RELATED CONSTRUCTS AND METHODS INVOLVING GENES ENCODING DTP21 POLYPEPTIDES

CROSS REFERENCE TO RELATED APPLICATIONS

This application is a Continuation of U.S. application Ser. No. 12/915,547, filed Oct. 29, 2010, now allowed, which claims the benefit of U.S. Provisional Application No. 61/256,348, filed Oct. 30, 2009, the entire content of which is herein incorporated by reference.

REFERENCE TO SEQUENCE LISTING SUBMITTED ELECTRONICALLY

The official copy of the sequence listing is submitted electronically via EFS-Web as an ASCII formatted sequence listing with a file named 20141209_BB1739USDIV_SequenceListing created on Dec. 9, 2014 and having a size of 187 kilobytes and is filed concurrently with the specification. The sequence listing contained in this ASCII formatted document is part of the specification and is herein incorporated by reference in its entirety.

FIELD OF THE INVENTION

The field of invention relates to plant breeding and genetics and, in particular, relates to recombinant DNA constructs useful in plants for conferring tolerance to drought.

BACKGROUND OF THE INVENTION

Abiotic stress is the primary cause of crop loss worldwide, causing average yield losses of more than 50% for major crops (Boyer, J. S. (1982) Science 218:443-448; Bray, E. A. et al. (2000) In Biochemistry and Molecular Biology of Plants, Edited by Buchannan, B. B. et al., Amer. Soc. Plant Biol., pp. 1158-1249). Among the various abiotic stresses, drought is the major factor that limits crop productivity worldwide. Exposure of plants to a water-limiting environment during various developmental stages appears to activate various physiological and developmental changes. Understanding of the basic biochemical and molecular mechanism for drought stress perception, transduction and tolerance is a major challenge in biology. Reviews on the molecular mechanisms of abiotic stress responses and the genetic regulatory networks of drought stress tolerance have been published (Valliyodan, B., and Nguyen, H. T., (2006) Curr. Opin. Plant Biol. 9:189-195; Wang, W., et al. (2003) Planta 218:1-14); Vinocur, B., and Altman, A. (2005) Curr. Opin. Biotechnol. 16:123-132; Chaves, M. M., and Oliveira, M. M. (2004) J. Exp. Bot. 55:2365-2384; Shinozaki, K., et al. (2003) Curr. Opin. Plant Biol. 6:410-417; Yamaguchi-Shinozaki, K., and Shinozaki, K. (2005) Trends Plant Sci. 10:88-94).

It is well known that responses to abiotic stress vary significantly among plant species and among varieties and cultivars within a plant species. Certain species, varieties or cultivars are more tolerant to abiotic stress such as drought than others. The genotypes of such plants are attractive sources of genes involved in unique responses to abiotic stress. Identification of stress response genes and expression of them in transgenic plants have been tried quite extensively to date. However, stress response genes introduced into plants are often not expressed very well. Reasons for the poor expression may include inappropriate choice of promoters and/or other regulatory elements and destruction of exon-intron structure. Introduction of a plant genomic segment, which retains the native promoter, entire coding region and intact exon-intron structure, into plants may be an effective approach for good expression of a foreign stress responsive gene. For example, it was reported that an enzyme involved in photosynthesis was expressed much higher from a genomic clone than from a corresponding cDNA clone in rice (Ku et al. Nature Biotechnol. 17:76-80, 1999).

Recently, a method for efficient screening of genomic DNA fragments capable of providing plants with an agriculturally advantageous phenotypic variation was developed (U.S. Patent Publication No. US2008/0301832A1). In this method, plants are transformed with genomic fragments from a genomic library constructed from a higher plant, and the resultant transgenic plants are screened for an agriculturally advantageous phenotypic variation. The resultant plants could be screened for a unique response to abiotic stress, such as drought tolerance, and eventually, a genomic fragment, which may carry a stress responsive gene readily expressible in plants, may be identified. In order to identify a unique stress responsive gene and utilize this gene in transgenic plants, considerable experimentation is required. Among the many factors to consider include the following: choice of a plant from which a genomic library is constructed; how the transgenic plants are screened; how the genomic fragments are examined; and how the a stress responsive gene is pinpointed, characterized and used.

SUMMARY OF THE INVENTION

The present invention includes:

In one embodiment, a plant comprising in its genome a recombinant DNA construct comprising a polynucleotide operably linked to at least one regulatory element, wherein said polynucleotide comprises a nucleotide sequence selected from the group consisting of: (a) a nucleotide sequence encoding a polypeptide with drought tolerance activity, wherein the polypeptide has an amino acid sequence of at least 60%, 80%, 85%, 90%, 95% or 100% sequence identity, based on the Clustal V method of alignment with pairwise alignment default parameters of KTUPLE=1, GAP PENALTY=3, WINDOW=5 and DIAGONALS SAVED=5, when compared to SEQ ID NO:27, 32, 46, 56, 60, 64, 81, 83, 85 or 87; (b) a nucleotide sequence encoding a polypeptide with drought tolerance activity, wherein the nucleotide sequence is hybridizable under stringent conditions with a DNA molecule comprising the full complement of SEQ ID NO:26, 31, 44, 55, 59, 63, 80, 82, 84 or 86; (c) a nucleotide sequence encoding a polypeptide with drought tolerance activity, wherein the nucleotide sequence is derived from SEQ ID NO:26, 31, 44, 55, 59, 63, 80, 82, 84 or 86 by alteration of one or more nucleotides by at least one method selected from the group consisting of: deletion, substitution, addition and insertion; (d) a nucleotide sequence encoding a polypeptide wherein the amino acid sequence of the polypeptide comprises SEQ ID NO:27, 32, 46, 56, 60, 64, 81, 83, 85 or 87; and (e) a nucleotide sequence comprising SEQ ID NO:26, 31, 44, 55, 59, 63, 80, 82, 84 or 86; and wherein said plant exhibits increased drought tolerance when compared to a control plant not comprising said recombinant DNA construct. The plant may be a monocot or dicot.

In another embodiment, a plant comprising in its genome a recombinant DNA construct comprising a polynucleotide operably linked to at least one regulatory element, wherein said polynucleotide comprises a nucleotide sequence selected from the group consisting of: (a) a nucleotide sequence encoding a polypeptide with drought tolerance activity, wherein the polypeptide has an amino acid sequence of at least 60%, 80%, 85%, 90%, 95% or 100% sequence identity, based on the Clustal V method of alignment with pairwise alignment default parameters of KTUPLE=1, GAP PENALTY=3, WINDOW=5 and DIAGONALS SAVED=5, when compared to SEQ ID NO:27, 32, 46, 56, 60, 64, 81, 83, 85 or 87; (b) a nucleotide sequence encoding a polypeptide with drought tolerance activity, wherein the nucleotide sequence is hybridizable under stringent conditions with a DNA molecule comprising the full complement of SEQ ID NO:26, 31, 44, 55, 59, 63, 80, 82, 84 or 86; (c) a nucleotide sequence encoding a polypeptide with drought tolerance activity, wherein the nucleotide sequence is derived from SEQ ID NO:26, 31, 44, 55, 59, 63, 80, 82, 84 or 86 by alteration of one or more nucleotides by at least one method selected from the group consisting of: deletion, substitution, addition and insertion; (d) a nucleotide sequence encoding a polypeptide wherein the amino acid sequence of the polypeptide comprises SEQ ID NO:27, 32, 46, 56, 60, 64, 81, 83, 85 or 87; and (e) a nucleotide sequence comprising SEQ ID NO:26, 31, 44, 55, 59, 63, 80, 82, 84 or 86; and wherein said plant exhibits an increase in yield when compared to a control plant not comprising said recombinant DNA construct. The plant may exhibit said increase in yield when compared, under water limiting conditions, to said control plant not comprising said recombinant DNA construct. The plant may be a monocot or dicot.

In another embodiment, a method of increasing drought tolerance in a plant, comprising: (a) introducing into a regenerable plant cell a recombinant DNA construct comprising a polynucleotide operably linked to at least one regulatory element, wherein said polynucleotide comprises a nucleotide sequence selected from the group consisting of: (i) a nucleotide sequence encoding a polypeptide with drought tolerance activity, wherein the polypeptide has an amino acid sequence of at least 60%, 80%, 85%, 90%, 95% or 100% sequence identity, based on the Clustal V method of alignment with pairwise alignment default parameters of KTUPLE=1, GAP PENALTY=3, WINDOW=5 and DIAGONALS SAVED=5, when compared to SEQ ID NO:27, 32, 46, 56, 60, 64, 81, 83, 85 or 87; (ii) a nucleotide sequence encoding a polypeptide with drought tolerance activity, wherein the nucleotide sequence is hybridizable under stringent conditions with a DNA molecule comprising the full complement of SEQ ID NO:26, 31, 44, 55, 59, 63, 80, 82, 84 or 86; (iii) a nucleotide sequence encoding a polypeptide with drought tolerance activity, wherein the nucleotide sequence is derived from SEQ ID NO:26, 31, 44, 55, 59, 63, 80, 82, 84 or 86 by alteration of one or more nucleotides by at least one method selected from the group consisting of: deletion, substitution, addition and insertion; (iv) a nucleotide sequence encoding a polypeptide wherein the amino acid sequence of the polypeptide comprises SEQ ID NO:27, 32, 46, 56, 60, 64, 81, 83, 85 or 87; and (v) a nucleotide sequence comprising SEQ ID NO:26, 31, 44, 55, 59, 63, 80, 82, 84 or 86; and (b) regenerating a transgenic plant from the regenerable plant cell after step (a), wherein the transgenic plant comprises in its genome the recombinant DNA construct and exhibits increased drought tolerance when compared to a control plant not comprising the recombinant DNA construct. The method may further comprise: (c) obtaining a progeny plant derived from the transgenic plant, wherein said progeny plant comprises in its genome the recombinant DNA construct and exhibits increased drought tolerance when compared to a control plant not comprising the recombinant DNA construct.

In another embodiment, a method of evaluating drought tolerance in a plant, comprising: (a) obtaining a transgenic plant, wherein the transgenic plant comprises in its genome a recombinant DNA construct comprising a polynucleotide operably linked to at least one regulatory element, wherein said polynucleotide comprises a nucleotide sequence selected from the group consisting of: (i) a nucleotide sequence encoding a polypeptide with drought tolerance activity, wherein the polypeptide has an amino acid sequence of at least 60%, 80%, 85%, 90%, 95% or 100% sequence identity, based on the Clustal V method of alignment with pairwise alignment default parameters of KTUPLE=1, GAP PENALTY=3, WINDOW=5 and DIAGONALS SAVED=5, when compared to SEQ ID NO:27, 32, 46, 56, 60, 64, 81, 83, 85 or 87; (ii) a nucleotide sequence encoding a polypeptide with drought tolerance activity, wherein the nucleotide sequence is hybridizable under stringent conditions with a DNA molecule comprising the full complement of SEQ ID NO:26, 31, 44, 55, 59, 63, 80, 82, 84 or 86; (iii) a nucleotide sequence encoding a polypeptide with drought tolerance activity, wherein the nucleotide sequence is derived from SEQ ID NO:26, 31, 44, 55, 59, 63, 80, 82, 84 or 86 by alteration of one or more nucleotides by at least one method selected from the group consisting of: deletion, substitution, addition and insertion; (iv) a nucleotide sequence encoding a polypeptide wherein the amino acid sequence of the polypeptide comprises SEQ ID NO:27, 32, 46, 56, 60, 64, 81, 83, 85 or 87; and (v) a nucleotide sequence comprising SEQ ID NO:26, 31, 44, 55, 59, 63, 80, 82, 84 or 86; and (b) obtaining a progeny plant derived from the transgenic plant of (a), wherein the progeny plant comprises in its genome the recombinant DNA construct; and (c) evaluating the progeny plant for drought tolerance compared to a control plant not comprising the recombinant DNA construct.

In another embodiment, a method of determining an alteration of an agronomic characteristic in a plant, comprising: (a) obtaining a transgenic plant, wherein the transgenic plant comprises in its genome a recombinant DNA construct comprising a polynucleotide operably linked to at least one regulatory element, wherein said polynucleotide comprises a nucleotide sequence selected from the group consisting of: (i) a nucleotide sequence encoding a polypeptide with drought tolerance activity, wherein the polypeptide has an amino acid sequence of at least 60%, 80%, 85%, 90%, 95% or 100% sequence identity, based on the Clustal V method of alignment with pairwise alignment default parameters of KTUPLE=1, GAP PENALTY=3, WINDOW=5 and DIAGONALS SAVED=5, when compared to SEQ ID NO:27, 32, 46, 56, 60, 64, 81, 83, 85 or 87; (ii) a nucleotide sequence encoding a polypeptide with drought tolerance activity, wherein the nucleotide sequence is hybridizable under stringent conditions with a DNA molecule comprising the full complement of SEQ ID NO:26, 31, 44, 55, 59, 63, 80, 82, 84 or 86; (iii) a nucleotide sequence encoding a polypeptide with drought tolerance activity, wherein the nucleotide sequence is derived from SEQ ID NO:26, 31, 44, 55, 59, 63, 80, 82, 84 or 86 by alteration of one or more nucleotides by at least one method selected from the group consisting of: deletion, substitution, addition and insertion; (iv) a nucleotide sequence encoding a polypeptide wherein the amino acid sequence of the polypeptide comprises SEQ ID NO:27, 32, 46, 56, 60, 64, 81, 83, 85 or 87; and (v) a nucleotide sequence comprising SEQ ID NO:26, 31, 44, 55, 59, 63, 80, 82, 84 or 86; and (b) obtaining a progeny plant derived from the transgenic plant of step (a), wherein the progeny plant comprises in its genome the recombinant DNA construct; and (c) determining whether the progeny plant exhibits an alteration of at least one agronomic characteristic when compared to a control plant not comprising the recombinant DNA construct. Said determining step (c) may comprise determining whether the transgenic plant exhibits an alteration of at least one agronomic characteristic when compared, under water limiting conditions, to a control plant not comprising the recombinant DNA construct. Said at least one agronomic trait may be yield and furthermore may be an increase in yield.

In another embodiment, an isolated polynucleotide comprising a nucleotide sequence selected from the group consisting of: (a) a nucleotide sequence encoding a polypeptide with drought tolerance activity, wherein the polypeptide has an amino acid sequence of at least 60%, 80%, 85%, 90% or 95% sequence identity, based on the Clustal V method of alignment with pairwise alignment default parameters of KTUPLE=1, GAP PENALTY=3, WINDOW=5 and DIAGONALS SAVED=5, when compared to SEQ ID NO:27, 32, 46, 56, 60, 64, 81, 83, 85 or 87; (b) a nucleotide sequence encoding a polypeptide with drought tolerance activity, wherein the nucleotide sequence is hybridizable under stringent conditions with a DNA molecule comprising the full complement of SEQ ID NO:26, 31, 44, 55, 59, 63, 80, 82, 84 or 86; (c) a nucleotide sequence encoding a polypeptide with drought tolerance activity, wherein the nucleotide sequence is derived from SEQ ID NO:26, 31, 44, 55, 59, 63, 80, 82, 84 or 86 by alteration of one or more nucleotides by at least one method selected from the group consisting of: deletion, substitution, addition and insertion; (d) a nucleotide sequence encoding a polypeptide wherein the amino acid sequence of the polypeptide comprises SEQ ID NO:27, 32, 46, 56, 60, 64, 81, 83, 85 or 87; and (e) a nucleotide sequence comprising SEQ ID NO:26, 31, 44, 55, 59, 63, 80, 82, 84 or 86.

In another embodiment, an isolated polynucleotide comprising the full complement of the nucleotide sequence of the invention, wherein the full complement and the nucleotide sequence of the invention consist of the same number of nucleotides and are 100% complementary.

In another embodiment, a recombinant DNA construct comprising the isolated polynucleotide of the invention operably linked to at least one regulatory element.

In another embodiment, a cell comprising the recombinant DNA construct of the invention, wherein the cell is selected from the group consisting of a bacterial cell, a yeast cell, and insect cell and a plant cell.

In another embodiment, a plant or a seed comprising the recombinant DNA construct of the invention. The plant or seed may be a monocot or a dicot plant or seed.

In another embodiment, a method for isolating a polypeptide encoded by the recombinant DNA construct of the invention, wherein the method comprises the following: (a) transforming a cell with the recombinant DNA construct of the invention; (b) growing the transformed cell of step (a) under conditions suitable for expression of the recombinant DNA construct; and (c) isolating the polypeptide from the transformed cell of step (b).

In another embodiment, an isolated polypeptide selected from the group consisting of: (a) a polypeptide with drought tolerance activity, wherein the polypeptide has an amino acid sequence of at least 60%, 80%, 85%, 90% or 95% sequence identity, based on the Clustal V method of alignment with pairwise alignment default parameters of KTUPLE=1, GAP PENALTY=3, WINDOW=5 and DIAGONALS SAVED=5, when compared to SEQ ID NO:27, 32, 46, 56, 60, 64, 81, 83, 85 or 87; (b) a polypeptide with drought tolerance activity, wherein the amino acid sequence is derived from SEQ ID NO:27, 32, 46, 56, 60, 64, 81, 83, 85 or 87 by alteration of one or more amino acids by at least one method selected from the group consisting of: deletion, substitution, addition and insertion; and (c) a polypeptide wherein the amino acid sequence of the polypeptide comprises SEQ ID NO:27, 32, 46, 56, 60, 64, 81, 83, 85 or 87.

In another embodiment, a vector comprising the polynucleotide of the invention.

In another embodiment, a method for producing a transgenic plant comprising transforming a plant cell with the recombinant DNA construct of the invention and regenerating a transgenic plant from the transformed plant cell.

In another embodiment, the present invention includes any of the plants of the present invention wherein the plant is selected from the group consisting of: maize, soybean, sunflower, *sorghum*, canola, wheat, alfalfa, cotton, rice, barley, millet, sugarcane, switchgrass, tobacco, potato and sugar beet.

In another embodiment, the present invention includes any of the methods of the present invention wherein the plant is selected from the group consisting of: maize, soybean, sunflower, *sorghum*, canola, wheat, alfalfa, cotton, rice, barley, millet, sugarcane, switchgrass, tobacco, potato and sugar beet.

In another embodiment, the present invention includes seed of any of the plants of the present invention, wherein said seed comprises in its genome a recombinant DNA construct comprising a polynucleotide operably linked to at least one regulatory element, wherein said polynucleotide encodes a polypeptide having an amino acid sequence of at least 60% sequence identity, based on the Clustal V method of alignment, when compared to SEQ ID NO:27, 32, 46, 56, 60, 64, 81, 83, 85 or 87, and wherein a plant produced from said seed exhibits either an increased drought tolerance, or an increase in yield, or both, when compared to a control plant not comprising said recombinant DNA construct.

BRIEF DESCRIPTION OF THE DRAWINGS AND SEQUENCE LISTING

The invention can be more fully understood from the following detailed description and the accompanying drawings and Sequence Listing which form a part of this application.

FIG. 3 shows the structure of the drought tolerant gene which encodes the SS-DTP21-1 polypeptide of 209 amino acids.

Figure 4C:
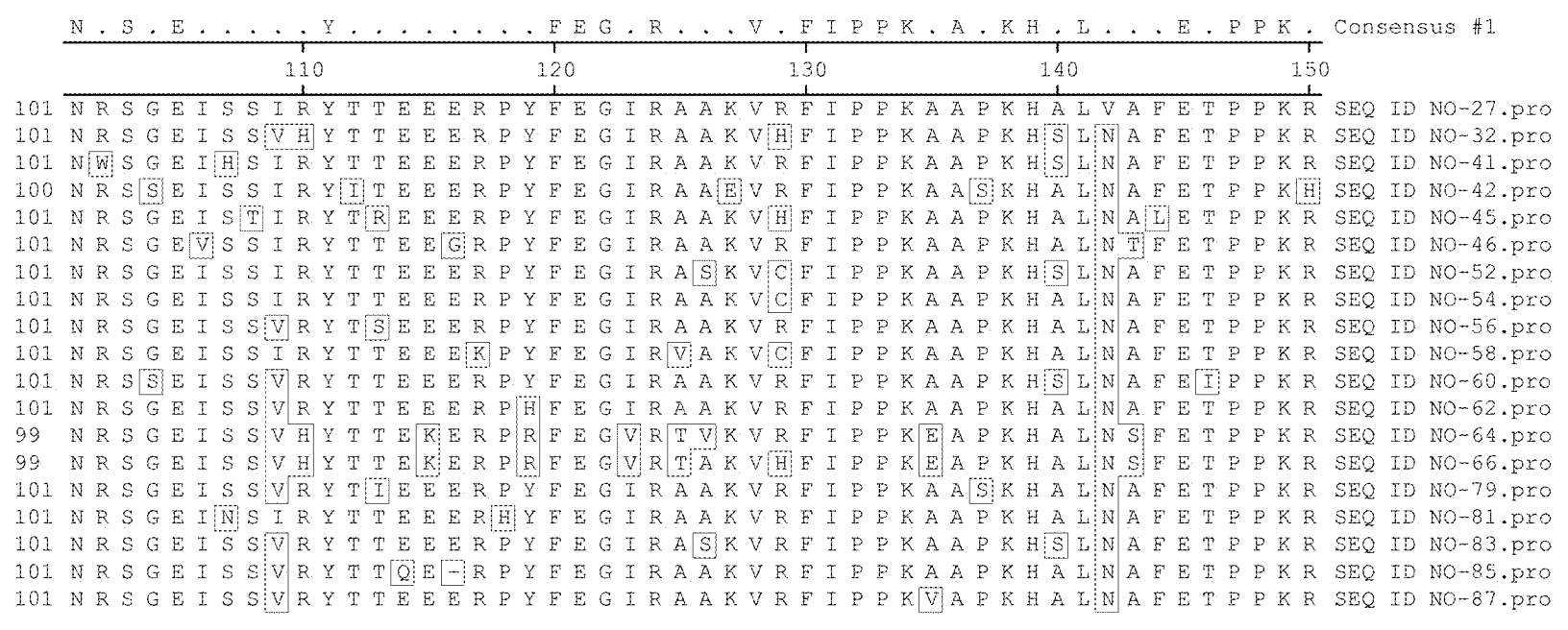

FIGS. 4A-4E present an alignment of the amino acid sequences of DTP21 polypeptides set forth in SEQ ID NOs: 27, 32, 41, 42, 45, 46, 52, 54, 56, 58, 60, 62, 64, 66, 79, 81, 83, 85 and 87. Residues that are different from the residue of SEQ ID NO:27 at a given position are enclosed in a box.

A consensus sequence is presented where a residue is shown if identical in all sequences, otherwise, a period is shown.

Figure 5:
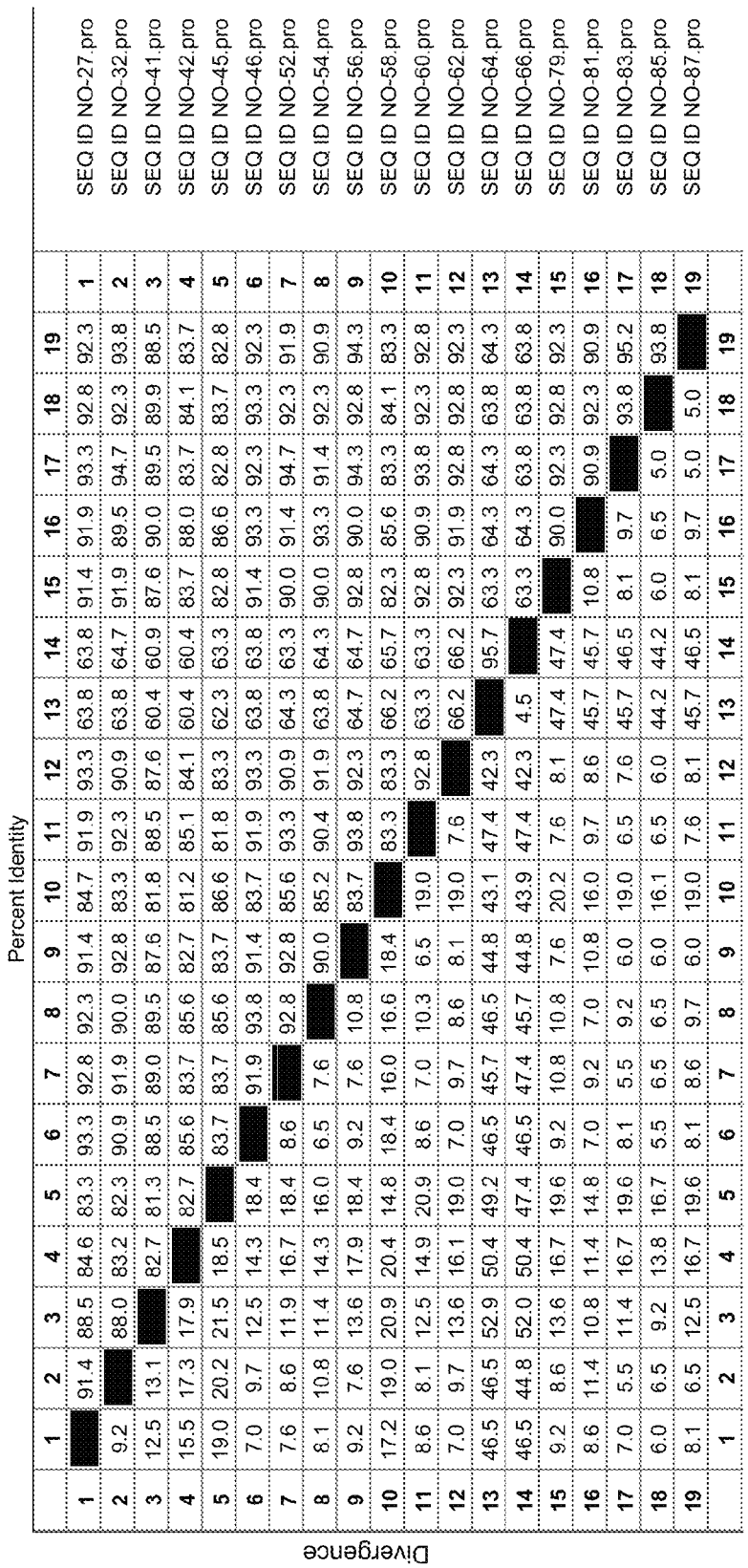

FIG. 5 presents the percent sequence identities and divergence values for each sequence pair presented in FIGS. 4A-4E.

FIGS. 6A-6B show an evaluation of individual Gaspe Flint derived maize lines transformed with PHP29675.

FIGS. 7A-7B show a summary evaluation of Gaspe Flint derived maize lines transformed with PHP29675.

SEQ ID NO:1 is the nucleotide sequence of a recombinant DNA fragment which contains the Genomic Fragment IS125 at nucleotide positions 10-40049.

Figure 1:
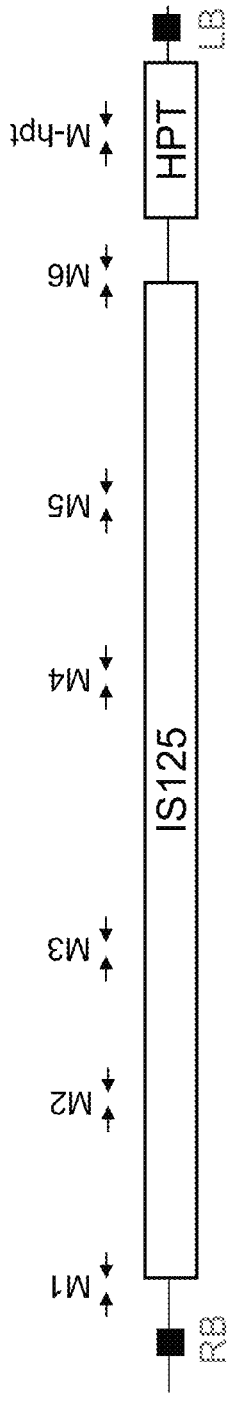
FIG. 1 shows the position and sequence of the PCR primer pairs used to genotype rice transformed with Genomic Fragment IS125.

SEQ ID NO:2 is the nucleotide sequence of the forward primer for the M1 primer pair of FIG. 1.

SEQ ID NO:3 is the nucleotide sequence of the reverse primer for the M1 primer pair of FIG. 1.

SEQ ID NO:4 is the nucleotide sequence of the forward primer for the M2 primer pair of FIG. 1.

SEQ ID NO:5 is the nucleotide sequence of the reverse primer for the M2 primer pair of FIG. 1.

SEQ ID NO:6 is the nucleotide sequence of the forward primer for the M3 primer pair of FIG. 1.

SEQ ID NO:7 is the nucleotide sequence of the reverse primer for the M3 primer pair of FIG. 1.

SEQ ID NO:8 is the nucleotide sequence of the forward primer for the M4 primer pair of FIG. 1.

SEQ ID NO:9 is the nucleotide sequence of the reverse primer for the M4 primer pair of FIG. 1.

SEQ ID NO:10 is the nucleotide sequence of the forward primer for the M5 primer pair of FIG. 1.

SEQ ID NO:11 is the nucleotide sequence of the reverse primer for the M5 primer pair of FIG. 1.

SEQ ID NO:12 is the nucleotide sequence of the forward primer for the M6 primer pair of FIG. 1.

SEQ ID NO:13 is the nucleotide sequence of the reverse primer for the M6 primer pair of FIG. 1.

SEQ ID NO:14 is the nucleotide sequence of the forward primer for the M-hpt primer pair of FIG. 1.

SEQ ID NO:15 is the nucleotide sequence of the reverse primer for the M-hpt primer pair of FIG. 1.

SEQ ID NO:16 is the nucleotide sequence of the forward primer for producing the Sub8 fragment.

SEQ ID NO:17 is the nucleotide sequence of the reverse primer for producing the Sub8 fragment.

SEQ ID NO:18 is the nucleotide sequence of the forward primer for producing the Sub7 fragment.

SEQ ID NO:19 is the nucleotide sequence of the reverse primer for producing the Sub7 fragment.

SEQ ID NO:20 is the nucleotide sequence of the forward primer for RT-PCR of transcripts encoded by the Sub7 fragment.

SEQ ID NO:21 is the nucleotide sequence of the reverse primer for RT-PCR of transcripts encoded by the Sub7 fragment.

SEQ ID NO:22 is the nucleotide sequence of an initial primer used for 5'-RACE of the transcript encoding SS-DTP21-1.

SEQ ID NO:23 is the nucleotide sequence of a nested primer used for 5'-RACE of the transcript encoding SS-DTP21-1.

SEQ ID NO:24 is the nucleotide sequence of an initial primer used for 3'-RACE of the transcript encoding SS-DTP21-1.

SEQ ID NO:25 is the nucleotide sequence of a nested primer used for 3'-RACE of the transcript encoding SS-DTP21-1.

SEQ ID NO:26 is the nucleotide sequence within Genomic Fragment IS125 that encodes the SS-DTP21-1 polypeptide.

SEQ ID NO:27 is the amino acid sequence of the SS-DTP21-1 polypeptide encoded by SEQ ID NO:26.

SEQ ID NO:28 is the nucleotide sequence of the forward primer for RT-PCR of transcripts encoded by the Sub5 fragment (Table 17).

SEQ ID NO:29 is the nucleotide sequence of the reverse primer for RT-PCR of transcripts encoded by the Sub5 fragment (Table 17).

SEQ ID NO:30 is the nucleotide sequence of a recombinant DNA fragment which contains the Genomic Fragment IS127 at nucleotide positions 3075-37662.

SEQ ID NO:31 is the nucleotide sequence of the region of Genomic Fragment IS127 that encode the SS-DTP21-2 polypeptide, a polypeptide with sequence homology to SS-DTP21-1.

SEQ ID NO:32 is the amino acid sequence of the SS-DTP21-2 polypeptide encoded by SEQ ID NO:31.

SEQ ID NO:33 is the nucleotide sequence of the forward primer used to amplify the region encoding SS-DTP21-2.

SEQ ID NO:34 is the nucleotide sequence of the reverse primer used to amplify the region encoding SS-DTP21-2.

SEQ ID NO:35 is the nucleotide sequence of the forward primer used to prepare a linearized vector for cloning of regions from *Sorghum bicolor* that encode polypeptides homologous to SS-DTP21-1.

SEQ ID NO:36 is the nucleotide sequence of the reverse primer used to prepare a linearized vector for cloning of regions from *Sorghum bicolor* that encode polypeptides homologous to SS-DTP21-1.

SEQ ID NO:37 is the nucleotide sequence of the forward primer used to amplify regions from *Sorghum bicolor* (Gold sorgho) that encode polypeptides homologous to SS-DTP21-1.

SEQ ID NO:38 is the nucleotide sequence of the reverse primer used to amplify regions from *Sorghum bicolor* that encode polypeptides homologous to SS-DTP21-1.

SEQ ID NO:39 is the nucleotide sequence from *Sorghum bicolor* (Gold sorgho) that encodes SB-DTP21-1, a polypeptide homologous to SS-DTP21-1 from Sudan grass.

SEQ ID NO:40 is the nucleotide sequence from *Sorghum bicolor* (Gold sorgho) that encodes SB-DTP21-2, a polypeptide homologous to SS-DTP21-1 from Sudan grass.

SEQ ID NO:41 is the amino acid sequence of the SB-DTP21-1 polypeptide from *Sorghum bicolor* (Gold sorgho) encoded by SEQ ID NO:39.

SEQ ID NO:42 is the amino acid sequence of the SB-DTP21-2 polypeptide from *Sorghum bicolor* (Gold sorgho) encoded by SEQ ID NO:40.

SEQ ID NO:43 is the nucleotide sequence from *Sorghum bicolor* (B35) that encodes SB-DTP21-3, a polypeptide homologous to SS-DTP21-1 from Sudan grass.

SEQ ID NO:44 is the nucleotide sequence from *Sorghum bicolor* (B35) that encodes SB-DTP21-4, a polypeptide homologous to SS-DTP21-1 from Sudan grass.

SEQ ID NO:45 is the amino acid sequence of the SB-DTP21-3 polypeptide from *Sorghum bicolor* (B35) encoded by SEQ ID NO:43.

SEQ ID NO:46 is the amino acid sequence of the SB-DTP21-4 polypeptide from *Sorghum bicolor* (B35) encoded by SEQ ID NO:44.

SEQ ID NO:47 is the nucleotide sequence from positions 24904 to 25530 of NCBI GI No. 124359063 for *Sorghum bicolor* clone SB_BBc0073F19.

SEQ ID NO:48 is the nucleotide sequence from positions 44114 to 44740 of NCBI GI No. 124359064 for *Sorghum bicolor* clone SB_BBc0109L12.

SEQ ID NO:49 is the amino acid sequence of a polypeptide encoded by SEQ ID NO:47, and is homologous to the SS-DTP21-1 polypeptide.

SEQ ID NO:50 is the amino acid sequence of a polypeptide encoded by SEQ ID NO:48, and is homologous to the SS-DTP21-1 polypeptide; however, this translation includes two in-frame stop codons.

SEQ ID NO:51 is the nucleotide sequence from Sudan grass that encodes SS-DTP21-3, a polypeptide homologous to SS-DTP21-1.

SEQ ID NO:52 is the amino acid sequence of the polypeptide encoded by SEQ ID NO:51.

SEQ ID NO:53 is the nucleotide sequence from Sudan grass that encodes SS-DTP21-4, a polypeptide homologous to SS-DTP21-1.

SEQ ID NO:54 is the amino acid sequence of the polypeptide encoded by SEQ ID NO:53.

SEQ ID NO:55 is the nucleotide sequence from Sudan grass that encodes SS-DTP21-5, a polypeptide homologous to SS-DTP21-1.

SEQ ID NO:56 is the amino acid sequence of the polypeptide encoded by SEQ ID NO:55.

SEQ ID NO:57 is the nucleotide sequence from Sudan grass that encodes SS-DTP21-7, a polypeptide homologous to SS-DTP21-1.

SEQ ID NO:58 is the amino acid sequence of the polypeptide encoded by SEQ ID NO:57.

SEQ ID NO:59 is the nucleotide sequence from Johnson grass that encodes SH-DTP21-1, a polypeptide homologous to SS-DTP21-1.

SEQ ID NO:60 is the amino acid sequence of the polypeptide encoded by SEQ ID NO:59.

SEQ ID NO:61 is the nucleotide sequence from Johnson grass that encodes SH-DTP21-2, a polypeptide homologous to SS-DTP21-1.

SEQ ID NO:62 is the amino acid sequence of the polypeptide encoded by SEQ ID NO:61.

SEQ ID NO:63 is the nucleotide sequence from sugarcane that encodes SO-DTP21-1, a polypeptide homologous to SS-DTP21-1.

SEQ ID NO:64 is the amino acid sequence of the polypeptide encoded by SEQ ID NO:63.

SEQ ID NO:65 is the nucleotide sequence from sugarcane that encodes SO-DTP21-2, a polypeptide homologous to SS-DTP21-1.

SEQ ID NO:66 is the amino acid sequence of the polypeptide encoded by SEQ ID NO:65.

SEQ ID NO:67 is the nucleotide sequence of the SS-DTP21-1-5'attB forward primer, containing the attB1 sequence, used to amplify the SS-DTP21-1 protein-coding region.

SEQ ID NO:68 is the nucleotide sequence of the SS-DTP21-1-3'attB reverse primer, containing the attB2 sequence, used to amplify the SS-DTP21-1 protein-coding region.

SEQ ID NO:69 is the nucleotide sequence of the attB1 site.

SEQ ID NO:70 is the nucleotide sequence of the attB2 site.

SEQ ID NO:71 is the nucleotide sequence of pBC-yellow, a destination vector for use with *Arabidopsis*.

SEQ ID NO:72 is the nucleotide sequence of the SS-DTP21-2-5'attB forward primer, containing the attB1 sequence, used to amplify the SS-DTP21-2 protein-coding region.

SEQ ID NO:73 is the nucleotide sequence of the SS-STP21-2-3'attB reverse primer, containing the attB2 sequence, used to amplify the SS-DTP21-2 protein-coding region.

SEQ ID NO:74 is the nucleotide sequence of the GENERACER™ 5' primer.

SEQ ID NO:75 is the nucleotide sequence of the GENERACER™ 5' nested primer.

SEQ ID NO:76 is the nucleotide sequence of the GENERACER™ 3' primer.

SEQ ID NO:77 is the nucleotide sequence of the GENERACER™ 3' nested primer.

SEQ ID NO:78 is the nucleotide sequence from Sudan grass that encodes SS-DTP21-6, a polypeptide homologous to SS-DTP21-1.

SEQ ID NO:79 is the amino acid sequence of the polypeptide encoded by SEQ ID NO:78.

SEQ ID NO:80 is the nucleotide sequence from *Sorghum bicolor* (Gold sorgho) that encodes SB-DTP21-5, a polypeptide homologous to SS-DTP21-1.

SEQ ID NO:81 is the amino acid sequence of the polypeptide encoded by SEQ ID NO:80.

SEQ ID NO:82 is the nucleotide sequence from *Sorghum bicolor* (B35) that encodes SB-DTP21-6, a polypeptide homologous to SS-DTP21-1.

SEQ ID NO:83 is the amino acid sequence of the polypeptide encoded by SEQ ID NO:82.

SEQ ID NO:84 is the nucleotide sequence from *Sorghum bicolor* (hoki) that encodes SB-DTP21-9, a polypeptide homologous to SS-DTP21-1.

SEQ ID NO:85 is the amino acid sequence of the polypeptide encoded by SEQ ID NO:84.

SEQ ID NO:86 is the nucleotide sequence from *Sorghum bicolor* (hoki) that encodes SB-DTP21-10, a polypeptide homologous to SS-DTP21-1.

SEQ ID NO:87 is the amino acid sequence of the polypeptide encoded by SEQ ID NO:86.

SEQ ID NO:88 is the nucleotide sequence of a first primer used to amplify a region of Sub8 plasmid DNA in Example 20.

SEQ ID NO:89 is the nucleotide sequence of a second primer used to amplify a region of Sub8 plasmid DNA in Example 20.

SEQ ID NO:90 is the nucleotide sequence of a first primer used to amplify a region of pSB31 (Ishida et al. 1996 Nature Biotechnology 14:745-750) plasmid DNA in Example 20.

SEQ ID NO:91 is the nucleotide sequence of a second primer used to amplify a region of pSB31 plasmid DNA in Example 20.

The sequence descriptions and Sequence Listing attached hereto comply with the rules governing nucleotide and/or amino acid sequence disclosures in patent applications as set forth in 37 C.F.R. §1.821-1.825.

The Sequence Listing contains the one letter code for nucleotide sequence characters and the three letter codes for amino acids as defined in conformity with the IUPAC-IUBMB standards described in *Nucleic Acids Res.* 13:3021-3030 (1985) and in the *Biochemical J.* 219 (No. 2):345-373 (1984) which are herein incorporated by reference. The symbols and format used for nucleotide and amino acid sequence data comply with the rules set forth in 37 C.F.R. §1.822.

DETAILED DESCRIPTION

The disclosure of each reference set forth herein is hereby incorporated by reference in its entirety.

As used herein and in the appended claims, the singular forms "a", "an", and "the" include plural reference unless the context clearly dictates otherwise. Thus, for example, reference to "a plant" includes a plurality of such plants, reference to "a cell" includes one or more cells and equivalents thereof known to those skilled in the art, and so forth.

As used herein:

"Genomic Fragment IS125" refers to a genomic DNA fragment from *Sorghum sudanense* cv. Sugar Slim (Sudan grass) that upon transformation conveys a drought tolerant phenotype to rice cultivar Yukihikari. The "SS-DTP21-1 polypeptide" refers to a 209 amino acid polypeptide encoded by Genomic Fragment IS125 that is a drought tolerant candidate protein.

"Genomic Fragment IS127" refers to a genomic DNA fragment from *Sorghum sudanense* cv. Sugar Slim (Sudan grass) that upon transformation conveys a drought tolerant phenotype to rice cultivar Yukihikari. The "SS-DTP21-2 polypeptide" refers to a 209 amino acid polypeptide encoded by Genomic Fragment IS127 that is highly homologous to the SS-DTP21-1 drought tolerant candidate protein.

"SB-DTP21-1 polypeptide" and "SB-DTP21-2 polypeptide" refer to two polypeptides encoded by genomic DNA from *Sorghum bicolor* (Gold sorgho), each of which is highly homologous to the SS-DTP21-1 polypeptide.

"SB-DTP21-3 polypeptide" and "SB-DTP21-4 polypeptide" refer to two polypeptides encoded by genomic DNA from *Sorghum bicolor* (B35), each of which is highly homologous to the SS-DTP21-1 polypeptide.

"DTP21 polypeptide" refers to a protein with sequence homology to SS-DTP21-1 and which is capable upon transformation of conveying a drought tolerant phenotype in rice cultivar Yukihikari and/or in other plant species or cultivars. The terms "DTP21 polypeptide" and "DTP21 protein" are used interchangeably herein.

"Drought tolerance activity" of a polypeptide indicates that over-expression of the polypeptide in a transgenic plant confers increased drought tolerance to the transgenic plant relative to a reference or control plant.

The terms "monocot" and "monocotyledonous plant" are used interchangeably herein. A monocot of the current invention includes the Gramineae.

The terms "dicot" and "dicotyledonous plant" are used interchangeably herein. A dicot of the current invention includes the following families: Brassicaceae, Leguminosae, and Solanaceae.

The terms "full complement" and "full-length complement" are used interchangeably herein, and refer to a complement of a given nucleotide sequence, wherein the complement and the nucleotide sequence consist of the same number of nucleotides and are 100% complementary.

"*Arabidopsis*" and "*Arabidopsis thaliana*" are used interchangeably herein, unless otherwise indicated.

An "Expressed Sequence Tag" ("EST") is a DNA sequence derived from a cDNA library and therefore is a sequence which has been transcribed. An EST is typically obtained by a single sequencing pass of a cDNA insert. The sequence of an entire cDNA insert is termed the "Full-Insert Sequence" ("FIS"). A "Contig" sequence is a sequence assembled from two or more sequences that can be selected from, but not limited to, the group consisting of an EST, FIS and PCR sequence. A sequence encoding an entire or functional protein is termed a "Complete Gene Sequence" ("CGS") and can be derived from an FIS or a contig.

"Agronomic characteristic" is a measurable parameter including but not limited to, greenness, yield, growth rate, biomass, fresh weight at maturation, dry weight at maturation, fruit yield, seed yield, total plant nitrogen content, fruit nitrogen content, seed nitrogen content, nitrogen content in a vegetative tissue, total plant free amino acid content, fruit free amino acid content, seed free amino acid content, free amino acid content in a vegetative tissue, total plant protein content, fruit protein content, seed protein content, protein content in a vegetative tissue, drought tolerance, nitrogen uptake, root lodging, harvest index, stalk lodging, plant height, ear height, ear length, salt tolerance, early seedling vigor and seedling emergence under low temperature stress.

"Transgenic" refers to any cell, cell line, callus, tissue, plant part or plant, the genome of which has been altered by the presence of a heterologous nucleic acid, such as a recombinant DNA construct, including those initial transgenic events as well as those created by sexual crosses or asexual propagation from the initial transgenic event. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

"Genome" as it applies to plant cells encompasses not only chromosomal DNA found within the nucleus, but organelle DNA found within subcellular components (e.g., mitochondrial, plastid) of the cell.

"Plant" includes reference to whole plants, plant organs, plant tissues, seeds and plant cells and progeny of same. Plant cells include, without limitation, cells from seeds, suspension cultures, embryos, meristematic regions, callus tissue, leaves, roots, shoots, gametophytes, sporophytes, pollen, and microspores.

"Progeny" comprises any subsequent generation of a plant.

"Transgenic plant" includes reference to a plant which comprises within its genome a heterologous polynucleotide. For example, the heterologous polynucleotide is stably integrated within the genome such that the polynucleotide is passed on to successive generations. The heterologous polynucleotide may be integrated into the genome alone or as part of a recombinant DNA construct.

"Heterologous" with respect to sequence means a sequence that originates from a foreign species, or, if from the same species, is substantially modified from its native form in composition and/or genomic locus by deliberate human intervention.

"Polynucleotide", "nucleic acid sequence", "nucleotide sequence", or "nucleic acid fragment" are used interchangeably and is a polymer of RNA or DNA that is single- or double-stranded, optionally containing synthetic, non-natural or altered nucleotide bases. Nucleotides (usually found in their 5'-monophosphate form) are referred to by their single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

"Polypeptide", "peptide", "amino acid sequence" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The terms "polypeptide", "peptide", "amino acid sequence", and "protein" are also inclusive of modifications including, but not limited to, glycosylation, lipid attachment, sulfation, gamma-carboxylation of glutamic acid residues, hydroxylation and ADP-ribosylation.

"Messenger RNA (mRNA)" refers to the RNA that is without introns and that can be translated into protein by the cell.

"cDNA" refers to a DNA that is complementary to and synthesized from a mRNA template using the enzyme reverse transcriptase. The cDNA can be single-stranded or converted into the double-stranded form using the Klenow fragment of DNA polymerase I.

"Mature" protein refers to a post-translationally processed polypeptide; i.e., one from which any pre- or pro-peptides present in the primary translation product have been removed.

"Precursor" protein refers to the primary product of translation of mRNA; i.e., with pre- and pro-peptides still present. Pre- and pro-peptides may be and are not limited to intracellular localization signals.

"Isolated" refers to materials, such as nucleic acid molecules and/or proteins, which are substantially free or otherwise removed from components that normally accompany or interact with the materials in a naturally occurring environment. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

"Recombinant" refers to an artificial combination of two otherwise separated segments of sequence, e.g., by chemical synthesis or by the manipulation of isolated segments of nucleic acids by genetic engineering techniques. "Recombinant" also includes reference to a cell or vector, that has been modified by the introduction of a heterologous nucleic acid or a cell derived from a cell so modified, but does not encompass the alteration of the cell or vector by naturally occurring events (e.g., spontaneous mutation, natural transformation/transduction/transposition) such as those occurring without deliberate human intervention.

"Recombinant DNA construct" refers to a combination of nucleic acid fragments that are not normally found together in nature. Accordingly, a recombinant DNA construct may comprise regulatory sequences and coding sequences that are derived from different sources, or regulatory sequences and coding sequences derived from the same source, but arranged in a manner different than that normally found in nature.

The terms "entry clone" and "entry vector" are used interchangeably herein.

"Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to, promoters, translation leader sequences, introns, and polyadenylation recognition sequences. The terms "regulatory sequence" and "regulatory element" are used interchangeably herein.

"Promoter" refers to a nucleic acid fragment capable of controlling transcription of another nucleic acid fragment.

"Promoter functional in a plant" is a promoter capable of controlling transcription in plant cells whether or not its origin is from a plant cell.

"Tissue-specific promoter" and "tissue-preferred promoter" are used interchangeably, and refer to a promoter that is expressed predominantly but not necessarily exclusively in one tissue or organ, but that may also be expressed in one specific cell.

"Developmentally regulated promoter" refers to a promoter whose activity is determined by developmental events.

"Operably linked" refers to the association of nucleic acid fragments in a single fragment so that the function of one is regulated by the other. For example, a promoter is operably linked with a nucleic acid fragment when it is capable of regulating the transcription of that nucleic acid fragment.

"Expression" refers to the production of a functional product. For example, expression of a nucleic acid fragment may refer to transcription of the nucleic acid fragment (e.g., transcription resulting in mRNA or functional RNA) and/or translation of mRNA into a precursor or mature protein.

"Phenotype" means the detectable characteristics of a cell or organism.

"Introduced" in the context of inserting a nucleic acid fragment (e.g., a recombinant DNA construct) into a cell, means "transfection" or "transformation" or "transduction" and includes reference to the incorporation of a nucleic acid fragment into a eukaryotic or prokaryotic cell where the nucleic acid fragment may be incorporated into the genome of the cell (e.g., chromosome, plasmid, plastid or mitochondrial DNA), converted into an autonomous replicon, or transiently expressed (e.g., transfected mRNA).

A "transformed cell" is any cell into which a nucleic acid fragment (e.g., a recombinant DNA construct) has been introduced.

"Transformation" as used herein refers to both stable transformation and transient transformation.

"Stable transformation" refers to the introduction of a nucleic acid fragment into a genome of a host organism resulting in genetically stable inheritance. Once stably transformed, the nucleic acid fragment is stably integrated in the genome of the host organism and any subsequent generation.

"Transient transformation" refers to the introduction of a nucleic acid fragment into the nucleus, or DNA-containing organelle, of a host organism resulting in gene expression without genetically stable inheritance.

"Allele" is one of several alternative forms of a gene occupying a given locus on a chromosome. When the alleles present at a given locus on a pair of homologous chromosomes in a diploid plant are the same that plant is homozygous at that locus. If the alleles present at a given locus on a pair of homologous chromosomes in a diploid plant differ that plant is heterozygous at that locus. If a transgene is present on one of a pair of homologous chromosomes in a diploid plant that plant is hemizygous at that locus.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels (1991) *Ann. Rev. Plant Phys. Plant Mol. Biol.* 42:21-53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys.* 100:1627-1632). A "mitochondrial signal peptide" is an amino acid sequence which directs a precursor protein into the mitochondria (Zhang and Glaser (2002) *Trends Plant Sci* 7:14-21).

The percent identity between two amino acid or nucleic acid sequences may be determined by visual inspection and mathematical calculation.

Alternatively, sequence alignments and percent identity calculations may be determined using a variety of comparison methods designed to detect homologous sequences including, but not limited to, the MEGALIGN® program of the LASERGENE® bioinformatics computing suite (DNASTAR® Inc., Madison, Wis.). Unless stated otherwise, multiple alignment of the sequences provided herein were performed using the Clustal V method of alignment (Higgins and Sharp (1989) CABIOS. 5:151 153) with the default parameters (GAP PENALTY=10, GAP LENGTH PENALTY=10). Default parameters for pairwise alignments and calculation of percent identity of protein sequences using the Clustal V method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences, using the Clustal V program, it is possible to obtain "percent identity" and "divergence" values by viewing the "sequence distances" table on the same program; unless stated otherwise, percent identities and divergences provided and claimed herein were calculated in this manner.

Alternatively, the percent identity of two protein sequences may be determined by comparing sequence information based on the algorithm of Needleman, S. B. and Wunsch, C. D. (J. Mol. Biol., 48:443-453, 1970) and using the GAP computer program available from the University of Wisconsin Genetics Computer Group (UWGCG). The preferred default parameters for the GAP program include: (1) a scoring matrix, blosum62, as described by Henikoff, S. and Henikoff, J. G. (Proc. Natl. Acad. Sci. USA, 89:10915-10919, 1992); (2) a gap weight of 12; (3) a gap length weight of 4; and (4) no penalty for end gaps.

Other programs used by those skilled in the art of sequence comparison may also be used. The percent identity can be determined by comparing sequence information using, e.g., the BLAST program described by Altschul et al. (Nucl. Acids. Res., 25, p. 3389-3402, 1997). This program is available on the Internet at the web site of the National Center for Biotechnology Information (NCBI) or the DNA Data Bank of Japan (DDBJ). The details of various conditions (parameters) for identity search using the BLAST program are shown on these web sites, and default values are commonly used for search although part of the settings may be changed as appropriate. Alternatively, the percent identity of two amino acid sequences may be determined by using a program such as genetic information processing software GENETYX Ver.7 (Genetyx Corporation, Japan) or using an algorithm such as FASTA. In this case, default values may be used for search.

The percent identity between two nucleic acid sequences can be determined by visual inspection and mathematical calculation, or more preferably, the comparison is done by comparing sequence information using a computer program. An exemplary, preferred computer program is the Genetic Computer Group (GCG®; Madison, Wis.) WISCONSIN PACKAGE® version 10.0 program, "GAP" (Devereux et al., 1984, Nucl. Acids Res., 12:387). In addition to making a comparison between two nucleic acid sequences, this "GAP" program can be used for comparison between two amino acid sequences and between a nucleic acid sequence and an amino acid sequence. The preferred default parameters for the "GAP" program include: (1) the GCG® implementation of a unary comparison matrix (containing a value of 1 for identities and 0 for non-identities) for nucleotides, and the weighted amino acid comparison matrix of Gribskov and Burgess, Nucl. Acids Res., 14:6745, 1986, as described by Schwartz and Dayhoff, eds., "Atlas of Polypeptide Sequence and Structure," National Biomedical Research Foundation, pp. 353-358, 1979, or other comparable comparison matrices; (2) a penalty of 30 for each gap and an additional penalty of 1 for each symbol in each gap for amino acid sequences, or penalty of 50 for each gap and an additional penalty of 3 for each symbol in each gap for nucleotide sequences; (3) no penalty for end gaps; and (4) no maximum penalty for long gaps. Other programs used by those skilled in the art of sequence comparison can also be used, such as, for example, the BLASTN program version 2.2.7, available for use via the National Library of Medicine website, or the WU-BLAST 2.0 algorithm (Advanced Biocomputing, LLC). In addition, the BLAST algorithm uses the BLOSUM62 amino acid scoring matrix, and optional parameters that can be used are as follows: (A) inclusion of a filter to mask segments of the query sequence that have low compositional complexity (as determined by the SEG program of Wootton and Federhen (Computers and Chemistry, 1993); also see Wootton and Federhen, 1996, "Analysis of compositionally biased regions in sequence databases," Methods Enzymol., 266: 554-71) or segments consisting of short-periodicity internal repeats (as determined by the XNU program of Claverie and States (Computers and Chemistry, 1993)), and (B) a statistical significance threshold for reporting matches against database sequences, or E-score (the expected probability of matches being found merely by chance, according to the stochastic model of Karlin and Altschul, 1990; if the statistical significance ascribed to a match is greater than this E-score threshold, the match will not be reported); preferred E-score threshold values are 0.5, or in order of increasing preference, 0.25, 0.1, 0.05, 0.01, 0.001, 0.0001, 1e-5, 1e-10, 1e-15, 1e-20, 1e-25, 1e-30, 1e-40, 1e-50, 1e-75, or 1e-100.

Standard recombinant DNA and molecular cloning techniques used herein are well known in the art and are described more fully in Sambrook, J., Fritsch, E. F. and Maniatis, T. *Molecular Cloning: A Laboratory Manual*; Cold Spring Harbor Laboratory Press: Cold Spring Harbor, 1989 (hereinafter "Sambrook").

Turning now to the embodiments:

Embodiments include isolated polynucleotides and polypeptides, recombinant DNA constructs useful for conferring drought tolerance, compositions (such as plants or seeds) comprising these recombinant DNA constructs, and methods utilizing these recombinant DNA constructs.

Isolated Polynucleotides and Polypeptides:

The present invention includes the following isolated polynucleotides and polypeptides:

An isolated polynucleotide comprising: (i) a nucleic acid sequence encoding a polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO:27, 32, 46, 56, 60, 64, 81, 83, 85 or 87; or (ii) a full complement of the nucleic acid sequence of (i), wherein the full complement and the nucleic acid sequence of (i) consist of the same number of nucleotides and are 100% complementary. Any of the foregoing isolated polynucleotides may be utilized in any recombinant DNA constructs of the present invention. The polypeptide is preferably a DTP21 polypeptide.

An isolated polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO:27, 32, 46, 56, 60, 64, 81, 83, 85 or 87. The polypeptide is preferably a DTP21 polypeptide.

An isolated polypeptide wherein the amino acid sequence is derived from SEQ ID NO:27, 32, 46, 56, 60, 64, 81, 83, 85 or 87 by alteration of one or more amino acids by at least one method selected from the group consisting of: deletion, substitution, addition and insertion; and (c) a polypeptide wherein the amino acid sequence of the polypeptide comprises SEQ ID NO:27, 32, 46, 56, 60, 64, 81, 83, 85 or 87. The polypeptide is preferably a DTP21 polypeptide.

An isolated polynucleotide comprising (i) a nucleic acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO:26, 31, 44, 55, 59, 63, 80, 82, 84 or 86; or (ii) a full complement of the nucleic acid sequence of (i). Any of the foregoing isolated polynucleotides may be utilized in any recombinant DNA constructs of the present invention. The isolated polynucleotide preferably encodes a DTP21 polypeptide.

An isolated polynucleotide comprising a nucleotide sequence encoding a polypeptide with drought tolerance activity, wherein the nucleotide sequence is hybridizable under stringent conditions with a DNA molecule comprising the full complement of SEQ ID NO:26, 31, 44, 55, 59, 63, 80, 82, 84 or 86;

An isolated polynucleotide comprising a nucleotide sequence encoding a polypeptide with drought tolerance activity, wherein the nucleotide sequence is derived from SEQ ID NO:26, 31, 44, 55, 59, 63, 80, 82, 84 or 86 by alteration of one or more nucleotides by at least one method selected from the group consisting of: deletion, substitution, addition and insertion.

Recombinant DNA Constructs:

In one aspect, the present invention includes recombinant DNA constructs.

In one embodiment, a recombinant DNA construct comprises a polynucleotide operably linked to at least one regulatory sequence (e.g., a promoter functional in a plant), wherein the polynucleotide comprises (i) a nucleic acid sequence encoding an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO:27, 32, 46, 56, 60, 64, 81, 83, 85 or 87; or (ii) a full complement of the nucleic acid sequence of (i).

In another embodiment, a recombinant DNA construct comprises a polynucleotide operably linked to at least one regulatory sequence (e.g., a promoter functional in a plant), wherein said polynucleotide comprises (i) a nucleic acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO:26, 31, 44, 55, 59, 63, 80, 82, 84 or 86; or (ii) a full complement of the nucleic acid sequence of (i).

In another embodiment, a recombinant DNA construct comprises a polynucleotide operably linked to at least one regulatory sequence (e.g., a promoter functional in a plant), wherein said polynucleotide encodes a DTP21 polypeptide. The DTP21 polypeptide may be from *Arabidopsis thaliana, Zea mays, Glycine max, Glycine tabacina, Glycine soja* and *Glycine tomentella.*

It is understood, as those skilled in the art will appreciate, that the invention encompasses more than the specific exemplary sequences. Alterations in a nucleic acid fragment which result in the production of a chemically equivalent amino acid at a given site, but do not affect the functional properties of the encoded polypeptide, are well known in the art. For example, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products.

The protein of the current invention may also be a protein which comprises an amino acid sequence comprising deletion, substitution, insertion and/or addition of one or more amino acids in an amino acid sequence selected from the group consisting of SEQ ID NO:27, 32, 41, 42, 45, 46, 52, 54, 56, 58, 60, 62, 64 and 66. The substitution may be conservative, which means the replacement of a certain amino acid residue by another residue having similar physical and chemical characteristics. Non-limiting examples of conservative substitution include replacement between aliphatic group-containing amino acid residues such as Ile, Val, Leu or Ala, and replacement between polar residues such as Lys-Arg, Glu-Asp or Gln-Asn replacement.

Proteins derived by amino acid deletion, substitution, insertion and/or addition can be prepared when DNAs encoding their wild-type proteins are subjected to, for example, well-known site-directed mutagenesis (see, e.g., Nucleic Acid Research, Vol. 10, No. 20, p. 6487-6500, 1982, which is hereby incorporated by reference in its entirety). As used herein, the term "one or more amino acids" is intended to mean a possible number of amino acids which may be deleted, substituted, inserted and/or added by site-directed mutagenesis.

Site-directed mutagenesis may be accomplished, for example, as follows using a synthetic oligonucleotide primer that is complementary to single-stranded phage DNA to be mutated, except for having a specific mismatch (i.e., a desired mutation). Namely, the above synthetic oligonucleotide is used as a primer to cause synthesis of a complementary strand by phages, and the resulting duplex DNA is then used to transform host cells. The transformed bacterial culture is plated on agar, whereby plaques are allowed to form from phage-containing single cells. As a result, in theory, 50% of new colonies contain phages with the mutation as a single strand, while the remaining 50% have the original sequence. At a temperature which allows hybridization with DNA completely identical to one having the above desired mutation, but not with DNA having the original strand, the resulting plaques are allowed to hybridize with a synthetic probe labeled by kinase treatment. Subsequently, plaques hybridized with the probe are picked up and cultured for collection of their DNA.

Techniques for allowing deletion, substitution, insertion and/or addition of one or more amino acids in the amino acid sequences of biologically active peptides such as enzymes while retaining their activity include site-directed mutagenesis mentioned above, as well as other techniques such as those for treating a gene with a mutagen, and those in which a gene is selectively cleaved to remove, substitute, insert or add a selected nucleotide or nucleotides, and then ligated.

The protein of the present invention may also be a protein which is encoded by a nucleic acid comprising a nucleotide sequence comprising deletion, substitution, insertion and/or addition of one or more nucleotides in a nucleotide sequence selected from the group consisting of SEQ ID NO:26, 31, 39, 40, 43, 44, 51, 53, 55, 57, 59, 60, 63 and 65. Nucleotide deletion, substitution, insertion and/or addition may be accomplished by site-directed mutagenesis or other techniques as mentioned above.

The protein of the present invention may also be a protein which is encoded by a nucleic acid comprising a nucleotide sequence hybridizable under stringent conditions with the complementary strand of a nucleotide sequence selected from the group consisting of SEQ ID NO:26, 31, 39, 40, 43, 44, 51, 53, 55, 57, 59, 60, 63 and 65.

The term "under stringent conditions" means that two sequences hybridize under moderately or highly stringent conditions. More specifically, moderately stringent conditions can be readily determined by those having ordinary skill in the art, e.g., depending on the length of DNA. The basic conditions are set forth by Sambrook et al., Molecular Cloning: A Laboratory Manual, third edition, chapters 6 and 7, Cold Spring Harbor Laboratory Press, 2001 and include the use of a prewashing solution for nitrocellulose filters 5×SSC, 0.5% SDS, 1.0 mM EDTA (pH 8.0), hybridization conditions of about 50% formamide, 2×SSC to 6×SSC at about 40-50° C. (or other similar hybridization solutions, such as Stark's solution, in about 50% formamide at about 42° C.) and washing conditions of, for example, about 40-60° C., 0.5-6×SSC, 0.1% SDS. Preferably, moderately stringent conditions include hybridization (and washing) at about 50° C. and 6×SSC. Highly stringent conditions can also be readily determined by those skilled in the art, e.g., depending on the length of DNA.

Generally, such conditions include hybridization and/or washing at higher temperature and/or lower salt concentration (such as hybridization at about 65° C., 6×SSC to 0.2×SSC, preferably 6×SSC, more preferably 2×SSC, most preferably 0.2×SSC), compared to the moderately stringent conditions. For example, highly stringent conditions may include hybridization as defined above, and washing at approximately 65-68° C., 0.2×SSC, 0.1% SDS. SSPE (1×SSPE is 0.15 M NaCl, 10 mM NaH2PO4, and 1.25 mM EDTA, pH 7.4) can be substituted for SSC (1×SSC is 0.15 M NaCl and 15 mM sodium citrate) in the hybridization and washing buffers; washing is performed for 15 minutes after hybridization is completed.

It is also possible to use a commercially available hybridization kit which uses no radioactive substance as a probe. Specific examples include hybridization with an ECL direct labeling & detection system (Amersham). Stringent conditions include, for example, hybridization at 42° C. for 4 hours using the hybridization buffer included in the kit, which is supplemented with 5% (w/v) Blocking reagent and 0.5 M NaCl, and washing twice in 0.4% SDS, 0.5×SSC at 55° C. for 20 minutes and once in 2×SSC at room temperature for 5 minutes.

The protein of the present invention is preferably a protein with drought tolerance activity.

"Suppression DNA construct" is a recombinant DNA construct which when transformed or stably integrated into the genome of the plant, results in "silencing" of a target gene in the plant. The target gene may be endogenous or transgenic to the plant. "Silencing," as used herein with respect to the target gene, refers generally to the suppression of levels of mRNA or protein/enzyme expressed by the target gene, and/or the level of the enzyme activity or protein functionality. The terms "suppression", "suppressing" and "silencing", used interchangeably herein, include lowering, reducing, declining, decreasing, inhibiting, eliminating or preventing. "Silencing" or "gene silencing" does not specify mechanism and is inclusive, and not limited to, anti-sense, cosuppression, viral-suppression, hairpin suppression, stem-loop suppression, RNAi-based approaches, and small RNA-based approaches.

A suppression DNA construct may comprise a region derived from a target gene of interest and may comprise all or part of the nucleic acid sequence of the sense strand (or antisense strand) of the target gene of interest. Depending upon the approach to be utilized, the region may be 100% identical or less than 100% identical (e.g., at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical) to all or part of the sense strand (or antisense strand) of the gene of interest.

Suppression DNA constructs are well-known in the art, are readily constructed once the target gene of interest is selected, and include, without limitation, cosuppression constructs, antisense constructs, viral-suppression constructs, hairpin suppression constructs, stem-loop suppression constructs, double-stranded RNA-producing constructs, and more generally, RNAi (RNA interference) constructs and small RNA constructs such as sRNA (short interfering RNA) constructs and miRNA (microRNA) constructs.

"Antisense inhibition" refers to the production of antisense RNA transcripts capable of suppressing the expression of the target gene or gene product. "Antisense RNA" refers to an RNA transcript that is complementary to all or part of a target primary transcript or mRNA and that blocks the expression of a target isolated nucleic acid fragment (U.S. Pat. No. 5,107,065). The complementarity of an antisense RNA may be with any part of the specific gene transcript, i.e., at the 5' non-coding sequence, 3' non-coding sequence, introns, or the coding sequence.

"Cosuppression" refers to the production of sense RNA transcripts capable of suppressing the expression of the target gene or gene product. "Sense" RNA refers to RNA transcript that includes the mRNA and can be translated into protein within a cell or in vitro. Cosuppression constructs in plants have been previously designed by focusing on overexpression of a nucleic acid sequence having homology to a native mRNA, in the sense orientation, which results in the reduction of all RNA having homology to the overexpressed sequence (see Vaucheret et al., *Plant J.* 16:651-659 (1998); and Gura, *Nature* 404:804-808 (2000)).

Another variation describes the use of plant viral sequences to direct the suppression of proximal mRNA encoding sequences (PCT Publication No. WO 98/36083 published on Aug. 20, 1998).

Regulatory Sequences:

A recombinant DNA construct of the present invention may comprise at least one regulatory sequence.

A regulatory sequence may be a promoter.

A number of promoters can be used in recombinant DNA constructs of the present invention. The promoters can be selected based on the desired outcome, and may include constitutive, tissue-specific, inducible, or other promoters for expression in the host organism.

Promoters that cause a gene to be expressed in most cell types at most times are commonly referred to as "constitutive promoters".

High level, constitutive expression of the candidate gene under control of the 35S or UBI promoter may have pleiotropic effects, although candidate gene efficacy may be estimated when driven by a constitutive promoter. Use of tissue-specific and/or stress-specific promoters may eliminate undesirable effects but retain the ability to enhance drought tolerance. This effect has been observed in *Arabidopsis* (Kasuga et al. (1999) Nature Biotechnol. 17:287-91).

Suitable constitutive promoters for use in a plant host cell include, for example, the core promoter of the Rsyn7 promoter and other constitutive promoters disclosed in WO 99/43838 and U.S. Pat. No. 6,072,050; the core CaMV 35S promoter (Odell et al., Nature 313:810-812 (1985)); rice actin (McElroy et al., Plant Cell 2:163-171 (1990)); ubiquitin (Christensen et al., Plant Mol. Biol. 12:619-632 (1989) and Christensen et al., Plant Mol. Biol. 18:675-689 (1992)); pEMU (Last et al., Theor. Appl. Genet. 81:581-588 (1991)); MAS (Velten et al., EMBO J. 3:2723-2730 (1984)); ALS promoter (U.S. Pat. No. 5,659,026), and the like. Other constitutive promoters include, for example, those discussed in U.S. Pat. Nos. 5,608,149; 5,608,144; 5,604,121; 5,569,597; 5,466,785; 5,399,680; 5,268,463; 5,608,142; and 6,177,611.

In choosing a promoter to use in the methods of the invention, it may be desirable to use a tissue-specific or developmentally regulated promoter.

A tissue-specific or developmentally regulated promoter is a DNA sequence which regulates the expression of a DNA sequence selectively in the cells/tissues of a plant critical to tassel development, seed set, or both, and limits the expression of such a DNA sequence to the period of tassel development or seed maturation in the plant. Any identifiable promoter may be used in the methods of the present invention which causes the desired temporal and spatial expression.

Promoters which are seed or embryo-specific and may be useful in the invention include soybean Kunitz trypsin inhibitor (Kti3, Jofuku and Goldberg, Plant Cell 1:1079-1093 (1989)), patatin (potato tubers) (Rocha-Sosa, M., et al. (1989) EMBO J. 8:23-29), convicilin, vicilin, and legumin (pea cotyledons) (Rerie, W. G., et al. (1991) Mol. Gen. Genet. 259:149-157; Newbigin, E. J., et al. (1990) Planta 180:461-470; Higgins, T. J. V., et al. (1988) Plant. Mol. Biol. 11:683-695), zein (maize endosperm) (Schemthaner, J. P., et al. (1988) EMBO J. 7:1249-1255), phaseolin (bean cotyledon) (Segupta-Gopalan, C., et al. (1985) Proc. Natl. Acad. Sci. U.S.A. 82:3320-3324), phytohemagglutinin (bean cotyledon) (Voelker, T. et al. (1987) EMBO J. 6:3571-3577), B-conglycinin and glycinin (soybean cotyledon) (Chen, Z-L, et al. (1988) EMBO J. 7:297-302), glutelin (rice endosperm), hordein (barley endosperm) (Marris, C., et al. (1988) Plant Mol. Biol. 10:359-366), glutenin and gliadin (wheat endosperm) (Colot, V., et al. (1987) EMBO J. 6:3559-3564), and sporamin (sweet potato tuberous root) (Hattori, T., et al. (1990) Plant Mol. Biol. 14:595-604). Promoters of seed-specific genes operably linked to heterologous coding regions in chimeric gene constructions maintain their temporal and spatial expression pattern in transgenic plants. Such examples include *Arabidopsis thaliana* 2S seed storage protein gene promoter to express enkephalin peptides in *Arabidopsis* and *Brassica napus* seeds (Vanderkerckhove et al., Bio/Technology 7:L929-932 (1989)), bean lectin and bean beta-phaseolin promoters to express luciferase (Riggs et al., Plant Sci. 63:47-57 (1989)), and wheat glutenin promoters to express chloramphenicol acetyl transferase (Colot et al., EMBO J 6:3559-3564 (1987)).

Inducible promoters selectively express an operably linked DNA sequence in response to the presence of an endogenous or exogenous stimulus, for example by chemical compounds (chemical inducers) or in response to environmental, hormonal, chemical, and/or developmental signals. Inducible or regulated promoters include, for example, promoters regulated by light, heat, stress, flooding or drought, phytohormones, wounding, or chemicals such as ethanol, jasmonate, salicylic acid, or safeners.

Promoters for use in the current invention include the following: 1) the stress-inducible RD29A promoter (Kasuga et al. (1999) Nature Biotechnol. 17:287-91); 2) the barley promoter, B22E; expression of B22E is specific to the pedicel in developing maize kernels ("Primary Structure of a Novel Barley Gene Differentially Expressed in Immature Aleurone Layers". Klemsdal, S. S. et al., Mol. Gen. Genet. 228(1/2):9-16 (1991)); and 3) maize promoter, Zag2 ("Identification and molecular characterization of ZAG1, the maize homolog of the *Arabidopsis* floral homeotic gene AGAMOUS", Schmidt, R. J. et al., Plant Cell 5(7):729-737 (1993); "Structural characterization, chromosomal localization and phylogenetic evaluation of two pairs of AGAMOUS-like MADS-box genes from maize", Theissen et al. Gene 156(2):155-166 (1995); NCBI GenBank Accession No. X80206)). Zag2 transcripts can be detected 5 days prior to pollination to 7 to 8 days after pollination ("DAP"), and directs expression in the carpel of developing female inflorescences and Ciml which is specific to the nucleus of developing maize kernels. Ciml transcript is detected 4 to 5 days before pollination to 6 to 8 DAP. Other useful promoters include any promoter which can be derived from a gene whose expression is maternally associated with developing female florets.

Additional promoters for regulating the expression of the nucleotide sequences of the present invention in plants are stalk-specific promoters. Such stalk-specific promoters include the alfalfa S2A promoter (GenBank Accession No.

EF030816; Abrahams et al., Plant Mol. Biol. 27:513-528 (1995)) and S2B promoter (GenBank Accession No. EF030817) and the like, herein incorporated by reference.

Promoters may be derived in their entirety from a native gene, or be composed of different elements derived from different promoters found in nature, or even comprise synthetic DNA segments.

Promoters for use in the current invention may include: RIP2, mLIP15, ZmCOR1, Rab17, CaMV 35S, RD29A, B22E, Zag2, SAM synthetase, ubiquitin, CaMV 19S, nos, Adh, sucrose synthase, R-allele, the vascular tissue preferred promoters S2A (Genbank accession number EF030816) and S2B (Genbank accession number EF030817), and the constitutive promoter GOS2 from *Zea mays*. Other promoters include root preferred promoters, such as the maize NAS2 promoter, the maize Cyclo promoter (US 2006/0156439, published Jul. 13, 2006), the maize ROOTMET2 promoter (WO05063998, published Jul. 14, 2005), the CR1BIO promoter (WO06055487, published May 26, 2006), the CRWAQ81 (WO005035770, published Apr. 21, 2005) and the maize ZRP2.47 promoter (NCBI accession number: U38790; GI No. 1063664), Recombinant DNA constructs of the present invention may also include other regulatory sequences, including but not limited to, translation leader sequences, introns, and polyadenylation recognition sequences. In another embodiment of the present invention, a recombinant DNA construct of the present invention further comprises an enhancer or silencer.

An intron sequence can be added to the 5' untranslated region, the protein-coding region or the 3' untranslated region to increase the amount of the mature message that accumulates in the cytosol. Inclusion of a spliceable intron in the transcription unit in both plant and animal expression constructs has been shown to increase gene expression at both the mRNA and protein levels up to 1000-fold. Buchman and Berg, *Mol. Cell Biol.* 8:4395-4405 (1988); Callis et al., *Genes Dev.* 1:1183-1200 (1987).

Any plant can be selected for the identification of regulatory sequences and DTP21 polypeptide genes to be used in recombinant DNA constructs of the present invention. Examples of suitable plant targets for the isolation of genes and regulatory sequences would include but are not limited to alfalfa, apple, apricot, *Arabidopsis*, artichoke, arugula, asparagus, avocado, banana, barley, beans, beet, blackberry, blueberry, broccoli, brussels sprouts, cabbage, canola, cantaloupe, carrot, cassava, castorbean, cauliflower, celery, cherry, chicory, cilantro, citrus, clementines, clover, coconut, coffee, corn, cotton, cranberry, cucumber, Douglas fir, eggplant, endive, escarole, eucalyptus, fennel, figs, garlic, gourd, grape, grapefruit, honey dew, jicama, kiwifruit, lettuce, leeks, lemon, lime, Loblolly pine, linseed, mango, melon, mushroom, nectarine, nut, oat, oil palm, oil seed rape, okra, olive, onion, orange, an ornamental plant, palm, papaya, parsley, parsnip, pea, peach, peanut, pear, pepper, persimmon, pine, pineapple, plantain, plum, pomegranate, poplar, potato, pumpkin, quince, radiata pine, radicchio, radish, rapeseed, raspberry, rice, rye, *sorghum*, Southern pine, soybean, spinach, squash, strawberry, sugarbeet, sugarcane, sunflower, sweet potato, sweetgum, tangerine, tea, tobacco, tomato, triticale, turf, turnip, a vine, watermelon, wheat, yams, and zucchini.

Compositions:

A composition of the present invention is a plant comprising in its genome any of the recombinant DNA constructs of the present invention (such as any of the constructs discussed above). Compositions also include any progeny of the plant, and any seed obtained from the plant or its progeny, wherein the progeny or seed comprises within its genome the recombinant DNA construct. Progeny includes subsequent generations obtained by self-pollination or outcrossing of a plant. Progeny also includes hybrids and inbreds.

In hybrid seed propagated crops, mature transgenic plants can be self-pollinated to produce a homozygous inbred plant. The inbred plant produces seed containing the newly introduced recombinant DNA construct. These seeds can be grown to produce plants that would exhibit an altered agronomic characteristic (e.g., an increased agronomic characteristic optionally under water limiting conditions), or used in a breeding program to produce hybrid seed, which can be grown to produce plants that would exhibit such an altered agronomic characteristic. The seeds may be maize seeds.

The plant may be a monocotyledonous or dicotyledonous plant, for example, a maize, rice or soybean plant, such as a maize hybrid plant or a maize inbred plant. The plant may also be sunflower, *sorghum*, canola, wheat, alfalfa, cotton, barley, millet, sugarcane, switchgrass, tobacco, potato and sugar beet.

The recombinant DNA construct may be stably integrated into the genome of the plant.

Particularly embodiments include but are not limited to the following:

1. A plant (for example, a maize, rice or soybean plant) comprising in its genome a recombinant DNA construct comprising a polynucleotide operably linked to at least one regulatory sequence, wherein said polynucleotide encodes a polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO:27, 32, 46, 56, 60, 64, 81, 83, 85 or 87, and wherein said plant exhibits increased drought tolerance when compared to a control plant not comprising said recombinant DNA construct. The plant may further exhibit an alteration of at least one agronomic characteristic when compared to the control plant.

2. A plant (for example, a maize, rice or soybean plant) comprising in its genome a recombinant DNA construct comprising a polynucleotide operably linked to at least one regulatory sequence, wherein said polynucleotide encodes a DTP21 polypeptide, and wherein said plant exhibits increased drought tolerance when compared to a control plant not comprising said recombinant DNA construct. The plant may further exhibit an alteration of at least one agronomic characteristic when compared to the control plant.

3. A plant (for example, a maize, rice or soybean plant) comprising in its genome a recombinant DNA construct comprising a polynucleotide operably linked to at least one regulatory sequence, wherein said polynucleotide encodes a DTP21 polypeptide, and wherein said plant exhibits an alteration of at least one agronomic characteristic when compared to a control plant not comprising said recombinant DNA construct.

4. A plant (for example, a maize, rice or soybean plant) comprising in its genome a recombinant DNA construct comprising a polynucleotide operably linked to at least one regulatory element, wherein said polynucleotide encodes a polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO:27, 32, 46, 56, 60, 64, 81, 83, 85 or 87, and wherein said plant exhibits an alteration of at least one agronomic characteristic when compared to a control plant not comprising said recombinant DNA construct.

5. A plant (for example, a maize, rice or soybean plant) comprising in its genome a recombinant DNA construct comprising a polynucleotide operably linked to at least one regulatory element, wherein said polynucleotide comprises a nucleotide sequence encoding a polypeptide with drought tolerance activity, wherein the nucleotide sequence is: (a) hybridizable under stringent conditions with a DNA molecule comprising the full complement of SEQ ID NO:26, 31, 44, 55, 59, 63, 80, 82, 84 or 86; or (b) derived from SEQ ID NO:26, 31, 44, 55, 59, 63, 80, 82, 84 or 86 by alteration of one or more nucleotides by at least one method selected from the group consisting of: deletion, substitution, addition and insertion; and wherein said plant exhibits increased drought tolerance when compared to a control plant not comprising said recombinant DNA construct.

6. A plant (for example, a maize, rice or soybean plant) comprising in its genome a recombinant DNA construct comprising a polynucleotide operably linked to at least one regulatory element, wherein said polynucleotide comprises a nucleotide sequence encoding a polypeptide with drought tolerance activity, wherein the nucleotide sequence is: (a) hybridizable under stringent conditions with a DNA molecule comprising the full complement of SEQ ID NO:26, 31, 44, 55, 59, 63, 80, 82, 84 or 86; or (b) derived from SEQ ID NO:26, 31, 44, 55, 59, 63, 80, 82, 84 or 86 by alteration of one or more nucleotides by at least one method selected from the group consisting of: deletion, substitution, addition and insertion; and wherein said plant exhibits an alteration of at least one agronomic characteristic when compared to a control plant not comprising said recombinant DNA construct.

7. A plant (for example, a maize, rice or soybean plant) comprising in its genome a recombinant DNA construct comprising a polynucleotide, wherein said polynucleotide comprises at least one nucleotide sequence selected from the group consisting of: (a) Genomic Fragment IS125; (b) Sub2 of Genomic Fragment IS125; (c) Sub3 of Genomic Fragment IS125; (d) Sub5 of Genomic Fragment IS125; (e) Sub7 of Genomic Fragment IS125; (f) Sub8 of Genomic Fragment IS125; and (g) Genomic Fragment IS127.

8. Any progeny of the above plants in embodiments 1-7, any seeds of the above plants in embodiments 1-7, any seeds of progeny of the above plants in embodiments 1-7, and cells from any of the above plants in embodiments 1-6 and progeny thereof.

In any of the foregoing embodiments 1-8 or any other embodiments of the present invention, the DTP21 polypeptide may be from *Arabidopsis thaliana, Zea mays, Glycine max, Glycine tabacina, Glycine soja* or *Glycine tomentella*.

In any of the foregoing embodiments 1-8 or any other embodiments of the present invention, the recombinant DNA construct may comprise at least a promoter functional in a plant as a regulatory sequence.

In any of the foregoing embodiments 1-8 or any other embodiments of the present invention, the alteration of at least one agronomic characteristic is either an increase or decrease.

In any of the foregoing embodiments 1-8 or any other embodiments of the present invention, the at least one agronomic characteristic may be selected from the group consisting of: greenness, yield, growth rate, biomass, fresh weight at maturation, dry weight at maturation, fruit yield, seed yield, total plant nitrogen content, fruit nitrogen content, seed nitrogen content, nitrogen content in a vegetative tissue, total plant free amino acid content, fruit free amino acid content, seed free amino acid content, free amino acid content in a vegetative tissue, total plant protein content, fruit protein content, seed protein content, protein content in a vegetative tissue, drought tolerance, nitrogen uptake, root lodging, harvest index, stalk lodging, plant height, ear height, ear length, salt tolerance, early seedling vigor and seedling emergence under low temperature stress. For example, the alteration of at least one agronomic characteristic may be an increase in yield, greenness or biomass.

In any of the foregoing embodiments 1-8 or any other embodiments of the present invention, the plant may exhibit the alteration of at least one agronomic characteristic when compared, under water limiting conditions, to a control plant not comprising said recombinant DNA construct.

"Drought" refers to a decrease in water availability to a plant that, especially when prolonged, can cause damage to the plant or prevent its successful growth (e.g., limiting plant growth or seed yield).

"Drought tolerance" is a trait of a plant to survive under drought conditions over prolonged periods of time without exhibiting substantial physiological or physical deterioration.

"Increased drought tolerance" of a plant is measured relative to a reference or control plant, and is a trait of the plant to survive under drought conditions over prolonged periods of time, without exhibiting the same degree of physiological or physical deterioration relative to the reference or control plant grown under similar drought conditions. Typically, when a transgenic plant comprising a recombinant DNA construct in its genome exhibits increased drought tolerance relative to a reference or control plant, the reference or control plant does not comprise in its genome the recombinant DNA construct.

One of ordinary skill in the art is familiar with protocols for simulating drought conditions and for evaluating drought tolerance of plants that have been subjected to simulated or naturally-occurring drought conditions. For example, one can simulate drought conditions by giving plants less water than normally required or no water over a period of time, and one can evaluate drought tolerance by looking for differences in physiological and/or physical condition, including (but not limited to) vigor, growth, size, or root length, or in particular, leaf color or leaf area size. Other techniques for evaluating drought tolerance include measuring chlorophyll fluorescence, photosynthetic rates and gas exchange rates.

A drought stress experiment may involve a chronic stress (i.e., slow dry down) and/or may involve two acute stresses (i.e., abrupt removal of water) separated by a day or two of recovery. Chronic stress may last 8-10 days. Acute stress may last 3-5 days. The following variables may be measured during drought stress and well watered treatments of transgenic plants and relevant control plants:

The variable "% area chg_start chronic—acute2" is a measure of the percent change in total area determined by remote visible spectrum imaging between the first day of chronic stress and the day of the second acute stress The variable "% area chg_start chronic—end chronic" is a measure of the percent change in total area determined by remote visible spectrum imaging between the first day of chronic stress and the last day of chronic stress.

The variable "% area chg_start chronic—harvest" is a measure of the percent change in total area determined by remote visible spectrum imaging between the first day of chronic stress and the day of harvest.

The variable "% area chg_start chronic—recovery24 hr" is a measure of the percent change in total area determined by remote visible spectrum imaging between the first day of chronic stress and 24 hrs into the recovery (24 hrs after acute stress 2).

The variable "psii_acute1" is a measure of Photosystem II (PSII) efficiency at the end of the first acute stress period. It provides an estimate of the efficiency at which light is absorbed by PSII antennae and is directly related to carbon dioxide assimilation within the leaf.

The variable "psii_acute2" is a measure of Photosystem II (PSII) efficiency at the end of the second acute stress period. It provides an estimate of the efficiency at which light is absorbed by PSII antennae and is directly related to carbon dioxide assimilation within the leaf.

The variable "fv/fm_acute1" is a measure of the optimum quantum yield (Fv/Fm) at the end of the first acute stress—(variable fluorescence difference between the maximum and minimum fluorescence/maximum fluorescence).

The variable "fv/fm_acute2" is a measure of the optimum quantum yield (Fv/Fm) at the end of the second acute stress—(variable flourescence difference between the maximum and minimum fluorescence/maximum fluorescence).

The variable "leaf rolling_harvest" is a measure of the ratio of top image to side image on the day of harvest.

The variable "leaf rolling_recovery24 hr" is a measure of the ratio of top image to side image 24 hours into the recovery.

The variable "Specific Growth Rate (SGR)" represents the change in total plant surface area (as measured by Lemna Tec Instrument) over a single day ($Y(t)=Y0*e^{r*t}$). $Y(t)=Y0*e^{r*t}$ is equivalent to % change in $Y/\Delta t$ where the individual terms are as follows: Y(t)=Total surface area at t; Y0=Initial total surface area (estimated); r=Specific Growth Rate day$^{-1}$, and t=Days After Planting ("DAP").

The variable "shoot dry weight" is a measure of the shoot weight 96 hours after being placed into a 104° C. oven.

The variable "shoot fresh weight" is a measure of the shoot weight immediately after being cut from the plant.

The Examples below describe some representative protocols and techniques for simulating drought conditions and/or evaluating drought tolerance.

One can also evaluate drought tolerance by the ability of a plant to maintain sufficient yield (at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% yield) in field testing under simulated or naturally-occurring drought conditions (e.g., by measuring for substantially equivalent yield under drought conditions compared to non-drought conditions, or by measuring for less yield loss under drought conditions compared to a control or reference plant).

One of ordinary skill in the art would readily recognize a suitable control or reference plant to be utilized when assessing or measuring an agronomic characteristic or phenotype of a transgenic plant in any embodiment of the present invention in which a control plant is utilized (e.g., compositions or methods as described herein). For example, by way of non-limiting illustrations:

1. Progeny of a transformed plant which is hemizygous with respect to a recombinant DNA construct, such that the progeny are segregating into plants either comprising or not comprising the recombinant DNA construct: the progeny comprising the recombinant DNA construct would be typically measured relative to the progeny not comprising the recombinant DNA construct (i.e., the progeny not comprising the recombinant DNA construct is the control or reference plant).

2. Introgression of a recombinant DNA construct into an inbred line, such as in maize, or into a variety, such as in soybean: the introgressed line would typically be measured relative to the parent inbred or variety line (i.e., the parent inbred or variety line is the control or reference plant).

3. Two hybrid lines, where the first hybrid line is produced from two parent inbred lines, and the second hybrid line is produced from the same two parent inbred lines except that one of the parent inbred lines contains a recombinant DNA construct: the second hybrid line would typically be measured relative to the first hybrid line (i.e., the first hybrid line is the control or reference plant).

4. A plant comprising a recombinant DNA construct: the plant may be assessed or measured relative to a control plant not comprising the recombinant DNA construct but otherwise having a comparable genetic background to the plant (e.g., sharing at least 90%, 91%, 92%, 93%, 94%, 95%, 96%, 97%, 98%, 99%, or 100% sequence identity of nuclear genetic material compared to the plant comprising the recombinant DNA construct. There are many laboratory-based techniques available for the analysis, comparison and characterization of plant genetic backgrounds; among these are Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLP®s), and Simple Sequence Repeats (SSRs) which are also referred to as Microsatellites.

Furthermore, one of ordinary skill in the art would readily recognize that a suitable control or reference plant to be utilized when assessing or measuring an agronomic characteristic or phenotype of a transgenic plant would not include a plant that had been previously selected, via mutagenesis or transformation, for the desired agronomic characteristic or phenotype.

Methods:

Methods include but are not limited to methods for increasing drought tolerance in a plant, methods for evaluating drought tolerance in a plant, methods for altering an agronomic characteristic in a plant, methods for determining an alteration of an agronomic characteristic in a plant, and methods for producing seed. The plant may be a monocotyledonous or dicotyledonous plant, for example, a maize, rice or soybean plant. The plant may also be sunflower, *sorghum*, canola, wheat, alfalfa, cotton, barley or millet. The seed may be a maize, rice or soybean seed, for example, a maize hybrid seed or maize inbred seed.

Methods include but are not limited to the following:

A method for transforming a cell comprising transforming a cell with any of the isolated polynucleotides of the present invention. The cell transformed by this method is also included. In particular embodiments, the cell is eukaryotic cell, e.g., a yeast, insect or plant cell, or prokaryotic, e.g., a bacterial cell.

A method for producing a transgenic plant comprising transforming a plant cell with any of the isolated polynucleotides or recombinant DNA constructs of the present invention and regenerating a transgenic plant from the transformed plant cell. The invention is also directed to the transgenic plant produced by this method, and transgenic seed obtained from this transgenic plant.

A method for isolating a polypeptide of the invention from a cell or culture medium of the cell, wherein the cell comprises a recombinant DNA construct comprising a polynucleotide of the invention operably linked to at least one regulatory sequence, and wherein the transformed host cell is grown under conditions that are suitable for expression of the recombinant DNA construct.

A method of altering the level of expression of a polypeptide of the invention in a host cell comprising: (a) transforming a host cell with a recombinant DNA construct of the present invention; and (b) growing the transformed host cell under conditions that are suitable for expression of the recombinant DNA construct wherein expression of the recombinant DNA construct results in production of altered levels of the polypeptide of the invention in the transformed host cell.

A method of increasing drought tolerance in a plant, comprising: (a) introducing into a regenerable plant cell a recombinant DNA construct comprising a polynucleotide operably linked to at least one regulatory sequence (for example, a promoter functional in a plant), wherein the polynucleotide encodes a polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO:27, 32, 46, 56, 60, 64, 81, 83, 85 or 87; and (b) regenerating a transgenic plant from the regenerable plant cell after step (a), wherein the transgenic plant comprises in its genome the recombinant DNA construct and exhibits increased drought tolerance when compared to a control plant not comprising the recombinant DNA construct. The method may further comprise (c) obtaining a progeny plant derived from the transgenic plant, wherein said progeny plant comprises in its genome the recombinant DNA construct and exhibits increased drought tolerance when compared to a control plant not comprising the recombinant DNA construct.

A method of increasing drought tolerance in a plant, comprising: (a) introducing into a regenerable plant cell a recombinant DNA construct comprising a polynucleotide operably linked to at least one regulatory element, wherein said polynucleotide comprises a nucleotide sequence encoding a polypeptide with drought tolerance activity, wherein the nucleotide sequence is: (a) hybridizable under stringent conditions with a DNA molecule comprising the full complement of SEQ ID NO:26, 31, 44, 55, 59, 63, 80, 82, 84 or 86; or (b) derived from SEQ ID NO:26, 31, 44, 55, 59, 63, 80, 82, 84 or 86 by alteration of one or more nucleotides by at least one method selected from the group consisting of: deletion, substitution, addition and insertion; and (b) regenerating a transgenic plant from the regenerable plant cell after step (a), wherein the transgenic plant comprises in its genome the recombinant DNA construct and exhibits increased drought tolerance when compared to a control plant not comprising the recombinant DNA construct. The method may further comprise (c) obtaining a progeny plant derived from the transgenic plant, wherein said progeny plant comprises in its genome the recombinant DNA construct and exhibits increased drought tolerance when compared to a control plant not comprising the recombinant DNA construct.

A method of evaluating drought tolerance in a plant, comprising (a) obtaining a transgenic plant, wherein the transgenic plant comprises in its genome a recombinant DNA construct comprising a polynucleotide operably linked to at least one regulatory sequence (for example, a promoter functional in a plant), wherein said polynucleotide encodes a polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO:27, 32, 46, 56, 60, 64, 81, 83, 85 or 87; (b) obtaining a progeny plant derived from said transgenic plant, wherein the progeny plant comprises in its genome the recombinant DNA construct; and (c) evaluating the progeny plant for drought tolerance compared to a control plant not comprising the recombinant DNA construct.

A method of evaluating drought tolerance in a plant, comprising (a) obtaining a transgenic plant, wherein the transgenic plant comprises in its genome a recombinant DNA construct comprising a polynucleotide operably linked to at least one regulatory element, wherein said polynucleotide comprises a nucleotide sequence encoding a polypeptide with drought tolerance activity, wherein the nucleotide sequence is: (a) hybridizable under stringent conditions with a DNA molecule comprising the full complement of SEQ ID NO:26, 31, 44, 55, 59, 63, 80, 82, 84 or 86; or (b) derived from SEQ ID NO:26, 31, 44, 55, 59, 63, 80, 82, 84 or 86 by alteration of one or more nucleotides by at least one method selected from the group consisting of: deletion, substitution, addition and insertion; (b) obtaining a progeny plant derived from said transgenic plant, wherein the progeny plant comprises in its genome the recombinant DNA construct; and (c) evaluating the progeny plant for drought tolerance compared to a control plant not comprising the recombinant DNA construct.

A method of determining an alteration of an agronomic characteristic in a plant, comprising (a) obtaining a transgenic plant, wherein the transgenic plant comprises in its genome a recombinant DNA construct comprising a polynucleotide operably linked to at least one regulatory sequence (for example, a promoter functional in a plant), wherein said polynucleotide encodes a polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO:27, 32, 46, 56, 60, 64, 81, 83, 85 or 87; (b) obtaining a progeny plant derived from said transgenic plant, wherein the progeny plant comprises in its genome the recombinant DNA construct; and (c) determining whether the progeny plant exhibits an alteration in at least one agronomic characteristic when compared, optionally under water limiting conditions, to a control plant not comprising the recombinant DNA construct.

A method of determining an alteration of an agronomic characteristic in a plant, comprising (a) obtaining a transgenic plant, wherein the transgenic plant comprises in its genome a recombinant DNA construct comprising a polynucleotide operably linked to at least one regulatory element, wherein said polynucleotide comprises a nucleotide sequence encoding a polypeptide with drought tolerance activity, wherein the nucleotide sequence is: (a) hybridizable under stringent conditions with a DNA molecule comprising the full complement of SEQ ID NO:26, 31, 44, 55, 59, 63, 80, 82, 84 or 86; or (b) derived from SEQ ID NO:26, 31, 44, 55, 59, 63, 80, 82, 84 or 86 by alteration of one or more nucleotides by at least one method selected from the group consisting of: deletion, substitution, addition and insertion; (b) obtaining a progeny plant derived from said transgenic plant, wherein the progeny plant comprises in its genome the recombinant DNA construct; and (c) determining whether the progeny plant exhibits an alteration in at least one agronomic characteristic when compared, optionally under water limiting conditions, to a control plant not comprising the recombinant DNA construct.

A method of producing seed (for example, seed that can be sold as a drought tolerant product offering) comprising any of the preceding methods, and further comprising obtaining seeds from said progeny plant, wherein said seeds comprise in their genome said recombinant DNA construct.

In any of the preceding methods or any other embodiments of methods of the present invention, in said introducing step said regenerable plant cell may comprise a callus cell, an embryogenic callus cell, a gametic cell, a meristematic cell, or a cell of an immature embryo. The regenerable plant cells may derive from an inbred maize plant.

In any of the preceding methods or any other embodiments of methods of the present invention, said regenerating step may comprise the following: (i) culturing said transformed plant cells in a media comprising an embryogenic promoting hormone until callus organization is observed; (ii) transferring said transformed plant cells of step (i) to a first media which includes a tissue organization promoting hormone; and (iii) subculturing said transformed plant cells after step (ii) onto a second media, to allow for shoot elongation, root development or both.

In any of the preceding methods or any other embodiments of methods of the present invention, the at least one agronomic characteristic may be selected from the group consisting of greenness, yield, growth rate, biomass, fresh weight at maturation, dry weight at maturation, fruit yield, seed yield, total plant nitrogen content, fruit nitrogen content, seed nitrogen content, nitrogen content in a vegetative tissue, total plant free amino acid content, fruit free amino acid content, seed free amino acid content, amino acid content in a vegetative tissue, total plant protein content, fruit protein content, seed protein content, protein content in a vegetative tissue, drought tolerance, nitrogen uptake, root lodging, harvest index, stalk lodging, plant height, ear height, ear length, salt tolerance, early seedling vigor and seedling emergence under low temperature stress. The alteration of at least one agronomic characteristic may be an increase in yield, greenness or biomass.

In any of the preceding methods or any other embodiments of methods of the present invention, the plant may exhibit the alteration of at least one agronomic characteristic when compared, under water limiting conditions, to a control plant not comprising said recombinant DNA construct.

In any of the preceding methods or any other embodiments of methods of the present invention, alternatives exist for introducing into a regenerable plant cell a recombinant DNA construct comprising a polynucleotide operably linked to at least one regulatory sequence. For example, one may introduce into a regenerable plant cell a regulatory sequence (such as one or more enhancers, optionally as part of a transposable element), and then screen for an event in which the regulatory sequence is operably linked to an endogenous gene encoding a polypeptide of the instant invention.

The introduction of recombinant DNA constructs of the present invention into plants may be carried out by any suitable technique, including but not limited to direct DNA uptake, chemical treatment, electroporation, microinjection, cell fusion, infection, vector-mediated DNA transfer, bombardment, or Agrobacterium-mediated transformation. Techniques for plant transformation and regeneration have been described in International Patent Publication WO 2009/006276, the contents of which are herein incorporated by reference.

The development or regeneration of plants containing the foreign, exogenous isolated nucleic acid fragment that encodes a protein of interest is well known in the art. The regenerated plants may be self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the present invention containing a desired polypeptide is cultivated using methods well known to one skilled in the art.

EXAMPLES

The present invention is further illustrated in the following Examples, in which parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

Example 1

Creation of a Sudan Grass Cosmid Library

Seeds of *Sorghum sudanense* cv. Sugar Slim (Sudan grass) were purchased from Kaneko Seeds Co., Ltd. and planted for cultivation in a greenhouse. Genomic DNA was extracted from leaves of the plants. The extracted genomic DNA was subjected to partial digestion with restriction enzyme TaqI and, thereafter, fractions containing DNA of 30 kb to 50 kb were prepared by sucrose density gradient centrifugation. DNA from those fractions was cloned into cosmid vector pSB200 that had been digested by Nsp (7524)V (also designated as "NspV" herein) to construct a genomic DNA library.

The cloning vector pSB200 was constructed from pSB11 (Komari et al. Plant J. 10:165-174, 1996). Specifically, a maize ubiquitin promoter was placed before a hygromycin resistance gene and the 3' terminal signal of NOS gene. A Nsp(7524)V cleavage site was added to the construct, which was then inserted into pSB11 thereby to construct pSB200. Using pSB200, one can construct a genomic DNA library having an average fragment length of about 40 kb. Vector pSB200 is also a transformation vector for higher plants and contains the hygromycin resistance gene for use as a selection marker. Most of the DNA fragments cloned in the library had sizes from about 30 kb to about 50 kb and the total number of clones was about 30,000. The *E. coli* strains used were DH5α™ and GENEHOGS®.

Example 2

Screens to Identify Transgenic Rice Lines with Enhanced Drought Tolerance

Original seeds of rice cultivar Yukihikari are purchased from a food retailer, and the progeny seeds are harvested in greenhouses. Original seeds of rice cultivar Suweon 287 are obtained from the National Institute of Agribiological Resources of Japan, and the progeny seeds are harvested in greenhouses.

The capability of rice plants to survive severe shortage of water in small containers is examined by the following method.

1) Six transgenic plants and one each of control plants Suweon 287 and Yukihikari are cultured together in soil in a small pot (10.5 cm in diameter, 9 cm in height, 570 ml in volume). Suweon 287 is a drought tolerant control cultivar, and Yukihikari is a drought susceptible control cultivar. Under this condition, roots are contained in a limited space so that the difference in capability to extend roots deep into the soil is not a factor in the assay. The overall condition of plants in this method is quite uniform because the variation in water content in soil within a pot is very small.

2) When the sixth leaf is extended, watering is withheld for between three and four days until leaves of control Yukihikari lose any apparent sign of viability. The level of dehydration may vary from pot to pot to some extent, but the appearance of control Yukihikari provides a good indication of the level of drought stress in the pot.

3) To facilitate scoring, plants are watered again and examined on the following day.

4) On the following day, plants are visually examined and scored according to the criteria described in Table 1.

TABLE 1

Criteria for Scoring in Rice Drought Assay

Appearance of top four leaves of a plant, which was watered again after drought stress

| Score | Viable part of leaf blade | Viable part of exposed area of leaf sheath |
|---|---|---|
| 0 | None | None |
| 1 | None | Less than half of sum of the four leaves |
| 2 | None | Half or more of sum of the four leaves |
| 3 | One leaf | Three quarters or more of sum of the four leaves |
| 4 | Two leaves | Three quarters or more of sum of the four leaves |
| 5 | Three or four leaves | All |

This assay is simple and highly reproducible. The scores of more than half of Suweon 287 plants are usually 2 or higher in this assay whereas the scores of susceptible plants rarely exceed 2. Therefore, when the scores of two or more plants in a tested line are 2 or higher, the line is recorded as drought tolerant.

Example 3

Identification of Sudan Grass Cosmids that Confer Drought Tolerance to Rice

The clones constituting the genomic DNA library derived from Sudan grass described in Example 1 were individually transferred into *Agrobacterium* strain LBA4404(pSB1) (Komari et al. Plant J. 10:165-174, 1996). The method used for transfer was triparental mating (Ditta et al. Proc. Natl. Acad. Sci. U.S.A. 77:7347-7351, 1980). The genomic DNA fragments in the resulting *Agrobacterium* lines carrying the clones were individually introduced into rice cultivar Yukihikari. The method of transformation was in accordance with Hiei et al. (Plant J. 6:271-282, 1994) and based on inoculation of immature embryos with *Agrobacterium*. A hygromycin resistance gene was used as a selection marker gene. The immature embryos of cultivar Yukihikari were obtained from plants cultivated in a greenhouse. Original seeds of rice cultivar Yukihikari were purchased from a food retailer, and the progeny seeds harvested in greenhouses were used.

Transgenic plants were obtained which contained individual genomic DNA fragments from Sudan grass. For each genomic DNA fragment, one or two individual plants from independent transformation events were obtained. Hereinafter, the transgenic plants of the initial generation will be referred to as T0 generation plants and their progeny as T1 generation, T2 generation and so on, according to the general rule.

T1 progeny plants derived from the transgenic plants were examined for drought tolerance. For each of the T0 transformants described above, six T1 plants were assayed. A total of 1045 of the genomic fragments from Sudan grass were thus ordered according to the scores in the first T1 assay, and 128 of them were selected from the top of the list for another T1 assay. Subsequently, 25 fragments were selected for further study.

T2 seeds were obtained from hygromycin-resistant T1 plants derived from rice transformed with each one of the 25 fragments. From each of the 25 T2 lines, 12 hygromycin-resistant plants were examined for drought tolerance. The T2 assay was repeated.

The progeny line of rice cultivar Yukihikari transformed with a particular genomic fragment from Sudan grass, which was designated as genomic fragment "IS125", was detected repeatedly as being drought tolerant in the T1 and T2 assays. The transgenic rice event containing genomic fragment IS125, as screened from these assays, was designated as "IS125 Event No. 1".

Tables 2, 3 and 4 show the results of the drought tolerance tests of transgenic rice IS125 Event No. 1 in the T1, T2, and T3 generations, respectively. In the T3 assay, 12 plants each of hygromycin-resistant and hygromycin-sensitive phenotypes were examined. As clearly demonstrated in this table, the drought tolerance trait conferred by genomic fragment IS125 was repeatedly detected and stably inherited up to the T3 generation and the drought tolerance and hygromycin resistance traits co-segregated.

TABLE 2

T1 Drought Assay of a Rice Line Transformed with Genomic Fragment IS125

| Exp. No. | Line | Total No. of Plants Tested | No. of Plants Scoring 2 or Higher | Drought Response |
|---|---|---|---|---|
| 1 | Yukihikari | 6 | 0 | Susceptible |
| 1 | Suweon 287 | 6 | 5 | Tolerant |
| 1 | IS125 Event No. 1 | 6 | 2 | Tolerant |
| 2 | Yukihikari | 6 | 0 | Susceptible |
| 2 | Suweon 287 | 6 | 3 | Tolerant |
| 2 | IS125 Event No. 1 | 6 | 4 | Tolerant |

TABLE 3

T2 Drought Assay of a Rice Line Transformed with Genomic Fragment IS125

| Exp. No. | Line | Total No. of Plants Tested | No. of Plants Scoring 2 or Higher | Drought Response |
|---|---|---|---|---|
| 1 | Yukihikari | 12 | 0 | Susceptible |
| 1 | Suweon 287 | 12 | 6 | Tolerant |
| 1 | IS125 Event No. 1 | 12 | 9 | Tolerant |
| 2 | Yukihikari | 12 | 0 | Susceptible |
| 2 | Suweon 287 | 12 | 10 | Tolerant |
| 2 | IS125 Event No. 1 | 12 | 10 | Tolerant |

TABLE 4

T3 Drought Assay of a Rice Line Transformed with Genomic Fragment IS125

| Exp. No. | Line | Total No. of Plants Tested | No. of Plants Scoring 2 or Higher | Drought Response |
|---|---|---|---|---|
| 1 | Yukihikari | 12 | 0 | Susceptible |
| 1 | Suweon 287 | 10 | 6 | Tolerant |
| 1 | Hygromycin-resistant progeny from IS125 Event No. 1 | 12 | 8 | Tolerant |
| 1 | Hygromycin-sensitive progeny from IS125 Event No. 1 | 12 | 1 | Susceptible |
| 2 | Yukihikari | 12 | 0 | Susceptible |
| 2 | Suweon 287 | 12 | 3 | Tolerant |
| 2 | Hygromycin-resistant progeny from IS125 Event No. 1 | 12 | 11 | Tolerant |
| 2 | Hygromycin-sensitive progeny from IS125 Event No. 1 | 12 | 0 | Susceptible |

Additionally, the rice cultivar Yukihikari was again transformed with genomic fragment IS125 as described above, and the additional events were examined for drought tolerance in the T1 generation. One of the transgenic rice events, designated as "IS125 Event No. 3", was clearly drought tolerant in the T1 generation (Table 5).

TABLE 5

T1 Drought Assay of Additional Rice Lines Transformed with Genomic Fragment IS125

| Line | Total No. of Plants Tested | No. of Plants Scoring 2 or Higher | Drought Response |
|---|---|---|---|
| Yukihikari | 12 | 0 | Susceptible |
| Suweon 287 | 12 | 8 | Tolerant |
| IS125 Event No. 2 | 12 | 0 | Susceptible |
| IS125 Event No. 3 | 12 | 10 | Tolerant |
| IS125 Event No. 4 | 12 | 0 | Susceptible |
| IS125 Event No. 5 | 12 | 1 | Susceptible |

The progeny line of rice cultivar Yukihikari transformed with a different genomic fragment from Sudan grass, which was designated as genomic fragment "IS127", also was detected repeatedly as drought tolerant in the T1 and T2 assays. The transgenic rice event of genomic fragment IS127 screened from these assays was designated as "IS127 Event No. 1". Table 6 shows the results of the drought tolerance test of transgenic rice IS127 Event No. 1 in the T3 generation. Thus, it was clearly demonstrated that the drought tolerance conferred by genomic fragment IS127 was repeatedly detected and stably inherited up to the T3 generation.

TABLE 6

T3 Drought Assay of a Rice Line Transformed with Genomic Fragment IS127

| Exp. No. | Line | Total No. of Plants Tested | No. of Plants Scoring 2 or Higher | Drought Response |
|---|---|---|---|---|
| 1 | Yukihikari | 12 | 0 | Susceptible |
| 1 | Suweon 287 | 12 | 3 | Tolerant |
| 1 | IS127 Event No. 1 | 12 | 10 | Tolerant |
| 2 | Yukihikari | 12 | 0 | Susceptible |
| 2 | Suweon 287 | 12 | 3 | Tolerant |
| 2 | IS127 Event No. 1 | 12 | 8 | Tolerant |

Additionally, rice cultivar Yukihikari was again transformed with genomic fragment IS127 as described above and the additional events were examined for drought tolerance in the T1 generation. All of the 3 transgenic rice events tested, designated "IS127 Event No. 2", "IS127 Event No. 3" and "IS127 Event No. 4", were clearly drought tolerant in the T1 generation (Table 7).

TABLE 7

T1 Drought Assay of Additional Rice Lines Transformed with Genomic Fragment IS127

| Line | Total No. of Plants Tested | No. of Plants Scoring 2 or Higher | Drought Response |
|---|---|---|---|
| Yukihikari | 12 | 0 | Susceptible |
| Suweon 287 | 12 | 8 | Tolerant |
| IS127 Event No. 2 | 12 | 4 | Tolerant |
| IS127 Event No. 3 | 12 | 7 | Tolerant |
| IS127 Event No. 4 | 12 | 6 | Tolerant |

Example 4

Identification of DTP21 as a Drought Tolerant Gene Candidate

As shown in EXAMPLE 3, it was found that genomic fragment IS125 from Sudan grass was capable of giving rice cultivar Yukihikari drought tolerance. Genomic fragment IS125 was fully sequenced by a standard procedure to obtain the sequence of SEQ ID NO:1 consisting of 42,104 nucleotides. PCR analysis was conducted to identify the regions of genomic fragment IS125 that are present in the transgenic rice line, IS125 Event No. 3. Six pairs of PCR primers (M1, M2, M3, M4, M5 and M6) were designed based on the sequence of genomic fragment IS125 as shown in FIG. 1. Additionally, primer pair M-Hpt is derived from the sequence of the selectable marker gene, HPT. DNA samples were isolated from T2 progeny plants derived from a drought tolerant T1 progeny plant of IS125 Event No. 3 and were examined by the primer pairs listed in FIG. 1. Primer pairs M1, M2 and M-Hpt were able to amplify the expected DNA fragments from all of the progeny. However, primer pairs M3, M4, M5 and M6 failed to amplify the expected products. These results are consistent with the hypothesis that the segment between M1 and M2 is present in IS125 Event No. 3 whereas the segment between M3 and M6 is not. Thus, it is possible that the drought-tolerance gene is located in the region between M1 and M2.

Figure 2:
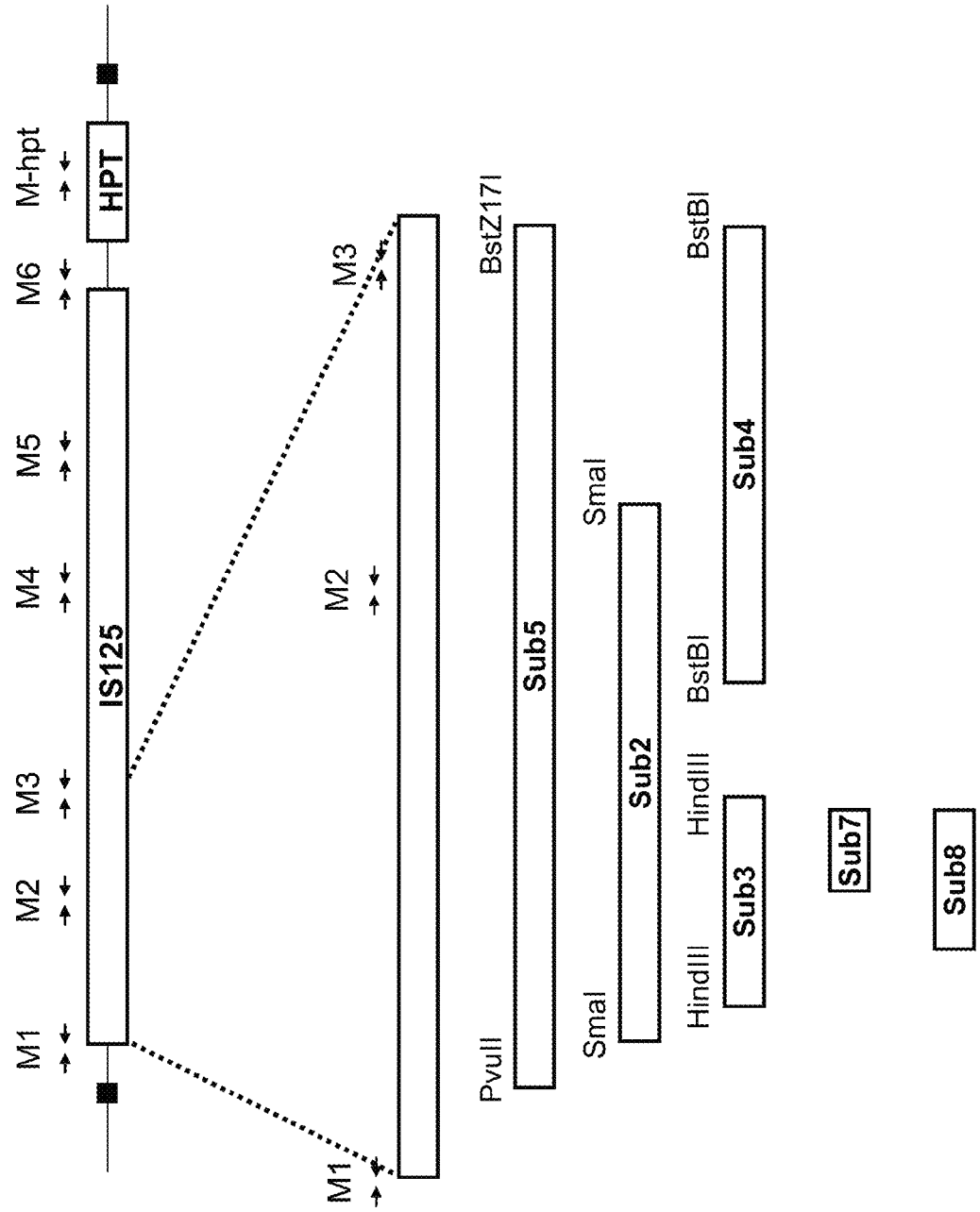
FIG. 2 shows the various regions of Genomic Fragment IS125 that were subcloned into rice to define the region responsible for the drought tolerant phenotype.
Figure 4A:
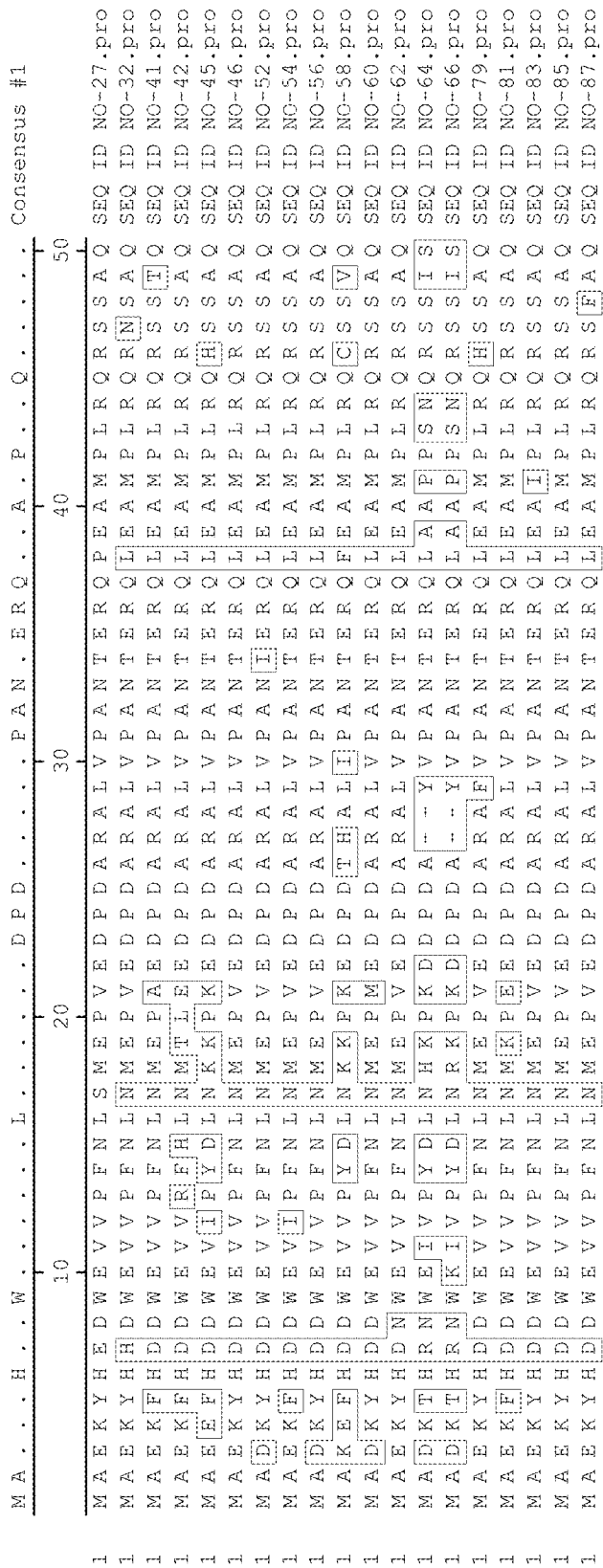

Next, fragments were subcloned from genomic fragment IS125 (FIG. 2) and were introduced into rice cultivar Yukihikari to confirm the hypothesis described above. Table 8 shows the summary of drought tolerance assay of rice transformed with genomic fragment IS125 and various subfragments of IS125.

TABLE 8

Drought Tolerance Assay of Rice Transformed with Genomic Fragment IS125 and Various Subfragments

| DNA Fragment | Size (bp) | SEQ ID NO: 1 Co-ordinates From | To | Drought Tolerant Event(s) |
| --- | --- | --- | --- | --- |
| IS125 | 40,040 | 10 | 40,049 | Yes |
| Sub5 | 12,938 | 1,659 | 14,596 | Yes |
| Sub2 | 8,068 | 2,343 | 10,410 | Yes |
| Sub4 | 6,833 | 7,738 | 14,570 | No |
| Sub3 | 3,158 | 2,868 | 6,025 | Yes |
| Sub8 | 2,083 | 3,735 | 5,817 | Yes |
| Sub7 | 1,210 | 4,608 | 5,817 | Yes |

A subclone fragment, the 12.9-kb PvuII-BstZ17I fragment, which is hereinafter designated "Sub5" and covers most of the M1-M3 region (FIG. 2), was inserted into pSB200 and the sequences at the junction regions were confirmed. The resultant plasmid was introduced into *Agrobacterium* strain LBA4404 (pSB1) by tri-parental mating. The recombinant *Agrobacterium* was used to transform rice cultivar Yukihikari as described in Example 3. Rice cultivar Yukihikari was also transformed with *Agrobacterium* LBA4404 that carried pSB134 (Hiei and Komari, Plant Cell Tissue and Organ Cult. 85:271-283, 2006), which contained a hygromycin resistance gene and a GUS gene.

Rice transformed with Sub5 was assayed for drought tolerance in the T0 and T1 generations. For the T0 generation, ten out of 48 regenerants of Sub5 transformants scored 2 or higher whereas none of 48 regenerants of GUS transformants, which were drought susceptible control plants, did so (Table 9). Therefore, Sub5 was sufficient to generate drought tolerant rice transformation events.

TABLE 9

Drought Tolerance Assay of T0 Regenerants of Rice Transformed with Sub5

| DNA Used in Transformation | Total No. of Regenerants Tested | No. of Regenerants Scoring 2 or Higher | Drought Tolerant Regenerants |
| --- | --- | --- | --- |
| GUS (Control) | 48 | 0 | No |
| Sub5 | 48 | 10 | Yes |

Tables 10 shows the results of drought tolerance assays of the T1 generation of rice transformed with subfragment Sub5 of genomic fragment IS125. Seven lines (designated "Sub5 Event No. 1"-"Sub5 Event No. 7") derived from seven events that scored 2 or higher in the T0 generation were tested. Six out of the seven lines clearly showed drought tolerance. Transgenic rice IS125 Event No. 3 in the T5 generation was also assayed in these subfragment evaluation trials and was distinctly drought tolerant in each of the experiments. Consequently, drought tolerance conferred by genomic fragment IS125 was stably inherited to the T5 generation and this series of drought tolerance assays were well controlled.

TABLE 10

Drought Tolerance Assay of the T1 Generation of Seven Transgenic Rice Lines Transformed with Sub5

| Exp. No. | Line | T0 Score | Total No. Plants Tested | No. Plants Scoring 2 or Higher | Drought Response |
| --- | --- | --- | --- | --- | --- |
| 1 | Yukihikari | — | 12 | 0 | Susceptible |
| 1 | IS125 Event No. 3 (T5) | — | 12 | 12 | Tolerant |
| 1 | Sub5 Event No. 1 | 2 | 12 | 1 | Susceptible |
| 1 | Sub5 Event No. 2 | 3 | 12 | 8 | Tolerant |
| 1 | Sub5 Event No. 3 | 3 | 12 | 2 | Tolerant |
| 2 | Yukihikari | — | 12 | 0 | Susceptible |
| 2 | IS125 Event No. 3 (T5) | — | 12 | 11 | Tolerant |
| 2 | Sub5 Event No. 4 | 2 | 12 | 5 | Tolerant |
| 2 | Sub5 Event No. 5 | 3 | 12 | 11 | Tolerant |
| 2 | Sub5 Event No. 6 | 4 | 12 | 9 | Tolerant |
| 2 | Sub5 Event No. 7 | 3 | 12 | 10 | Tolerant |

In order to further define the region containing the drought-tolerance gene, smaller subfragments were tested. The 8.1-kb SmaI fragment (hereinafter designated "Sub2"), the 3.2-kb HindIII fragment (hereinafter designated "Sub3"), and the 6.8-kb BstBI fragment (hereinafter designated "Sub4"), each of which is a subfragment of Sub5, were inserted into pSB200 that was pretreated with EcoRV, HindIII and BstBI, respectively, and then with CIAP. In a similar way described for Sub5, each of the three subfragments was introduced into rice cultivar Yukihikari by the *Agrobacterium*-mediated transformation method.

Sixteen events of rice transformed with subfragment Sub2 were examined for drought tolerance in the T1 generation (Table 11). Six events (Sub2 Events No. 5, No. 7, No. 9, No. 12, No. 15 and No. 16) were clearly drought tolerant.

TABLE 11

Drought Tolerance Assay of the T1 Generation of Sixteen Transgenic Rice Lines Transformed with Sub2

| Exp. No. | Line | Total No. Plants Tested | No. Plants Scoring 2 or Higher | Drought Response |
|---|---|---|---|---|
| 1 | Yukihikari | 12 | 0 | Susceptible |
| 1 | IS125 Event No. 1 (T5) | 12 | 8 | Tolerant |
| 1 | Sub2 Event No. 1 | 12 | 0 | Susceptible |
| 1 | Sub2 Event No. 2 | 12 | 1 | Susceptible |
| 1 | Sub2 Event No. 3 | 12 | 1 | Susceptible |
| 1 | Sub2 Event No. 4 | 12 | 0 | Susceptible |
| 2 | Yukihikari | 12 | 0 | Susceptible |
| 2 | IS125 Event No. 1 (T5) | 12 | 12 | Tolerant |
| 2 | Sub2 Event No. 5 | 12 | 4 | Tolerant |
| 2 | Sub2 Event No. 6 | 12 | 1 | Susceptible |
| 2 | Sub2 Event No. 7 | 12 | 2 | Tolerant |
| 2 | Sub2 Event No. 8 | 12 | 1 | Susceptible |
| 3 | Yukihikari | 12 | 0 | Susceptible |
| 3 | IS125 Event No. 3 (T5) | 12 | 12 | Tolerant |
| 3 | Sub2 Event No. 9 | 12 | 5 | Tolerant |
| 3 | Sub2 Event No. 10 | 12 | 0 | Susceptible |
| 3 | Sub2 Event No. 11 | 12 | 0 | Susceptible |
| 3 | Sub2 Event No. 12 | 12 | 4 | Tolerant |
| 4 | Yukihikari | 12 | 0 | Susceptible |
| 4 | IS125 Event No. 3 (T5) | 12 | 12 | Tolerant |
| 4 | Sub2 Event No. 13 | 12 | 0 | Susceptible |
| 4 | Sub2 Event No. 14 | 12 | 0 | Susceptible |
| 4 | Sub2 Event No. 15 | 12 | 5 | Tolerant |
| 4 | Sub2 Event No. 16 | 11 | 5 | Tolerant |

Sixteen events of rice transformed with subfragment Sub3 were examined for drought tolerance in the T1 generation (Table 12). Eight events (Sub3 Events No. 3, No. 4, No. 6, No. 7, No. 9, No. 10, No. 12 and No. 16) were clearly drought tolerant.

TABLE 12

Drought Tolerance Assay of the T1 Generation of Sixteen Transgenic Rice Lines Transformed with Sub3

| Exp. No. | Line | Total No. Plants Tested | No. Plants Scoring 2 or Higher | Drought Response |
|---|---|---|---|---|
| 1 | Yukihikari | 12 | 0 | Susceptible |
| 1 | IS125 Event No. 1 (T5) | 12 | 6 | Tolerant |
| 1 | Sub3 Event No. 1 | 12 | 0 | Susceptible |
| 1 | Sub3 Event No. 2 | 12 | 1 | Susceptible |
| 1 | Sub3 Event No. 3 | 12 | 2 | Tolerant |
| 1 | Sub3 Event No. 4 | 12 | 3 | Tolerant |
| 2 | Yukihikari | 12 | 0 | Susceptible |
| 2 | IS125 Event No. 1 (T5) | 12 | 8 | Tolerant |
| 2 | Sub3 Event No. 5 | 12 | 0 | Susceptible |
| 2 | Sub3 Event No. 6 | 12 | 5 | Tolerant |
| 2 | Sub3 Event No. 7 | 12 | 4 | Tolerant |
| 2 | Sub3 Event No. 8 | 12 | 1 | Susceptible |
| 3 | Yukihikari | 12 | 0 | Susceptible |
| 3 | IS125 Event No. 1 (T5) | 12 | 7 | Tolerant |
| 3 | Sub3 Event No. 9 | 12 | 6 | Tolerant |
| 3 | Sub3 Event No. 10 | 12 | 7 | Tolerant |
| 3 | Sub3 Event No. 11 | 12 | 1 | Susceptible |
| 3 | Sub3 Event No. 12 | 12 | 6 | Tolerant |
| 4 | Yukihikari | 12 | 0 | Susceptible |
| 4 | IS125 Event No. 1 (T5) | 12 | 9 | Tolerant |
| 4 | Sub3 Event No. 13 | 12 | 0 | Susceptible |
| 4 | Sub3 Event No. 14 | 10 | 0 | Susceptible |
| 4 | Sub3 Event No. 15 | 12 | 1 | Susceptible |
| 4 | Sub3 Event No. 16 | 12 | 5 | Tolerant |

Sixteen events of rice transformed with subfragment Sub4 were examined for drought tolerance in the T1 generation (Table 13). None of the Sub4 Events were drought tolerant.

TABLE 13

Drought Tolerance Assay of the T1 Generation of Sixteen Transgenic Rice Lines Transformed with Sub4

| Exp. No. | Line | Total No. Plants Tested | No. Plants Scoring 2 or Higher | Drought Response |
|---|---|---|---|---|
| 1 | Yukihikari | 12 | 0 | Susceptible |
| 1 | IS125 Event No. 1 (T5) | 12 | 6 | Tolerant |
| 1 | Sub4 Event No. 1 | 12 | 0 | Susceptible |
| 1 | Sub4 Event No. 2 | 12 | 0 | Susceptible |
| 1 | Sub4 Event No. 3 | 12 | 0 | Susceptible |
| 1 | Sub4 Event No. 4 | 12 | 0 | Susceptible |
| 2 | Yukihikari | 12 | 0 | Susceptible |
| 2 | IS125 Event No. 1 (T5) | 12 | 10 | Tolerant |
| 2 | Sub4 Event No. 5 | 12 | 0 | Susceptible |
| 2 | Sub4 Event No. 6 | 12 | 0 | Susceptible |
| 2 | Sub4 Event No. 7 | 12 | 0 | Susceptible |
| 2 | Sub4 Event No. 8 | 12 | 0 | Susceptible |
| 3 | Yukihikari | 12 | 0 | Susceptible |
| 3 | IS125 Event No. 3 (T5) | 12 | 11 | Tolerant |
| 3 | Sub4 Event No. 9 | 12 | 0 | Susceptible |
| 3 | Sub4 Event No. 10 | 12 | 0 | Susceptible |
| 3 | Sub4 Event No. 11 | 12 | 0 | Susceptible |
| 3 | Sub4 Event No. 12 | 12 | 0 | Susceptible |
| 4 | Yukihikari | 12 | 0 | Susceptible |
| 4 | IS125 Event No. 3 (T5) | 12 | 11 | Tolerant |
| 4 | Sub4 Event No. 13 | 12 | 0 | Susceptible |
| 4 | Sub4 Event No. 14 | 12 | 0 | Susceptible |
| 4 | Sub4 Event No. 15 | 12 | 0 | Susceptible |
| 4 | Sub4 Event No. 16 | 12 | 0 | Susceptible |

To more precisely define the drought tolerant gene region, two subfragments of Sub3 were created as follows. PCR with Pyrobest DNA Polymerase (TAKARA-BIO) was carried out using Sub5 plasmid DNA as a template and primers SEQ ID NO:16 (5'-TACCTTGTTAACCTCATAGGTTCT-TCTCAG-3') and SEQ ID NO:17 (5'-TCCCATGGAGAGT-TAACGCCCGACCTT-3'), and then the PCR products were digested with HpaI to give a 2.1-kb fragment (hereafter designated as "Sub8"). In a similar way, primers SEQ ID NO:18 (5'-CCCCATACTTGTTAACTGCTTTCTTGC-3') and SEQ ID NO:19 (5'-TCCCATGGAGAGTTAACGC-CCGACCTT-3') were used in PCR, and then the PCR products were digested with HpaI, to give a 1.2-kb fragment (hereafter designated as "Sub7"). Sub7 is a sub-segment of Sub8. Sub8 and Sub7 were inserted into pSB200 that had been digested with EcoRV and then pre-treated with CIAP. After the sequences of the PCR-amplified regions and the junction regions were confirmed, Sub8 and Sub7 were introduced into rice cultivar Yukihikari by the *Agrobacterium*-mediated transformation method as described above.

Drought response evaluation of rice transformed with Sub8 and Sub7 was conducted in the T0 generation. Seventeen of the 48 Sub8 events were clearly drought tolerant whereas none of the GUS transformation events were drought tolerant (Table 14). Three of the 48 Sub7 events were clearly drought tolerant whereas none of the GUS transformation events were drought tolerant (Table 15).

TABLE 14

Drought Tolerance Assay of the T0 Generation of Rice Transformed with Sub8

| DNA Used in Transformation | Total No. of Events Tested | No. of Events Scoring 2 or Higher | Drought Tolerant Events |
|---|---|---|---|
| GUS (Control) | 48 | 0 | No |
| Sub8 | 48 | 17 | Yes |

TABLE 15

Drought Tolerance Assay of the T0 Generation of Rice Transformed with Sub7

| DNA Used in Transformation | Total No. of Events Tested | No. of Events Scoring 2 or Higher | Drought Tolerant Events |
|---|---|---|---|
| GUS (Control) | 48 | 0 | No |
| Sub7 | 48 | 3 | Yes |

From these results, it is evident that the drought tolerance gene in genomic clone IS125 is present in the region of subfragment Sub7.

The presence of transcripts encoded by Sub7 was examined by RT-PCR. Using RNEASY® Mini Kit (QIAGEN), total RNA was prepared from a whole T0 transgenic rice plant that contained subfragment Sub5 and showed drought tolerance. RNA of a transgenic rice plant that carried a GUS gene and an HPT gene was used as a negative control. The RNA samples were subjected to cDNA synthesis with SuperScript™ III First-Strand Synthesis System for RT-PCR (Invitrogen). RT-PCR was performed with two primers, SEQ ID NO:20 (5'-TCCCTAATCTTCTTGTTGGCACTG-3') and SEQ ID NO:21 (5'-TTAGTTCCTTGCTGCTC-CAATGGC-3'), which were designed based on the sequence of Sub7. As a result, a fragment of about 0.6 kb was amplified from the cDNA of the Sub5 transformant but not from the cDNA of the GUS transformant (FIG. 3; Table 16). In addition, the amplification was not observed when the reverse transcriptase was not included in the reaction, indicating that the fragment was amplified from the RNA. Sequence analysis of the 0.6-kb fragment confirmed that the RT-PCR product was from the Sub7 sequence.

TABLE 16

RT-PCR of Transcripts Containing Nucleotides No. 4,827 Through No. 5,459 of SEQ ID NO: 1

| Source of RNA for Template | Pre-treated with Reverse Transcriptase | Amplification of 0.6-kb DNA |
|---|---|---|
| Sub5 Transformant | Yes | Yes |
| Sub5 Transformant | No | No |
| GUS Transformant | Yes | No |
| GUS Transformant | No | No |

Experiments employing 5' and 3' RACE (rapid amplification of cDNA ends) were carried out with GENER-ACER™ Kit (Invitrogen) for characterization of the gene encoding the drought-tolerance polypeptide (hereinafter designated as the "SS-DTP21-1" polypeptide). For 5' RACE, the primer SEQ ID NO:22 (5'-CCTTTGGAGGGAT-GAAACGGACTTTG-3') was combined with a GENER-ACER™ 5' primer, SEQ ID NO:74 (5'-CGACTGGAG-CACGAGGACACTGA-3'), and then the primer SEQ ID NO:23 (5'-TGATCTCACCGCTCCGGTTGGTCTTG-3') was combined with a GENERACER™ 5' nested primer, SEQ ID NO:75 (5'-GGACACTGACATGGACT-GAAGGAGTA-3'). For 3' RACE, the primer SEQ ID NO:24 (5'-TCCTTGCTGCTCCAATGGCCGAGAAG-3') was combined with a GENERACER™ 3' primer, SEQ ID NO:76 (5'-GCTGTCAACGATACGCTACGTAACG-3'), and then the primer SEQ ID NO:25 (5'-ACCTCAGCATG-GAGCCTGTGGAAGAC-3') was combined with a GEN-ERACER™ 3' nested primer, SEQ ID NO:77 (5'-CGC-TACGTAACGGCATGACAGTG-3'). The amplified fragments of the nested PCRs were inserted into pCR®4-TOPO® (Invitrogen) and subjected to sequence analysis. A single transcription initiation site was identified at nucleotide No. 5,499 of SEQ ID NO:1, and seven 3' end sites were found at nucleotides No. 4,655, No. 4,652, No. 4,471, No. 4,464, No. 4,069, No. 4,011 and No. 3,956 of SEQ ID NO:1 (FIG. 3), indicating that 7 types of transcripts were present in the drought tolerant rice. Nevertheless, all of the transcripts appeared to encode the same protein because the diversity was within the 3'-untranslated region. The nucleotide sequence encoding the SS-DTP21-1 polypeptide is presented as SEQ ID NO:26. The amino acid sequence of SS-DTP21-1 is presented as SEQ ID NO:27.

Based on these results, two primers, SEQ ID NO:28 (5'-TGCGAGGTTGTCGAGCACTTGCTCCT-3') and SEQ ID NO:29 (5'-CAAGCCTTCTCTTCTTCAGTTAGAGC-3') were designed and RT-PCR was carried out using RNA from the Sub5 transformant and the GUS transformant described above. A band of the expected size (1.5 kb) was observed only when the RNA from the Sub5 transformant was treated with reverse transcriptase (Table 17), which confirmed the existence of transcripts spanning the two primers.

TABLE 17

RT-PCR of Transcripts Containing Nucleotides No. 4,019 Through No. 5,489 of SEQ ID NO: 1

| Source of RNA for Template | Pre-treated with Reverse Transcriptase | Amplification of 1.5-kb DNA |
|---|---|---|
| Sub5 Transformant | Yes | Yes |
| Sub5 Transformant | No | No |
| GUS Transformant | Yes | No |
| GUS Transformant | No | No |

Example 5

Identification of the SS-DTP21-2 Gene as a Drought Tolerant Gene Candidate

As described in EXAMPLE 3, genomic fragment IS127 from Sudan grass also was capable of conferring drought tolerance to rice cultivar Yukihikari. Genomic fragment IS127 was fully sequenced by a standard procedure and a sequence of 34,231 nucleotides was elucidated (SEQ ID NO:30).

Genomic fragment IS127 (SEQ ID NO:30) contains a region that is highly homologous with subfragment Sub8 of genomic fragment IS125. This IS127 homologous region contains a nucleotide sequence (SEQ ID NO:31) that encodes a polypeptide (SEQ ID NO:32), hereinafter designated the "SS-DTP21-2" polypeptide, that is homologous to the SS-DTP21-1 polypeptide. This region was subcloned as follows. The homologous region was amplified with two primers derived from genomic fragment IS127, SEQ ID NO:33 (5'-ATACCTTGTTAACCTCATAGGT-TCTCTCAG-3') and SEQ ID NO:34 (5'-CCTTCCCATG-GAGAGTTAACGCCCGACACT-3'), and the resulting PCR fragment was then subcloned into pSB200 by the methods described above.

Example 6

Identification of *Sorghum* Genes Encoding Polypeptides Homologous to SS-DTP21-1

Using standard DNA sequence analysis methods, *Sorghum bicolor* genes encoding polypeptides homologous to SS-DTP21-1 were identified. A TBLASTN analysis of publically available nucleotide sequences indicated that the amino acid sequence of SS-DTP21-1, SEQ ID NO:27, is highly homologous to the amino acid sequences encoded by the following: nucleotides 25530-24904 of *Sorghum bicolor* genomic BAC clone SB_BBc0073F19 (NCBI GI No. 124359063); and nucleotides 44114-44740 of *Sorghum bicolor* genomic BAC clone SB_BBc0109L12 (NCBI GI No. 124359064). A TBLASTN analysis of publically available *sorghum* EST sequences indicated that sub-fragments of SEQ ID NO:27 are highly homologous to the amino acid sequences encoded by the following: two *sorghum* EST sequences obtained from water-stressed plants, i.e., 5-week-old plants on days 7 and 8 after water was withheld (NCBI GI No. 7659303; NCBI GI No. 7659212); and an EST sequence obtained from ovaries of varying immature stages from 8-week-old plants (NCBI GI No. 11922211).

The region encoding SS-DTP21-1 in subclone Sub8 of genomic fragment IS125 was replaced with various protein-coding regions of *Sorghum bicolor* genes encoding polypeptides homologous to SS-DTP-21-1. The Clontech IN-FUSION™ PCR Cloning System, in which the ends of a PCR fragment are fused to the homologous ends of a linearized vector, was used for vector construction.

The linearized vector was prepared as follows. PCR amplification was performed with the following: PRIME-STAR® Max (TAKARA-BIO) enzyme; the plasmid containing subfragment Sub8 in pSB200, which was constructed in EXAMPLE 4, as a template; and the following two primers:

```
                                       (SEQ ID NO: 35)
5'-GCTCTAACTGAAGAAGAGAAGGCTTGGTGGCTTGGTGTTTG-3';
and (SEQ ID NO: 36)
5'-GCTATCATTTAAATCGGTTTAGGTTTACTATTATCATCAG-3'.
```

The PCR products were self-ligated with DNA Ligation Kit "Mighty Mix" (TAKARA-BIO) after treatment with T4 polynucleotide kinase (TAKARA-BIO). The resultant DNA was used to transform *E. coli* MACH1™-T1R (Invitrogen) by electroporation. Among the recombinant colonies that appeared on LB plates containing spectinomycin (50 µg/ml), one colony was selected based on the results of colony PCR and sequence analysis of the plasmid with respect to the junction regions. Plasmids of the selected colony were digested with SwaI and AfeI, and the digest was treated with BAP (TAKARA-BIO) and purified from an agarose gel after electrophoresis.

The protein-coding regions of *Sorghum bicolor* (Gold sorgho) genes encoding polypeptides homologous to SS-DTP21-1 were prepared by PCR amplification using the following: PRIMESTAR® Max (TAKARA-BIO) enzyme; genomic DNA of *Sorghum bicolor* (Gold sorgho) as template; and the following two primers:

```
                                       (SEQ ID NO: 37)
5'-TTCTTCAGTTAGAGCTTGATTAGTTCCTTGCTGCTCCAATG-3';
and (SEQ ID NO: 38)
5'-AAACCTAAACCGATTTTAAAGATAGATAACTAAGATGCATTGC
CTCAATGTCTAATCTAGATAAATTA-3'.
```

The PCR products were purified from an agarose gel after electrophoresis.

The linearized vector and PCR products encoding polypeptides homologous to SS-DTP21-1, each of which shared 15-16 base pairs of sequence identity in the terminal regions, were fused to each other using an IN-FUSION™ Advantage PCR Cloning Kit (Clontech) according to the instruction manual. The resultant DNA was used to transform *E. coli* MACH1™-T1R (Invitrogen) by electroporation. Among the recombinant colonies that appeared on LB plates containing spectinomycin (50 µg/ml), two colonies were selected based on the results of colony PCR and sequence analysis of the plasmids. The nucleotide sequences of the coding regions of the selected colonies are presented as SEQ ID NO:39 (encoding the SB-DTP21-1 polypeptide) and SEQ ID NO:40 (encoding the SB-DTP21-2 polypeptide). The corresponding amino acid sequences of the two proteins are presented as SEQ ID NO:41 (SB-DTP21-1) and SEQ ID NO:42 (SB-DTP21-2), respectively.

The colonies were used in triparental mating together with *Agrobacterium* strain LBA4404 (pSB1) and helper *E. coli* strain HB101 (pRK2013), and the resultant *Agrobacterium* strains were used to transform a rice variety as described above.

In a similar manner, the protein-coding regions of two genes homologous to SS-DTP21-1 were obtained from *Sorghum bicolor* (B35). The two homologous nucleotide sequences from *Sorghum bicolor* (B35) are presented as SEQ ID NO:43 (encoding the SB-DTP21-3 polypeptide) and SEQ ID NO:44 (encoding the SB-DTP21-4 polypeptide). The corresponding amino acid sequences of the two proteins are presented as SEQ ID NO:45 (SB-DTP21-3) and SEQ ID NO:46 (SB-DTP21-4), respectively.

Example 7

Identification of Additional Genes Encoding Polypeptides Homologous to SS-DTP21-1

In a manner similar to the above Examples, the protein-coding regions of other genes homologous to SS-DTP21-1 were identified from Sudan grass (*Sorghum sudanense*), Johnson grass (*Sorghum halepense*), sugarcane (*Saccharum officinarum*), and sorghum (*Sorghum bicolor* (Gold sorgho); *Sorghum bicolor* (B35); and *Sorghum bicolor* (hoki)). The SEQ ID NOs for the the amino acid sequences for SS-DTP21-1 and the various homologous proteins, as well as for the corresponding nucleotide sequences encoding SS-DTP21-1 and the various homologous proteins, are presented in the following Table.

TABLE 18

SS-DTP21-1 and Homologous Proteins from Various Organisms

| Protein Designation | Organism | Nucleotide SEQ ID NO | Amino Acid SEQ ID NO |
|---|---|---|---|
| SS-DTP21-1 | Sudan grass | 26 | 27 |
| SS-DTP21-2 | Sudan grass | 31 | 32 |
| SB-DTP21-1 | *Sorghum bicolor* (Gold sorgho) | 39 | 41 |
| SB-DTP21-2 | *Sorghum bicolor* (Gold sorgho) | 40 | 42 |
| SB-DTP21-3 | *Sorghum bicolor* (B35) | 43 | 45 |
| SB-DTP21-4 | *Sorghum bicolor* (B35) | 44 | 46 |
| SS-DTP21-3 | Sudan grass | 51 | 52 |
| SS-DTP21-4 | Sudan grass | 53 | 54 |
| SS-DTP21-5 | Sudan grass | 55 | 56 |
| SS-DTP21-7 | Sudan grass | 57 | 58 |
| SH-DTP21-1 | Johnson grass | 59 | 60 |
| SH-DTP21-2 | Johnson grass | 61 | 62 |

TABLE 18-continued

SS-DTP21-1 and Homologous Proteins from Various Organisms

| Protein Designation | Organism | Nucleotide SEQ ID NO | Amino Acid SEQ ID NO |
|---|---|---|---|
| SO-DTP21-1 | Sugarcane | 63 | 64 |
| SO-DTP21-2 | Sugarcane | 65 | 66 |
| SS-DTP21-6 | Sudan grass | 78 | 79 |
| SB-DTP21-5 | Sorghum bicolor (Gold sorgho) | 80 | 81 |
| SB-DTP21-6 | Sorghum bicolor (B35) | 82 | 83 |
| SB-DTP21-9 | Sorghum bicolor (hoki) | 84 | 85 |
| SB-DTP21-10 | Sorghum bicolor (hoki) | 86 | 87 |

Example 8

Characterization of Polypeptides Homologous to SS-DTP21-1

FIGS. 4A-4E present an alignment of the amino acid sequences set forth in SEQ ID NOs:27, 32, 41, 42, 45, 46, 52, 54, 56, 58, 60, 62, 64, 66, 79, 81, 83, 85 and 87, for DTP21 polypeptides from Sudan grass, *sorghum*, Johnson grass and sugarcane. FIG. 5 presents the percent sequence identities and divergence values for each sequence pair presented in FIGS. 4A-4E.

Sequence alignments and percent identity calculations were performed using the MEGALIGN® program of the LASERGENE® bioinformatics computing suite (DNASTAR® Inc., Madison, Wis.). Multiple alignment of the sequences was performed using the Clustal V method of alignment (Higgins and Sharp (1989) *CABIOS.* 5:151-153) with the default parameters (GAP PENALTY=10, GAP LENGTH PENALTY=10). Default parameters for pairwise alignments using the Clustal method were KTUPLE=1, GAP PENALTY=3, WINDOW=5 and DIAGONALS SAVED=5.

The amino acid sequence of SS-DTP21-1 has the following percent sequence identity with the homologs presented in FIGS. 4A-4E: 91.4% (SS-DTP21-2); 88.5% (SB-DTP21-1); 84.6% (SB-DTP21-2); 83.3% (SB-DTP21-3); 93.3% (SB-DTP21-4); 92.8% (SS-DTP21-3); 92.3% (SS-DTP21-4); 91.4% (SS-DTP21-5); 84.7% (SS-DTP21-7); 91.9% (SH-DPT21-1); 93.3% (SH-DTP21-2); 63.8% (SO-DTP21-1), 63.8% (SO-DTP21-2), 91.4% (SS-DTP21-6), 91.9% (SB-DTP21-5), 93.3% (SB-DTP21-6), 92.8% (SB-DTP21-9) and 92.3% (SB-DTP21-10).

Example 9

Electroporation of *Agrobacterium tumefaciens* LBA4404

Electroporation competent cells (40 µL), such as *Agrobacterium tumefaciens* LBA4404 containing PHP10523 ("pSB1"; Komari et al., *Plant J.* 10:165-174 (1996); NCBI General Identifier No. 59797027), are thawed on ice (20-30 min). PHP10523 contains VIR genes for T-DNA transfer, an *Agrobacterium* low copy number plasmid origin of replication, a tetracycline resistance gene, and a Cos site for in vivo DNA bimolecular recombination. Meanwhile the electroporation cuvette is chilled on ice. The electroporator settings are adjusted to 2.1 kV. A DNA aliquot (0.5 µL parental DNA at a concentration of 0.2 µg-1.0 µg in low salt buffer or twice distilled H$_2$O) is mixed with the thawed *Agrobacterium tumefaciens* LBA4404 cells while still on ice. The mixture is transferred to the bottom of electroporation cuvette and kept at rest on ice for 1-2 min. The cells are electroporated (Eppendorf electroporator 2510) by pushing the "pulse" button twice (ideally achieving a 4.0 millisecond pulse). Subsequently, 0.5 mL of room temperature 2xYT medium (or SOC medium) are added to the cuvette and transferred to a 15 mL snap-cap tube (e.g., FALCON™ tube). The cells are incubated at 28-30° C., 200-250 rpm for 3 h.

Aliquots of 250 µL are spread onto plates containing YM medium and 50 µg/mL spectinomycin and incubated three days at 28-30° C. To increase the number of transformants one of two optional steps can be performed:

Option 1: Overlay plates with 30 µL of 15 mg/mL rifampicin. LBA4404 has a chromosomal resistance gene for rifampicin. This additional selection eliminates some contaminating colonies observed when using poorer preparations of LBA4404 competent cells.

Option 2: Perform two replicates of the electroporation to compensate for poorer electrocompetent cells.

Identification of Transformants:

Four independent colonies are picked and streaked on plates containing AB minimal medium and 50 µg/mL spectinomycin for isolation of single colonies. The plates are incubated at 28° C. for two to three days. A single colony for each putative co-integrate is picked and inoculated with 4 mL of 10 g/L bactopeptone, 10 g/L yeast extract, 5 g/L sodium chloride and 50 mg/L spectinomycin. The mixture is incubated for 24 h at 28° C. with shaking. Plasmid DNA from 4 mL of culture is isolated using QIAGEN® Miniprep and an optional Buffer PB wash. The DNA is eluted in 30 µL. Aliquots of 2 µL are used to electroporate 20 µL of DH10b+20 µL of twice distilled H$_2$O as per above. Optionally a 15 µL aliquot can be used to transform 75-100 µL of INVITROGEN™ Library Efficiency DH5α. The cells are spread on plates containing LB medium and 50 µg/mL spectinomycin and incubated at 37° C. overnight.

Three to four independent colonies are picked for each putative co-integrate and inoculated 4 mL of 2xYT medium (10 g/L bactopeptone, 10 g/L yeast extract, 5 g/L sodium chloride) with 50 µg/mL spectinomycin. The cells are incubated at 37° C. overnight with shaking. Next, isolate the plasmid DNA from 4 mL of culture using QIAPREP® Miniprep with optional Buffer PB wash (elute in 50 µL). Use 8 µL for digestion with SalI (using parental DNA and PHP10523 as controls). Three more digestions using restriction enzymes BamHI, EcoRI, and HindIII are performed for 4 plasmids that represent 2 putative co-integrates with correct SalI digestion pattern (using parental DNA and PHP10523 as controls). Electronic gels are recommended for comparison.

Example 10

Transformation of Maize with Genomic Fragment IS125 Using *Agrobacterium* Triparental Mating Due to the large size of the Genomic Fragment IS125, maize may be transformed via triparental mating with *Agrobacterium* using the following protocol (Ditta et al. Proc. Natl. Acad. Sci. U.S.A. 77:7347-7351, 1980).

Day 1: Streak *Agrobacterium* strain LBA4404 (pAL4404, pSB1) on minimal medium agar plus tetracycline (10 µg/ml) and incubate at 28° C. for 3 days.

Day 2: Inoculate *E. coli* strain GENEHOGS® with IS125-containing DNA on LB agar with spectinomycin (100 µg/ml) and incubate 2 days at 25° C.

Day 3: Streak *E. coli* (pRK2013) onto LB agar plus kanamycin (50 μg/ml) and incubate overnight at 37° C.

Day 4: Mix one loopful each of the 3 strains on a Nutrient Agar plate and incubate overnight at 28° C.

Day 5: Streak out the mixture on a minimal medium agar plus spectinomycin (50 μg/ml) plate and incubate at 28° C. for 3 days.

Day 8: Pick up a single colony, streak out on the same medium and incubate at 28° C. for 3 days.

Day 11: Pick up a single colony, streak out on the same medium and incubate at 28° C. for 3 days.

Day 14: Pick up single colonies and start 2 ml 2XYT Broth culture with spectinomycin (100 μg/ml) at 28° C. overnight to 1 day.

Day 15: Miniprepare DNA of the overnight culture. Use 1 μl to electroporate 20 μl GENEHOGS® cells.

Day 16: Pick up single colonies and start 1.2 ml 2XYT Broth culture with spectinomycin (100 μg/ml) at 37° C. overnight.

Day 17: Miniprepare DNA of the overnight culture and perform restriction analysis with BamHI, EcoRI, and HindIII.

Example 11

Transformation of Maize Using *Agrobacterium*

*Agrobacterium*-mediated transformation of maize is performed essentially as described by Zhao et al. in *Meth. Mol. Biol.* 318:315-323 (2006) (see also Zhao et al., *Mol. Breed.* 8:323-333 (2001) and U.S. Pat. No. 5,981,840 issued Nov. 9, 1999, incorporated herein by reference). The transformation process involves bacterium innoculation, co-cultivation, resting, selection and plant regeneration.

1. Immature Embryo Preparation:

Immature maize embryos are dissected from caryopses and placed in a 2 mL microtube containing 2 mL PHI-A medium.

2. *Agrobacterium* Infection and Co-Cultivation of Immature Embryos:

2.1 Infection Step:

PHI-A medium of (1) is removed with 1 mL micropipettor, and 1 mL of *Agrobacterium* suspension is added. The tube is gently inverted to mix. The mixture is incubated for 5 min at room temperature.

2.2 Co-Culture Step:

The *Agrobacterium* suspension is removed from the infection step with a 1 mL micropipettor. Using a sterile spatula the embryos are scraped from the tube and transferred to a plate of PHI-B medium in a 100×15 mm Petri dish. The embryos are oriented with the embryonic axis down on the surface of the medium. Plates with the embryos are cultured at 20° C., in darkness, for three days. L-Cysteine can be used in the co-cultivation phase. With the standard binary vector, the co-cultivation medium supplied with 100-400 mg/L L-cysteine is critical for recovering stable transgenic events.

3. Selection of Putative Transgenic Events:

To each plate of PHI-D medium in a 100×15 mm Petri dish, 10 embryos are transferred, maintaining orientation and the dishes are sealed with PARAFILM®. The plates are incubated in darkness at 28° C. Actively growing putative events, as pale yellow embryonic tissue, are expected to be visible in six to to eight weeks. Embryos that produce no events may be brown and necrotic, and little friable tissue growth is evident. Putative transgenic embryonic tissue is subcultured to fresh PHI-D plates at two-three week intervals, depending on growth rate. The events are recorded.

4. Regeneration of T0 Plants:

Embryonic tissue propagated on PHI-D medium is subcultured to PHI-E medium (somatic embryo maturation medium), in 100×25 mm Petri dishes and incubated at 28° C., in darkness, until somatic embryos mature, for about ten to eighteen days. Individual, matured somatic embryos with well-defined scutellum and coleoptile are transferred to PHI-F embryo germination medium and incubated at 28° C. in the light (about 80 μE from cool white or equivalent fluorescent lamps). In seven to ten days, regenerated plants, about 10 cm tall, are potted in horticultural mix and hardened-off using standard horticultural methods.

Media for Plant Transformation:

1. PHI-A: 4 g/L CHU basal salts, 1.0 mL/L 1000× Eriksson's vitamin mix, 0.5 mg/L thiamin HCl, 1.5 mg/L 2,4-D, 0.69 g/L L-proline, 68.5 g/L sucrose, 36 g/L glucose, pH 5.2. Add 100 μM acetosyringone (filter-sterilized).
2. PHI-B: PHI-A without glucose, increase 2,4-D to 2 mg/L, reduce sucrose to 30 g/L and supplemented with 0.85 mg/L silver nitrate (filter-sterilized), 3.0 g/L GELRITE®, 100 μM acetosyringone (filter-sterilized), pH 5.8.
3. PHI-C: PHI-B without GELRITE® and acetosyringonee, reduce 2,4-D to 1.5 mg/L and supplemented with 8.0 g/L agar, 0.5 g/L 2-[N-morpholino]ethanesulfonic acid (MES) buffer, 100 mg/L carbenicillin (filter-sterilized).
4. PHI-D: PHI-C supplemented with 3 mg/L bialaphos (filter-sterilized).
5. PHI-E: 4.3 g/L of Murashige and Skoog (MS) salts, (Gibco, BRL 11117-074), 0.5 mg/L nicotinic acid, 0.1 mg/L thiamine HCl, 0.5 mg/L pyridoxine HCl, 2.0 mg/L glycine, 0.1 g/L myo-inositol, 0.5 mg/L zeatin (Sigma, Cat. No. Z-0164), 1 mg/L indole acetic acid (IAA), 26.4 μg/L abscisic acid (ABA), 60 g/L sucrose, 3 mg/L bialaphos (filter-sterilized), 100 mg/L carbenicillin (filter-sterilized), 8 g/L agar, pH 5.6.
6. PHI-F: PHI-E without zeatin, IAA, ABA; reduce sucrose to 40 g/L; replacing agar with 1.5 g/L GELRITE®; pH 5.6.

Plants can be regenerated from the transgenic callus by first transferring clusters of tissue to N6 medium supplemented with 0.2 mg per liter of 2,4-D. After two weeks the tissue can be transferred to regeneration medium (Fromm et al., *Bio/Technology* 8:833-839 (1990)).

Transgenic T0 plants can be regenerated and their phenotype determined. T1 seed can be collected. T1 plants, and/or their progeny, can be grown and their phenotype determined.

Example 12

Transformation of Gaspe Flint Derived Maize Lines with a Validated Drought Tolerant Lead Gene Maize plants can be transformed to overexpress the drought tolerant lead gene or the corresponding homologs from other species in order to examine the resulting phenotype.

Recipient Plants:

Recipient plant cells can be from a uniform maize line having a short life cycle ("fast cycling"), a reduced size, and high transformation potential. Typical of these plant cells for maize are plant cells from any of the publicly available Gaspe Flint (GBF) line varieties. One possible candidate plant line variety is the F1 hybrid of GBF×QTM (Quick Turnaround Maize, a publicly available form of Gaspe Flint selected for growth under greenhouse conditions) disclosed in Tomes et al. U.S. Patent Application Publication No. 2003/0221212. Transgenic plants obtained from this line are of such a reduced size that they can be grown in four inch pots (¼ the space needed for a normal sized maize plant) and mature in less than 2.5 months. (Traditionally 3.5 months is required to obtain transgenic T0 seed once the transgenic plants are acclimated to the greenhouse.) Another suitable line is a double haploid line of GS3 (a highly transformable line)×Gaspe Flint. Yet another suitable line is a transformable elite inbred line carrying a transgene which causes early flowering, reduced stature, or both.

Transformation Protocol:

Any suitable method may be used to introduce the transgenes into the maize cells, including but not limited to inoculation type procedures using *Agrobacterium* based vectors. Transformation may be performed on immature embryos of the recipient (target) plant.

Precision Growth and Plant Tracking:

The event population of transgenic (T0) plants resulting from the transformed maize embryos is grown in a controlled greenhouse environment using a modified randomized block design to reduce or eliminate environmental error. A randomized block design is a plant layout in which the experimental plants are divided into groups (e.g., thirty plants per group), referred to as blocks, and each plant is randomly assigned a location with the block.

For a group of thirty plants, twenty-four transformed, experimental plants and six control plants (plants with a set phenotype) (collectively, a "replicate group") are placed in pots which are arranged in an array (a.k.a. a replicate group or block) on a table located inside a greenhouse. Each plant, control or experimental, is randomly assigned to a location with the block which is mapped to a unique, physical greenhouse location as well as to the replicate group. Multiple replicate groups of thirty plants each may be grown in the same greenhouse in a single experiment. The layout (arrangement) of the replicate groups should be determined to minimize space requirements as well as environmental effects within the greenhouse. Such a layout may be referred to as a compressed greenhouse layout.

An alternative to the addition of a specific control group is to identify those transgenic plants that do not express the gene of interest. A variety of techniques such as RT-PCR can be applied to quantitatively assess the expression level of the introduced gene. T0 plants that do not express the transgene can be compared to those which do.

Each plant in the event population is identified and tracked throughout the evaluation process, and the data gathered from that plant is automatically associated with that plant so that the gathered data can be associated with the transgene carried by the plant. For example, each plant container can have a machine readable label (such as a Universal Product Code (UPC) bar code) which includes information about the plant identity, which in turn is correlated to a greenhouse location so that data obtained from the plant can be automatically associated with that plant.

Alternatively any efficient, machine readable, plant identification system can be used, such as two-dimensional matrix codes or even radio frequency identification tags (RFID) in which the data is received and interpreted by a radio frequency receiver/processor. See U.S. Published Patent Application No. 2004/0122592, incorporated herein by reference.

Phenotypic Analysis Using Three-Dimensional Imaging:

Each greenhouse plant in the T0 event population, including any control plants, is analyzed for agronomic characteristics of interest, and the agronomic data for each plant is recorded or stored in a manner so that it is associated with the identifying data (see above) for that plant. Confirmation of a phenotype (gene effect) can be accomplished in the T1 generation with a similar experimental design to that described above.

The T0 plants are analyzed at the phenotypic level using quantitative, non-destructive imaging technology throughout the plant's entire greenhouse life cycle to assess the traits of interest. A digital imaging analyzer may be used for automatic multi-dimensional analyzing of total plants. The imaging may be done inside the greenhouse. Two camera systems, located at the top and side, and an apparatus to rotate the plant, are used to view and image plants from all sides. Images are acquired from the top, front and side of each plant. All three images together provide sufficient information to evaluate the biomass, size and morphology of each plant.

Due to the change in size of the plants from the time the first leaf appears from the soil to the time the plants are at the end of their development, the early stages of plant development are best documented with a higher magnification from the top. This may be accomplished by using a motorized zoom lens system that is fully controlled by the imaging software.

In a single imaging analysis operation, the following events occur: (1) the plant is conveyed inside the analyzer area, rotated 360 degrees so its machine readable label can be read, and left at rest until its leaves stop moving; (2) the side image is taken and entered into a database; (3) the plant is rotated 90 degrees and again left at rest until its leaves stop moving, and (4) the plant is transported out of the analyzer.

Plants are allowed at least six hours of darkness per twenty four hour period in order to have a normal day/night cycle.

Imaging Instrumentation:

Any suitable imaging instrumentation may be used, including but not limited to light spectrum digital imaging instrumentation commercially available from LemnaTec GmbH of Wurselen, Germany. The images are taken and analyzed with a LemnaTec Scanalyzer HTS LT-0001-2 having a ½" IT Progressive Scan IEE CCD imaging device. The imaging cameras may be equipped with a motor zoom, motor aperture and motor focus. All camera settings may be made using LemnaTec software. For example, the instrumental variance of the imaging analyzer is less than about 5% for major components and less than about 10% for minor components.

Software:

The imaging analysis system comprises a LemnaTec HTS Bonit software program for color and architecture analysis and a server database for storing data from about 500,000 analyses, including the analysis dates. The original images and the analyzed images are stored together to allow the user to do as much reanalyzing as desired. The database can be connected to the imaging hardware for automatic data collection and storage. A variety of commercially available software systems (e.g. Matlab, others) can be used for quantitative interpretation of the imaging data, and any of these software systems can be applied to the image data set.

Conveyor System:

A conveyor system with a plant rotating device may be used to transport the plants to the imaging area and rotate them during imaging. For example, up to four plants, each with a maximum height of 1.5 m, are loaded onto cars that travel over the circulating conveyor system and through the imaging measurement area. In this case the total footprint of the unit (imaging analyzer and conveyor loop) is about 5 m×5 m.

The conveyor system can be enlarged to accommodate more plants at a time. The plants are transported along the conveyor loop to the imaging area and are analyzed for up to 50 seconds per plant. Three views of the plant are taken. The conveyor system, as well as the imaging equipment, should be capable of being used in greenhouse environmental conditions.

Illumination:

Any suitable mode of illumination may be used for the image acquisition. For example, a top light above a black background can be used. Alternatively, a combination of top- and backlight using a white background can be used. The illuminated area should be housed to ensure constant illumination conditions. The housing should be longer than the measurement area so that constant light conditions prevail without requiring the opening and closing or doors. Alternatively, the illumination can be varied to cause excitation of either transgene (e.g., green fluorescent protein (GFP), red fluorescent protein (RFP)) or endogenous (e.g. Chlorophyll) fluorophores.

Biomass Estimation Based on Three-Dimensional Imaging:

For best estimation of biomass the plant images should be taken from at least three axes, for example, the top and two side (sides 1 and 2) views. These images are then analyzed to separate the plant from the background, pot and pollen control bag (if applicable). The volume of the plant can be estimated by the calculation:

$$\text{Volume(voxels)} = \sqrt{\text{TopArea(pixels)}} \times \sqrt{\text{Side1Area(pixels)}} \times \sqrt{\text{Side2Area(pixels)}}$$

In the equation above the units of volume and area are "arbitrary units". Arbitrary units are entirely sufficient to detect gene effects on plant size and growth in this system because what is desired is to detect differences (both positive-larger and negative-smaller) from the experimental mean, or control mean. The arbitrary units of size (e.g. area) may be trivially converted to physical measurements by the addition of a physical reference to the imaging process. For instance, a physical reference of known area can be included in both top and side imaging processes. Based on the area of these physical references a conversion factor can be determined to allow conversion from pixels to a unit of area such as square centimeters ($cm^2$). The physical reference may or may not be an independent sample. For instance, the pot, with a known diameter and height, could serve as an adequate physical reference.

Color Classification:

The imaging technology may also be used to determine plant color and to assign plant colors to various color classes. The assignment of image colors to color classes is an inherent feature of the LemnaTec software. With other image analysis software systems color classification may be determined by a variety of computational approaches.

For the determination of plant size and growth parameters, a useful classification scheme is to define a simple color scheme including two or three shades of green and, in addition, a color class for chlorosis, necrosis and bleaching, should these conditions occur. A background color class which includes non plant colors in the image (for example pot and soil colors) is also used and these pixels are specifically excluded from the determination of size. The plants are analyzed under controlled constant illumination so that any change within one plant over time, or between plants or different batches of plants (e.g. seasonal differences) can be quantified.

In addition to its usefulness in determining plant size growth, color classification can be used to assess other yield component traits. For these other yield component traits additional color classification schemes may be used. For instance, the trait known as "staygreen", which has been associated with improvements in yield, may be assessed by a color classification that separates shades of green from shades of yellow and brown (which are indicative of senescing tissues). By applying this color classification to images taken toward the end of the T0 or T1 plants' life cycle, plants that have increased amounts of green colors relative to yellow and brown colors (expressed, for instance, as Green/Yellow Ratio) may be identified. Plants with a significant difference in this Green/Yellow ratio can be identified as carrying transgenes which impact this important agronomic trait.

The skilled plant biologist will recognize that other plant colors arise which can indicate plant health or stress response (for instance anthocyanins), and that other color classification schemes can provide further measures of gene action in traits related to these responses.

Plant Architecture Analysis:

Transgenes which modify plant architecture parameters may also be identified using the present invention, including such parameters as maximum height and width, internodal distances, angle between leaves and stem, number of leaves starting at nodes and leaf length. The LemnaTec system software may be used to determine plant architecture as follows. The plant is reduced to its main geometric architecture in a first imaging step and then, based on this image, parameterized identification of the different architecture parameters can be performed. Transgenes that modify any of these architecture parameters either singly or in combination can be identified by applying the statistical approaches previously described.

Pollen Shed Date:

Pollen shed date is an important parameter to be analyzed in a transformed plant, and may be determined by the first appearance on the plant of an active male flower. To find the male flower object, the upper end of the stem is classified by color to detect yellow or violet anthers. This color classification analysis is then used to define an active flower, which in turn can be used to calculate pollen shed date.

Alternatively, pollen shed date and other easily visually detected plant attributes (e.g. pollination date, first silk date) can be recorded by the personnel responsible for performing plant care. To maximize data integrity and process efficiency this data is tracked by utilizing the same barcodes utilized by the LemnaTec light spectrum digital analyzing device. A computer with a barcode reader, a palm device, or a notebook PC may be used for ease of data capture recording time of observation, plant identifier, and the operator who captured the data.

Orientation of the Plants:

Mature maize plants grown at densities approximating commercial planting often have a planar architecture. That is, the plant has a clearly discernable broad side, and a narrow side. The image of the plant from the broadside is determined. To each plant a well defined basic orientation is assigned to obtain the maximum difference between the broadside and edgewise images. The top image is used to determine the main axis of the plant, and an additional rotating device is used to turn the plant to the appropriate orientation prior to starting the main image acquisition.

Example 13

Evaluation of Gaspe Flint Derived Maize Lines for Drought Tolerance

Transgenic Gaspe Flint derived maize lines containing the candidate drought tolerant gene can be screened for tolerance to drought stress in the following manner.

Transgenic maize plants are subjected to well-watered conditions (control) and to drought-stressed conditions. Transgenic maize plants are screened at the T1 stage or later.

For plant growth, the soil mixture consists of ⅓ TURFACE®, ⅓ SB300 and ⅓ sand. All pots are filled with the same amount of soil ±10 grams. Pots are brought up to 100% field capacity ("FC") by hand watering. All plants are maintained at 60% FC using a 20-10-20 (N-P-K) 125 ppm N nutrient solution. Throughout the experiment pH is monitored at least three times weekly for each table. Starting at 13 days after planting (DAP), the experiment can be divided into two treatment groups, well watered and reduce watered. All plants comprising the reduced watered treatment are maintained at 40% FC while plants in the well watered treatment are maintained at 80% FC. Reduced watered plants are grown for 10 days under chronic drought stress conditions (40% FC). All plants are imaged daily throughout chronic stress period. Plants are sampled for metabolic profiling analyses at the end of chronic drought period, 22 DAP. At the conclusion of the chronic stress period all plants are imaged and measured for chlorophyll fluorescence. Reduced watered plants are subjected to a severe drought stress period followed by a recovery period, 23-31 DAP and 32-34 DAP respectively. During the severe drought stress, water and nutrients are withheld until the plants reached 8% FC. At the conclusion of severe stress and recovery periods all plants are again imaged and measured for chlorophyll fluorescence. The probability of a greater Student's t Test is calculated for each transgenic mean compared to the appropriate null mean (either segregant null or construct null). A minimum (P<t) of 0.1 is used as a cut off for a statistically significant result.

Example 14

Transformation and Evaluation of Gaspe Flint Derived Maize Lines Transformed with PHP29675

A Gaspe Flint derived maize line was transformed via *Agrobacterium* using plasmid DNA PHP29675, containing the Sudan grass genomic DNA fragment IS125. Four transformation events for the plasmid construct were evaluated for drought tolerance in a manner similar to that described in Example 13.

Tables 19-20 show the variables for each transgenic event that were significantly altered, as compared to the segregant nulls. A "positive effect" was defined as statistically significant improvement in that variable for the transgenic event relative to the null control. A "negative effect" was defined as a statistically significant improvement in that variable for the null control relative to the transgenic event. Table 19 presents the number of variables with a significant change for individual events transformed with the plasmid DNA construct. Table 20 presents the number of events for the construct that showed a significant change for each individual variable.

TABLE 19

Number of Variables with a Significant Change* for Individual Events Transformed with PHP29675 Containing Genomic Fragment IS125

| | Reduced Water | | Well Watered | |
|---|---|---|---|---|
| Event | Positive Effect | Negative Effect | Positive Effect | Negative Effect |
| EA2393.324.2.1 | 3 | 1 | 2 | 3 |
| EA2393.324.3.2 | 1 | 1 | 0 | 2 |
| EA2393.324.4.2 | 0 | 1 | 0 | 1 |
| EA2393.324.5.1 | 3 | 1 | 2 | 0 |

*P-value less than or equal to 0.1

TABLE 20

Number of Events Transformed with PHP29675 with a Significant Change* for Individual Variables

| | Reduced Water | | Well Watered | |
|---|---|---|---|---|
| Variable | Positive Effect | Negative Effect | Positive Effect | Negative Effect |
| % area chg_start chronic - end chronic | 1 | 0 | 0 | 2 |
| % area chg_start chronic - harvest | 1 | 0 | 0 | 1 |
| % area chg_start chronic - recovery24 hr | 0 | 0 | 0 | 0 |
| % area chg_start chronic - recovery48 hr | 0 | 0 | 0 | 0 |
| fv/fm_acute1 | 2 | 0 | 2 | 1 |
| fv/fm_acute2 | 0 | 0 | 0 | 0 |
| leaf rolling_recovery24 hr | 0 | 1 | 0 | 0 |
| leaf rolling_recovery48 hr | 0 | 0 | 0 | 0 |
| psii_acute1 | 2 | 0 | 1 | 0 |
| psii_acute2 | 0 | 0 | 0 | 0 |
| sgr - r2 > 0.9 | 0 | 2 | 0 | 2 |
| shoot dry weight | 1 | 1 | 0 | 0 |
| shoot fresh weight | 0 | 0 | 1 | 0 |

*P-value less than or equal to 0.1

For the construct evaluated, PHP29675, the statistical value associated with each improved variable is presented in FIGS. 6A, 6B, 7A and 7B. A significant positive result had a P-value of less than or equal to 0.1. The results for individual transformed maize lines are presented in FIGS. 6A and 6B. The summary evaluation for the construct PHP30853 is presented in FIGS. 7A and 7B. As shown in Table 18 and FIGS. 6A and 6B, under reduced water conditions corn transformation events EA2393.324.2.1 and EA2393.324.5.1 had significant positive values for three of the thirteen variables listed.

Example 15

Yield Analysis of Maize Lines Transformed with the Drought Tolerant Lead Gene A recombinant DNA construct containing a validated drought tolerant gene can be introduced into an elite maize inbred line either by direct transformation or introgression from a separately transformed line.

Transgenic plants, either inbred or hybrid, can undergo more vigorous field-based experiments to study yield enhancement and/or stability under well-watered and water-limiting conditions.

Subsequent yield analysis can be done to determine whether plants that contain the validated drought tolerant lead gene have an improvement in yield performance under water-limiting conditions, when compared to the control plants that do not contain the validated drought tolerant lead gene. Specifically, drought conditions can be imposed during the flowering and/or grain fill period for plants that contain the validated drought tolerant lead gene and the control plants. Reduction in yield can be measured for both. Plants containing the validated drought tolerant lead gene have less yield loss relative to the control plants, for example, at least 25% less yield loss, under water limiting conditions, or would have increased yield relative to the control plants under water non-limiting conditions.

The above method may be used to select transgenic plants with increased yield, under water-limiting conditions and/or well-watered conditions, when compared to a control plant not comprising said recombinant DNA construct.

Example 16

Screens to Identify Transgenic *Arabidopsis* Lines with Enhanced Drought Tolerance Quantitative Drought Screen: From each transgenic *Arabidopsis* line, nine glufosinate resistant T2 plants are sown, each in a single pot on SCOTTS® METRO-MIX® 200 soil. Flats are configured with 8 square pots each. Each of the square pots is filled to the top with soil. Each pot (or cell) is sown to produce 9 glufosinate resistant seedlings in a 3×3 array.

The soil is watered to saturation and then plants are grown under standard conditions (i.e., 16 hour light, 8 hour dark cycle; 22° C.; ~60% relative humidity). No additional water is given.

Digital images of the plants are taken at the onset of visible drought stress symptoms. Images are taken once a day (at the same time of day), until the plants appear dessicated. Typically, four consecutive days of data is captured.

Color analysis is employed for identifying potential drought tolerant lines. Color analysis can be used to measure the increase in the percentage of leaf area that falls into a yellow color bin. Using hue, saturation and intensity data ("HSI"), the yellow color bin consists of hues 35 to 45.

Maintenance of leaf area is also used as another criterion for identifying potential drought tolerant lines, since *Arabidopsis* leaves wilt during drought stress. Maintenance of leaf area can be measured as reduction of rosette leaf area over time.

Leaf area is measured in terms of the number of green pixels obtained using the LemnaTec imaging system. Activation-tagged and control (e.g., wild-type) plants are grown side by side in flats that contain 72 plants (9 plants/pot). When wilting begins, images are measured for a number of days to monitor the wilting process. From these data wilting profiles are determined based on the green pixel counts obtained over four consecutive days for activation-tagged and accompanying control plants. The profile is selected from a series of measurements over the four day period that gives the largest degree of wilting. The ability to withstand drought is measured by the tendency of activation-tagged plants to resist wilting compared to control plants.

LemnaTec HTSBonitUV software is used to analyze CCD images. Estimates of the leaf area of the *Arabidopsis* plants are obtained in terms of the number of green pixels. The data for each image is averaged to obtain estimates of mean and standard deviation for the green pixel counts for activation-tagged and wild-type plants. Parameters for a noise function are obtained by straight line regression of the squared deviation versus the mean pixel count using data for all images in a batch. Error estimates for the mean pixel count data are calculated using the fit parameters for the noise function. The mean pixel counts for activation-tagged and wild-type plants are summed to obtain an assessment of the overall leaf area for each image. The four-day interval with maximal wilting is obtained by selecting the interval that corresponds to the maximum difference in plant growth. The individual wilting responses of the activation-tagged and wild-type plants are obtained by normalization of the data using the value of the green pixel count of the first day in the interval. The drought tolerance of the activation-tagged plant compared to the wild-type plant is scored by summing the weighted difference between the wilting response of activation-tagged plants and wild-type plants over day two to day four; the weights are estimated by propagating the error in the data. A positive drought tolerance score corresponds to an activation-tagged plant with slower wilting compared to the wild-type plant. Significance of the difference in wilting response between activation-tagged and wild-type plants is obtained from the weighted sum of the squared deviations.

Lines with a significant delay in yellow color accumulation and/or with significant maintenance of rosette leaf area, when compared to the average of the whole flat, are designated as Phase 1 hits. Phase 1 hits are re-screened in duplicate under the same assay conditions. When either or both of the Phase 2 replicates show a significant difference (score of greater than 0.9) from the whole flat mean, the line is then considered a validated drought tolerant line.

Example 17

Validation of SS-DTP21-1 Via Transformation into *Arabidopsis*

The candidate gene that encodes SS-DTP21-1 (SEQ ID NO:27) was tested for its ability to confer drought tolerance in *Arabidopsis* in the following manner.

A 16.8-kb T-DNA based binary vector, called pBC-yellow was constructed with a 1.3-kb 35S promoter immediately upstream of the INVITROGEN™ GATEWAY® C1 conversion insert. The vector also contains the RD29a promoter driving expression of the gene for ZS-Yellow (INVITROGEN™), which confers yellow fluorescence to transformed seed.

The SS-DTP21-1 protein-coding region was amplified from genomic DNA from Sudan grass by RT-PCR with the following primers:

(1) SS-DTP21-1-5'attB forward primer (SEQ ID NO:67):

GGGGACAAGTTTGTACAAAAAAGCAGGCTATGGCCGAGAAGTACCA

CGAAG (2) SS-DTP21-1-3'attB reverse primer (SEQ ID NO:68):

GGGGACCACTTTGTACAAGAAAGCTGGGTTTAGCGGCGCTCTAATT

CCCTAATC

The forward primer contains the attB1 sequence (ACAAGTTTGTACAAAAAAGCAGGCT; SEQ ID NO:69) adjacent to the first 22 nucleotides of the protein-coding region, beginning with the ATG start codon.

The reverse primer contains the attB2 sequence (ACCACTTTGTACAAGAAAGCTGGGT; SEQ ID NO:70) adjacent to the reverse complement of the last 25 nucleotides of the protein-coding region, beginning with the reverse complement of the stop codon.

Using the INVITROGEN™ GATEWAY® CLONASE™ technology, a BP Recombination Reaction was performed with pDONR™/Zeo. This process removed the bacteria lethal ccdB gene, as well as the chloramphenicol resistance gene (CAM) from pDONR™/Zeo and directionally cloned the PCR product with flanking attB1 and attB2 sites creating an entry clone, pDONR™/Zeo-SS-DTP21-1. This entry clone was used for a subsequent LR Recombination Reaction with a destination vector, as follows.

A 16.8-kb T-DNA based binary vector (destination vector), called pBC-yellow (SEQ ID NO:71), was constructed with a 1.3-kb 35S promoter immediately upstream of the INVITROGEN™ GATEWAY® C1 conversion insert, which contains the bacterial lethal ccdB gene as well as the chloramphenicol resistance gene (CAM) flanked by attR1 and attR2 sequences. The vector also contains the RD29a promoter driving expression of the gene for ZS-Yellow (INVITROGEN™), which confers yellow fluorescence to transformed seed. Using the INVITROGEN™ GATEWAY® technology, an LR Recombination Reaction was performed on the pDONR™/Zeo-SS-DTP21-1 entry clone, containing the directionally cloned PCR product, and pBC-yellow. This allowed for rapid and directional cloning of the candidate gene behind the 35S promoter in pBC-yellow to create the 35S promoter::SS-DTP21-1 expression construct, pBC-Yellow-SS-DTP21-1.

The 35S promoter::SS-DTP21-1 expression construct was then introduced into wild-type *Arabidopsis* ecotype Col-0 using a whole plant *Agrobacterium*-mediated transformation procedure (International Patent Publication WO 2009/006276, the contents of which are herein incorporated by reference). Transgenic T1 seeds were selected by yellow fluorescence, and T1 seeds were plated next to wild-type seeds and grown under water limiting conditions. Growth conditions and imaging analysis were as described in Example 16. Transgenic *Arabidopsis* plants that were transformed with a construct where SS-DTP21-1 was directly expressed by the 35S promoter were found to be drought tolerant. The drought tolerance score, as determined by the method of Example 16, was 1.0.

Example 18

Validation of SS-DTP21-2 Via Transformation into *Arabidopsis*

The candidate gene that encodes SS-DTP21-2 (SEQ ID NO:32) was tested for its ability to confer drought tolerance in *Arabidopsis* in the following manner.

A 16.8-kb T-DNA based binary vector, called pBC-yellow was constructed with a 1.3-kb 35S promoter immediately upstream of the INVITROGEN™ GATEWAY® C1 conversion insert. The vector also contains the RD29a promoter driving expression of the gene for ZS-Yellow (INVITROGEN™), which confers yellow fluorescence to transformed seed.

The SS-DTP21-2 protein-coding region was amplified from genomic DNA from Sudan grass by RT-PCR with the following primers:

(3) SS-DTP21-2-5'attB forward primer (SEQ ID NO:72):

```
GGGGACAAGTTTGTACAAAAAAGCAGGCTATGGCCGAGAAGTACCA
CCATG
```

(4) SS-DTP21-2-3'attB reverse primer (SEQ ID NO:73):

```
GGGGACCACTTTGTACAAGAAAGCTGGGTTTAGCGGTGCTCTAATT
CCTTG
```

The forward primer contains the attB1 sequence (ACAAGTTTGTACAAAAAAGCAGGCT; SEQ ID NO:69) adjacent to the first 22 nucleotides of the protein-coding region, beginning with the ATG start codon.

The reverse primer contains the attB2 sequence (ACCACTTTGTACAAGAAAGCTGGGT; SEQ ID NO:70) adjacent to the reverse complement of the last 22 nucleotides of the protein-coding region, beginning with the reverse complement of the stop codon.

Using the INVITROGEN™ GATEWAY® CLONASE™ technology, a BP Recombination Reaction was performed with pDONR™/Zeo, to create an entry clone, pDONR™/Zeo-SS-DTP21-2. An LR Recombination Reaction was then performed on the pDONR™/Zeo-SS-DTP21-2 entry clone, containing the directionally cloned PCR product, and the destination vector pBC-yellow (SEQ ID NO:71; Example 17). This allowed for rapid and directional cloning of the candidate gene behind the 35S promoter in pBC-yellow to create the 35S promoter::SS-DTP21-2 expression construct, pBC-Yellow-SS-DTP21-2.

The 35S promoter::SS-DTP21-2 expression construct was then introduced into wild-type *Arabidopsis* ecotype Col-0 using a whole plant *Agrobacterium*-mediated transformation procedure (International Patent Publication WO 2009/006276, the contents of which are herein incorporated by reference). Transgenic T1 seeds were selected by yellow fluorescence, and T1 seeds were plated next to wild-type seeds and grown under water limiting conditions. Growth conditions and imaging analysis were as described in Example 16. Transgenic *Arabidopsis* plants that were transformed with a construct where SS-DTP21-2 was directly expressed by the 35S promoter were found to be drought tolerant. The drought tolerance score, as determined by the method of Example 16, was 2.2.

Example 19

Drought Tolerance Assay of SS-DTP21-1 Homologs in Rice

SS-DTP21-1 homologs described in Example 7 were introduced into a rice cultivar Yukihikari by *Agrobacterium*-mediated transformation, as described in Example 3. For these experiments, the region encoding SS-DTP21-1 in subclone Sub8 of genomic fragment IS125 was replaced with the protein-coding regions of various genes encoding polypeptides homologous to SS-DTP21-1. Transgenic rice plants were assayed for drought tolerance in the T0 generation. Details of the drought tolerance assay are described in Example 2. More than one transgenic plant out of 36, 42 or 48 regenerants of eight homologs (SS-DTP21-5, SB-DTP21-4, SB-DTP21-5, SB-DTP21-6, SB-DTP21-9, SB-DTP21-10, SH-DTP21-1, SO-DTP21-1) scored 2 or higher, whereas none of 42 regenerants of non-transgenic Yukihikari did so (Table 21). Therefore, each of these eight homologs were sufficient to produce drought tolerant transgenic rice.

TABLE 21

Drought Tolerance Assay of T0 Regenerants Transformed with SS-DTP21-1 Homologs

| DNA[1] | Homolog SEQ ID NO | Total No.[2] | No. ≥2[3] | Drought Response |
|---|---|---|---|---|
| Yukihikari (Control) | — | 42 | 0 | Susceptible |
| SS-DTP21-3 | 52 | 36 | 0 | Susceptible |
| SS-DTP21-4 | 54 | 36 | 0 | Susceptible |
| SS-DTP21-5 | 56 | 36 | 7 | Tolerant |
| SS-DTP21-6 | 79 | 48 | 0 | Susceptible |
| SS-DTP21-7 | 58 | 36 | 0 | Susceptible |
| SB-DTP21-1 | 41 | 36 | 0 | Susceptible |
| SB-DTP21-2 | 42 | 36 | 0 | Susceptible |
| SB-DTP21-3 | 45 | 36 | 0 | Susceptible |
| SB-DTP21-4 | 46 | 36 | 17 | Tolerant |
| SB-DTP21-5 | 81 | 42 | 12 | Tolerant |
| SB-DTP21-6 | 83 | 42 | 9 | Tolerant |
| SB-DTP21-9 | 85 | 42 | 16 | Tolerant |
| SB-DTP21-10 | 87 | 42 | 9 | Tolerant |
| SH-DTP21-1 | 60 | 48 | 21 | Tolerant |
| SH-DTP21-2 | 62 | 36 | 0 | Susceptible |
| SO-DTP21-1 | 64 | 36 | 6 | Tolerant |
| SO-DTP21-2 | 66 | 36 | 0 | Susceptible |

[1]DNA used in transformation.
[2]Total number of regenerants tested.
[3]Number of regenerants scoring 2 or higher.

Example 20

Drought Tolerance Assay of the T1 Generation of Tobacco Lines Transformed with SS-DTP21-1

The promoter region of subfragment Sub8 of genomic fragment IS125, encoding SS-DTP21-1, was replaced with 35S promoter as follows. PCR with Pyrobest DNA Polymerase (TAKARA-BIO) was carried out using Sub8 plasmid DNA as a template and a primer pair, SEQ ID NO:88 (5'-ACCTTTTTATCCTCAAAGCTTCTTCTCAGA-3') and SEQ ID NO:89 (5'-ACCCCTGACCTCAATTGT-CAAACACCAAGC-3'), and then the PCR products were inserted into pCR4 Blunt-TOPO (Invitrogen). After confirmation of the sequence of the PCR-amplified region, the resultant plasmid was digested with HindIII and MfeI to give a 1.8-kb fragment. In a similar way, PCR was carried out using pSB31 (Ishida et al. 1996 Nature Biotechnology 14:745-750) plasmid DNA as a template and a primer pair, SEQ ID NO:90 (5'-GGGCGTCGTTCTGGGTCAATTGT-TATAGAG-3') and SEQ ID NO:91 (5'-GGACGTTTT-TAAGGTACCGAATTCCAATCC-3'), and then the PCR products were inserted into pCR4 Blunt-TOPO, followed by treatment with KpnI and MfeI to give a 1.4-kb fragment. The two fragments (1.8-kb and 1.4-kb fragments) were inserted into pSB200 that had been digested with HindIII and KpnI and then pre-treated with CIAP (calf intestine alkaline phosphatase). The resultant chimeric gene (hereafter designated as "35S+Sub8" or "35S promoter::SS-DTP21-1 construct", these terms used interchangeably herein) was introduced into tobacco variety SR1 by *Agrobacterium*-mediated transformation. The transgenic tobacco plants were assayed for drought tolerance in the T1 generation.

The genetically modified plants and wild-type plants were cultivated in 12 cm pots, and only hygromycin resistant genetically modified plants were used for drought tolerance assay. During the drought treatment, in which watering was stopped, photographs were taken from the top by using Scanalyzer (LemnaTec GmbH) and the leaf area was measured in units of pixel numbers. The leaf areas relative to the leaf areas measured on the first day of the drought treatment were statistically examined. The leaves of the wild type plants shrank quickly after the drought treatment, whereas one of the nine T1 lines retained the leaf size even 3 days after the drought treatment, as presented in the following table. This line, T1 line No. 9, was also statistically different from the wild type plants on day 6 in the relative leaf area. Therefore, T1 line No. 9, a transgenic tobacco line containing the 35S promoter::SS-DTP21-1 construct, was clearly drought tolerant.

TABLE 22

Ratio (%) of Leaf Area Relative to Leaf Area for the First Day

| | Days after watering was stopped | | | | | | | |
|---|---|---|---|---|---|---|---|---|
| | 3 | | 6 | | 7 | | 9 | |
| | mean | SD | mean | SD | mean | SD | mean | SD |
| T1 line (No. 9) | 105.0 | 1.6 | 68.0 | 11.0 | 54.4 | 9.2 | 36.9 | 3.5 |
| wild-type | 92.4 | 10.2 | 54.2 | 7.3 | 46.7 | 6.2 | 35.5 | 3.8 |
| t-test | ** | | * | | NS | | NS | |

What is claimed is:

1. A plant comprising in its genome a recombinant DNA construct comprising a polynucleotide operably linked to at least one heterologous regulatory element, wherein said polynucleotide comprises a nucleotide sequence selected from the group consisting of:
   (a) a nucleotide sequence encoding a polypeptide with drought tolerance activity, wherein the polypeptide has an amino acid sequence of at least 90% sequence identity, based on the Clustal V method of alignment with pairwise alignment default parameters of KTUPLE=1, GAP PENALTY=3, WINDOW=5 and DIAGONALS SAVED=5, when compared to SEQ ID NO:32;
   (b) a nucleotide sequence encoding a polypeptide wherein the amino acid sequence of the polypeptide comprises SEQ ID NO:32; and
   (c) a nucleotide sequence comprising SEQ ID NO:31;
and wherein said plant exhibits increased drought tolerance when compared to a control plant not comprising said recombinant DNA construct.

2. A plant comprising in its genome a recombinant DNA construct comprising a polynucleotide operably linked to at least one heterologous regulatory element, wherein said polynucleotide comprises a nucleotide sequence selected from the group consisting of:
   (a) a nucleotide sequence encoding a polypeptide with drought tolerance activity, wherein the polypeptide has an amino acid sequence of at least 90% sequence identity, based on the Clustal V method of alignment with pairwise alignment default parameters of KTUPLE=1, GAP PENALTY=3, WINDOW=5 and DIAGONALS SAVED=5, when compared to SEQ ID NO:32;
   (b) a nucleotide sequence encoding a polypeptide wherein the amino acid sequence of the polypeptide comprises SEQ ID NO:32; and
   (c) a nucleotide sequence comprising SEQ ID NO:31;
and wherein said plant exhibits an increase in yield when compared to a control plant not comprising said recombinant DNA construct.

3. The plant of claim 2, wherein said plant exhibits said increase in yield when compared, under water limiting conditions, to said control plant not comprising said recombinant DNA construct.

4. The plant of any one of claim 1, 2 or 3, wherein the plant is a monocot or dicot.

5. The plant of claim 4 wherein the plant is selected from the group consisting of: maize, soybean, sunflower, *sorghum*, canola, wheat, alfalfa, cotton, rice, barley, millet, sugarcane, switchgrass, tobacco, potato and sugar beet.

6. A method of increasing drought tolerance in a plant, comprising:
   (a) introducing into a regenerable plant cell a recombinant DNA construct comprising a polynucleotide operably linked to at least one heterologous regulatory element, wherein said polynucleotide comprises a nucleotide sequence selected from the group consisting of:
       (i) a nucleotide sequence encoding a polypeptide with drought tolerance activity, wherein the polypeptide has an amino acid sequence of at least 90% sequence identity, based on the Clustal V method of alignment with pairwise alignment default parameters of KTUPLE=1, GAP PENALTY=3, WINDOW=5 and DIAGONALS SAVED=5, when compared to SEQ ID NO:32;
       (ii) a nucleotide sequence encoding a polypeptide wherein the amino acid sequence of the polypeptide comprises SEQ ID NO:32; and (iii) a nucleotide sequence comprising SEQ ID NO:31; and (b) regenerating a transgenic plant from the regenerable plant cell after step (a), wherein the transgenic plant comprises in its genome the recombinant DNA construct and exhibits increased drought tolerance when compared to a control plant not comprising the recombinant DNA construct.

7. The method of claim 6, further comprising:

(c) obtaining a progeny plant derived from the transgenic plant, wherein said progeny plant comprises in its genome the recombinant DNA construct and exhibits increased drought tolerance when compared to a control plant not comprising the recombinant DNA construct.

8. A method of evaluating drought tolerance in a plant, comprising:

(a) obtaining a transgenic plant, wherein the transgenic plant comprises in its genome a recombinant DNA construct comprising a polynucleotide operably linked to at least one heterologous regulatory element, wherein said polynucleotide comprises a nucleotide sequence selected from the group consisting of:

(i) a nucleotide sequence encoding a polypeptide with drought tolerance activity, wherein the polypeptide has an amino acid sequence of at least 90% sequence identity, based on the Clustal V method of alignment with pairwise alignment default parameters of KTUPLE=1, GAP PENALTY=3, WINDOW=5 and DIAGONALS SAVED=5, when compared to SEQ ID NO:32;

(ii) a nucleotide sequence encoding a polypeptide wherein the amino acid sequence of the polypeptide comprises SEQ ID NO:32; and (iii) a nucleotide sequence comprising SEQ ID NO:31; and (b) obtaining a progeny plant derived from the transgenic plant of (a), wherein the progeny plant comprises in its genome the recombinant DNA construct; and (c) evaluating the progeny plant for drought tolerance compared to a control plant not comprising the recombinant DNA construct.

9. A method of determining an alteration of an agronomic characteristic in a plant, comprising:

(a) obtaining a transgenic plant, wherein the transgenic plant comprises in its genome a recombinant DNA construct comprising a polynucleotide operably linked to at least one heterologous regulatory element, wherein said polynucleotide comprises a nucleotide sequence selected from the group consisting of:

(i) a nucleotide sequence encoding a polypeptide with drought tolerance activity, wherein the polypeptide has an amino acid sequence of at least 90% sequence identity, based on the Clustal V method of alignment with pairwise alignment default parameters of KTUPLE=1, GAP PENALTY=3, WINDOW=5 and DIAGONALS SAVED=5, when compared to SEQ ID NO:32;

(ii) a nucleotide sequence encoding a polypeptide wherein the amino acid sequence of the polypeptide comprises SEQ ID NO: 32; and (iii) a nucleotide sequence comprising SEQ ID NO:31; and (b) obtaining a progeny plant derived from the transgenic plant of step (a), wherein the progeny plant comprises in its genome the recombinant DNA construct; and (c) determining whether the progeny plant exhibits an alteration of at least one agronomic characteristic when compared to a control plant not comprising the recombinant DNA construct.

10. The method of claim 9, wherein said at least one agronomic trait is yield and further wherein said alteration is an increase.

11. The method of any one of claim 9 or 10, wherein said determining step (c) comprises determining whether the transgenic plant exhibits an alteration of at least one agronomic characteristic when compared, under water limiting conditions, to a control plant not comprising the recombinant DNA construct.

12. The method of any one of claims 6 to 10, wherein the plant is a monocot or a dicot.

13. The method of claim 12, wherein the plant is selected from the group consisting of: maize, soybean, sunflower, *sorghum*, canola, wheat, alfalfa, cotton, rice, barley, millet, sugarcane, switchgrass, tobacco, potato and sugar beet.

14. A recombinant DNA construct comprising at least one heterologous regulatory element operably linked to a polynucleotide comprising:

(a) a nucleotide sequence encoding a polypeptide with drought tolerance activity, wherein the polypeptide has an amino acid sequence of at least 96% sequence identity, based on the Clustal V method of alignment with pairwise alignment default parameters of KTUPLE=1, GAP PENALTY=3, WINDOW=5 and DIAGONALS SAVED=5, when compared to SEQ ID NO:32; or (b) a full complement of the nucleotide sequence of part (a), wherein the full complement and the nucleotide sequence of part (a) consist of the same number of nucleotides and are 100% complementary.

15. The polynucleotide of claim 14, wherein the polypeptide of part (a) has an amino acid sequence of at least 97% sequence identity, based on the Clustal V method of alignment with the pairwise alignment default parameters, when compared to SEQ ID NO:32.

16. The polynucleotide of claim 14, wherein the polypeptide of part (a) has an amino acid sequence of at least 98% sequence identity, based on the Clustal V method of alignment with the pairwise alignment default parameters, when compared to SEQ ID NO:32.

17. The polynucleotide of claim 14, wherein the polypeptide of part (a) has an amino acid sequence of at least 99% sequence identity, based on the Clustal V method of alignment with the pairwise alignment default parameters, when compared to SEQ ID NO: 32.

18. The polynucleotide of claim 14, wherein the polypeptide of part (a) comprises SEQ ID NO: 32.

19. A cell comprising the recombinant DNA construct of claim 14, wherein the cell is selected from the group consisting of a bacterial cell, a yeast cell, an insect cell and a plant cell.

20. A seed comprising the recombinant DNA construct of claim 14.

21. A method for isolating a polypeptide encoded by the recombinant DNA construct of claim 14, wherein the method comprises the following:

(a) transforming a cell with the recombinant DNA construct of claim 14;

(b) growing the transformed cell of step (a) under conditions suitable for expression of the polypeptide encoded by the recombinant DNA construct; and (c) isolating the polypeptide from the transformed cell of step (b).

22. A vector comprising the recombinant DNA construct of claim 14.

23. Seed of the plant of any one of claims 1 to 3, wherein said seed comprises in its genome a recombinant DNA construct comprising a polynucleotide operably linked to at least one heterologous regulatory element, wherein said polynucleotide encodes a polypeptide having an amino acid sequence of at least 90% sequence identity, based on the Clustal V method of alignment, when compared to SEQ ID NO: 32, and wherein a plant produced from said seed exhibits either an increase in drought tolerance, or an increase in yield, or both, when compared to a control plant not comprising said recombinant DNA construct.

24. Seed of the plant of claim 4, wherein said seed comprises in its genome a recombinant DNA construct comprising a polynucleotide operably linked to at least one heterologous regulatory element, wherein said polynucleotide encodes a polypeptide having an amino acid sequence of at least 90% sequence identity, based on the Clustal V method of alignment, when compared to SEQ ID NO:32, and wherein a plant produced from said seed exhibits either an increase in drought tolerance, or an increase in yield, or both, when compared to a control plant not comprising said recombinant DNA construct.

25. Seed of the plant of claim 5, wherein said seed comprises in its genome a recombinant DNA construct comprising a polynucleotide operably linked to at least one heterologous regulatory element, wherein said polynucleotide encodes a polypeptide having an amino acid sequence of at least 90% sequence identity, based on the Clustal V method of alignment, when compared to SEQ ID NO:32, and wherein a plant produced from said seed exhibits either an increase in drought tolerance, or an increase in yield, or both, when compared to a control plant not comprising said recombinant DNA construct.

26. The method of claim 11, wherein the plant is a monocot or a dicot.

27. The method of claim 26, wherein the plant is selected from the group consisting of: maize, soybean, sunflower, *sorghum*, canola, wheat, alfalfa, cotton, rice, barley, millet, sugarcane, switchgrass, tobacco, potato and sugar beet.

* * * * *